United States Patent
Seko et al.

(10) Patent No.: US 7,166,590 B2
(45) Date of Patent: Jan. 23, 2007

(54) AMINO ACID DERIVATIVES

(75) Inventors: Takuya Seko, Osaka (JP); Masashi Kato, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 616 days.

(21) Appl. No.: 10/154,780

(22) Filed: May 28, 2002

(65) Prior Publication Data

US 2003/0013725 A1 Jan. 16, 2003

Related U.S. Application Data

(63) Continuation of application No. 09/462,447, filed as application No. PCT/JP98/03013 on Jul. 3, 1998, now abandoned.

(30) Foreign Application Priority Data

Jul. 8, 1997 (JP) ............................................. 9-197784
May 13, 1998 (JP) ........................................... 10-148405

(51) Int. Cl.
*A61K 31/54* (2006.01)
*C07D 279/12* (2006.01)

(52) U.S. Cl. ............................... 514/226.8; 514/227.5; 514/357; 514/365; 514/374; 514/399; 514/448; 544/54; 544/58.1; 544/58.4; 546/323; 548/200; 548/236; 548/333.5; 549/72

(58) Field of Classification Search .................. 544/54, 544/58.1, 58.4, 55, 56.4, 58.6, 313, 367; 546/323, 189, 194, 201, 208, 207, 210, 213; 548/200, 236, 333.5, 201, 204, 334.1, 340.1; 549/72, 76, 494; 514/226.8, 227.5, 357, 365, 514/374, 399, 448, 227.8, 257.7, 316, 254.01, 514/254.02, 318, 326, 327
See application file for complete search history.

(56) References Cited

U.S. PATENT DOCUMENTS

| | | | | |
|---|---|---|---|---|
| 4,962,225 A | 10/1990 | Okada et al. | ............... | 560/163 |
| 5,596,000 A | 1/1997 | Esser et al. | ................. | 514/312 |
| 5,731,340 A | 3/1998 | Bras et al. | | |
| 6,605,608 B1 * | 8/2003 | Seko et al. | ............. | 514/226.8 |

FOREIGN PATENT DOCUMENTS

| | | |
|---|---|---|
| EP | 0 194 464 | 9/1986 |
| EP | 0 237 082 A2 | 9/1987 |
| EP | 0 405 391 | 1/1991 |
| EP | 0 520 200 | 12/1992 |
| EP | 0 697 403 A1 | 2/1996 |
| EP | 0 757 037 | 2/1997 |
| EP | 0 780 386 | 6/1997 |
| EP | 0 805 147 | 11/1997 |
| JP | 6-80696 | 3/1994 |
| JP | 8-208690 | 8/1996 |
| JP | 8-217671 | 8/1996 |
| JP | 8-217751 | 8/1996 |
| WO | WO 89/02431 | 3/1989 |
| WO | WO 91/01976 | 2/1991 |
| WO | WO 93/15047 | 8/1993 |
| WO | WO 94/07815 | 4/1994 |
| WO | WO 94/12181 | 6/1994 |
| WO | WO 96/11940 | 4/1996 |
| WO | WO 97/49679 | 12/1997 |
| WO | WO 98/54123 | 12/1998 |

OTHER PUBLICATIONS

CAS printout for Wolfe et al. Chem. Abs. 110:18385 (1989).*
Gillessen et al., Chemical Abstracts, vol. 72:67256, 1970.*
Poroshin et al., Chemical Abstracts, vol. 63:89274, 1965.*
Gasc et al., Chemical Abstracts, vol. 114:82543, 1991.*
Shengeliya et al., Chemical Abstracts, vol. 107:77510, 1987.*
Kowollik et al., Chemical Abstracts, vol. 103:105274, 1985.*
Lau et al., Chemical Abstracts, vol. 99:64868, 1983.*
CAS printout for Connell et al, Oct. 1993, Chemical Abstracts, vol. 121:109676.
CAS printout for Ravi, et al, Apr. 1984, Chemical Abstracts, vol. 103:2340.
CAS printout for Bodanszky, et al, Feb. 1972, Chemical Abstracts, vol. 77:75449.
CAS printout for Aubury, et al, May 1987, Chemical Abstracts, vol. 109:73893.
PCT International Preliminary Examination Report, 1998.
CAS printout for Connell et al, Oct. 1993.
CAS printout for Ravi, et al, Apr. 1984.

(Continued)

*Primary Examiner*—Richard L. Raymond
(74) *Attorney, Agent, or Firm*—Sughrue Mion, PLLC

(57) ABSTRACT

A compound of the formula (I):

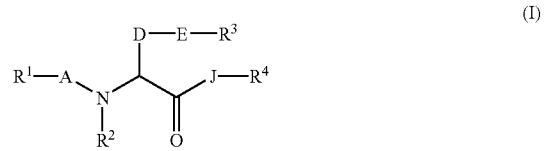

[wherein $R^1$ is (substituted) alkyl, alkoxy, phenyl, hetero ring etc.; A is bond, CO, $SO_2$; $R^2$ is H, (substituted) alkyl etc.; D is alkylene etc.; E is COO, OCO, O, S, SO, $SO_2$ etc.; $R^3$ is (substituted) alkyl, carbocyclic ring, hetero ring; J is O, $NR^{16}$ ($R^{16}$ is H, substituted alkyl); $R^4$ is (substituted) alkyl, carbocyclic ring, hetero ring.] or non-toxic salt thereof, and an N-type calcium channel blocker comprising it as an active ingredient.

The compounds of the formula (I) possess an inhibitory action on N-type calcium channel, so they are useful as agent for the prevention and/or treatment of cerebral infarct, transient ischemic attack, encephalomyelopathy after cardiac operation, spinal angiopathy, hypertension with stress, neurosis or epilepsy etc. or agent for the treatment of pain.

8 Claims, No Drawings

OTHER PUBLICATIONS

CAS printout for Bodanszky, et al, Feb. 1972.

CAS printout for Aubry, et al, May 1987.

PCT International Preliminary Examination Report, 1998.

M. Ashraf Shalaby et al., "Thiopeptide Synthesis. α–Amino Thionoacid Derivatives of Nitrobenzotriazole as Thioacylating Agents," *J. Org. Chem.*, (1996) 61(25), 9045–9048.

Kosaku Noda et al., "A facile method for preparation of t–butyloxycarbonylamino acid p–nitroanilides," *Int. j. Peptide Protein Res* (1990) 36(2), 197–200.

Shi Pu–Tao et al., "Opiate Multiple Receptor Binding Activity of Enkephalin Analogs," ACTA Biochimica and Biophysica Sinica (Jan. 1983), vol. 15, No. 1, 67–76.

Castelhano et al., "Synthesis, Chemistry, and Absolute Configuration of Novel Transglutaminase Inhibitors Containing a 3–Halo–4,5–dihydroisoxazole," *Bioorganic Chemistry* (1988), 16(3), 335–40.

V.F. Pozdnev et al., "Activation of carboxylic acids by pyrocarbonates. Synthesis of arylamides of N–protected amino acids and small peptides using dialkylk pyrocarbonates as condensing reagents," *Int. J. Peptide Protein Res.* (1994) 44(1), 36–48.

Václav Čeřovsky, et al., "Papain–Catalyzed Synthesis of 2–Naphthylamdes of N–Acylamino Acids and Dipeptides," *Collection Czech Chem. Comm.* (1987), vol. 52, 2309–16.

F. Orosz et al., "Derivatives of DL–1,2,3,4–Tetrahydro–2–Naphthylamine Acylated with Amino Acids," Acta Chimica Academiac Scientiarum Hungaricae (1966) 49(3), 291–302.

Michio Namikoshi et al., "Use of Tetrabutylammonium Fluoride as a Facile Deprotecting Reagent for 4–Nitrobenzyl, 2,2,2–Tricholorethyl, and Phenacyl Esters of Amino Acids," *J. Org. Chem* (1991), 56, 5464–5466.

Tohru Sugawara et al., "Application of a Unique Automated Synthesis System for Solution–phase Peptide Synthesis," *Chem. Pharm. Bull.* (1995), 43(8), 1272–1280.

Nobutaka Fujii et al., "Studies on Peptides. CXXXII. Evaluation of Two β–Carboxyl Protecting Groups of Aspartic Acid, Cycloheptyl and Cycloctyl, for Peptide Synthesis," *Chem. Pharm. Bull* (1985), 34(2), 864–8.

Haruaka Yajima et al Chem. Pharm. Bull., "Studies ofn Peptides. CXLIII. Evaluation of β–Menthylaspartate for Peptide Synthesis," (1986), 34(10) 4356–61.

Tam et al., "Mechanisms of Aspartimide Formation: The effects of Protecting Groups, Acid, Base, Temperature and Time," *Peptide Research* (1988), 1(1) 6–18.

\* cited by examiner

AMINO ACID DERIVATIVES

This is a continuation of application Ser. No. 09/462,447 filed Jan. 7, 2000, which is now abandoned, and which is a National Stage Application of International PCT Application No. PCT/JP98/03013, file Jul. 3, 1998; the above noted prior applications are all hereby incorporated by reference.

FIELD OF THE INVENTION

The present invention relates to an amino acid derivative of the formula (I), a process for the preparation thereof, and a pharmaceutical composition comprising it as an active ingredient.

More particularly, it relates to amino acid derivatives of the formula (I)

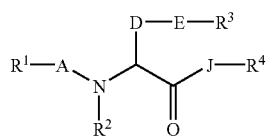

(I)

(wherein all the symbols are the same meanings as hereinafter described.), non-toxic salts thereof, and the hydrates thereof, processes for the preparation thereof, and N-type calcium channel blocker comprising them.

BACKGROUND OF THE INVENTION

Calcium ion has been known as an intracellular messenger for signal transduction, and it is suggested that various physiological events are triggered by the elevation of intracellular calcium concentration. Calcium influx from extracellular fluid is one of the mechanisms for the elevation of intracellular calcium concentration. The gate of calcium influx is the voltage-dependent calcium channels. The voltage-dependent calcium channel is opened by the polarization of plasma membrane, and calcium ion influxes from extracellular fluid into the cell selectively through the channel according to the electrochemical gradient. The voltage-dependent calcium channels are classified into N-, L-, P-, Q- and T-type at present. It is known that L- and T-type calcium channels are distributed in the various tissues ubiquitously, and especially, L-type calcium channel is enriched in the smooth muscle cells or the cardiac muscle cells. On the other hand, N- and P-type calcium channels are mainly located in the nervous system and related to the neurotransmitter release. This neurotransmitter is stored in synaptic vesicles of nerve terminals at resting state. When action potential by signal transmission on nerve is conducted in pre-synaptic fiber and reaches to the nerve terminal, the voltage-dependent calcium channels are activated and then, calcium ion influxes into the nerve terminals. By these mechanisms, synaptic vesicles are fused with pre-synaptic membrane, and neurotransmitters in the vesicles are released. The released neurotransmitters are related to signal transmission in synapse due to binding to their receptors in post-synaptic membrane. From the above, an N-type calcium channel blocker is thought to be effective on various diseases induced by an excessive release of neurotransmitter. For example, it may be useful as agent for the prevention and/or treatment of cerebral infarct (J. Cereb. Blood Flow Metab., Vol. 17, 421–429, 1997), transient ischemic attack, encephalomyelopathy after cardiac operation, spinal angiopathy, hypertension with stress (Science., 239, 57–61, 1988), neurosis or epilepsy etc. or agent for the treatment of pain (for example, acute pain, chronic pain, pain after operation, cancer pain, neuralgia, pain caused by infection etc.) (Pain, 60, 83–90, 1995).

The venoms isolated from the genus Conus, ω-conotoxin GVIA, MVIIA, are well known as N-type calcium channel blockers.

But, these ω-conotoxins are peptidic compounds, so it is expected that they have various problems (for example, they are not absorbed into the living body easily.). Therefore, there is a demand for arrangement of these blockers to non-peptidic compounds namely to small-molecule. There are some reports relate to small-molecule as follows:

For example, it is described in the specification of Japanese Patent Kokai Hei 8-217671 that glycine derivatives of the formula (A)

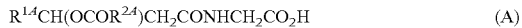

(A)

(wherein $R^{1A}$ and $R^{2A}$ are, same or different, C1–19 straight or branched alkyl, or C2–19 straight or branched alkenyl.) and salts thereof are N-type calcium channel blocker.

It is described In the specification of EP 805147 that the compounds of the formula (B)

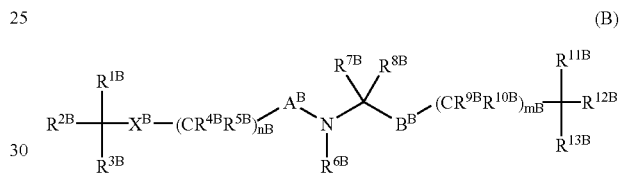

(B)

(wherein $R^{1B}$ is alkyl, $R^{2B}$ is hydrogen, optionally substituted alkyl, optionally substituted aryl or optionally substituted heteroaryl, $R^{3B}$ is hydrogen, CN, $X^B$ is bond or $SO_2$, $R^{4B}$, $R^{5B}$, $R^{6B}$, $R^{8B}$, $R^{9B}$ and $R^{10B}$ are each hydrogen or alkyl, $A^B$ is $CH_2$ or $Y^B CO$ (in which $Y^B$ is bond.), $R^{7B}$ is C-α substituent of amino acid or ester thereof, $R^{6B}$ and $R^{7B}$ together form C3–5 alkylene chain optionally substituted by C1-alkyl or hydroxy, or $CH_2$-$Z^B$-$CH_2$ (in which $Z^B$ is CO, S, SO, $SO_2$.), $R^{7B}$ and $R^{8B}$ together form C3–5 alkylene chain optionally substituted by C1–4 alkyl or hydroxy, $B^B$ is $CON(R^{21B})$, mB is 0~2, $R^{11B}$ is hydrogen or alkyl, $R^{12B}$ is hydrogen, alkyl, optionally substituted aryl or optionally substituted heteroaryl, $R^{13B}$ is alkyl, optionally substituted aryl, or optionally substituted heteroaryl, $R^{12B}$ and $R^{13B}$ together form C3–8 cycloalkyl.), the salts thereof, or the ester thereof are calcium channel modulator (necessary part is extracted in the explanation of the group.).

Also, it is described in the specification of Japanese Patent Kokai Sho 61-200950 that the compound of the formula (C)

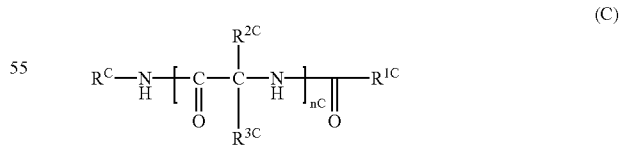

(C)

(wherein $R^C$ and $R^{1C}$ each independently, is lower alkyl, aryl-lower alkyl or phenyl optionally substituted by one or more electron-withdrawing or electron-donating group, $R^{2C}$ and $R^{3C}$ each independently, is hydrogen, lower alkyl, aryl-lower alkyl or phenyl optionally substituted with one or more electron-withdrawing or electron-donating group, and nC is 1~4.) and pharmaceutically acceptable salts thereof are anti-convulsant agent.

DISCLOSURE OF THE INVENTION

As the result of energetic investigations in order to find compounds possessing an N-type calcium channel blockery action, the present inventors have found that the purpose has been accomplished by the compound of the formula (I). Most of compounds of the formula (I) are new.

The present invention relates to:

1) an N-type calcium channel blocker comprising, as an active ingredient, an amino acid derivative of the formula (I)

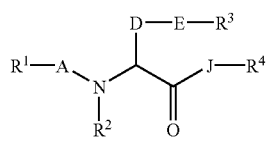

(I)

[wherein $R^1$ is
1) C1–15 alkyl,
2) C1–8 alkoxy,
3) phenyl,
4) C3–8 cycloalkyl,
5) hetero ring,
6) C1–4 alkyl substituted by phenyl, C3–8 cycloalkyl, or hetero ring,
7) C1–4 alkoxy substituted by phenyl, C3–8 cycloalkyl, or hetero ring, or
8) C2–4 alkenyl substituted by phenyl, C3–8 cycloalkyl, or hetero ring (with proviso that, all phenyl, C3–8 cycloalkyl and hetero ring in $R^1$ group may be substituted by 1~3 of substituent selected from the following (i)~(xi);
   (i) C1–4 alkyl,
   (ii) C1–4 alkoxy,
   (iii) phenyl,
   (iv) phenoxy,
   (v) benzyloxy,
   (vi) —$SR^5$ (in which $R^5$ is hydrogen or C1–4 alkyl.),
   (vii) C2–5 acyl,
   (viii) halogen,
   (ix) C1–4 alkoxycarbonyl,
   (x) nitro,
   (xi) —$NR^6R^7$ (in which $R^5$ and $R^7$ each independently, is hydrogen, C1–4 alkyl or C1–4 alkoxycarbonyl, or $R^6$ and $R^7$ taken together with the nitrogen atom to which they are attached may represent 5~7 membered saturated hetero ring containing another one nitrogen atom or one oxygen atom.).);
A is bond, —CO— or —$SO_2$—;
$R^2$ is hydrogen or C1–4 alkyl optionally substituted by one phenyl;
D is C1–4 alkylene or C2–4 alkenylene;
E is
1) —COO—,
2) —OCO—,
3) —$CONR^8$— (in which $R^8$ is hydrogen or C1–4 alkyl.),
4) —$NR^9CO$— (in which $R^9$ is hydrogen or C1–4 alkyl.),
5) —O—,
6) —S—,
7) —SO—,
8) —$SO_2$—,
9) —$NR^{10}$— (in which $R^{10}$ is hydrogen or C1–4 alkyl.),
10) —CO—,
11) —$SO_2NR^{11}$— (in which $R^{11}$ is hydrogen or C1–4 alkyl.), or
12) —$NR^{12}SO_2$— (in which $R^{12}$ is hydrogen or C1–4 alkyl.);
$R^3$ is
1) carbocyclic ring,
2) hetero ring, or
3) C1–4 alkyl substituted by carbocyclic ring or hetero ring (with proviso that, all carbocyclic ring and hetero ring in $R^3$, may be substituted by 1~3 of substituent selected from the following (i)~(xi);
   (i) C1–4 alkyl,
   (ii) C1–4 alkoxy,
   (iii) phenyl,
   (iv) phenoxy,
   (v) benzyloxy,
   (vi) —$SR^{13}$ (in which $R^{13}$ is hydrogen or C1–4 alkyl.),
   (vii) C2–5 acyl,
   (viii) halogen,
   (ix) C1–4 alkoxycarbonyl,
   (x) nitro,
   (xi) —$NR^{14}R^{15}$ (in which $R^{14}$ and $R^{15}$ each independently, is hydrogen, C1–4 alkyl or C1–4 alkoxycarbonyl, or $R^{14}$ and $R^{15}$ taken together with the nitrogen atom to which they are attached may represent 5~7 membered saturated hetero ring containing another one nitrogen atom or one oxygen atom.).);
J is —O— or —$NR^{16}$— (in which $R^{16}$ is hydrogen or C1–4 alkyl.);
$R^4$ is
1) C1–8 alkyl,
2) carbocyclic ring,
3) hetero ring,
4) C1–8 alkyl substituted by 1~3 of substituent selected from the following (i)~(v);
   (i) carbocyclic ring,
   (ii) hetero ring,
   (iii) $COOR^{17}$ (in which $R^{17}$ is hydrogen or C1–4 alkyl substituted by one phenyl (in which phenyl may be substituted by C1–4 alkoxy.),
   (iv) $SR^{18}$ (in which $R^{18}$ is hydrogen or C1–4 alkyl.),
   (v) $OR^{19}$ (in which $R^{19}$ is hydrogen or C1–4 alkyl.), or
when J represents —$NR^{16}$— group, $R^4$ and $R^{16}$ taken together with the nitrogen atom to which they are attached may represent hetero ring (with proviso that, all carbocyclic ring and hetero ring, and hetero ring represented by $R^4$ and $R^{16}$ taken together with the nitrogen atom to which they are attached may be substituted by 1~3 of substituent selected from the following (i)~(xi);
   (i) C1–4 alkyl,
   (ii) C1–4 alkoxy,
   (iii) phenyl,
   (iv) phenoxy,
   (v) benzyloxy,
   (vi) —$SR^{20}$ (in which $R^{20}$ is hydrogen or C1–4 alkyl.),
   (vii) C2–5 acyl,
   (viii) halogen,
   (ix) C1–4 alkoxycarbonyl,
   (x) nitro,
   (xi) —$NR^{21}R^{22}$ (in which $R^{21}$ and $R^{22}$ each independently, is hydrogen, C1–4 alkyl or C1–4 alkoxycarbonyl, or $R^{21}$ and $R^{22}$ taken together with the nitrogen atom to which they are attached may represent 5~7 membered saturated hetero ring containing another one nitrogen atom or one oxygen atom.).).], non-toxic salt thereof, or a hydrate thereof, and
2) an amino acid derivative of the formula (I)

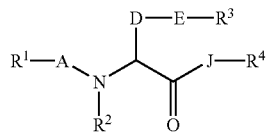

[wherein R¹ is
1) C1–15 alkyl,
2) C1–8 alkoxy,
3) phenyl,
4) C3–8 cycloalkyl,
5) hetero ring,
6) C1–4 alkyl substituted by phenyl, C3–8 cycloalkyl, or hetero ring,
7) C1–4 alkoxy substituted by phenyl, C3–8 cycloalkyl, or hetero ring, or
8) C2–4 alkenyl substituted by phenyl, C3–8 cycloalkyl, or hetero ring (with proviso that, all phenyl, C3–8 cycloalkyl and hetero ring in R¹ group may be substituted by 1~3 of substituent selected from the following (i)~(xi);
    (i) C1–4 alkyl,
    (ii) C1–4 alkoxy,
    (iii) phenyl,
    (iv) phenoxy,
    (v) benzyloxy,
    (vi) —SR⁵ (in which R⁵ is hydrogen or C1–4 alkyl.),
    (vii) C2–5 acyl,
    (viii) halogen,
    (ix) C1–4 alkoxycarbonyl,
    (x) nitro,
    (xi) —NR⁶R⁷ (in which R⁶ and R⁷ each independently, is hydrogen, C1–4 alkyl or C1–4 alkoxycarbonyl, or R⁶ and R⁷ taken together with the nitrogen atom to which they are attached may represent 5~7 membered saturated hetero ring containing another one nitrogen atom or one oxygen atom.).);
A is bond, —CO— or —SO₂—;
R² is hydrogen or C1–4 alkyl optionally substituted by one phenyl;
D is C1–4 alkylene or C2–4 alkenylene;
E is
1) —COO—,
2) —OCO—,
3) —CONR⁸— (in which R⁸ is hydrogen or C1–4 alkyl.),
4) —NR⁹CO— (in which R⁹ is hydrogen or C1–4 alkyl.),
5) —O—,
6) —S—,
7) —SO—,
8) —SO₂—,
9) —NR¹⁰— (in which R¹⁰ is hydrogen or C1–4 alkyl.),
10) —CO—,
11) —SO₂NR¹¹— (in which R¹¹ is hydrogen or C1–4 alkyl.), or
12) —NR¹²SO₂— (in which R¹² is hydrogen or C1–4 alkyl.);
R³ is
1) carbocyclic ring,
2) hetero ring, or
3) C1–4 alkyl substituted by carbocyclic ring or hetero ring (with proviso that, all carbocyclic ring and hetero ring in R³, may be substituted by 1~3 of substituent selected from the following (i)~(xi);
    (i) C1–4 alkyl,
    (ii) C1–4 alkoxy,
    (iii) phenyl,
    (iv) phenoxy,
    (v) benzyloxy,
    (vi) —SR¹³ (in which R¹³ is hydrogen or C1–4 alkyl.),
    (vii) C2–5 acyl,
    (viii) halogen,
    (ix) C1–4 alkoxycarbonyl,
    (x) nitro,
    (xi) —NR¹⁴R¹⁵ (in which R¹⁴ and R¹⁵ each independently, is hydrogen, C1–4 alkyl or C1–4 alkoxycarbonyl, or R¹⁴ and R¹⁵ taken together with the nitrogen atom to which they are attached may represent 5~7 membered saturated hetero ring containing another one nitrogen atom or one oxygen atom.).);
J is —O— or —NR¹⁶— (in which R¹⁶ is hydrogen or C1–4 alkyl.);
R⁴ is
1) C1–8 alkyl,
2) carbocyclic ring,
3) hetero ring,
4) C1–8 alkyl substituted by 1~3 of substituent selected from the following (i)~(v);
    (i) carbocyclic ring,
    (ii) hetero ring,
    (iii) COOR¹⁷ (in which R¹⁷ is hydrogen or C1–4 alkyl substituted by one phenyl (in which phenyl may be substituted by C1–4 alkoxy.),
    (iv) SR¹⁸ (in which R¹⁸ is hydrogen or C1–4 alkyl.),
    (v) OR¹⁹ (in which R¹⁹ is hydrogen or C1–4 alkyl.), or
when J represents —NR¹⁶— group, R⁴ and R¹⁶ taken together with the nitrogen atom to which they are attached may represent hetero ring (with proviso that, all carbocyclic ring and hetero ring, and hetero ring represented by R⁴ and R¹⁶ taken together with the nitrogen atom to which they are attached may be substituted by 1~3 of substituent selected from the following (i)~(xi);
    (i) C1–4 alkyl,
    (ii) C1–4 alkoxy,
    (iii) phenyl,
    (iv) phenoxy,
    (v) benzyloxy,
    (vi) —SR²⁰ (in which R²⁰ is hydrogen or C1–4 alkyl.),
    (vii) C2–5 acyl,
    (viii) halogen,
    (ix) C1–4 alkoxycarbonyl,
    (x) nitro,
    (xi) —NR²¹R²² (in which R²¹ and R²² each independently, is hydrogen, C1–4 alkyl or C1–4 alkoxycarbonyl, or R²¹ and R²² taken together with the nitrogen atom to which they are attached may represent 5~7 membered saturated hetero ring containing another one nitrogen atom or one oxygen atom.).).
With proviso that, the following compounds (1)–(37) are excluded:
(1) N-(2-amino-5-nitrophenyl)-3-benzyloxy-2-t-butoxycarbonylaminopropanamide,
(2) N-phenyl-3-benzyloxy-2-butoxycarbonylaminopropanamide,
(3) N-(2-aminophenyl)-3-benzyloxy-2-t-butoxycarbonylaminopropanamide, (4) N-(4-nitrophenyl)-3-benzyloxy-2-t-butoxycarbonylaminopropanamide,
(5) N-(adamantan-2-yl)-3-benzyloxy-2-t-butoxycarbonylaminopropanamide,
(6) N-(pyridin-4-yl)-3-benzyloxy-2-t-butoxycarbonylaminopropanamide,
(7) N-(2-aminophenyl)-3-benzyloxy-2-t-butoxycarbonylaminobutanamide,
(8) N-(4-nitrophenyl)-3-benzyloxy-2-t-butoxycarbonylaminobutanamide,
(9) N-(3-bromo-4,5-dihydroisoxazol-5-ylmethyl)-3-benzyloxy-2-t-butoxycarbonylaminobutanamide,
(10) N-methyl-N-(2,6-dimethoxy-4-methylphenyl)-3-benzyloxy-2-t-butoxycarbonylaminopropanamide,
(11) N-(4-nitrophenyl)-3-benzylthio-2-t-butoxycarbonylaminopropanamide,
(12) N-(quinolin-6-yl)-3-benzylthio-2-t-butoxycarbonylaminopropanamide,
(13) N-(2-aminophenyl)-3-benzylthio-2-t-butoxycarbonylaminopropanamide,
(14) N-(adamantan-2-yl)-3-(3-ethoxycarbonylpyridin-2-ylthio)-2-t-butoxycarbonylaminopropanamide,
(15) N-methyl-N-(2-ethoxyphenyl)-3-(3-methoxycarbonylpyridin-2-yl)-2-t-butoxycarbonylaminopropanamide,
(16) N-(4-methoxycarbonylphenyl)-3-benzylthio-2-benzyloxycarbonylaminopropanamide,
(17) N-(3-bromo-4,5-dihydroisoxazol-5-ylmethyl)-3-benzylthio-2-benzyloxycarbonylaminopropanamide,
(18) N-(2-methylphenyl)-3-benzylthio-2-benzyloxycarbonylaminopropanamide,
(19) N-(3-methylphenyl)-3-benzylthio-2-benzyloxycarbonylaminopropanamide,
(20) N-(4-methylphenyl)-3-benzylthio-2-benzyloxycarbonylaminopropanamide,
(21) N-phenyl-3-benzylthio-2-benzyloxycarbonylaminopropanamide,
(22) N-(naphthalen-2-yl)-3-benzylthio-2-benzyloxycarbonylaminopropanamide,
(23) N-(naphthalen-1-yl)-3-benzylthio-2-benzyloxycarbonylaminopropanamide,
(24) N-benzyl-3-benzylthio-2-benzyloxycarbonylaminopropanamide,
(25) N-(4-chlorophenyl)-3-benzylthio-2-benzyloxycarbonylaminopropanamide,
(26) N-(4-bromophenyl)-3-benzylthio-2-benzyloxycarbonylaminopropanamide,
(27) N-(4-nitrophenyl)-3-benzylthio-2-benzyloxycarbonylaminopropanamide,
(28) N-(1,2,3,4-tetrahydronaphthalen-2-yl)-3-benzylthio-2-(4-chlorobenzyloxycarbonylamino)propanamide,
(29) N-methyl-N-(2-ethoxyphenyl)-3-(3-methoxycarbonylpyridin-2-ylthio)-2-(3,4-dichlorophenylcarbonylamino)propanamide,
(30) 3-cyclohexyloxycarbonyl-2-t-butoxycarbonylaminopropanoic acid.4-nitrobenzyl ester,
(31) 3-cyclohexyloxycarbonyl-2-t-butoxycarbonylaminopropanoic acid.benzyl ester,
(32) 3-cycloheptyloxycarbonyl-2-t-butoxycarbonylaminopropanoic acid.benzyl ester,
(33) 3-cyclooctyloxycarbonyl-2-t-butoxycarbonylaminopropanoic acid.benzyl ester,
(34) 3-(2-isopropyl-5-methylcyclohexyloxycarbonyl)-2-t-butoxycarbonylaminopropanoic acid.benzyl ester,
(35) N-(benzyloxycarbonylmethyl)-3-(2-isopropyl-5-methylcyclohexyloxycarbonyl)-2-t-butoxycarbonylaminopropanamide,
(36) 3-cyclohexyloxycarbonyl-2-benzyloxycarbonylaminopropanoic acid.benzyl ester, and
(37) N-phenyl-2,3-bis(benzoylamino)propanamide.],
non-toxic salt thereof, or a hydrate thereof, and
3) processes for the preparation of an amino acid derivative of the formula (I) and a non-toxic salt thereof.

DETAILED EXPLANATION OF THE INVENTION

Unless otherwise specified, all isomers are included in the present invention. For example, alkyl, alkoxy, alkylene and alkenylene group include straight-chain or branched-chain ones. The double bond in alkenylene includes structure of configurations E, Z and EZ mixtures. The isomers (optical isomers) generated by asymmetric carbon atom(s) in branched alkyl, alkoxy, alkylene and alkenylene group are also included within the present invention.

In the formula (I), C1–15 alkyl group represented by $R^1$ means methyl, ethyl, propyl, butyl, pentyl, hexyl, heptyl, octyl, nonyl, decyl, undecyl, dodecyl, tridecyl, tetradecyl, pentadecyl and the isomers thereof.

In the formula (I), C1–8 alkoxy group represented by $R^1$ means methoxy, ethoxy, propoxy, butoxy, pentyloxy, hexyloxy, heptyloxy, octyloxy and the isomers thereof.

In the formula (i), C3–8 cycloalkyl group represented by $R^1$ or C3–8 cycloalkyl group as a substituent of C1–4 alkyl, C1–4 alkoxy or C2–4 alkenyl in $R^1$ group means cyclopropyl, cyclobutyl, cyclopentyl, cyclohexyl, cycloheptyl and cyclooctyl.

In the formula (I), C1–4 alkyl group represented by $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{18}$, $R^{19}$, $R^{20}$, $R^{21}$ or $R^{22}$ means methyl, ethyl, propyl, butyl and the isomers thereof.

In the formula (I), C1–4 alkyl group as a substituent of phenyl, C3–8 cycloalkyl or hetero ring in $R^1$ group, C1–4 alkyl group as a substituent of carbocyclic ring or hetero ring in $R^3$ or $R^4$ group, or C1–4 alkyl group as a substituent of hetero ring represented by $R^4$ and $R^{16}$ taken together with the nitrogen atom to which they are attached means methyl, ethyl, propyl, butyl and the isomers thereof.

In the formula (I), C1–4 alkyl substituted by phenyl, cycloalkyl or hetero ring represented by $R^1$ group means methyl, ethyl, propyl, butyl and the isomers thereof substituted by phenyl, C3–8 cycloalkyl or hetero ring.

In the formula (I), C1–4 alkyl optionally substituted by one phenyl represented by $R^2$ group means methyl, ethyl, propyl, butyl and the isomers thereof optionally substituted by one phenyl.

In the formula (I), C1–4 alkyl substituted by one phenyl represented by $R^{17}$ group means methyl, ethyl, propyl, butyl and the isomers thereof substituted by one phenyl.

In the formula (I), C1–4 alkyl substituted by carbocyclic ring or hetero ring represented by $R^3$ group means methyl, ethyl, propyl, butyl and the isomers thereof substituted by carbocyclic ring or hetero ring.

In the formula (I), C1–4 alkoxy substituted by phenyl, C3–8 cycloalkyl or hetero ring means methoxy, ethoxy, propoxy, butoxy and the isomers thereof substituted by phenyl, C3–8 cycloalkyl or hetero ring.

In the formula (I), C1–4 alkoxy as a substituent of phenyl, C3–8 cycloalkyl or hetero ring in $R^1$ group, C1–4 alkoxy as a substituent of carbocyclic ring or hetero ring in $R^3$ or $R^4$ group, or C1–4 alkoxy as a substituent of hetero ring represented by $R^4$ and $R^{16}$ taken together with the nitrogen atom to which they are attached means methoxy, ethoxy, propoxy, butoxy and the isomers thereof.

In the formula (I), C1–4 alkoxy as a substituent of phenyl in C1–4 alkyl substituted by one phenyl in $R^{17}$ group means methoxy, ethoxy, propoxy, butoxy and the isomers thereof.

In the formula (I), C2–4 alkenyl substituted by phenyl, cycloalkyl or hetero ring group means ethenyl, propenyl, butenyl and the isomers thereof.

In the formula (I), C2–5 acyl as a substituent of phenyl, C3–8 cycloalkyl or hetero ring in $R^1$ group, C2–5 acyl as a substituent of carbocyclic ring or hetero ring in $R^3$ or $R^4$ group, or C2–5 acyl as a substituent of hetero ring represented by $R^4$ and $R^{16}$ taken together with the nitrogen atom to which they are attached means acetyl, propionyl, butyryl, valeryl and the isomers thereof.

In the formula (I), halogen as a substituent of phenyl, C3–8 cycloalkyl or hetero ring in $R^1$ group, or halogen as a substituent of carbocyclic ring or hetero ring in $R^3$ or $R^4$ group, or halogen as a substituent of hetero ring represented by $R^4$ and $R^{16}$ taken together with the nitrogen atom to which they are attached means fluoro, chloro, bromo and iodo.

In the formula (I), C1–4 alkoxycarbonyl represented by $R^6$, $R^7$, $R^{14}$, $R^{15}$, $R^{21}$ or $R^{22}$ means methoxycarbonyl, ethoxycarbonyl, propoxycarbonyl, butoxycarbonyl and the isomers thereof.

In the formula (i), C1–4 alkoxycarbonyl as a substituent of phenyl, C3–8 cycloalkyl or hetero ring in $R^1$ group, or C1–4 alkoxycarbonyl as a substituent of carbocyclic ring or hetero ring in $R^3$ or $R^4$ group, or C1–4 alkoxycarbonyl as a substituent of hetero ring represented by $R^4$ and $R^{16}$ taken together with the nitrogen atom to which they are attached means methoxycarbonyl, ethoxycarbonyl, propoxycarbonyl, butoxycarbonyl and the isomers thereof.

In the formula (I), C1–4 alkylene represented by D group means methylene, ethylene, propylene, butylene and the isomers thereof.

In the formula (I), C2–4 alkenylene represented by D group means ethenylene, propenylene, butenylene and the isomers thereof.

In the formula (I), C1–8 alkyl represented by $R^4$ group means methyl, ethyl, propyl, butyl, pentyl, hexyl, heptyl, octyl and the isomers thereof.

In the formula (I), C1–8 alkyl substituted by 1~3 of substituent selected from (i)~(v) represented by $R^4$ group means methyl, ethyl, propyl, butyl, pentyl, hexyl, heptyl, octyl and the isomers thereof substituted by 1~3 of substituent selected from (i)~(v).

In the formula (I), 5~7 memebered saturated hetero ring optionally containing another one nitrogen atom or one oxygen atom represented by $R^6$ and $R^7$ taken together with the nitrogen atom to which they are attached, by $R^{14}$ and $R^{15}$ taken together with the nitrogen atom to which they are attached or by $R^{21}$ and $R^{22}$ taken together with the nitrogen atom to which they are attached means pyrrolidine, piperidine, piperazine, morpholine, perhydroazepine etc.

In the formula (I), carbocyclic ring in $R^3$ or $R^4$ means C3~10 mono-, bi- and bridged carbocyclic ring. For example, C3~10 mono, bi and bridged carbocyclic ring includes cyclopropane, cyclobutane, cyclopentane, cyclohexane, cycloheptane, cyclooctane, cyclononane, cyclodecane, cyclopentene, cyclohexene, cyclopentadiene, cyclohexadiene, benzene, pentalene, indene, naphthalene, azulene, dihydronaphthalene, tetrahydronaphthalene, perhydronaphthalene, indan (dihydroindene), perhydroindene, bicyclopentane, bicyclohexane, bicycloheptane (bicyclo[2.2.1]heptane), bicycloheptene (bicyclo[2.2.1]hept-2-ene.), bicyclooctane, bicyclononane, bicyclodecane, adamantane etc.

In the formula (I), hetero ring in $R^1$, $R^3$ or $R^4$ group means a 5~15 memebered unsaturated, partial saturated or saturated mono-cyclic or bi-cyclic hetero ring containing 1~2 nitrogen atom, 1~2 oxygen atom and/or one sulfur atom. For example, a 5~15 memebered unsaturated, partial saturated or saturated mono-cyclic or bi-cyclic hetero ring containing 1~2 nitrogen atom; 1~2 oxygen atom and/or one sulfur atom includes pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, dihydrofuran, tetrahydrofuran, dihydropyran, tetrrahydropyran, dihydrothiophene, tetrahydrothiophene, dihydrothiain (dihydrothiopyran), tetrahydrothiain (tetrahydrothiopyran), dihydroxazole, tetrahydroxazole, dihydroisoxazole, tetrahydroisoxazole, dihydrothiazole, tetrahydrothiazole, dihydroisothiazole, tetraisothiazole, morpholine, thiomorpholine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrobenzoxazine, dioxaindan, benzodioxane, quinuclidine, pyrrole, imidazole, pyrazole, pyridine, pyradine, pyrimidine, pyridazine, pyridazine, azepine, diazepine, furan, pyran, oxepin, oxazepine, thiophene, thiain (thiopyran), thiepin, oxazole, isoxazole, thiazole, isothiazole, oxadiazole, oxazine, oxadiazine, oxazepin oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, oxatetrahydrofuran, thiazolidinone, thiazolidinedione etc.

In the formula (I), hetero ring represented by $R^4$ and $R^{16}$ taken together with the nitrogen atom to which they are attached means a 5~15 memebered unsaturated, partial saturated or saturated mono-cyclic or bi-cyclic hetero ring necessarily containing one nitrogen atom and further containing one nitrogen atom, one oxygen atom and/or one sulfur atom. For example, a 5~15 memebered unsaturated, partial saturated or saturated mono-cyclic or bi-cyclic hetero ring necessarily containing one nitrogen atom and further containing one nitrogen atom, 1~2 oxygen atom and/or one sulfur atom includes pyrroline, pyrrolidine, imidazoline, imidazolidine, pyrazoline, pyrazolidine, piperidine, piperazine, tetrahydropyrimidine, hexahydropyrimidine, tetrahydropyridazine, hexahydropyridazine, hexahydroazepine, tetrahydroxazole, tetrahydroisoxazole, tetrahydrothiazole, tetrahydroisothiazole, morpholine, thiomorpholine, indoline, isoindoline, dihydroindazole, perhydroindazole, dihydroquinoine, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, pyrrole, imidazole, pyrazole, indole, isoindole, indazole, benzimidazole etc.

Preferred $R^1$ is C1–8 alkoxy, phenyl, C3–8 cycloalkyl, hetero ring, or C1–4 alkyl substituted by phenyl, C3–8 cycloalkyl or hetero ring. Particularly, preferred $R^1$ is hetero ring.

Preferred A is bond or —CO—. Particularly, preferred A is —CO—.

Preferred E is —COO—, —O—, —S—, —SO— or —SO$_2$—. Particularly, preferred E is —S—.

Preferred carbocyclic ring represented by $R^3$ and carbocyclic ring as substituent of C1–4 alkyl in $R^3$ is C3–10 cycloalkyl represented by cyclobutane, cyclopentane, cyclohexane, cycloheptane, cyclooctane, cyclononane and cyclodecane. Particularly, preferred carbocyclic ring is cyclopentane or cyclohexane.

Preferred J is —NR$^{16}$— (in which $R^{16}$ is the same meaning as hereinbefore described.).

Preferred $R^4$ is carbocyclic ring, hetero ring, or C1–8 alkyl substituted by carbocyclic ring or hetero ring. Particularly, preferred $R^4$ is C1–8 alkyl substituted by carbocyclic ring.

[Salts]

In the present invention, non-toxic salts includes all such salts.

For example, the compounds of the present invention of the formula (I) maybe converted into the corresponding salts by known method. Non toxic and water-soluble salts are preferable. Suitable salts include the salts of alkalimetal (sodium, potassium etc.), alkaline-earth metal (calcium, magnesium etc.), ammonium salts, salts of organic amine which is pharmacologically permitted (tetramethyl ammonium, triethylamine, methylamine, dimethylamine, cyclopentylamine, dicyclohexylamine, benzylamine, phenetylamine, piperidine, monoethanolamine, diethanolamine, tris(hydroxymethyl)amine, lysine, arginine, N-methyl-D-gulcamine etc.).

The compounds of the present invention of the formula (I) may be converted into the corresponding acid-addition salts by known method. Non toxic and water-soluble salts are preferable. Suitable acid-addition salts include the salts with inorganic acids such as hydrochloric acid, hydrobromic acid, sulphonic acid, phosphonic acid, nitric acid and the salts with organic acids such as acetic acid, trifluoroacetic acid, lactic acid, tartaric acid, oxalic acid, fumaric acid, maleic acid, citric acid, benzoic acid, methanesulfonic acid, ethanesulfonic acid, benzenesulfonic acid, toluenesulfonic acid, isethionic acid, glucuronic acid and gluconic acid.

The compounds of the present invention of the formula (I) or salts thereof may be converted into a corresponding hydrate by known methods.

In the compounds of the formula (I), preferred compounds are as follows:

the compound of the formula (Ia)

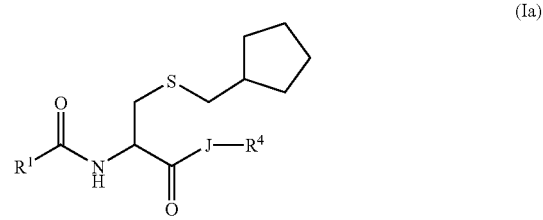

(Ia)

(wherein all the symbols are the same meanings as hereinbefore described.), the compound of the formula (Ib)

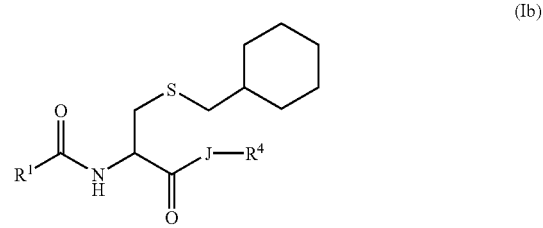

(Ib)

(wherein all the symbols are the same meanings as hereinbefore described.), the compound of the formula (Ic)

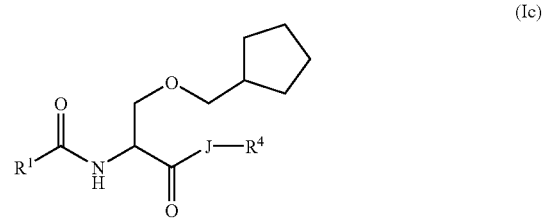

(Ic)

(wherein all the symbols are the same meanings as hereinbefore described.), the compound of the formula (Id)

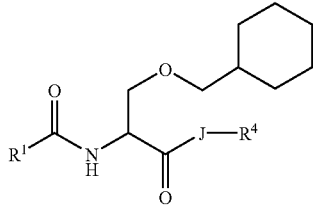
(Id)

(wherein all the symbols are the same meanings as hereinbefore described.), the compound of the formula (Ie)

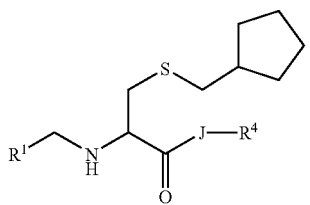
(Ie)

(wherein all the symbols are the same meanings as hereinbefore described.), the compound of the formula (If)

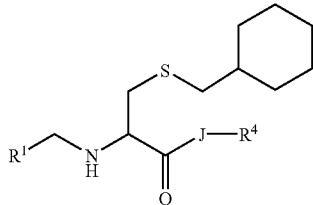
(If)

(wherein all the symbols are the same meanings as hereinbefore described.), the compound of the formula (Ig)

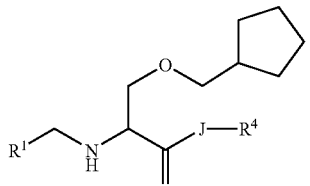
(Ig)

(wherein all the symbols are the same meanings as hereinbefore described.), the compound of the formula (Ih)

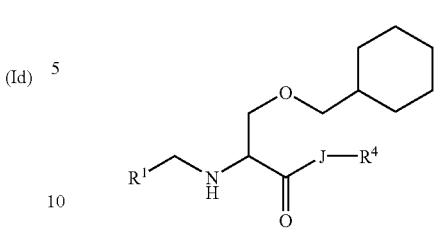
(Ih)

(wherein all the symbols are the same meanings as hereinbefore described.),
non-toxic salts thereof or the hydrates thereof.

The concrete compounds are ones shown in the following Tables 1–40, non-toxic salts thereof and the hydrates thereof and ones described in Example. Also, the following concrete compounds include the isomers generated by asymmetric carbon atom(s), i.e., R, S and RS form. In the following each Table, Me is methyl, Boc is t-butoxycarbonyl, i-Bu is isobutyl, Ac is acetyl.

TABLE 1

(Ia-1)

| No. | $R^1$ |
|---|---|
| 1 | Boc-thiazolidine |
| 2 | H-thiazolidine |
| 3 | CO$_2$Me-thiazolidine |
| 4 | i-BuO-C(=O)-thiazolidine |
| 5 | Ac-thiazolidine |

TABLE 1-continued
(Ia-1)
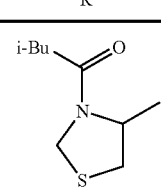
| No. | R¹ |
|---|---|
| 6 | 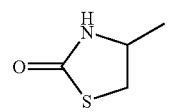 |
| 7 | 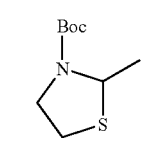 |
| 8 | 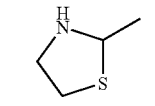 |
| 9 | 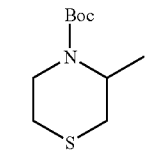 |
| 10 | 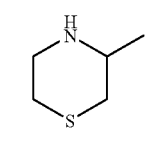 |
| 11 | 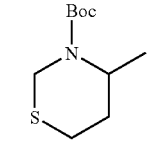 |
| 12 | 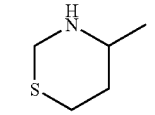 |
| 13 | 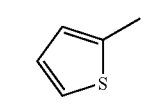 |
| 14 | 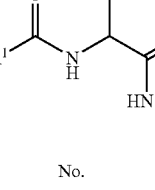 |
TABLE 1-continued
(Ia-1)
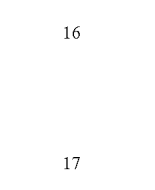
| No. | R¹ |
|---|---|
| 15 |  |
| 16 |  |
| 17 |  |
| 18 |  |
| 19 | 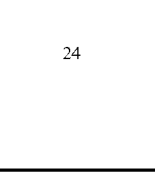 |
| 20 |  |
| 21 | |
| 22 | |
| 23 | |
| 24 | |

TABLE 2

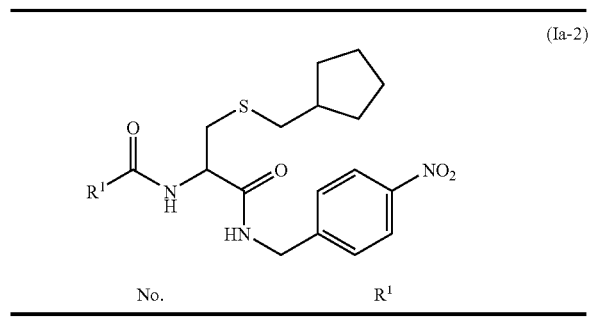

(Ia-2)

| No. | R¹ |
|---|---|
| 1 | Boc-thiazolidine-4-methyl |
| 2 | H-thiazolidine-4-methyl |
| 3 | CO₂Me-thiazolidine-4-methyl |
| 4 | i-BuO-C(O)-thiazolidine-4-methyl |
| 5 | Ac-thiazolidine-4-methyl |
| 6 | i-Bu-C(O)-thiazolidine-4-methyl |
| 7 | 2-oxo-thiazolidine-4-methyl |
| 8 | Boc-thiazolidine-2-methyl |
| 9 | H-thiazolidine-2-methyl |

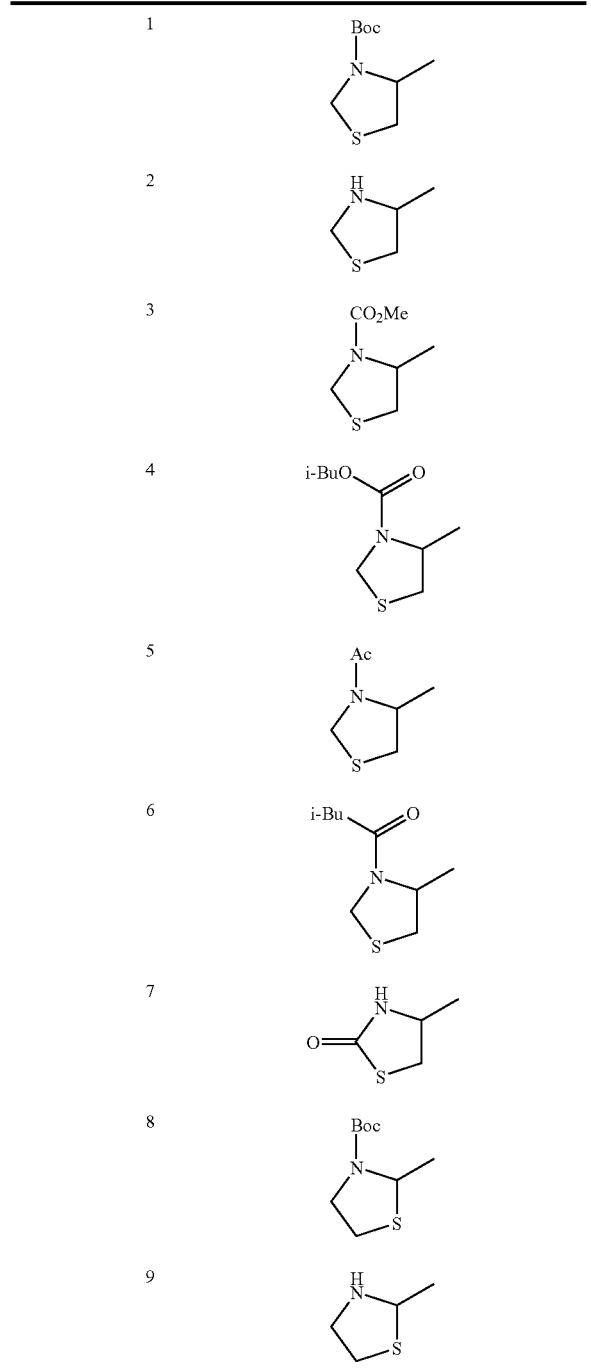

TABLE 2-continued

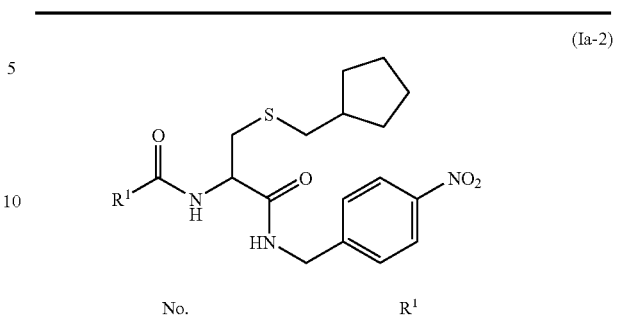

(Ia-2)

| No. | R¹ |
|---|---|
| 10 | Boc-thiomorpholine-3-methyl |
| 11 | H-thiomorpholine-3-methyl |
| 12 | Boc-thiazinane-4-methyl |
| 13 | H-thiazinane-4-methyl |
| 14 | 2-methylthiophene |
| 15 | 4-methylthiazole |
| 16 | 2-amino-4-methylthiazole |
| 17 | 4-methylimidazole (1H) |
| 18 | Boc-4-methylimidazole |
| 19 | 2-methylfuran |

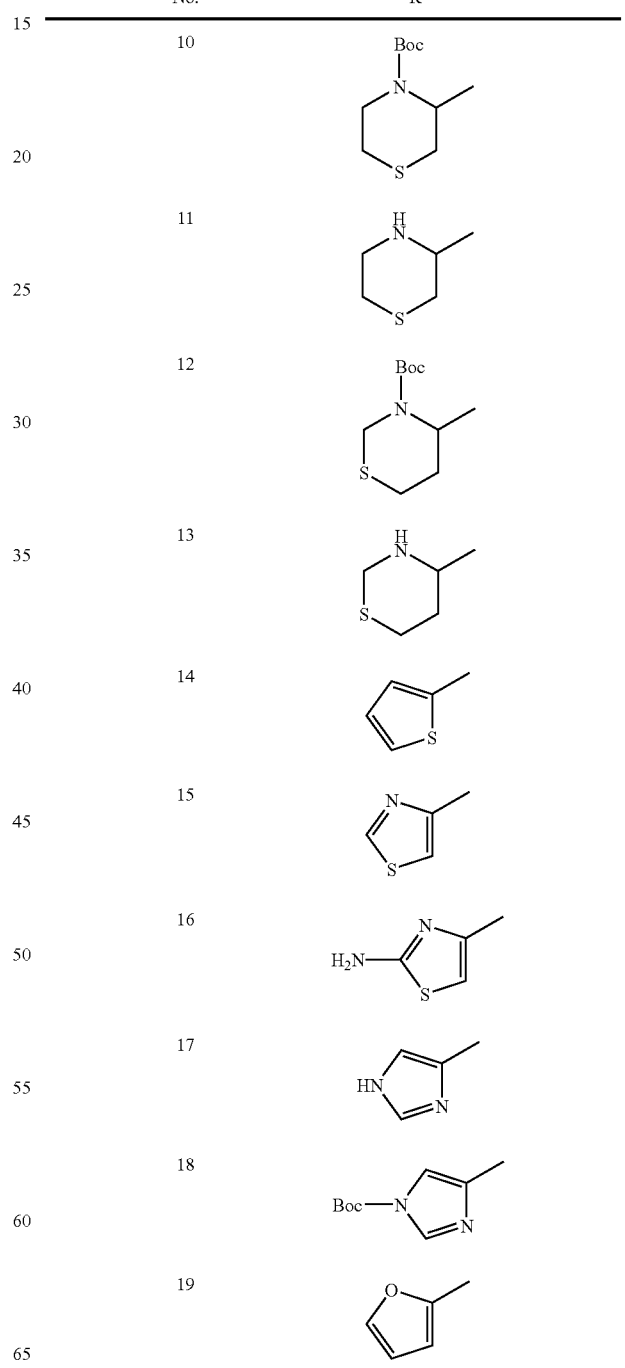

TABLE 2-continued
(Ia-2)
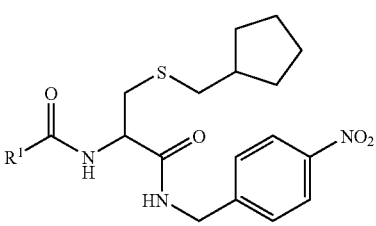
| No. | R¹ |
|---|---|
| 20 | 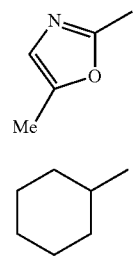 |
| 21 | 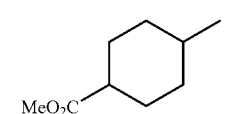 |
| 22 | 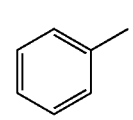 |
| 23 | 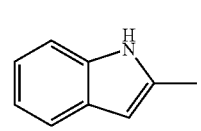 |
| 24 | 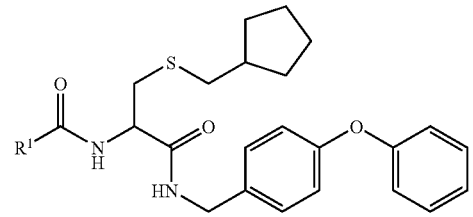 |
TABLE 3
(Ia-3)
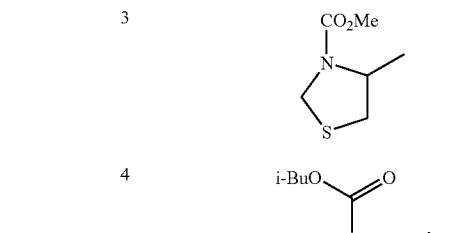
| No. | R¹ |
|---|---|
| 1 | 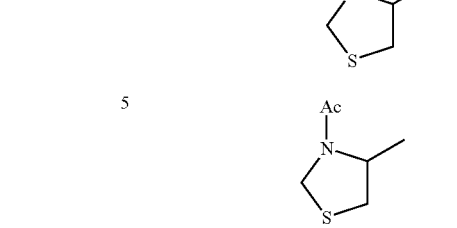 |
| 2 | 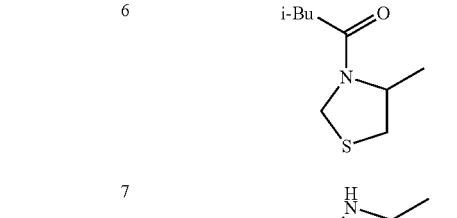 |
TABLE 3-continued
(Ia-3)
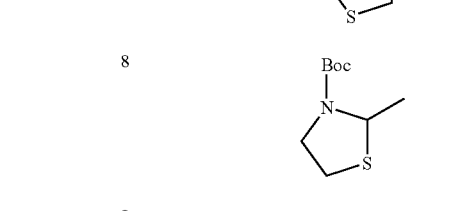
| No. | R¹ |
|---|---|
| 3 | 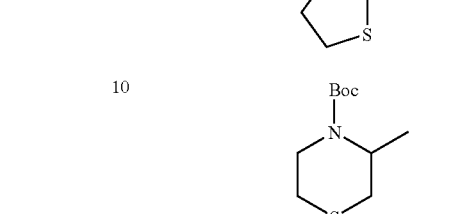 |
| 4 | 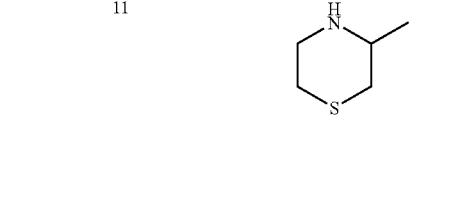 |
| 5 | 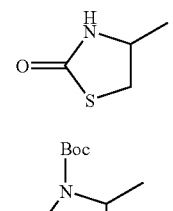 |
| 6 | 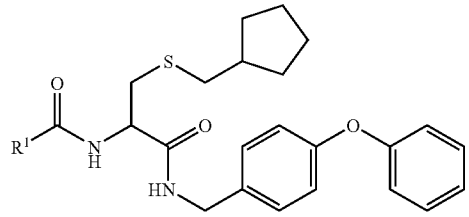 |
| 7 | 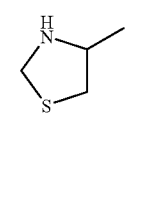 |
| 8 | 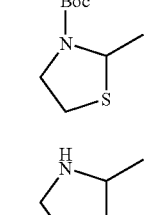 |
| 9 | 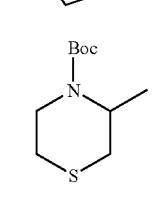 |
| 10 | 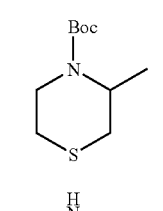 |
| 11 | 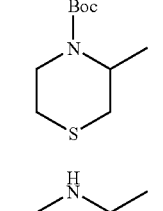 |

TABLE 3-continued (Ia-3)

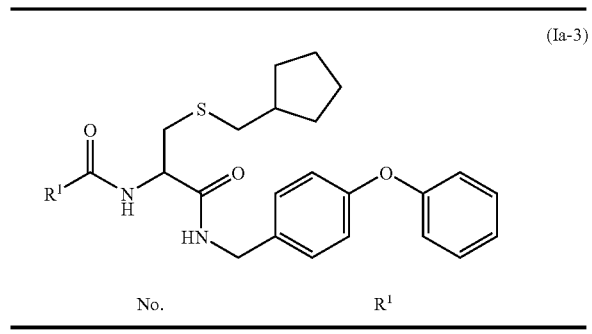

| No. | R¹ |
|---|---|
| 12 | Boc-N-(4-methyl-1,3-thiazinane) |
| 13 | 4-methyl-1,3-thiazinane (NH) |
| 14 | 2-methylthiophene |
| 15 | 4-methylthiazole |
| 16 | 2-amino-4-methylthiazole |
| 17 | 4-methyl-1H-imidazole |
| 18 | Boc-1-(4-methylimidazole) |
| 19 | 2-methylfuran |
| 20 | 2,5-dimethyloxazole |
| 21 | cyclohexyl |

TABLE 3-continued (Ia-3)

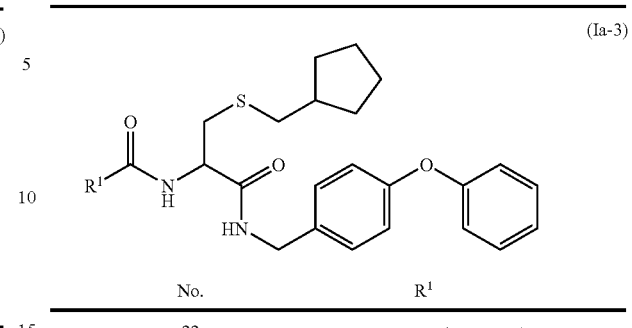

| No. | R¹ |
|---|---|
| 22 | 4-methyl-cyclohexanecarboxylic acid methyl ester (MeO₂C-) |
| 23 | 2-methylphenyl |
| 24 | 2-methyl-1H-indole |

TABLE 4

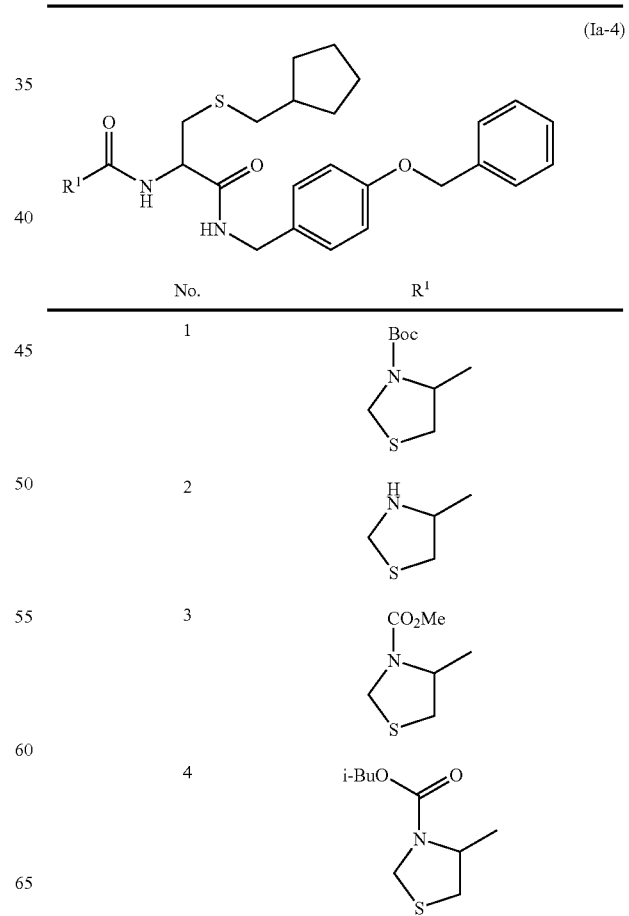

| No. | R¹ |
|---|---|
| 1 | Boc-N-(4-methylthiazolidine) |
| 2 | 4-methylthiazolidine (NH) |
| 3 | CO₂Me-N-(4-methylthiazolidine) |
| 4 | i-BuO-C(=O)-N-(4-methylthiazolidine) |

TABLE 4-continued (Ia-4)

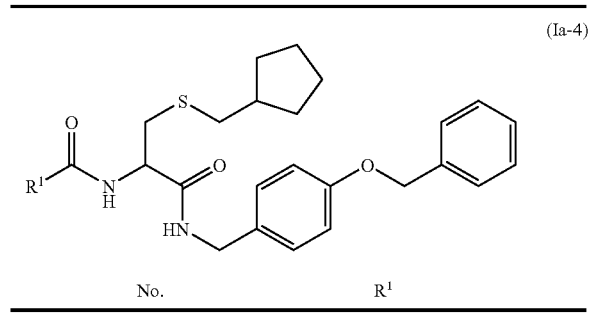

| No. | R¹ |
|---|---|
| 5 | N-Ac, 4-methyl thiazolidine |
| 6 | N-(i-Bu-C(O)), 4-methyl thiazolidine |
| 7 | 2-oxo-4-methyl thiazolidine (NH) |
| 8 | N-Boc, 2-methyl thiazolidine |
| 9 | NH, 2-methyl thiazolidine |
| 10 | N-Boc, 3-methyl thiomorpholine |
| 11 | NH, 3-methyl thiomorpholine |
| 12 | N-Boc, 4-methyl 1,3-thiazinane |
| 13 | NH, 4-methyl 1,3-thiazinane |
| 14 | 2-methyl thiophene |
| 15 | 4-methyl thiazole |
| 16 | 2-amino-4-methyl thiazole |
| 17 | 4-methyl imidazole (NH) |
| 18 | N-Boc 4-methyl imidazole |
| 19 | 2-methyl furan |
| 20 | 2,5-dimethyl oxazole |
| 21 | methyl cyclohexane |
| 22 | 4-methyl cyclohexane-1-CO₂Me |
| 23 | methyl benzene |
| 24 | 2-methyl indole |

TABLE 5
(Ia-5)
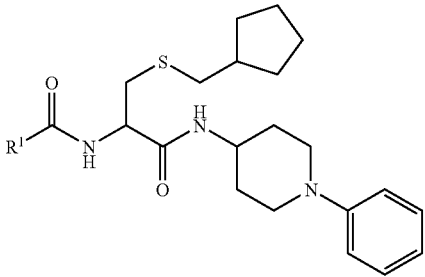
| No. | R¹ |
|---|---|
| 1 | 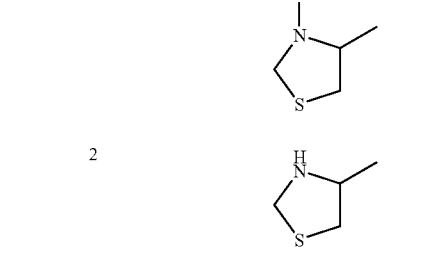 |
| 2 | 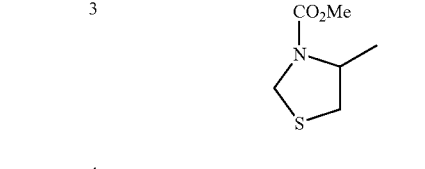 |
| 3 |  |
| 4 | 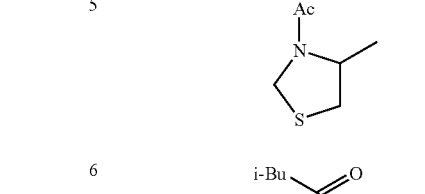 |
| 5 |  |
| 6 |  |
| 7 |  |
| 8 | 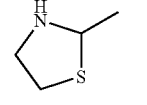 |
TABLE 5-continued
(Ia-5)
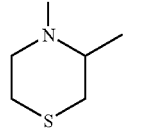
| No. | R¹ |
|---|---|
| 9 | 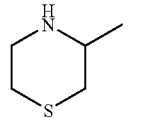 |
| 10 | 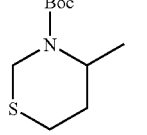 |
| 11 | 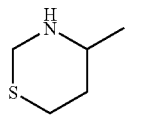 |
| 12 | 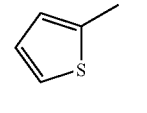 |
| 13 | 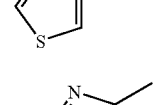 |
| 14 | 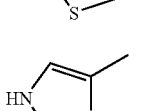 |
| 15 | 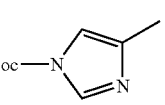 |
| 16 |  |
| 17 | |
| 18 | |

TABLE 5-continued (Ia-5)

| No. | R¹ |
|---|---|
| 19 | 2-methylfuran |
| 20 | 2,5-dimethyloxazole |
| 21 | methylcyclohexane |
| 22 | methyl 4-methylcyclohexanecarboxylate |
| 23 | toluyl |
| 24 | 2-methyl-1H-indole |

TABLE 6

(Ib-1)

| No. | R¹ |
|---|---|
| 1 | N-Boc-4-methylthiazolidine |
| 2 | 4-methylthiazolidine (NH) |
| 3 | N-CO₂Me-4-methylthiazolidine |
| 4 | N-(i-BuO-C(O))-4-methylthiazolidine |
| 5 | N-Ac-4-methylthiazolidine |
| 6 | N-(i-Bu-C(O))-4-methylthiazolidine |
| 7 | 4-methyl-2-oxo-thiazolidine |
| 8 | N-Boc-2-methylthiazolidine |
| 9 | 2-methylthiazolidine (NH) |

TABLE 6-continued (Ib-1)

| No. | R¹ |
|---|---|
| 10 | N-Boc, 3-methyl thiomorpholine |
| 11 | NH, 3-methyl thiomorpholine |
| 12 | N-Boc, 4-methyl thiazinane |
| 13 | NH, 4-methyl thiazinane |
| 14 | 2-thienyl |
| 15 | 4-methyl thiazolyl |
| 16 | 2-amino-4-methyl thiazolyl |
| 17 | 4-methyl imidazolyl (NH) |
| 18 | N-Boc 4-methyl imidazolyl |
| 19 | 2-methyl furyl |
| 20 | 2,5-dimethyl oxazolyl |
| 21 | cyclohexyl-methyl |
| 22 | 4-(MeO₂C)cyclohexyl-methyl |
| 23 | phenyl |
| 24 | 2-methyl-1H-indolyl |

TABLE 7

(Ib-2)

| No. | R¹ |
|---|---|
| 1 | N-Boc, 4-methyl thiazolidinyl |
| 2 | NH, 4-methyl thiazolidinyl |

TABLE 7-continued (Ib-2)

Structure: R¹-C(=O)-NH-CH(CH₂-S-CH₂-cyclohexyl)-C(=O)-NH-CH₂-(4-nitrophenyl)

| No. | R¹ |
|---|---|
| 3 | 3-(CO₂Me)-4-methyl-thiazolidin-3-yl |
| 4 | 3-(i-BuO-C(=O))-4-methyl-thiazolidin-3-yl |
| 5 | 3-Ac-4-methyl-thiazolidin-3-yl |
| 6 | 3-(i-Bu-C(=O))-4-methyl-thiazolidin-3-yl |
| 7 | 2-oxo-4-methyl-thiazolidin-3-yl (NH) |
| 8 | 3-Boc-2-methyl-thiazolidin-3-yl |
| 9 | 2-methyl-thiazolidin-2-yl (NH) |
| 10 | 4-Boc-3-methyl-thiomorpholin-4-yl |
| 11 | 3-methyl-thiomorpholin-3-yl (NH) |
| 12 | 3-Boc-4-methyl-1,3-thiazinan-3-yl |
| 13 | 4-methyl-1,3-thiazinan-4-yl (NH) |
| 14 | 2-thienyl-methyl |
| 15 | 4-methyl-thiazol-4-yl |
| 16 | 2-amino-4-methyl-thiazol-4-yl |
| 17 | 4-methyl-1H-imidazol-4-yl |
| 18 | 1-Boc-4-methyl-imidazol-4-yl |
| 19 | 2-furyl-methyl |
| 20 | 2-methyl-5-Me-oxazol-2-yl |
| 21 | cyclohexyl-methyl |

TABLE 7-continued
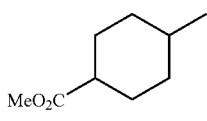
(Ib-2)
| No. | R¹ |
|---|---|
| 22 | 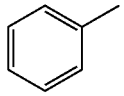 |
| 23 | 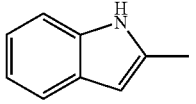 |
| 24 | 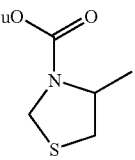 |
TABLE 8
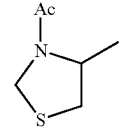
(Ib-3)
| No. | R¹ |
|---|---|
| 1 | 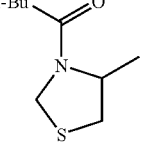 |
| 2 | 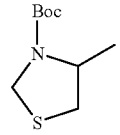 |
| 3 | 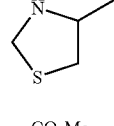 |
TABLE 8-continued
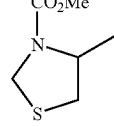
(Ib-3)
| No. | R¹ |
|---|---|
| 4 | 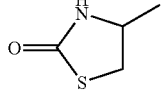 |
| 5 | 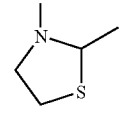 |
| 6 | 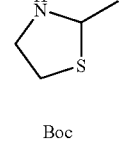 |
| 7 | 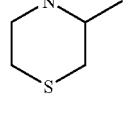 |
| 8 | 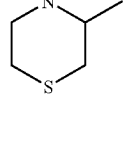 |
| 9 |  |
| 10 |  |
| 11 |  |

TABLE 8-continued (Ib-3)

| No. | R¹ |
|---|---|
| 12 | N-Boc, 4-methyl-1,3-thiazinane |
| 13 | 4-methyl-1,3-thiazinane (NH) |
| 14 | 2-methylthiophene |
| 15 | 4-methylthiazole |
| 16 | 2-amino-4-methylthiazole |
| 17 | 4-methylimidazole (NH) |
| 18 | N-Boc-4-methylimidazole |
| 19 | 2-methylfuran |
| 20 | 2,5-dimethyloxazole |
| 21 | methylcyclohexane |
| 22 | 4-(methoxycarbonyl)methylcyclohexane |

TABLE 8-continued (Ib-3)

| No. | R¹ |
|---|---|
| 23 | toluene (methylphenyl) |
| 24 | 2-methylindole |

TABLE 9

(Ib-4)

| No. | R¹ |
|---|---|
| 1 | N-Boc-4-methylthiazolidine |
| 2 | 4-methylthiazolidine (NH) |
| 3 | N-(CO₂Me)-4-methylthiazolidine |
| 4 | N-(i-BuO-CO)-4-methylthiazolidine |

TABLE 9-continued
(Ib-4)
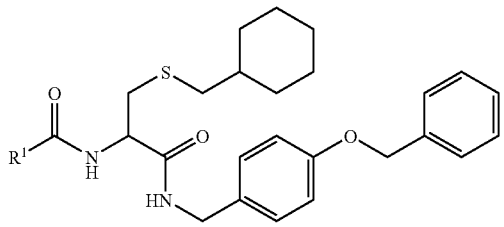
| No. | R[1] |
|---|---|
| 5 | 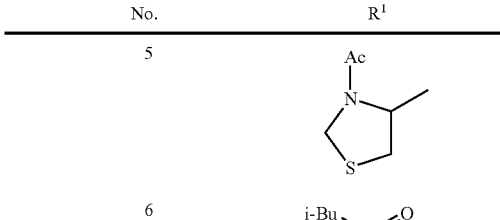 |
| 6 | 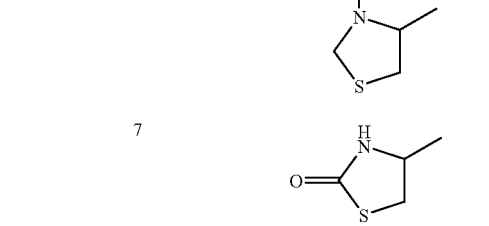 |
| 7 | 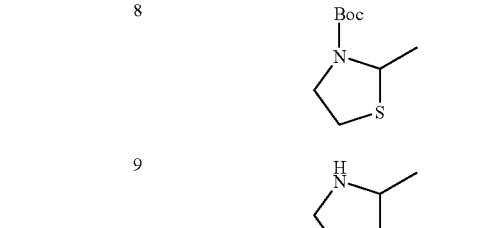 |
| 8 | 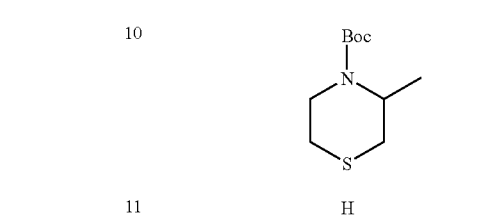 |
| 9 | 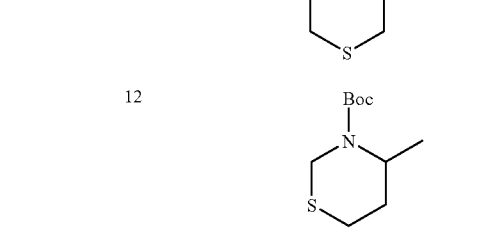 |
| 10 | 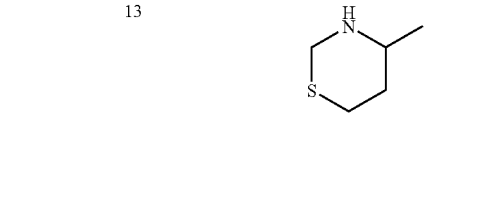 |
| 11 |  |
| 12 | 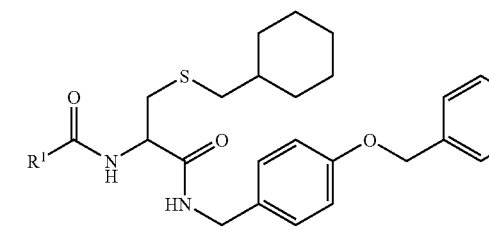 |
| 13 | 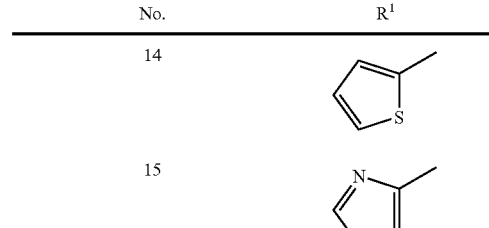 |
| 14 | 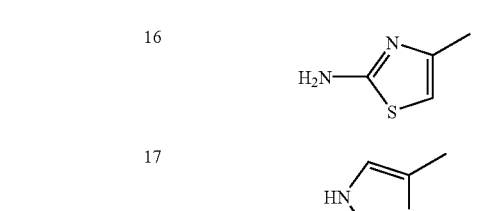 |
| 15 | 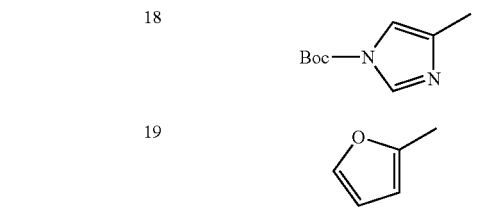 |
| 16 | 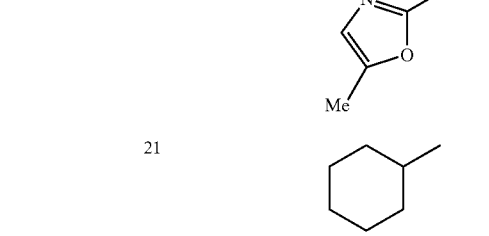 |
| 17 | 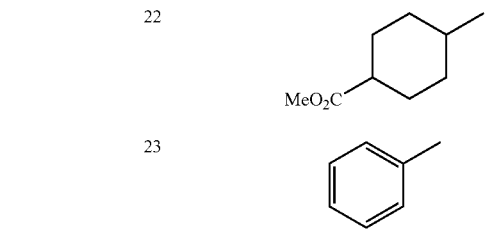 |
| 18 | 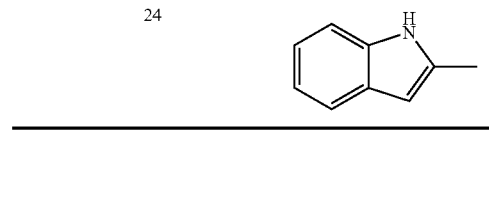 |
| 19 |  |
| 20 | |
| 21 | |
| 22 | |
| 23 | |
| 24 | |

TABLE 10

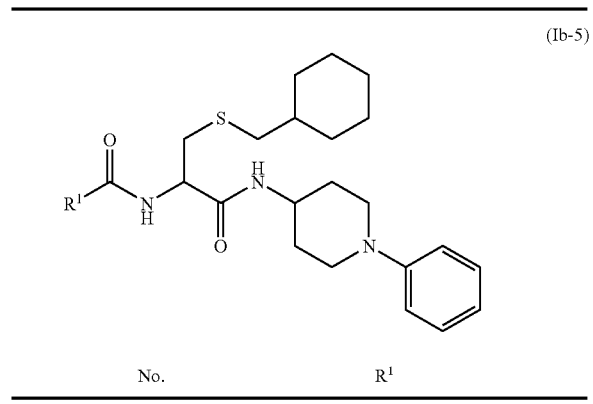

(Ib-5)

| No. | R¹ |
|---|---|
| 1 | Boc-N(thiazolidine-4-methyl) |
| 2 | HN(thiazolidine-4-methyl) |
| 3 | CO₂Me-N(thiazolidine-4-methyl) |
| 4 | i-BuO-C(=O)-N(thiazolidine-4-methyl) |
| 5 | Ac-N(thiazolidine-4-methyl) |
| 6 | i-Bu-C(=O)-N(thiazolidine-4-methyl) |
| 7 | 2-oxo-thiazolidine-4-methyl |
| 8 | Boc-N(thiazolidine-2-methyl) |

TABLE 10-continued

| No. | R¹ |
|---|---|
| 9 | HN(thiazolidine-2-methyl) |
| 10 | Boc-N(thiomorpholine-3-methyl) |
| 11 | HN(thiomorpholine-3-methyl) |
| 12 | Boc-N(thiazinane-4-methyl) |
| 13 | HN(thiazinane-4-methyl) |
| 14 | thiophene-2-methyl |
| 15 | thiazole-4-methyl |
| 16 | 2-amino-thiazole-4-methyl |
| 17 | imidazole-4-methyl |
| 18 | Boc-imidazole-4-methyl |

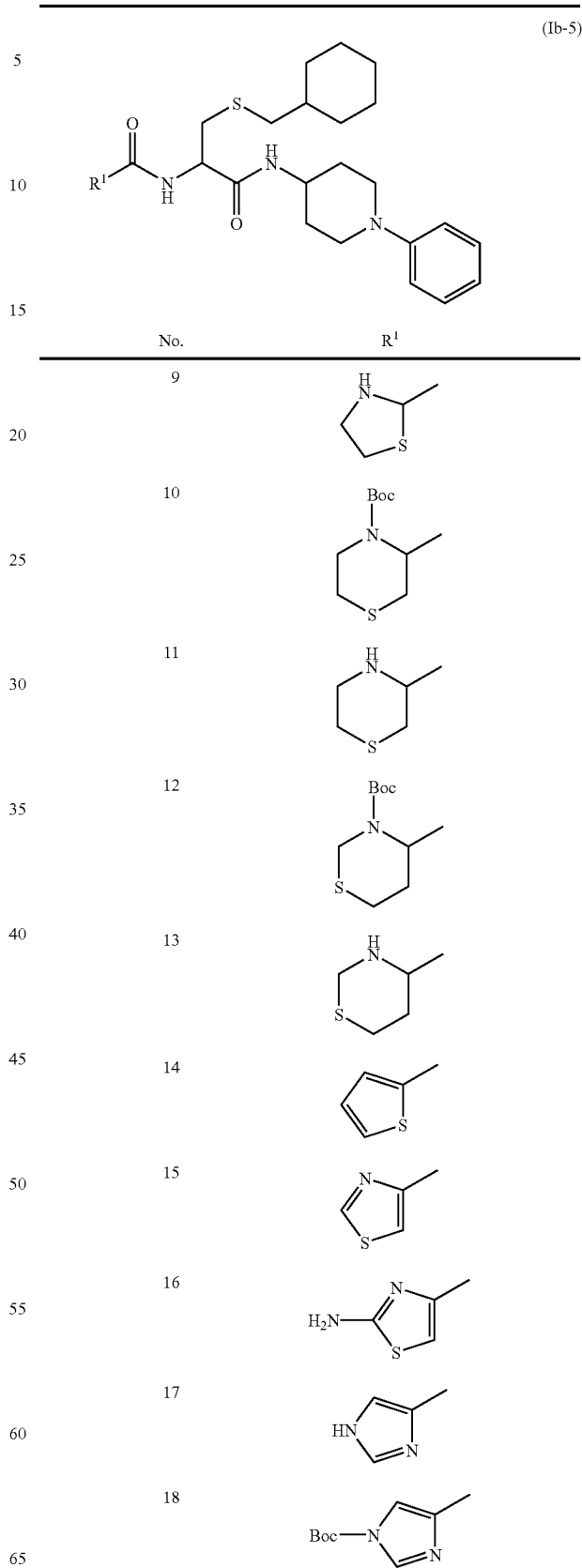

TABLE 10-continued (Ib-5)

[Structure: R¹-C(=O)-NH-CH(CH₂-S-CH₂-cyclohexyl)-C(=O)-NH-(4-piperidinyl)-N-phenyl]

| No. | R¹ |
|-----|-----|
| 19 | 2-furyl |
| 20 | 2,5-dimethyl-oxazol-4-yl (Me on 5-position) |
| 21 | cyclohexyl |
| 22 | 4-(methoxycarbonyl)cyclohexyl (MeO₂C) |
| 23 | 4-methylphenyl |
| 24 | 2-methyl-1H-indol-3-yl |

TABLE 11

(Ic-1)

[Structure: R¹-C(=O)-NH-CH(CH₂-O-CH₂-cyclopentyl)-C(=O)-NH-CH₂-(4-methoxyphenyl)]

| No. | R¹ |
|-----|-----|
| 1 | N-Boc-4-methylthiazolidin-3-yl |

TABLE 11-continued (Ic-1)

[Structure: R¹-C(=O)-NH-CH(CH₂-O-CH₂-cyclopentyl)-C(=O)-NH-CH₂-(4-methoxyphenyl)]

| No. | R¹ |
|-----|-----|
| 2 | 4-methylthiazolidin-3-yl (NH) |
| 3 | N-(CO₂Me)-4-methylthiazolidin-3-yl |
| 4 | N-(i-BuO-C(=O))-4-methylthiazolidin-3-yl |
| 5 | N-Ac-4-methylthiazolidin-3-yl |
| 6 | N-(i-Bu-C(=O))-4-methylthiazolidin-3-yl |
| 7 | 2-oxo-4-methylthiazolidin-3-yl |
| 8 | N-Boc-2-methylthiazolidin-3-yl |
| 9 | 2-methylthiazolidin-3-yl (NH) |
| 10 | N-Boc-3-methylthiomorpholin-4-yl |

TABLE 11-continued
(Ic-1)
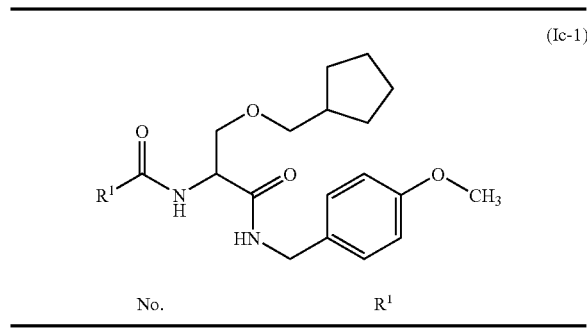
| No. | R¹ |
|---|---|
| 11 | 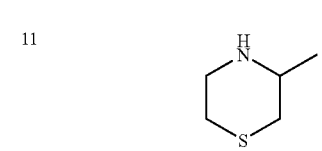 |
| 12 | 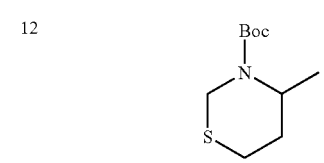 |
| 13 | 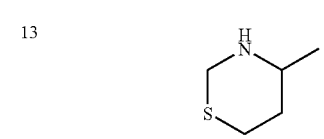 |
| 14 |  |
| 15 |  |
| 16 | 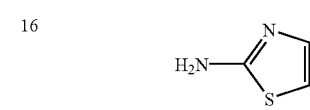 |
| 17 | 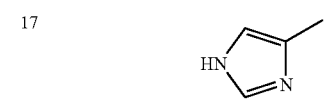 |
| 18 |  |
| 19 |  |
| 20 | 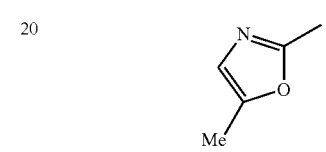 |
TABLE 11-continued
(Ic-1)
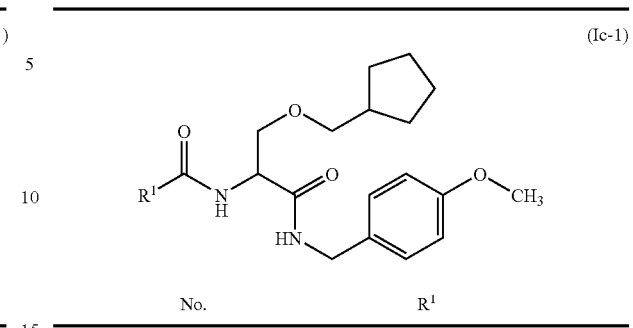
| No. | R¹ |
|---|---|
| 21 | 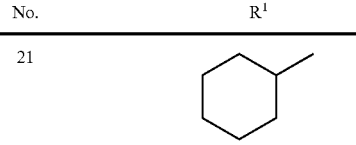 |
| 22 | 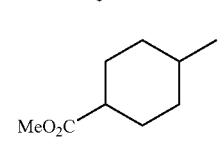 |
| 23 | 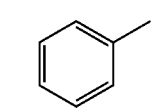 |
| 24 | 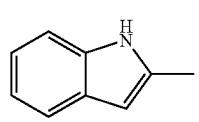 |
TABLE 12
(Ic-2)
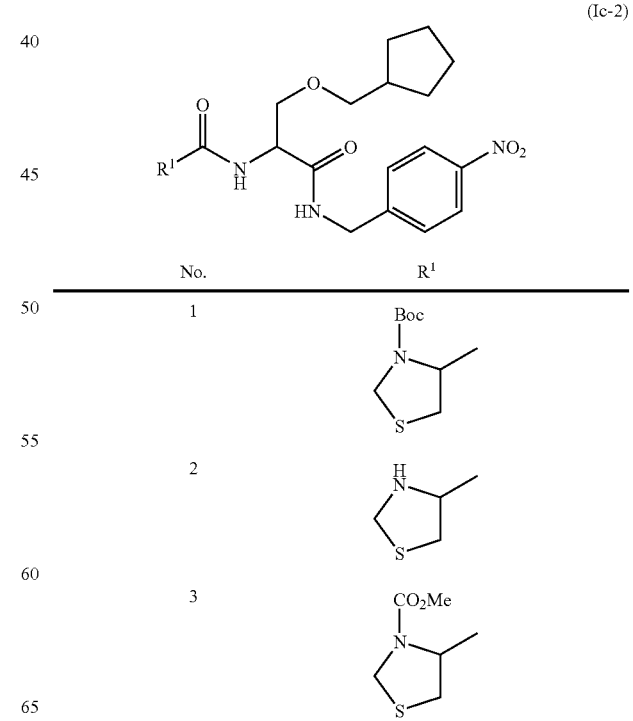
| No. | R¹ |
|---|---|
| 1 | 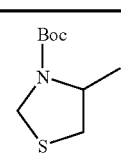 |
| 2 | 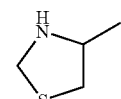 |
| 3 | 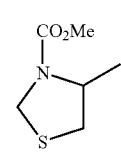 |

TABLE 12-continued (Ic-2)

| No. | R¹ |
|---|---|
| 4 | i-BuO-C(=O)-(4-methylthiazolidin-3-yl) |
| 5 | Ac-(4-methylthiazolidin-3-yl) |
| 6 | i-Bu-C(=O)-(4-methylthiazolidin-3-yl) |
| 7 | 2-oxo-4-methylthiazolidin-3-yl (NH) |
| 8 | Boc-(2-methylthiazolidin-3-yl) |
| 9 | 2-methylthiazolidin-3-yl (NH) |
| 10 | Boc-(3-methylthiomorpholin-4-yl) |
| 11 | 3-methylthiomorpholin-4-yl (NH) |
| 12 | Boc-(4-methyl-1,3-thiazinan-3-yl) |

TABLE 12-continued (Ic-2)

| No. | R¹ |
|---|---|
| 13 | 4-methyl-1,3-thiazinan-3-yl (NH) |
| 14 | 2-thienyl-methyl |
| 15 | 4-methylthiazol-2-yl |
| 16 | 2-amino-4-methylthiazol-5-yl |
| 17 | 4-methyl-1H-imidazol-5-yl |
| 18 | Boc-4-methylimidazol-1-yl |
| 19 | 2-methylfuran-5-yl |
| 20 | 2,5-dimethyloxazol-4-yl |
| 21 | cyclohexyl-methyl |
| 22 | 4-(methoxycarbonyl)cyclohexyl-methyl |
| 23 | phenyl-methyl |

TABLE 12-continued

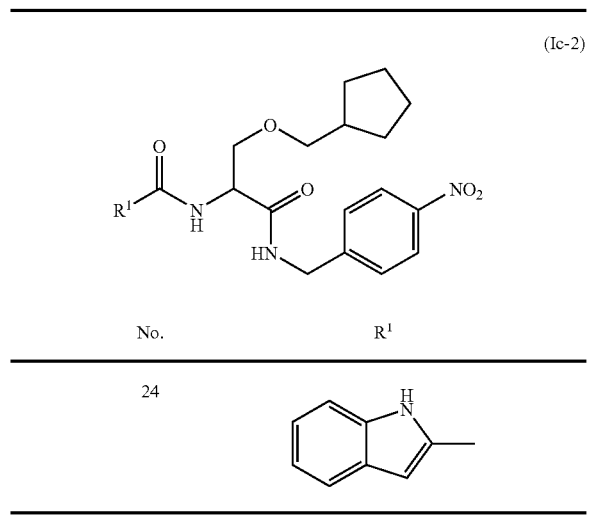

| No. | R¹ |
|---|---|
| 24 | 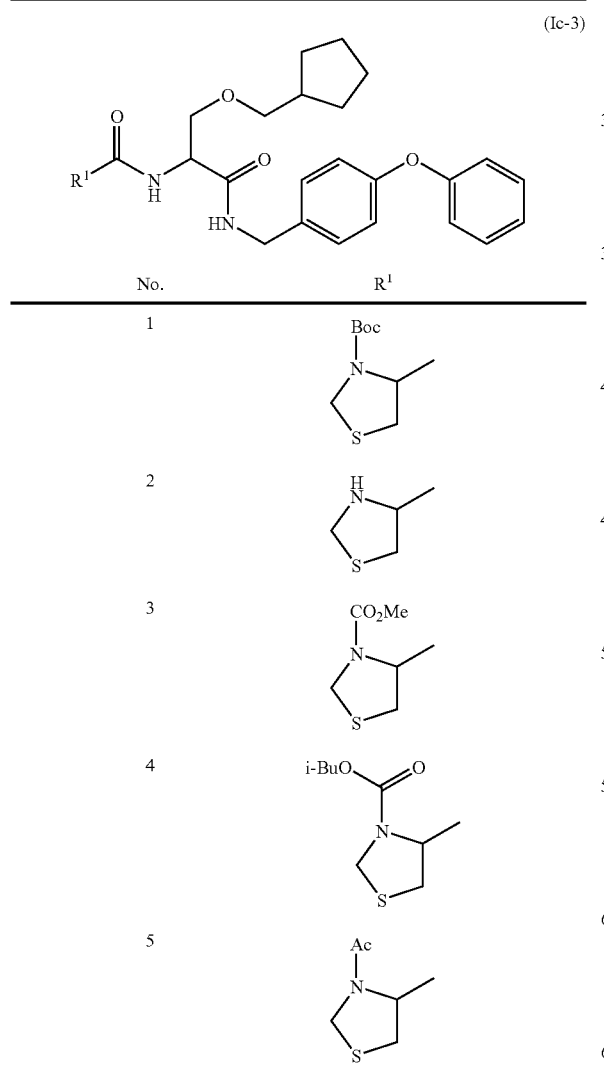 |

TABLE 13

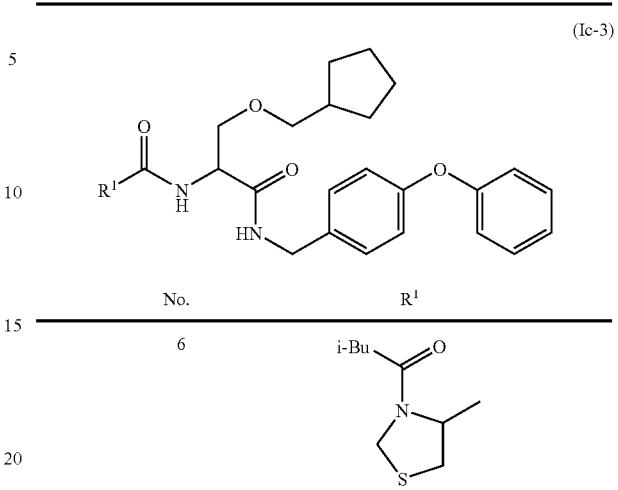

| No. | R¹ |
|---|---|
| 1 | (Boc-4-methylthiazolidine) |
| 2 | (4-methylthiazolidine) |
| 3 | (N-CO₂Me-4-methylthiazolidine) |
| 4 | (N-i-BuOC(O)-4-methylthiazolidine) |
| 5 | (N-Ac-4-methylthiazolidine) |

TABLE 13-continued

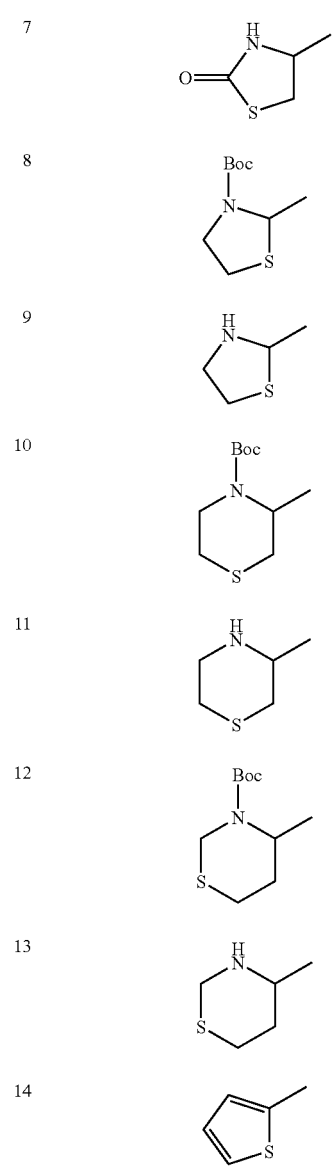

| No. | R¹ |
|---|---|
| 6 | (N-i-BuC(O)-4-methylthiazolidine) |
| 7 | (2-oxo-4-methylthiazolidine) |
| 8 | (N-Boc-2-methylthiazolidine) |
| 9 | (2-methylthiazolidine) |
| 10 | (N-Boc-3-methylthiomorpholine) |
| 11 | (3-methylthiomorpholine) |
| 12 | (N-Boc-4-methyl-1,3-thiazinane) |
| 13 | (4-methyl-1,3-thiazinane) |
| 14 | (2-methylthiophene) |

TABLE 13-continued
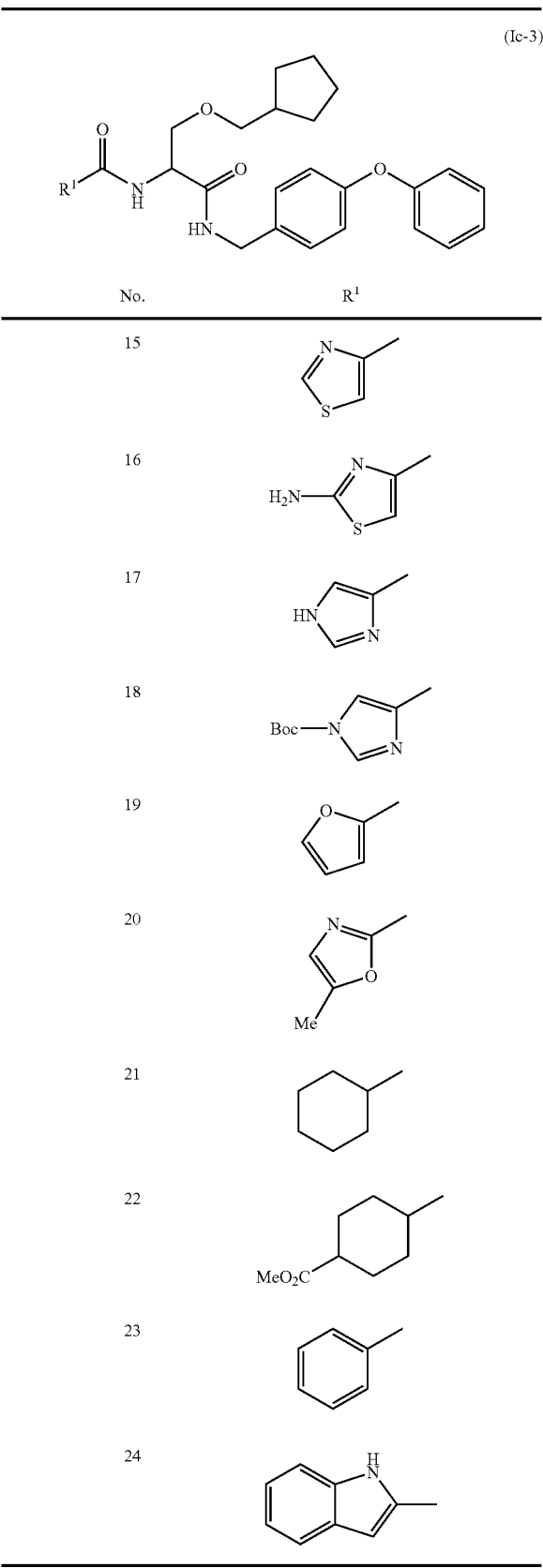
TABLE 14
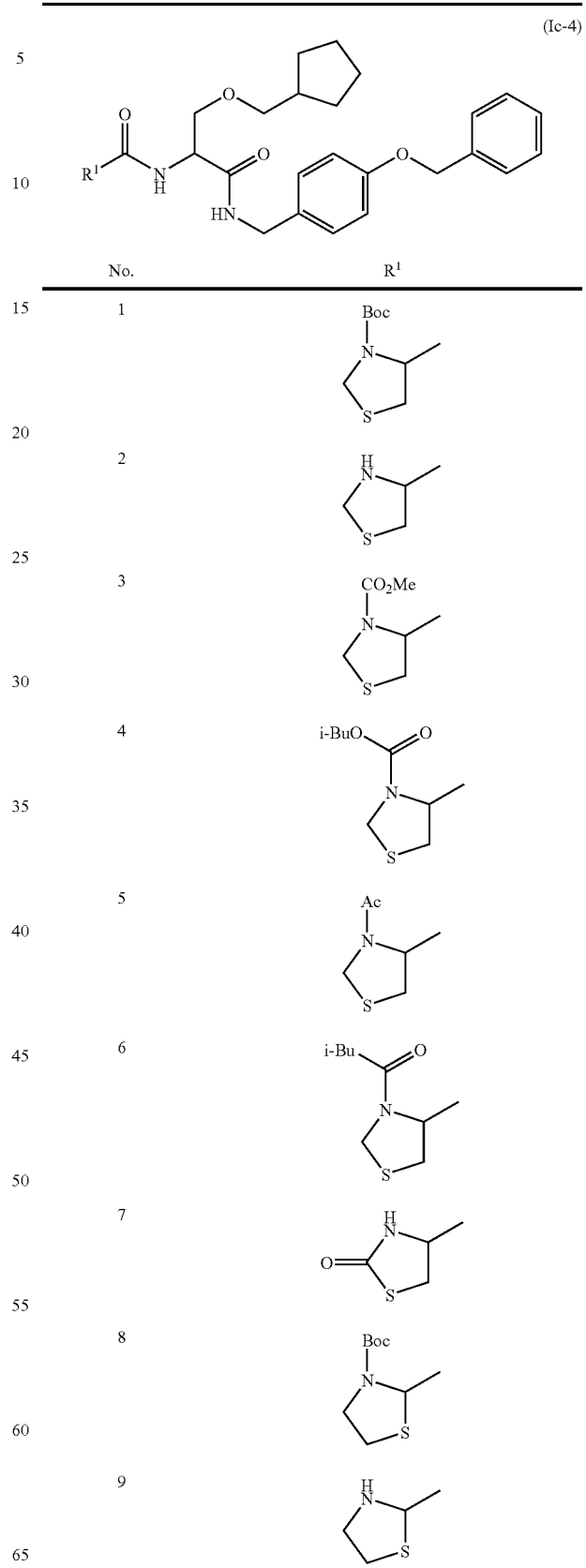

TABLE 14-continued (Ic-4)

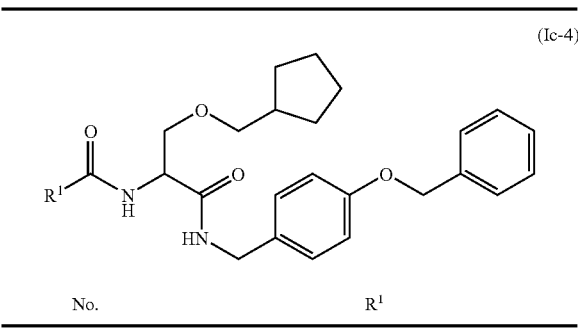

| No. | R¹ |
|---|---|
| 10 | N-Boc thiomorpholine-methyl |
| 11 | NH thiomorpholine-methyl |
| 12 | N-Boc thiazinane-methyl |
| 13 | NH thiazinane-methyl |
| 14 | 2-thienyl |
| 15 | 4-methylthiazol-2-yl |
| 16 | 2-amino-4-methylthiazol-5-yl |
| 17 | 4-methyl-1H-imidazol-2-yl |
| 18 | 1-Boc-4-methylimidazol-2-yl |
| 19 | 2-furyl |

TABLE 14-continued (Ic-4)

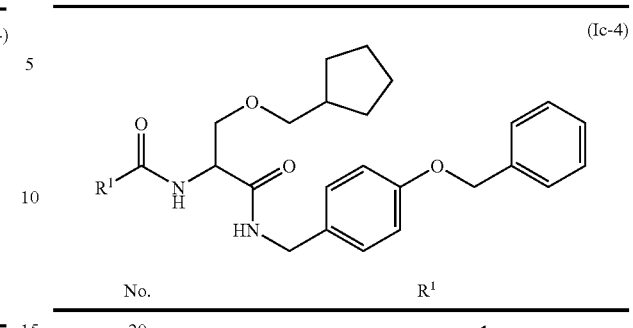

| No. | R¹ |
|---|---|
| 20 | 2,5-dimethyloxazol-4-yl |
| 21 | cyclohexyl-methyl |
| 22 | 4-(MeO₂C)cyclohexyl-methyl |
| 23 | phenyl-methyl |
| 24 | 2-methyl-1H-indol-3-yl |

TABLE 15

(Ic-5)

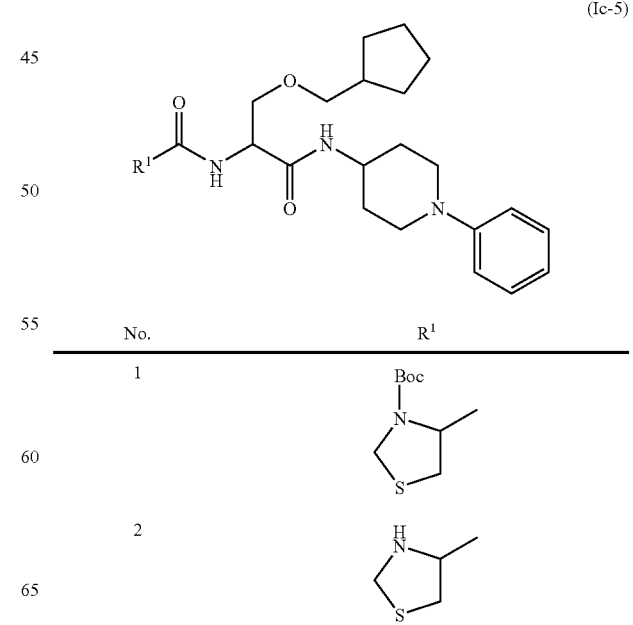

| No. | R¹ |
|---|---|
| 1 | N-Boc thiazolidine-methyl |
| 2 | NH thiazolidine-methyl |

TABLE 15-continued (Ic-5)

| No. | R¹ |
|---|---|
| 3 | N-CO₂Me, 4-methyl thiazolidine |
| 4 | N-C(O)O-i-Bu, 4-methyl thiazolidine |
| 5 | N-Ac, 4-methyl thiazolidine |
| 6 | N-C(O)-i-Bu, 4-methyl thiazolidine |
| 7 | 2-oxo-4-methyl thiazolidine |
| 8 | N-Boc, 2-methyl thiazolidine |
| 9 | 2-methyl thiazolidine (NH) |
| 10 | N-Boc, 3-methyl thiomorpholine |
| 11 | 3-methyl thiomorpholine (NH) |
| 12 | N-Boc, 4-methyl thiazinane |
| 13 | 4-methyl thiazinane (NH) |
| 14 | 2-methyl thiophene |
| 15 | 4-methyl thiazole |
| 16 | 2-amino-4-methyl thiazole |
| 17 | 4-methyl imidazole (NH) |
| 18 | N-Boc, 4-methyl imidazole |
| 19 | 2-methyl furan |
| 20 | 2,5-dimethyl oxazole |

TABLE 15-continued
(Ic-5)
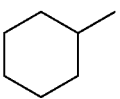
| No. | R¹ |
|---|---|
| 21 | 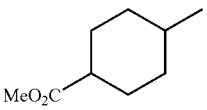 |
| 22 | 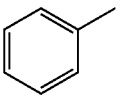 |
| 23 | 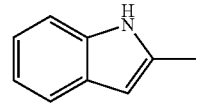 |
| 24 | 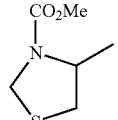 |
TABLE 16
(Id-1)
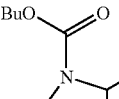
| No. | R¹ |
|---|---|
| 1 | 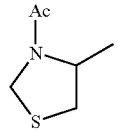 |
| 2 | 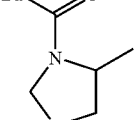 |
TABLE 16-continued
(Id-1)
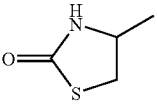
| No. | R¹ |
|---|---|
| 3 | 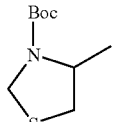 |
| 4 | 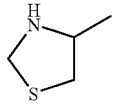 |
| 5 | 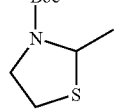 |
| 6 | 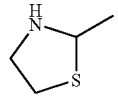 |
| 7 | 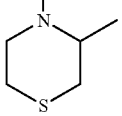 |
| 8 | 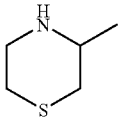 |
| 9 | |
| 10 | |
| 11 | |

TABLE 16-continued
(Id-1)
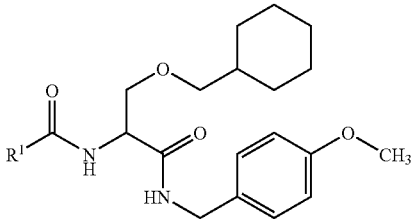
| No. | R¹ |
|---|---|
| 12 | 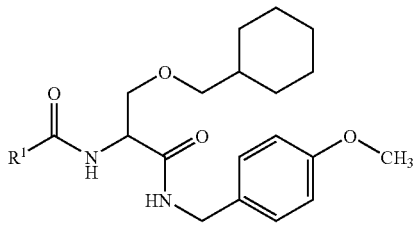 |
| 13 | 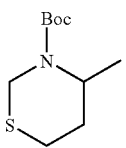 |
| 14 | 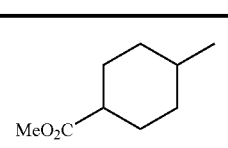 |
| 15 | 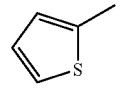 |
| 16 | 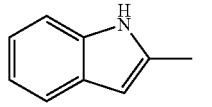 |
| 17 | 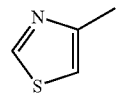 |
| 18 | 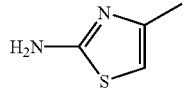 |
| 19 | 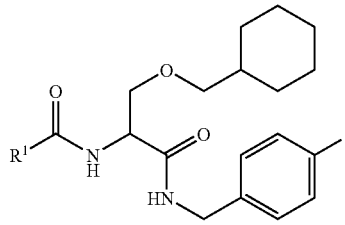 |
| 20 | 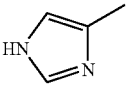 |
| 21 | 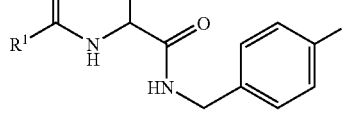 |
TABLE 16-continued
(Id-1)
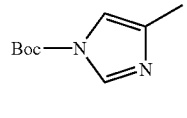
| No. | R¹ |
|---|---|
| 22 | 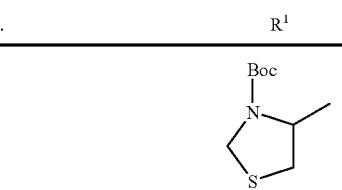 |
| 23 | 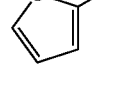 |
| 24 | 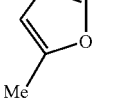 |
TABLE 17
(Id-2)
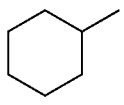
| No. | R¹ |
|---|---|
| 1 | 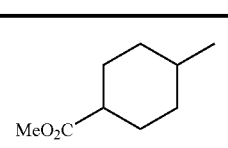 |
| 2 | 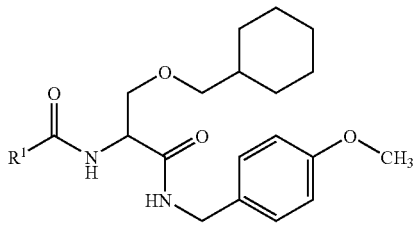 |
| 3 | 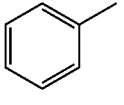 |

TABLE 17-continued (Id-2)

Structure: R¹-C(=O)-NH-CH(CH₂-O-CH₂-cyclohexyl)-C(=O)-NH-CH₂-(4-nitrophenyl)

| No. | R¹ |
|---|---|
| 4 | i-BuO-C(=O)-N(4-methylthiazolidine) |
| 5 | Ac-N(4-methylthiazolidine) |
| 6 | i-Bu-C(=O)-N(4-methylthiazolidine) |
| 7 | 2-oxo-4-methylthiazolidine (NH) |
| 8 | Boc-N(2-methylthiazolidine) |
| 9 | 2-methylthiazolidine (NH) |
| 10 | Boc-N(3-methylthiomorpholine) |
| 11 | 3-methylthiomorpholine (NH) |
| 12 | Boc-N(4-methyl-1,3-thiazinane) |
| 13 | 4-methyl-1,3-thiazinane (NH) |
| 14 | 2-methylthiophene |
| 15 | 4-methylthiazole |
| 16 | 2-amino-4-methylthiazole |
| 17 | 4-methyl-1H-imidazole |
| 18 | Boc-N(4-methylimidazole) |
| 19 | 2-methylfuran |
| 20 | 2,5-dimethyloxazole |
| 21 | methylcyclohexyl |
| 22 | 4-methylcyclohexyl-CO₂Me |

TABLE 17-continued (Id-2)

| No. | R¹ |
|---|---|
| 23 | phenyl |
| 24 | 2-methyl-1H-indol-3-yl |

TABLE 18

(Id-3)

| No. | R¹ |
|---|---|
| 1 | N-Boc-4-methylthiazolidin-3-yl |
| 2 | 4-methylthiazolidin-3-yl (NH) |
| 3 | N-CO₂Me-4-methylthiazolidin-3-yl |
| 4 | N-(i-BuO-C(O))-4-methylthiazolidin-3-yl |

TABLE 18-continued (Id-3)

| No. | R¹ |
|---|---|
| 5 | N-Ac-4-methylthiazolidin-3-yl |
| 6 | N-(i-Bu-C(O))-4-methylthiazolidin-3-yl |
| 7 | 4-methyl-2-oxo-thiazolidin-3-yl |
| 8 | N-Boc-2-methylthiazolidin-3-yl |
| 9 | 2-methylthiazolidin-3-yl (NH) |
| 10 | N-Boc-3-methylthiomorpholin-4-yl |
| 11 | 3-methylthiomorpholin-4-yl (NH) |
| 12 | N-Boc-4-methyl-1,3-thiazinan-3-yl |
| 13 | 4-methyl-1,3-thiazinan-3-yl (NH) |

TABLE 18-continued
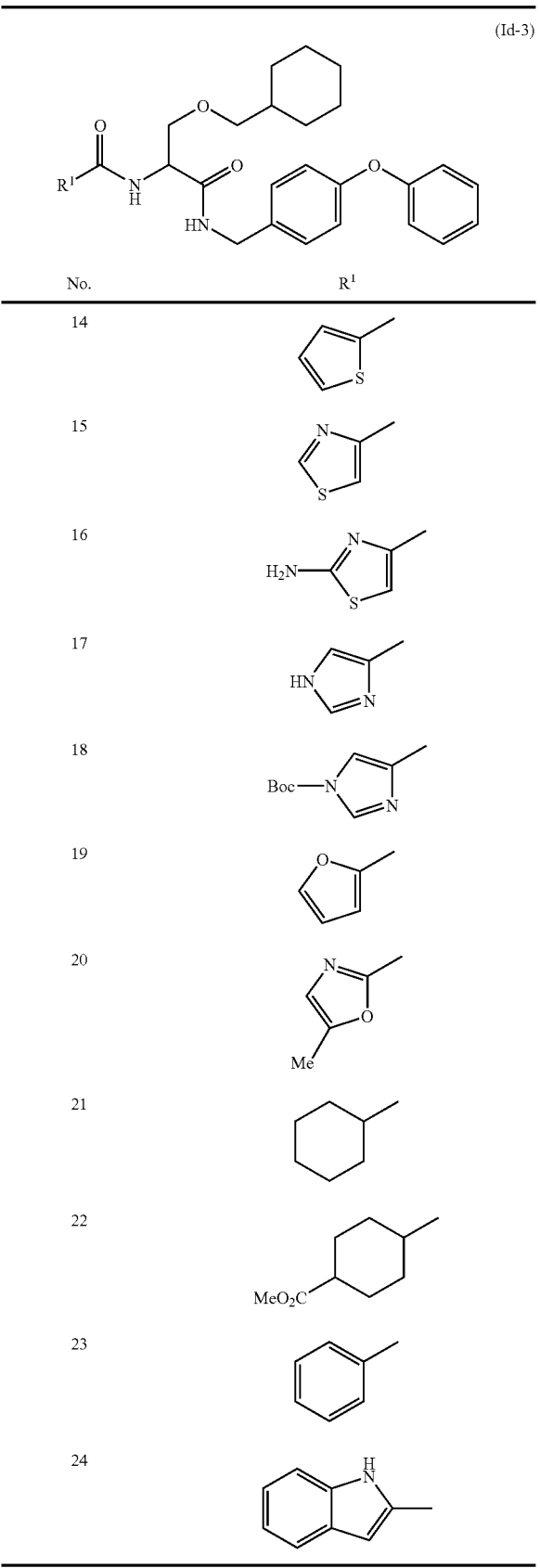
TABLE 19
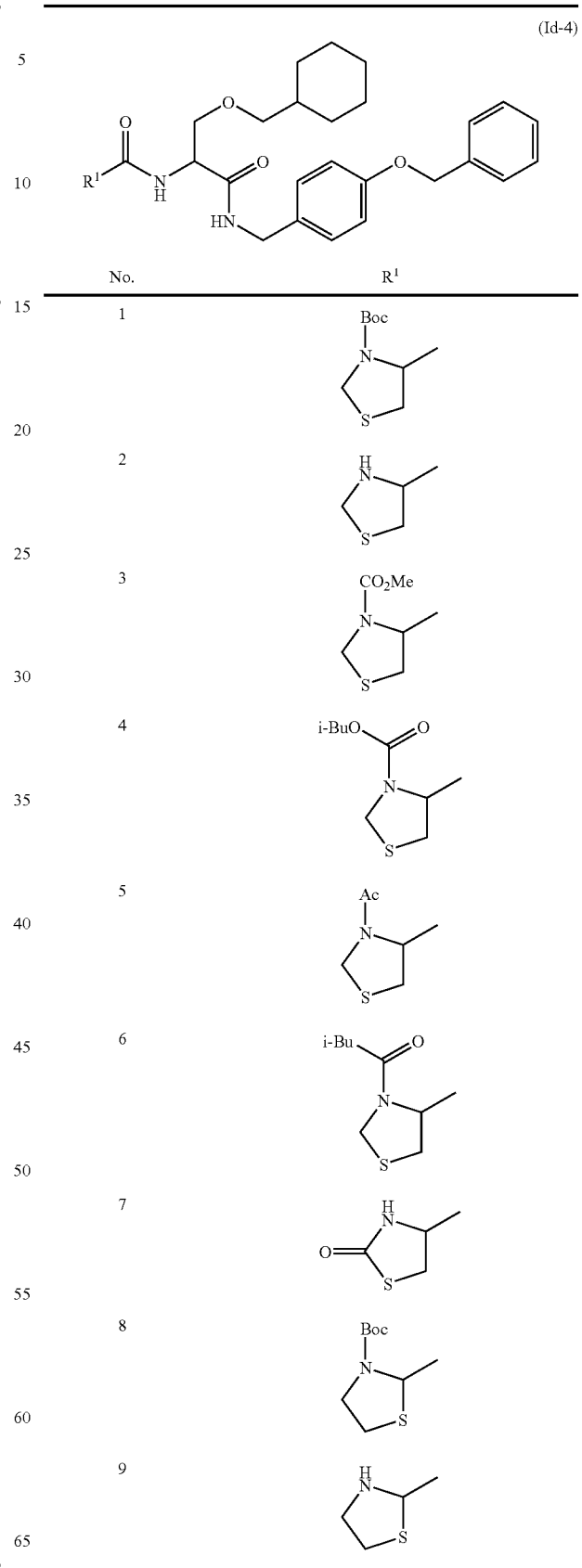

TABLE 19-continued (Id-4)

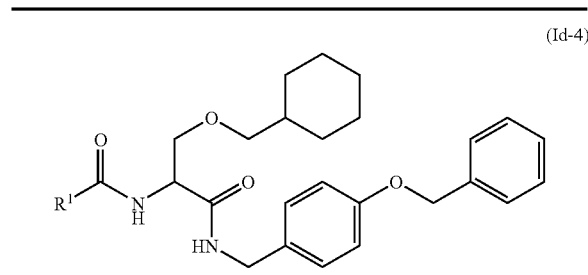

| No. | R¹ |
|---|---|
| 10 | N-Boc thiomorpholine with methyl |
| 11 | NH thiomorpholine with methyl |
| 12 | N-Boc thiazinane with methyl |
| 13 | NH thiazinane with methyl |
| 14 | 2-methylthiophene |
| 15 | 4-methylthiazole |
| 16 | 2-amino-4-methylthiazole |
| 17 | 4-methylimidazole (NH) |
| 18 | N-Boc-4-methylimidazole |
| 19 | 2-methylfuran |

TABLE 19-continued (Id-4)

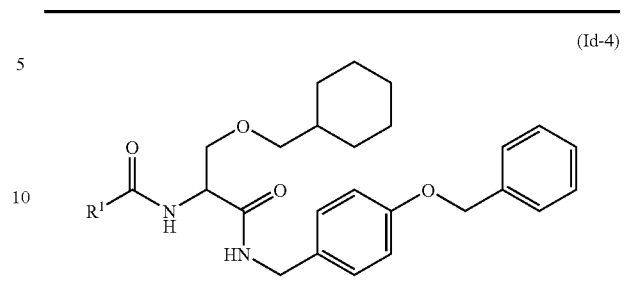

| No. | R¹ |
|---|---|
| 20 | 2,5-dimethyloxazole |
| 21 | methylcyclohexane |
| 22 | methyl 4-methylcyclohexanecarboxylate |
| 23 | methylbenzene |
| 24 | 2-methylindole |

TABLE 20

(Id-5)

R¹—C(=O)—NH—CH(CH₂—O—CH₂-cyclohexyl)—C(=O)—NH—(1-phenylpiperidin-4-yl)

| No. | R¹ |
|---|---|
| 1 | N-Boc-4-methylthiazolidine |

TABLE 20-continued (Id-5)

| No. | R¹ |
|---|---|
| 2 | 4-methylthiazolidine (NH) |
| 3 | 3-CO₂Me-4-methylthiazolidine |
| 4 | 3-(i-BuO-C(O))-4-methylthiazolidine |
| 5 | 3-Ac-4-methylthiazolidine |
| 6 | 3-(i-Bu-C(O))-4-methylthiazolidine |
| 7 | 2-oxo-4-methylthiazolidine |
| 8 | 3-Boc-2-methylthiazolidine |
| 9 | 2-methylthiazolidine (NH) |

TABLE 20-continued (Id-5)

| No. | R¹ |
|---|---|
| 10 | 4-Boc-3-methylthiomorpholine |
| 11 | 3-methylthiomorpholine (NH) |
| 12 | 3-Boc-4-methyl-1,3-thiazinane |
| 13 | 4-methyl-1,3-thiazinane (NH) |
| 14 | 2-methylthiophene |
| 15 | 4-methylthiazole |
| 16 | 2-amino-4-methylthiazole |
| 17 | 4-methylimidazole (NH) |
| 18 | 1-Boc-4-methylimidazole |
| 19 | 2-methylfuran |

TABLE 20-continued
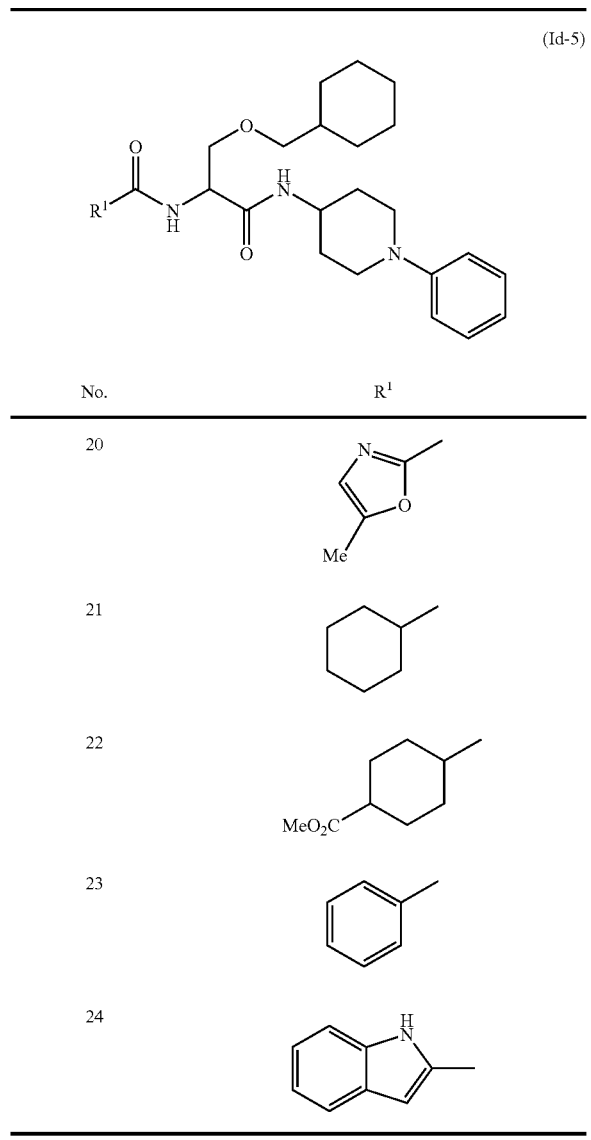
TABLE 21
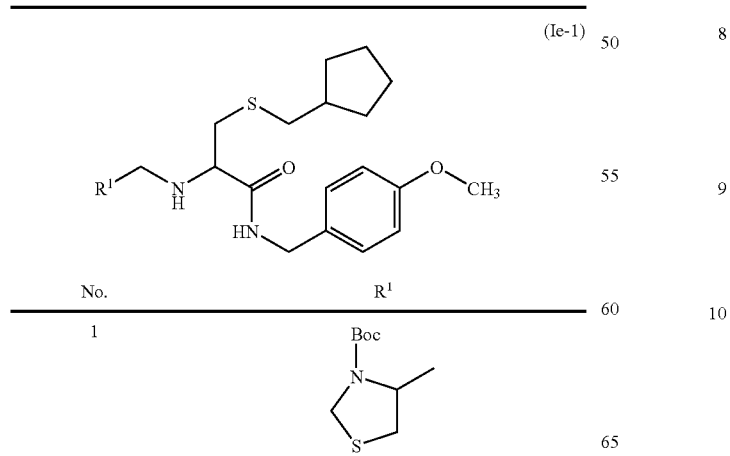
TABLE 21-continued
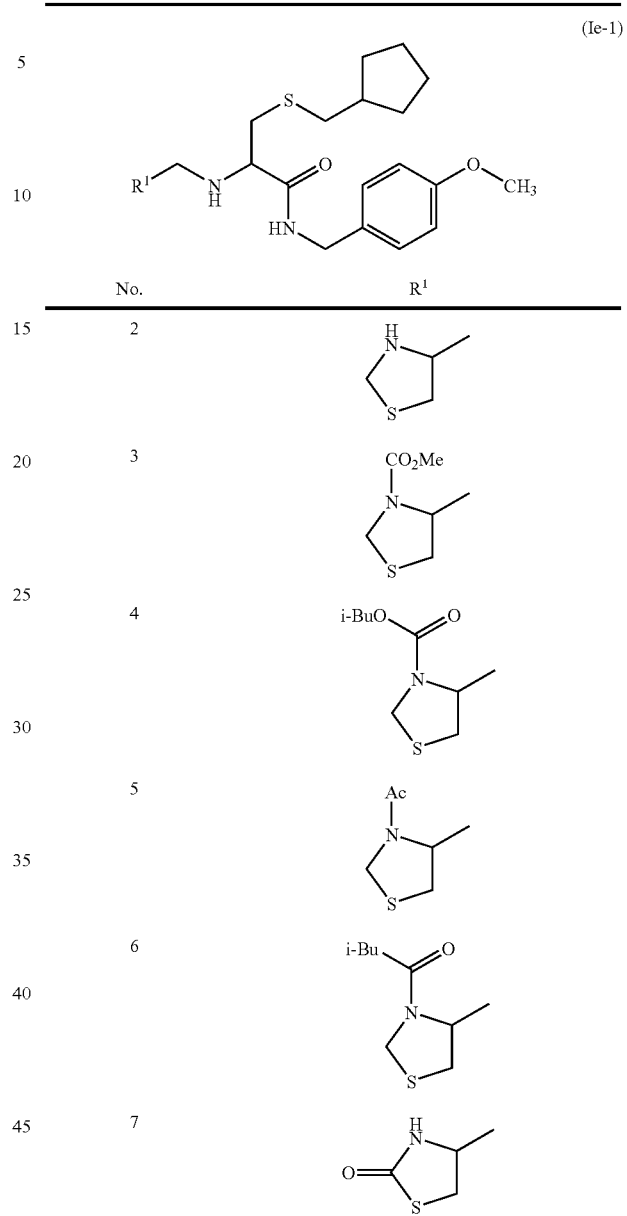

TABLE 21-continued
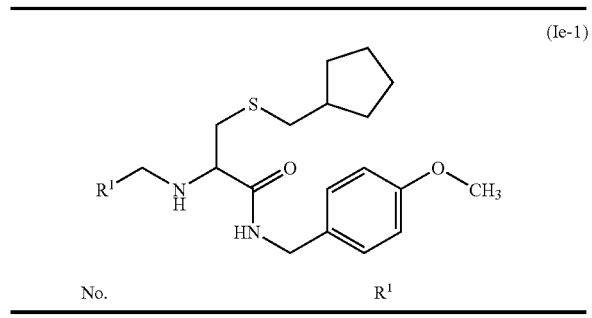
TABLE 21-continued
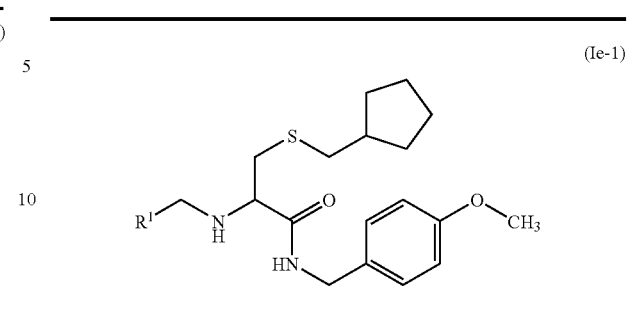
TABLE 22
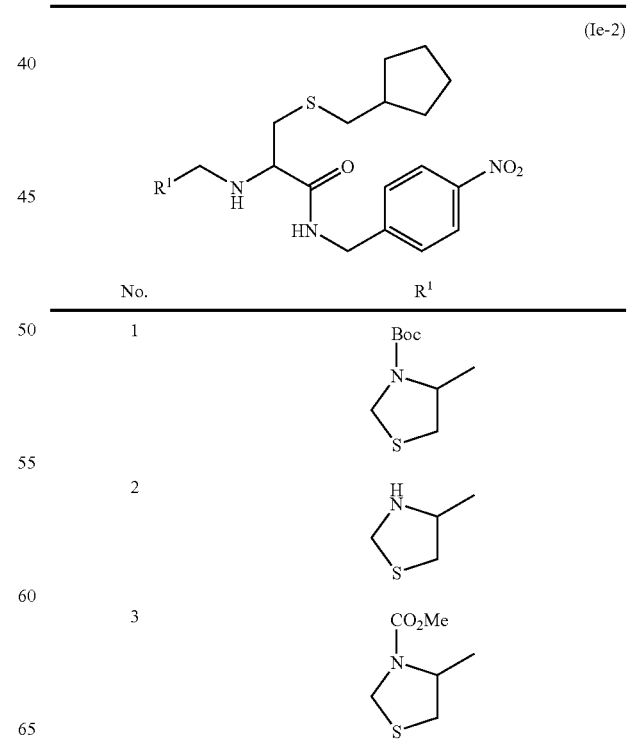

TABLE 22-continued (Ie-2)

| No. | R¹ |
|---|---|
| 4 | i-BuO-C(=O)-N(thiazolidine-4-yl-methyl) |
| 5 | Ac-N(thiazolidine-4-yl-methyl) |
| 6 | i-Bu-C(=O)-N(thiazolidine-4-yl-methyl) |
| 7 | 2-oxo-thiazolidine-4-yl-methyl |
| 8 | Boc-N(thiazolidine-2-yl-methyl) |
| 9 | thiazolidine-2-yl-methyl |
| 10 | Boc-N(thiomorpholine-3-yl-methyl) |
| 11 | thiomorpholine-3-yl-methyl |
| 12 | Boc-N(1,3-thiazinane-4-yl-methyl) |
| 13 | 1,3-thiazinane-4-yl-methyl |
| 14 | thiophen-2-yl-methyl |
| 15 | thiazol-4-yl-methyl |
| 16 | 2-amino-thiazol-4-yl-methyl |
| 17 | 1H-imidazol-4-yl-methyl |
| 18 | Boc-imidazol-4-yl-methyl |
| 19 | furan-2-yl-methyl |
| 20 | 2,5-dimethyl-oxazol-4-yl-methyl |
| 21 | cyclohexyl-methyl |
| 22 | 4-(methoxycarbonyl)-cyclohexyl-methyl |
| 23 | phenyl-methyl |

TABLE 22-continued
(Ie-2)
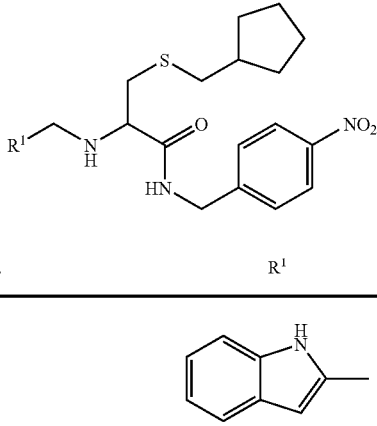
| No. | R¹ |
|---|---|
| 24 | 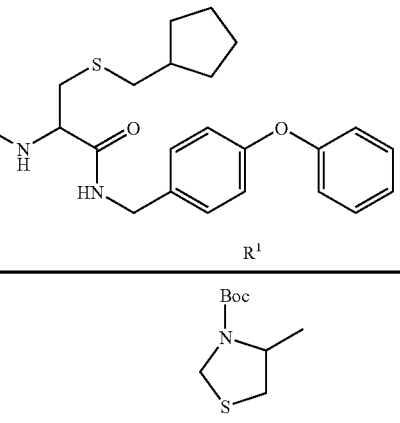 |
TABLE 23
(Ie-3)
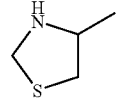
| No. | R¹ |
|---|---|
| 1 | 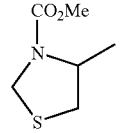 |
| 2 | 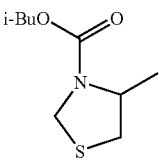 |
| 3 | 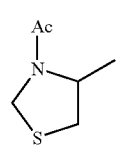 |
| 4 | 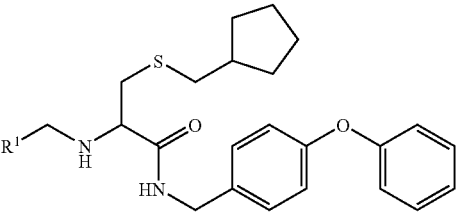 |
| 5 | 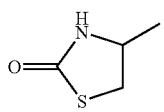 |
TABLE 23-continued
(Ie-3)
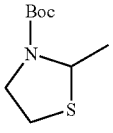
| No. | R¹ |
|---|---|
| 6 | 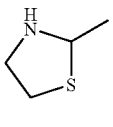 |
| 7 | 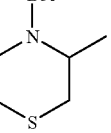 |
| 8 | 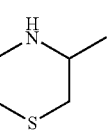 |
| 9 | 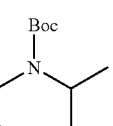 |
| 10 | 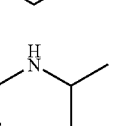 |
| 11 | 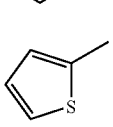 |
| 12 | |
| 13 | |
| 14 | |

TABLE 23-continued
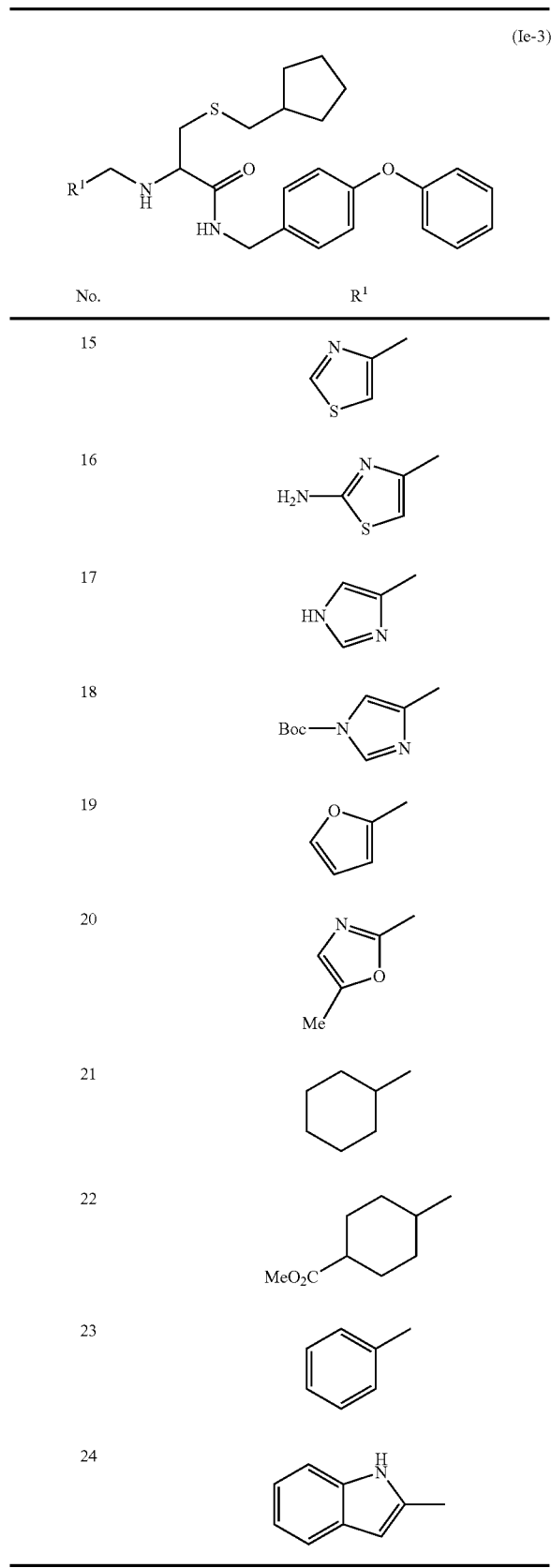
TABLE 24
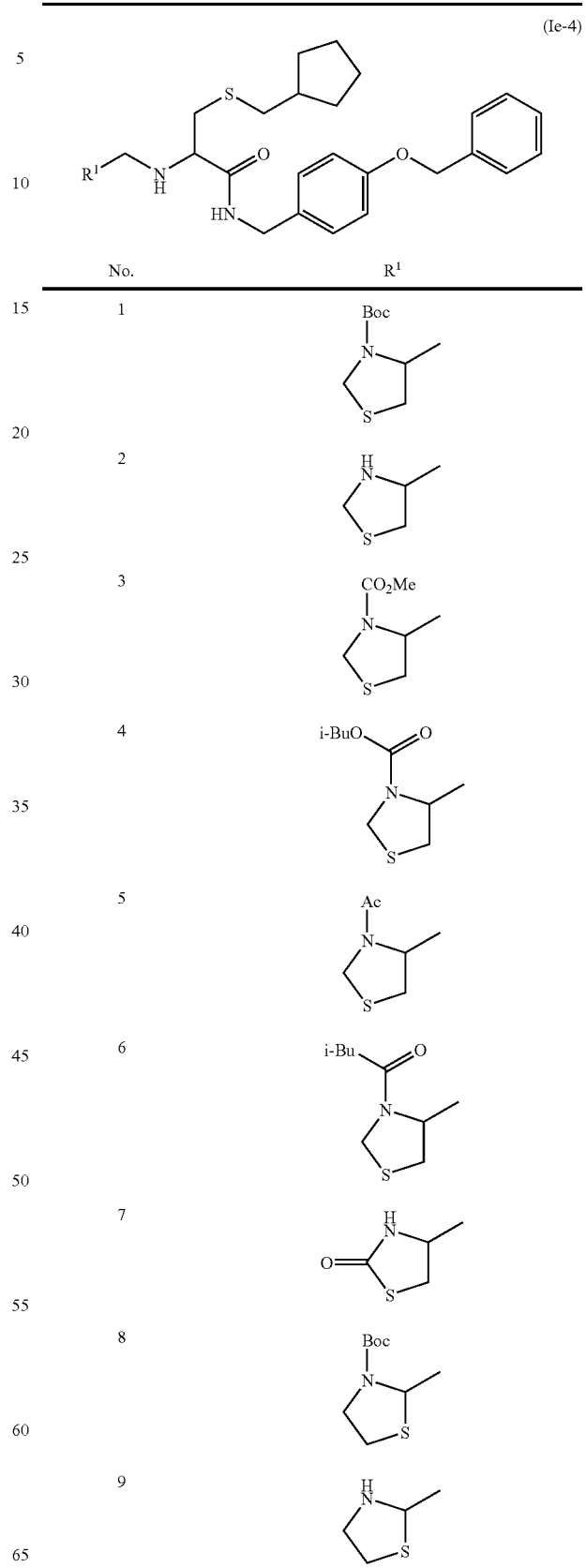

TABLE 24-continued
(Ie-4)
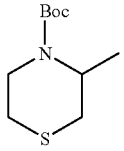
| No. | R¹ |
|---|---|
| 10 | 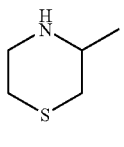 |
| 11 | 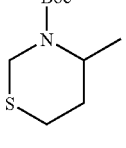 |
| 12 | 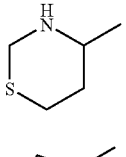 |
| 13 | 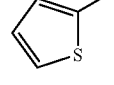 |
| 14 | 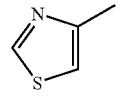 |
| 15 | 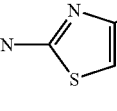 |
| 16 | 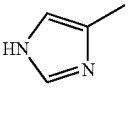 |
| 17 | 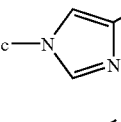 |
| 18 | 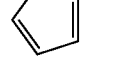 |
| 19 | 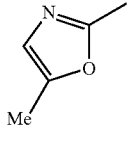 |
TABLE 24-continued
(Ie-4)
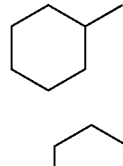
| No. | R¹ |
|---|---|
| 20 | 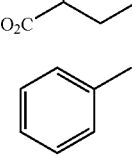 |
| 21 | 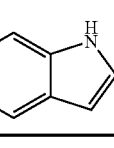 |
| 22 | 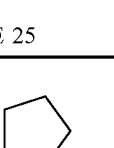 |
| 23 | 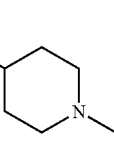 |
| 24 | 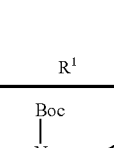 |
TABLE 25
(Ie-5)
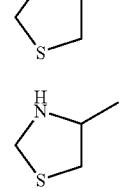
| No. | R¹ |
|---|---|
| 1 |  |
| 2 | 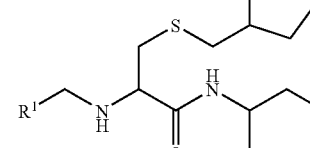 |

TABLE 25-continued
(Ie-5)
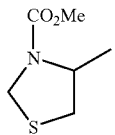
| No. | R¹ |
|---|---|
| 3 | 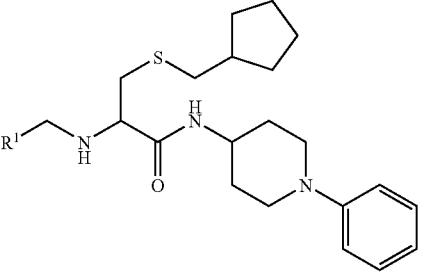 |
| 4 | 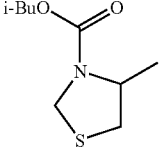 |
| 5 | 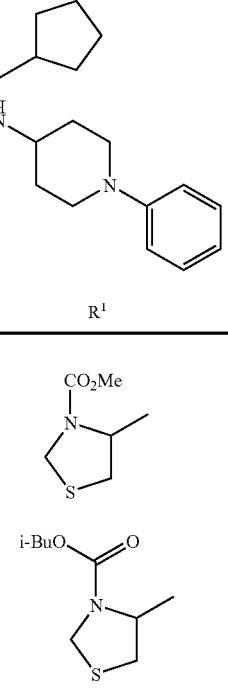 |
| 6 | 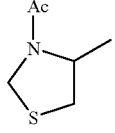 |
| 7 | 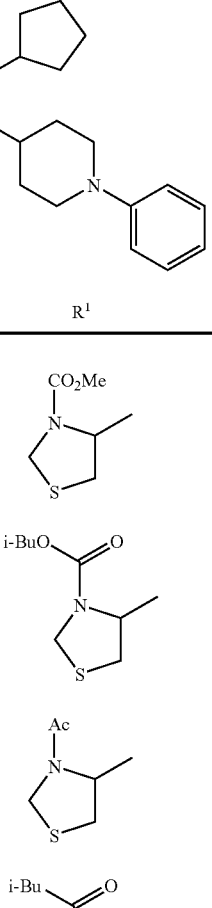 |
| 8 | 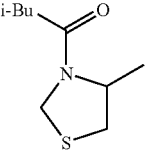 |
| 9 | 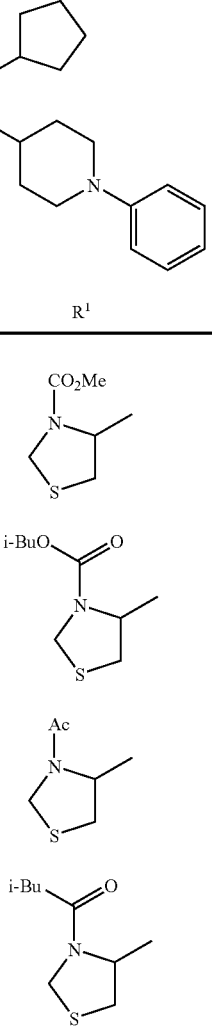 |
| 10 | 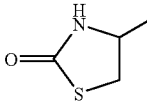 |
TABLE 25-continued
(Ie-5)
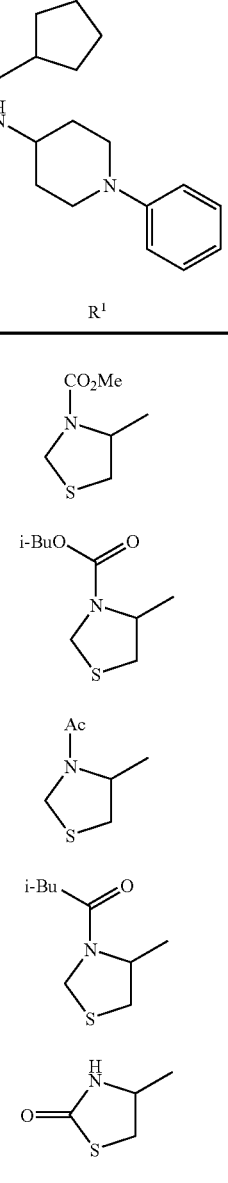
| No. | R¹ |
|---|---|
| 11 | 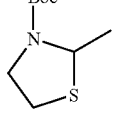 |
| 12 | 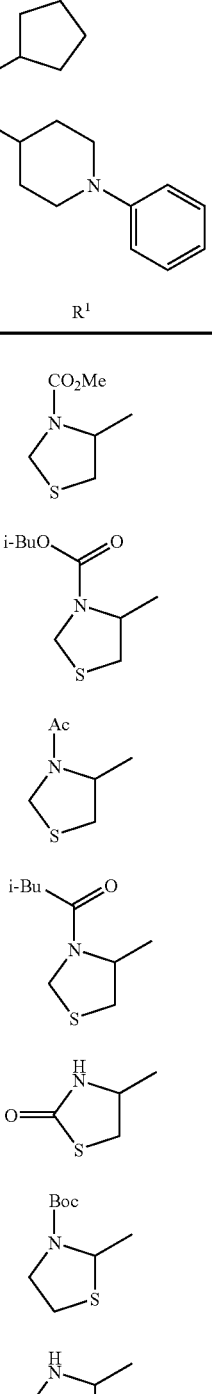 |
| 13 | 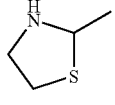 |
| 14 | 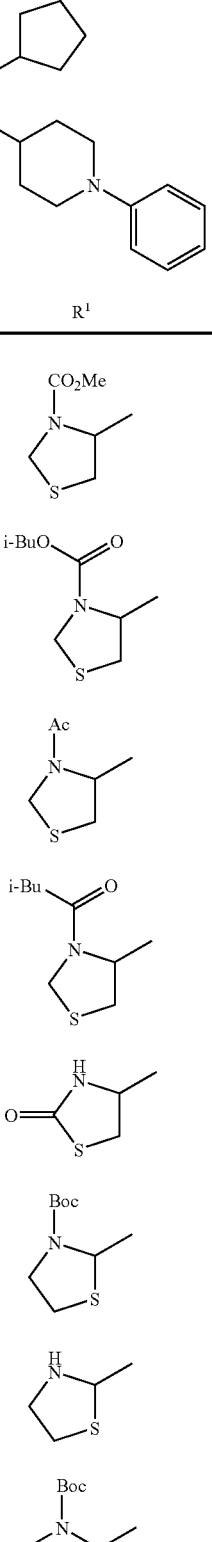 |
| 15 | 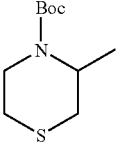 |
| 16 | 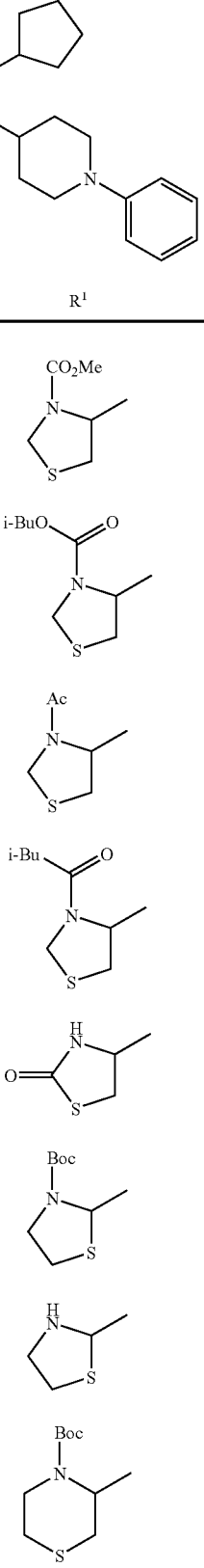 |
| 17 | 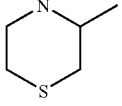 |
| 18 | 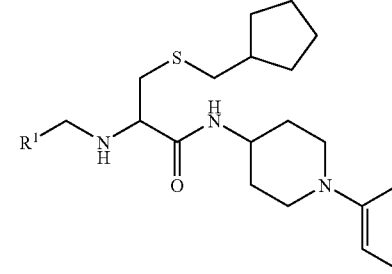 |
| 19 | 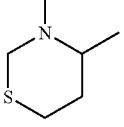 |
| 20 | 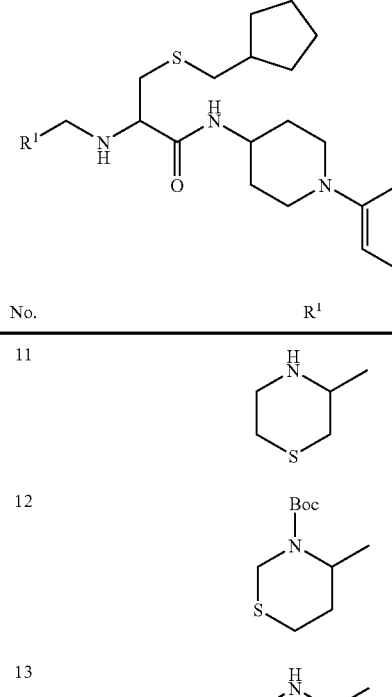 |

TABLE 25-continued
(Ie-5)
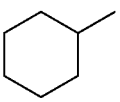
| No. | R¹ |
|---|---|
| 21 | 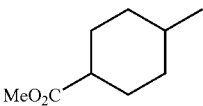 |
| 22 | 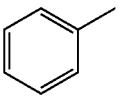 |
| 23 | 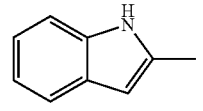 |
| 24 | 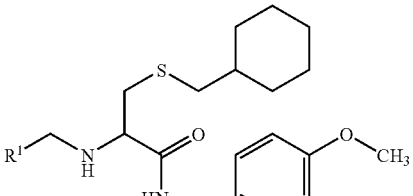 |
TABLE 26
(If-1)
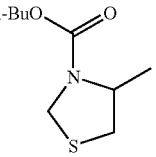
| No. | R¹ |
|---|---|
| 1 | 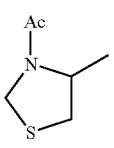 |
| 2 | 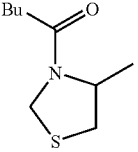 |
TABLE 26-continued
(If-1)
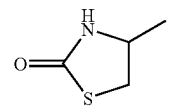
| No. | R¹ |
|---|---|
| 3 | 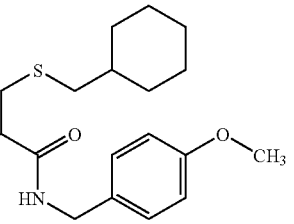 |
| 4 | 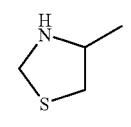 |
| 5 | 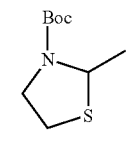 |
| 6 | 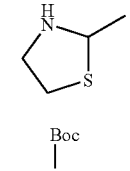 |
| 7 | 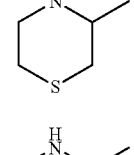 |
| 8 | 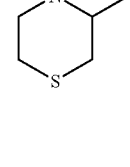 |
| 9 |  |
| 10 |  |
| 11 |  |

TABLE 26-continued (If-1)

| No. | R¹ |
|---|---|
| 12 | N-Boc, 4-methyl-1,3-thiazinane |
| 13 | 4-methyl-1,3-thiazinane |
| 14 | 2-methylthiophene |
| 15 | 4-methylthiazole |
| 16 | 2-amino-4-methylthiazole |
| 17 | 4-methylimidazole |
| 18 | N-Boc-4-methylimidazole |
| 19 | 2-methylfuran |
| 20 | 2,5-dimethyloxazole |
| 21 | methylcyclohexane |

TABLE 26-continued (If-1)

| No. | R¹ |
|---|---|
| 22 | methyl 4-methylcyclohexanecarboxylate |
| 23 | toluene |
| 24 | 2-methylindole |

TABLE 27

(If-2)

| No. | R¹ |
|---|---|
| 1 | N-Boc-4-methylthiazolidine |
| 2 | 4-methylthiazolidine |
| 3 | N-CO₂Me-4-methylthiazolidine |

TABLE 27-continued
(If-2)
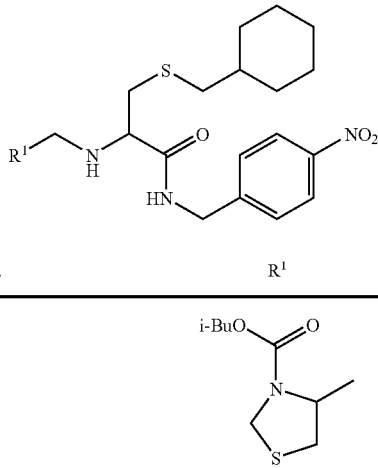
| No. | R¹ |
|---|---|
| 4 | 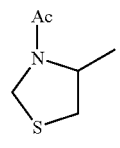 |
| 5 | 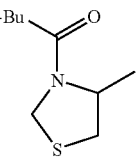 |
| 6 | 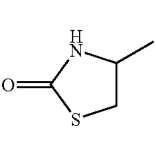 |
| 7 | 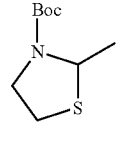 |
| 8 | 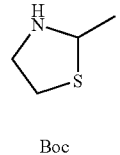 |
| 9 | 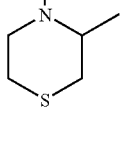 |
| 10 | 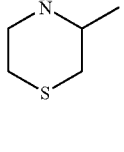 |
| 11 | 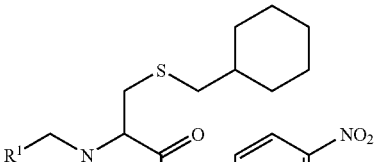 |
TABLE 27-continued
(If-2)
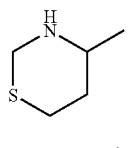
| No. | R¹ |
|---|---|
| 12 | 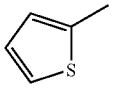 |
| 13 | 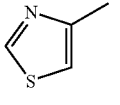 |
| 14 | 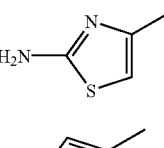 |
| 15 | 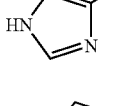 |
| 16 | 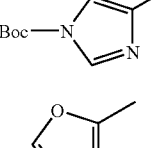 |
| 17 | 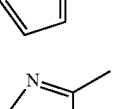 |
| 18 | 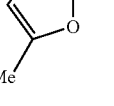 |
| 19 | 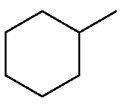 |
| 20 | 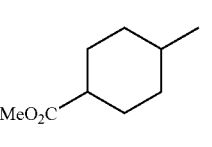 |
| 21 |  |
| 22 |  |

TABLE 27-continued
(If-2)
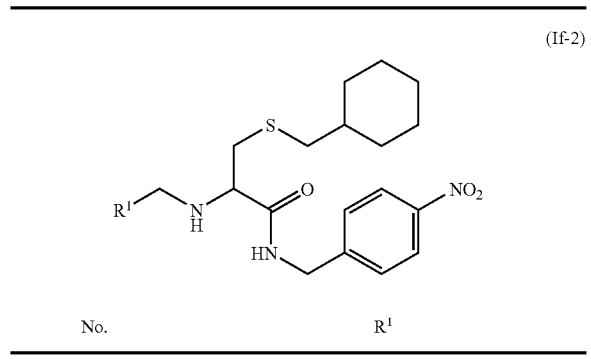
| No. | R¹ |
|---|---|
| 23 | 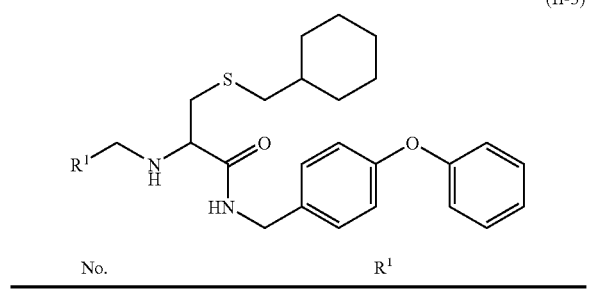 |
| 24 | |
TABLE 28
(If-3)
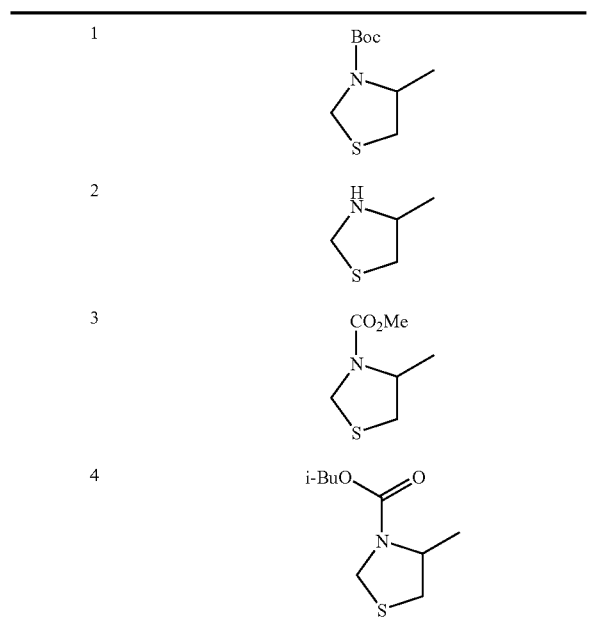
| No. | R¹ |
|---|---|
| 1 | |
| 2 | |
| 3 | |
| 4 | |
TABLE 28-continued
(If-3)
| No. | R¹ |
|---|---|
| 5 | 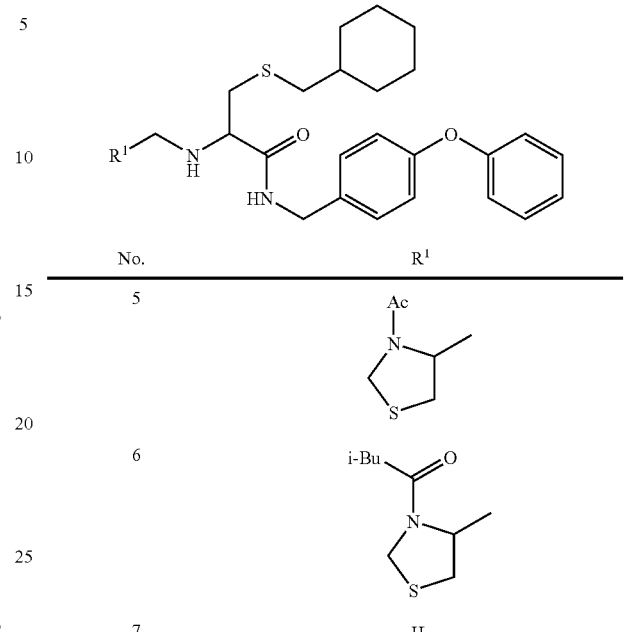 |
| 6 | |
| 7 | |
| 8 | |
| 9 | |
| 10 | 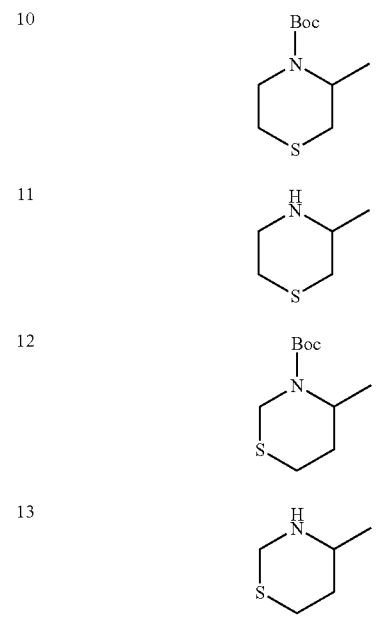 |
| 11 | |
| 12 | |
| 13 | |

TABLE 28-continued
(If-3)
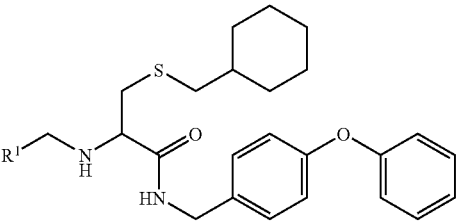
| No. | R¹ |
|---|---|
| 14 | 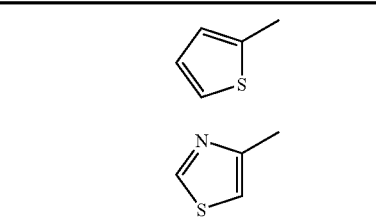 |
| 15 | 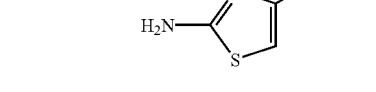 |
| 16 | 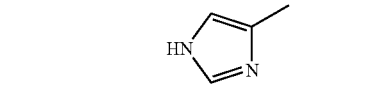 |
| 17 | 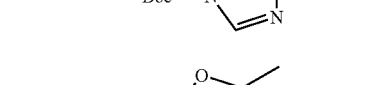 |
| 18 | 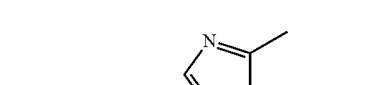 |
| 19 | 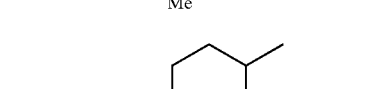 |
| 20 | 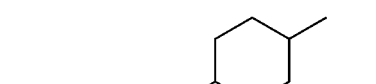 |
| 21 | 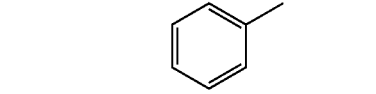 |
| 22 | 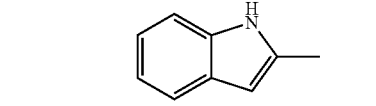 |
| 23 |  |
| 24 | 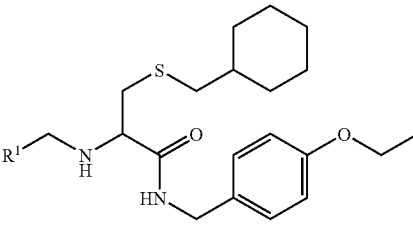 |
TABLE 29
(If-4)
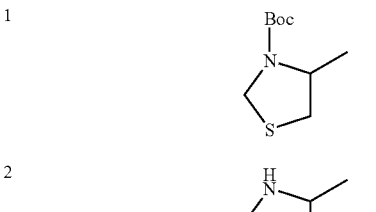
| No. | R¹ |
|---|---|
| 1 | 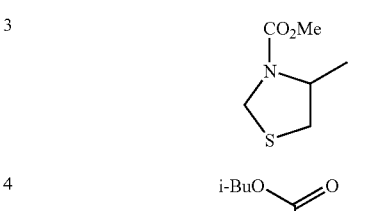 |
| 2 | 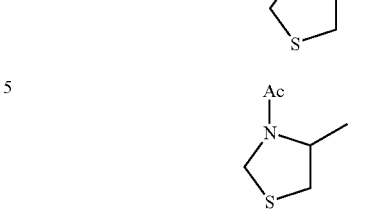 |
| 3 | 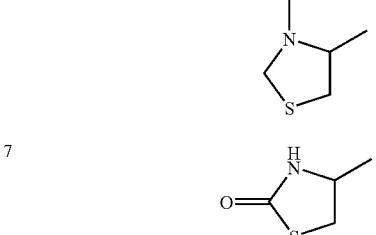 |
| 4 | 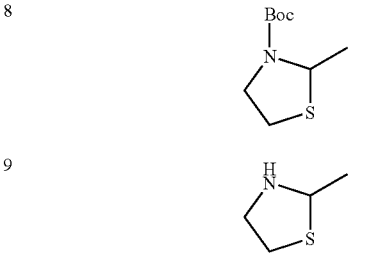 |
| 5 |  |
| 6 |  |
| 7 |  |
| 8 |  |
| 9 |  |

TABLE 29-continued
(If-4)
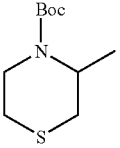
| No. | R¹ |
|---|---|
| 10 | 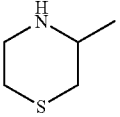 |
| 11 | 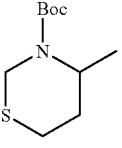 |
| 12 | 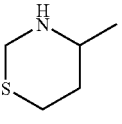 |
| 13 | 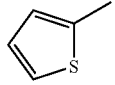 |
| 14 | 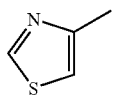 |
| 15 | 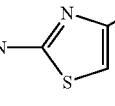 |
| 16 | 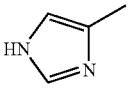 |
| 17 | 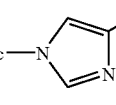 |
| 18 | 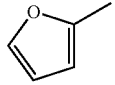 |
| 19 | 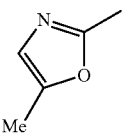 |
TABLE 29-continued
(If-4)
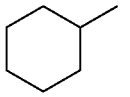
| No. | R¹ |
|---|---|
| 20 | 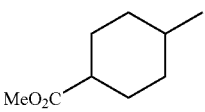 |
| 21 | 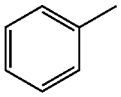 |
| 22 | 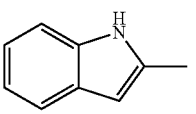 |
| 23 | (methylphenyl) |
| 24 | (2-methyl-1H-indole) |
TABLE 30
(If-5)
| No. | R¹ |
|---|---|
| 1 | (Boc-N-methylthiazolidine) |

TABLE 30-continued (If-5)

| No. | R¹ |
|---|---|
| 2 | 4-methylthiazolidine (NH) |
| 3 | N-CO₂Me 4-methylthiazolidine |
| 4 | N-C(O)O-i-Bu 4-methylthiazolidine |
| 5 | N-Ac 4-methylthiazolidine |
| 6 | N-C(O)-i-Bu 4-methylthiazolidine |
| 7 | 2-oxo-4-methylthiazolidine |
| 8 | N-Boc 2-methylthiazolidine |
| 9 | 2-methylthiazolidine (NH) |
| 10 | N-Boc 3-methylthiomorpholine |
| 11 | 3-methylthiomorpholine (NH) |
| 12 | N-Boc 4-methyl-1,3-thiazinane |
| 13 | 4-methyl-1,3-thiazinane (NH) |
| 14 | 2-methylthiophene |
| 15 | 4-methylthiazole |
| 16 | 2-amino-4-methylthiazole |
| 17 | 4-methylimidazole (NH) |
| 18 | N-Boc 4-methylimidazole |
| 19 | 2-methylfuran |

TABLE 30-continued
(If-5)
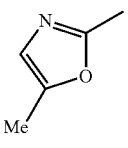
| No. | R¹ |
|---|---|
| 20 | 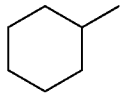 |
| 21 | 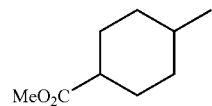 |
| 22 | 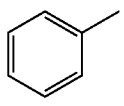 |
| 23 | 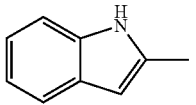 |
| 24 | 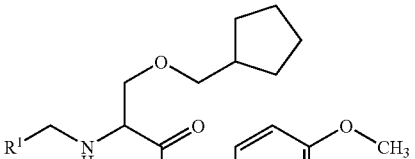 |
TABLE 31
(Ig-1)
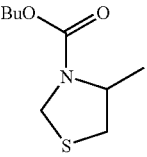
| No. | R¹ |
|---|---|
| 1 | 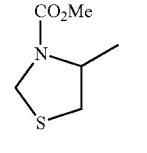 |
| 2 | 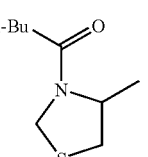 |
TABLE 31-continued
(Ig-1)
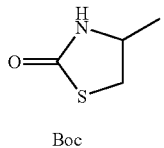
| No. | R¹ |
|---|---|
| 3 | 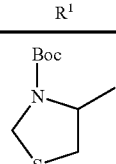 |
| 4 | 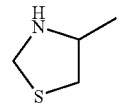 |
| 5 | |
| 6 | |
| 7 | |
| 8 | |
| 9 | |
| 10 | |
| 11 | |

TABLE 31-continued (Ig-1)

| No. | R¹ |
|-----|-----|
| 12 | N-Boc, 4-methyl-1,3-thiazinane |
| 13 | 4-methyl-1,3-thiazinane (NH) |
| 14 | 2-methylthiophene |
| 15 | 4-methylthiazole |
| 16 | 2-amino-4-methylthiazole |
| 17 | 4-methyl-1H-imidazole |
| 18 | N-Boc-4-methylimidazole |
| 19 | 2-methylfuran |
| 20 | 2,5-dimethyloxazole |
| 21 | methylcyclohexane |
| 22 | methyl 4-methylcyclohexanecarboxylate |
| 23 | methylbenzene |
| 24 | 2-methyl-1H-indole |

TABLE 32

(Ig-2)

| No. | R¹ |
|-----|-----|
| 1 | N-Boc-4-methylthiazolidine |
| 2 | 4-methylthiazolidine (NH) |
| 3 | N-CO₂Me-4-methylthiazolidine |
| 4 | N-(i-BuO-C(O))-4-methylthiazolidine |

TABLE 32-continued (Ig-2)

| No. | R¹ |
|---|---|
| 5 | N-Ac, 4-methyl thiazolidine |
| 6 | N-C(O)-i-Bu, 4-methyl thiazolidine |
| 7 | 2-oxo-4-methyl thiazolidine |
| 8 | N-Boc, 2-methyl thiazolidine |
| 9 | 2-methyl thiazolidine (NH) |
| 10 | N-Boc, 3-methyl thiomorpholine |
| 11 | 3-methyl thiomorpholine (NH) |
| 12 | N-Boc, 4-methyl 1,3-thiazinane |
| 13 | 4-methyl 1,3-thiazinane (NH) |

TABLE 32-continued (Ig-2)

| No. | R¹ |
|---|---|
| 14 | 2-thienyl |
| 15 | 4-methyl thiazole |
| 16 | 2-amino-4-methyl thiazole |
| 17 | 4-methyl imidazole (NH) |
| 18 | N-Boc, 4-methyl imidazole |
| 19 | 2-furyl |
| 20 | 2-methyl-5-Me oxazole |
| 21 | cyclohexyl |
| 22 | 4-(MeO₂C) cyclohexyl |
| 23 | phenyl |
| 24 | 2-methyl-1H-indole |

TABLE 33

(Ig-3) structure: cyclopentylmethoxy-substituted compound with R¹—NH—CH₂— group and —C(O)—NH—CH₂—(4-phenoxyphenyl) group.

| No. | R¹ |
|-----|----|
| 1 | N-Boc-4-methylthiazolidin-3-yl |
| 2 | 4-methylthiazolidin-3-yl (NH) |
| 3 | N-CO₂Me-4-methylthiazolidin-3-yl |
| 4 | N-(i-BuOC(O))-4-methylthiazolidin-3-yl |
| 5 | N-Ac-4-methylthiazolidin-3-yl |
| 6 | N-(i-BuC(O))-4-methylthiazolidin-3-yl |
| 7 | 2-oxo-4-methylthiazolidin-3-yl |
| 8 | N-Boc-2-methylthiazolidin-3-yl |
| 9 | 2-methylthiazolidin-3-yl (NH) |
| 10 | N-Boc-3-methylthiomorpholin-4-yl |
| 11 | 3-methylthiomorpholin-4-yl (NH) |
| 12 | N-Boc-4-methyl-1,3-thiazinan-3-yl |
| 13 | 4-methyl-1,3-thiazinan-3-yl (NH) |
| 14 | 2-thienyl-methyl |
| 15 | 4-thiazolyl-methyl |
| 16 | 2-amino-4-thiazolyl-methyl |
| 17 | 1H-imidazol-4-yl-methyl |
| 18 | N-Boc-imidazol-4-yl-methyl |
| 19 | 2-furyl-methyl |

TABLE 33-continued (Ig-3)

| No. | R¹ |
|---|---|
| 20 | 2,5-dimethyloxazole |
| 21 | cyclohexyl |
| 22 | 4-methyl-methoxycarbonylcyclohexyl |
| 23 | phenyl (tolyl) |
| 24 | 2-methyl-1H-indole |

TABLE 34

(Ig-4)

| No. | R¹ |
|---|---|
| 1 | N-Boc-4-methylthiazolidine |
| 2 | 4-methylthiazolidine (NH) |
| 3 | N-CO$_2$Me-4-methylthiazolidine |
| 4 | N-(i-BuOC(O))-4-methylthiazolidine |
| 5 | N-Ac-4-methylthiazolidine |
| 6 | N-(i-BuC(O))-4-methylthiazolidine |
| 7 | 4-methyl-2-oxothiazolidine |
| 8 | N-Boc-2-methylthiazolidine |
| 9 | 2-methylthiazolidine (NH) |
| 10 | N-Boc-3-methylthiomorpholine |
| 11 | 3-methylthiomorpholine (NH) |

TABLE 34-continued
(Ig-4)
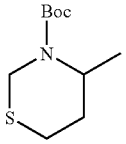
| No. | R¹ |
|---|---|
| 12 | 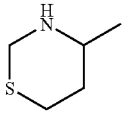 |
| 13 | 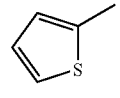 |
| 14 | 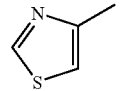 |
| 15 | 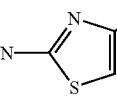 |
| 16 | 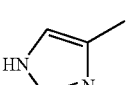 |
| 17 | 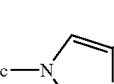 |
| 18 | 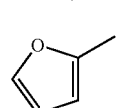 |
| 19 | 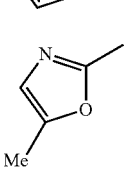 |
| 20 | 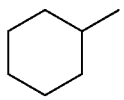 |
| 21 | 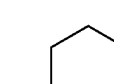 |
| 22 | 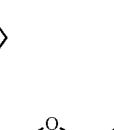 |
TABLE 34-continued
(Ig-4)
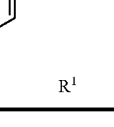
| No. | R¹ |
|---|---|
| 23 | 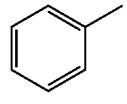 |
| 24 | 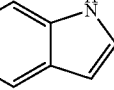 |
TABLE 35
(Ig-5)
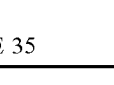
| No. | R¹ |
|---|---|
| 1 | 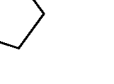 |
| 2 | 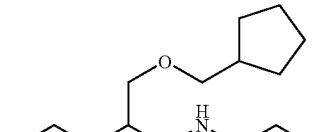 |
| 3 | 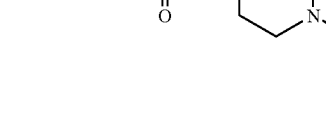 |
| 4 |  |

TABLE 35-continued (Ig-5)

| No. | R¹ |
|---|---|
| 5 | N-Ac, 4-methyl thiazolidine |
| 6 | N-(i-Bu-C(O)), 4-methyl thiazolidine |
| 7 | 2-oxo-4-methyl thiazolidine (NH) |
| 8 | N-Boc, 2-methyl thiazolidine |
| 9 | NH, 2-methyl thiazolidine |
| 10 | N-Boc, 3-methyl thiomorpholine |
| 11 | NH, 3-methyl thiomorpholine |
| 12 | N-Boc, 4-methyl thiazinane |
| 13 | NH, 4-methyl thiazinane |
| 14 | 2-methyl thiophene |
| 15 | 4-methyl thiazole |
| 16 | 2-amino-4-methyl thiazole |
| 17 | 4-methyl-1H-imidazole |
| 18 | N-Boc-4-methyl imidazole |
| 19 | 2-methyl furan |
| 20 | 2-methyl-5-Me oxazole |
| 21 | methyl cyclohexane |
| 22 | 4-(MeO₂C) methyl cyclohexane |

TABLE 35-continued (Ig-5)

[Structure: R¹-NH-CH(CH₂-O-CH₂-cyclopentyl)-C(=O)-NH-(4-piperidinyl)-N-phenyl]

| No. | R¹ |
|---|---|
| 23 | 2-methylphenyl |
| 24 | 2-methyl-1H-indol-3-yl |

TABLE 36

(Ih-1)

[Structure: R¹-NH-CH(CH₂-O-CH₂-cyclohexyl)-C(=O)-NH-CH₂-(4-methoxyphenyl)]

| No. | R¹ |
|---|---|
| 1 | N-Boc-4-methylthiazolidin-3-yl |
| 2 | 4-methylthiazolidin-3-yl (NH) |
| 3 | N-CO₂Me-4-methylthiazolidin-3-yl |
| 4 | N-(i-BuO-C(=O))-4-methylthiazolidin-3-yl |

TABLE 36-continued (Ih-1)

[Structure: R¹-NH-CH(CH₂-O-CH₂-cyclohexyl)-C(=O)-NH-CH₂-(4-methoxyphenyl)]

| No. | R¹ |
|---|---|
| 5 | N-Ac-4-methylthiazolidin-3-yl |
| 6 | N-(i-Bu-C(=O))-4-methylthiazolidin-3-yl |
| 7 | 2-oxo-4-methylthiazolidin-3-yl |
| 8 | N-Boc-2-methylthiazolidin-3-yl |
| 9 | 2-methylthiazolidin-3-yl (NH) |
| 10 | N-Boc-3-methylthiomorpholin-4-yl |
| 11 | 3-methylthiomorpholin-4-yl (NH) |
| 12 | N-Boc-4-methyl-1,3-thiazinan-3-yl |
| 13 | 4-methyl-1,3-thiazinan-3-yl (NH) |

TABLE 36-continued (Ih-1)

| No. | R¹ |
|---|---|
| 14 | 2-thienyl-methyl |
| 15 | (4-methylthiazol-... )methyl |
| 16 | (2-amino-4-methylthiazol-5-yl)methyl |
| 17 | (4-methyl-1H-imidazol-...)methyl |
| 18 | (1-Boc-4-methylimidazol-...)methyl |
| 19 | (5-methylfuran-2-yl)methyl |
| 20 | (2,5-dimethyloxazol-4-yl)methyl |
| 21 | cyclohexylmethyl |
| 22 | (4-methyl-4-methoxycarbonylcyclohexyl)methyl |
| 23 | benzyl (methylphenyl) |
| 24 | (2-methyl-1H-indol-3-yl)methyl |

TABLE 37

(Ih-2)

| No. | R¹ |
|---|---|
| 1 | 3-Boc-4-methylthiazolidin-... |
| 2 | 4-methylthiazolidin-... |
| 3 | 3-CO₂Me-4-methylthiazolidin-... |
| 4 | 3-(i-BuO-CO)-4-methylthiazolidin-... |
| 5 | 3-Ac-4-methylthiazolidin-... |
| 6 | 3-(i-Bu-CO)-4-methylthiazolidin-... |
| 7 | 4-methyl-2-oxothiazolidin-... |
| 8 | 3-Boc-2-methylthiazolidin-... |
| 9 | 2-methylthiazolidin-... |

TABLE 37-continued
(Ih-2)
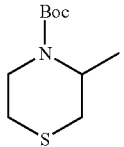
| No. | R¹ |
|---|---|
| 10 | 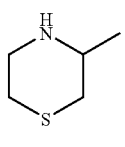 |
| 11 | 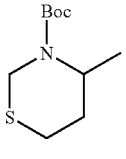 |
| 12 | 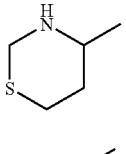 |
| 13 | 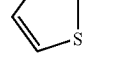 |
| 14 | 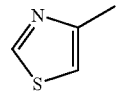 |
| 15 | 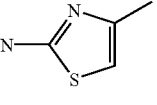 |
| 16 | 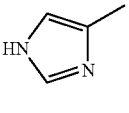 |
| 17 | 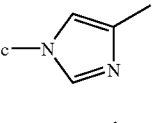 |
| 18 | 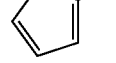 |
| 19 | 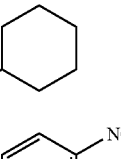 |
TABLE 37-continued
(Ih-2)
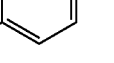
| No. | R¹ |
|---|---|
| 20 | 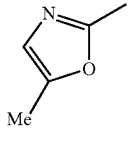 |
| 21 | 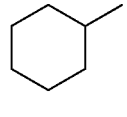 |
| 22 | 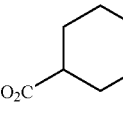 |
| 23 | 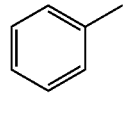 |
| 24 | 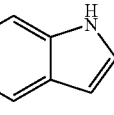 |
TABLE 38
(Ih-3)
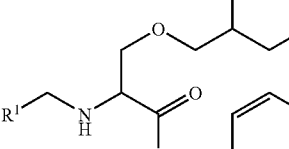
| No. | R¹ |
|---|---|
| 1 | 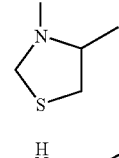 |
| 2 | 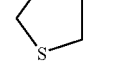 |

TABLE 38-continued (Ih-3)

| No. | R¹ |
|---|---|
| 3 | 3-(CO₂Me)-4-methyl-thiazolidine |
| 4 | 3-(i-BuOC(O))-4-methyl-thiazolidine |
| 5 | 3-Ac-4-methyl-thiazolidine |
| 6 | 3-(i-BuC(O))-4-methyl-thiazolidine |
| 7 | 2-oxo-4-methyl-thiazolidine |
| 8 | 3-Boc-2-methyl-thiazolidine |
| 9 | 2-methyl-thiazolidine |
| 10 | 4-Boc-3-methyl-thiomorpholine |
| 11 | 3-methyl-thiomorpholine |
| 12 | 3-Boc-4-methyl-[1,3]thiazinane |
| 13 | 4-methyl-[1,3]thiazinane |
| 14 | 2-methyl-thiophene |
| 15 | 4-methyl-thiazole |
| 16 | 2-amino-4-methyl-thiazole |
| 17 | 4-methyl-1H-imidazole |
| 18 | 1-Boc-4-methyl-imidazole |
| 19 | 2-methyl-furan |
| 20 | 2-methyl-5-Me-oxazole |
| 21 | cyclohexyl |

TABLE 38-continued
(Ih-3)
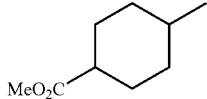
| No. | R¹ |
|---|---|
| 22 | 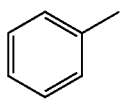 |
| 23 | 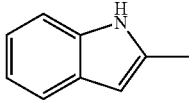 |
| 24 | 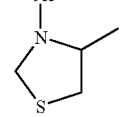 |
TABLE 39
(Ih-4)
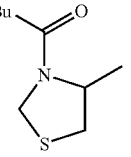
| No. | R¹ |
|---|---|
| 1 | 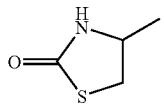 |
| 2 | 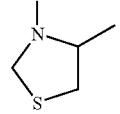 |
| 3 | 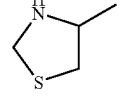 |
| 4 | 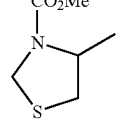 |
TABLE 39-continued
(Ih-4)
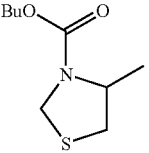
| No. | R¹ |
|---|---|
| 5 | 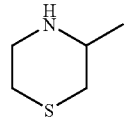 |
| 6 | 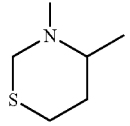 |
| 7 | 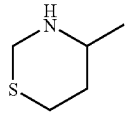 |
| 8 | Boc-N thiazolidine (2-methyl) |
| 9 | HN thiazolidine (2-methyl) |
| 10 | Boc-N thiomorpholine (3-methyl) |
| 11 | HN thiomorpholine (3-methyl) |
| 12 | Boc-N 1,3-thiazinane (4-methyl) |
| 13 | HN 1,3-thiazinane (4-methyl) |

TABLE 39-continued (Ih-4)

| No. | R¹ |
|---|---|
| 14 | 2-thienyl |
| 15 | 4-methylthiazol-2-yl |
| 16 | 2-amino-4-methylthiazol-5-yl |
| 17 | 4-methyl-1H-imidazol-2-yl |
| 18 | 1-Boc-4-methylimidazol-2-yl |
| 19 | 2-furyl |
| 20 | 2-methyl-5-methyl-oxazol-4-yl |
| 21 | cyclohexyl |
| 22 | 4-(methoxycarbonyl)cyclohexyl |
| 23 | phenyl |
| 24 | 2-methyl-1H-indol-3-yl |

TABLE 40

(Ih-5)

| No. | R¹ |
|---|---|
| 1 | 3-Boc-4-methylthiazolidin-3-yl |
| 2 | 4-methylthiazolidin-3-yl |
| 3 | 3-(CO₂Me)-4-methylthiazolidin-3-yl |
| 4 | 3-(i-BuOC(O))-4-methylthiazolidin-3-yl |
| 5 | 3-Ac-4-methylthiazolidin-3-yl |
| 6 | 3-(i-BuC(O))-4-methylthiazolidin-3-yl |
| 7 | 4-methyl-2-oxothiazolidin-3-yl |
| 8 | 3-Boc-2-methylthiazolidin-3-yl |

TABLE 40-continued (Ih-5)

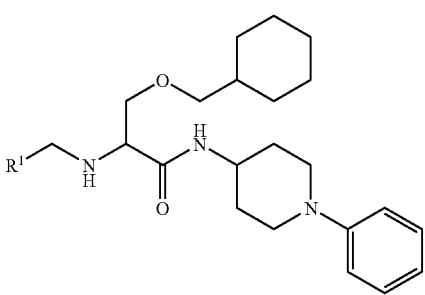

| No. | R¹ |
|---|---|
| 9 | 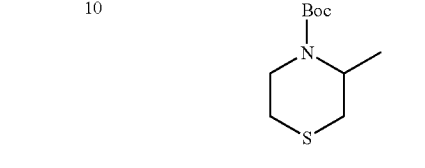 |
| 10 |  |
| 11 |  |
| 12 |  |
| 13 |  |
| 14 |  |
| 15 |  |
| 16 |  |
| 17 |  |
| 18 | 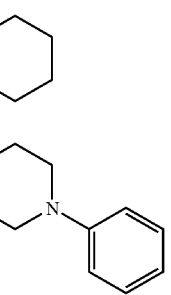 |
| 19 | 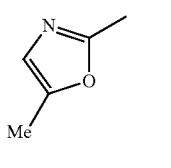 |
| 20 | 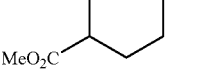 |
| 21 | 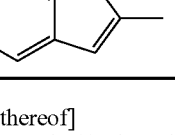 |
| 22 | 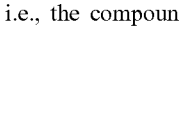 |
| 23 | 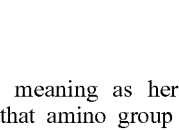 |
| 24 | 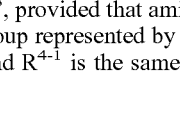 |

[Processes for the Preparation thereof]

(a) For the compounds of the formula (I), those in which E is —COO—, —OCO—, —CONR⁸—, —NR⁹CO—, —O—, —S—, or —CO—, i.e., the compounds of the formula (I-A)

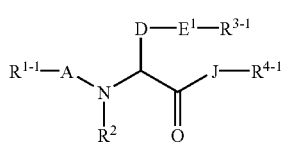

(I-A)

(wherein $R^{1-1}$ is the same meaning as hereinbefore described for $R^1$, provided that amino group which is comprised in the group represented by $R^{1-1}$ may be protected, if necessary, and $R^{3-1}$ is the same meaning as hereinbefore described for $R^3$, provided that amino group which is comprised in the group represented by $R^{3-1}$ may be protected, if necessary, and $R^{4-1}$ is the same meaning as hereinbefore described for $R^4$, provided that —COOH, hydroxy or amino group which is comprised in the group represented by $R^{4-1}$ may be protected, if necessary, and $E^1$ is —COO—, —OCO—, —CONR$^8$—, —NR$^9$CO—, —O—, —S— or —CO—, and the other symbols are the same meanings as hereinbefore described.) may be prepared by amidation or esterification of a compound of formula (II)

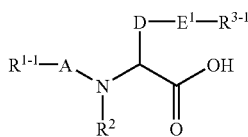
(II)

(wherein all the symbols are the same meanings as hereinbefore described.)
with a compound of formula (III)

(III)

(wherein $J^2$ is —OH, —NHR$^{16}$ or hetero ring containing NH group (this hetero ring is the same meaning as hereinbefore described for hetero ring represented by $R^4$, $R^{16}$ and nitrogen atom which $R^4$ and $R^{16}$ are bound to, together.), and the other symbol is the same meaning as hereinbefore described.), or by amidation or esterification of a compound of formula (IV)

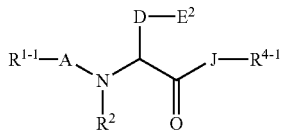
(IV)

(wherein $E^2$ is —COOH, —NHR$^9$ or —OH, and the other symbols are the same meanings as hereinbefore described.)
with a compound of formula (V)

(V)

(wherein $E^3$ is —OH, —NHR$^8$ or —COOH, and the other symbol is the same meaning as hereinbefore described.).

The above amidation is known per se and can be carried out by, for example:
(1) using an acid haride,
(2) using a mixed acid anhydride,
(3) using a condensing agent etc.

Each of those methods can be carried out, for example, as follows:
(1) the method using an acid halide may be carried out, for example, by reacting a carboxylic acid with an acid halide (e.g., oxalyl chloride, thionyl chloride etc.) in an organic solvent (e.g., chloroform, methylene chloride, diethyl ether, tetrahydrofuran, ethyl acetate etc.) or without a solvent at from −20° C. to the reflux temperature, and then by reacting the acid halide obtained with an amine in the presence of a tertiary amine (e.g., pyridine, triethylamine, dimethylaniline, dimethylaminopyridine, N-methylmorpholine etc.) in an organic solvent (e.g., chloroform, methylene chloride, diethyl ether, tetrahydrofuran etc.) at 0° C.~40° C.,
(2) the method using a mixed acid anhydride may be carried out, for example, by reacting a carboxylic acid and an acid halide (e.g., pivaloyl chloride, tosyl chloride, mesyl chloride, ethyl chloroformate, isobutyl chloroformate etc.) in the presence of a tertiary amine (e.g., pyridine, triethylamine, dimethylaniline, dimethylaminopyridine, N-methylmorpholine etc.) in an organic solvent (e.g., chloroform, methylene chloride, diethyl ether, tetrahydrofuran etc.) or without a solvent at −20° C.~40° C., and then by reacting the mixture of acid anhydride obtained with a corresponding amine in an organic solvent (e.g., chloroform, methylene chloride, diethyl ether, tetrahydrofuran etc.), at 0° C.~40° C.,
(3) the method using a condensing agent (e.g., 1,3-dicyclohexylcarbodiimide (DCC), 1-ethyl-3-[3-(dimethylamino)propyl]cabodiimide (EDC), 2-chloro-1-methylpyridinium iodide, 1,1'-carbonyldiimidazole (CDI) etc.) may be carried out, for example, by reacting a carboxylic acid with an amine using a condensing agent in the presence or absence of a tertiary amine (e.g., pyridine, triethylamine, dimethylaniline, dimethylaminopyridine etc.), in the presence or absence of 1-hydroxybenzotriazole (HOBt) in an organic solvent (e.g., chloroform, methylene chloride, dimethyl formamide, diethyl ether, tetrahydrofuran etc.) or without a solvent at 0° C.~40° C.

The reactions (1), (2) and (3) hereinbefore described may be preferably carried out in an atmosphere of inert gas (e.g., argon, nitrogen etc.) under anhydrous conditions.

The above esterification is known per se and can be carried out by, for example:
(1) using an acid haride,
(2) using a mixed acid anhydride,
(3) using a condensing agent etc.

Each of those methods can be carried out, for example, as follows:
(1) the method using an acid halide may be carried out, for example, by reacting a carboxylic acid with an acid halide (e.g., oxalyl chloride, thionyl chloride etc.) in an organic solvent (e.g., chloroform, methylene chloride, diethyl ether, tetrahydrofuran ethyl acetate etc.) or without a solvent at from −20° C. to the reflux temperature, and then by reacting the acid halide obtained with an alcohol in the presence of a tertiary amine (e.g., pyridine, triethylamine, dimethylaniline, dimethylaminopyridine, N-methylmorpholine etc.) in an organic solvent (e.g., chloroform, methylene chloride, diethyl ether, tetrahydrofuran etc.) at 0° C.~40° C.,
(2) the method using a mixed acid anhydride may be carried out, for example, by reacting a carboxylic acid and an acid halide (e.g., pivaloyl chloride, tosyl chloride, mesyl chloride, ethyl chloroformate, isobutyl chloroformate etc.) in the presence of a tertiary amine (e.g., pyridine, triethylamine, dimethylaniline, dimethylaminopyridine, N-methylmorpholine etc.) in an organic solvent (e.g., chloroform, methylene chloride, diethyl ether, tetrahydrofuran etc.) or without a solvent at −20° C.~40° C., and then by reacting the mixture of acid anhydride obtained with a corresponding alcohol in an organic solvent (e.g., chloroform, methylene chloride, diethyl ether, tetrahydrofuran etc.), at 0° C.~40° C.,
(3) the method using a condensing agent (e.g., 1,3-dicyclohexylcarbodiimide (DCC), 1-ethyl-3-[3-(dimethylamino)propyl]cabodiimide (EDC), 2-chloro-1-methylpyridinium iodide, 1,1'-carbonyldiimidazole (CDI) etc.) may be carried out, for example, by reacting a carboxylic acid with an alcohol using a condensing agent in the presence or absence of a tertiary amine (e.g., pyridine, triethylamine, dimethylaniline, dimethylaminopyridine etc.), in the presence or absence of 1-hydroxybenzotriazole (HOBt) in an organic solvent (e.g., chloroform, methylene chloride, dimethyl formamide, diethyl ether, tetrahydrofuran etc.) or without a solvent at 0° C.~40° C.

The reactions (1), (2) and (3) hereinbefore described may be preferably carried out in an atmosphere of inert gas (e.g., argon, nitrogen etc.) under anhydrous conditions.

Also, for the compounds of the formula (I-A), those in which E is —S—, i.e., the compounds of the formula (I-A-1)

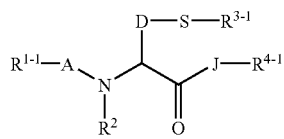
(I-A-1)

(wherein all the symbols are the same meanings as hereinbefore described.)
may be prepared by the reaction of a compound of formula (VI)

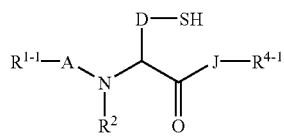
(VI)

(wherein all the symbols are the same meanings as hereinbefore described.)
with a compound of formula (VII)

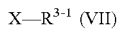
X—$R^{3-1}$ (VII)

(wherein X is halogen, and the other symbols is the same meaning as hereinbefore described.).

The reaction of a compound of formula (VI) with a compound of formula (VII) is known per se and can be carried out, for example, in an organic solvent (e.g., dimethylformamide, acetone etc.), in the presence of base (e.g., potassium carbonate etc.), at 0° C.~40° C.

(b) For the compounds of the formula (i), those in which E is —SO—, —SO$_2$—, i.e., the compounds of formula (I-B)

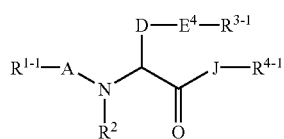
(I-B)

(wherein $E^4$ is —SO— or —SO$_2$— and the other symbols are the same meanings as hereinbefore described.) may be prepared by the oxidation of a compounds of formula (I-A) wherein $E^1$ is —S—.

The above oxidation is known per se, and in case of the oxidation from sulfide group to sulfoxide group, for example, it can be carried out in an organic solvent (e.g., methylene chloride, chloroform, benzene, hexane, t-butyl alcohol etc.), in the presence of 1 equivalent of oxidizing agent (e.g., hydrogen peroxide, sodium periodate, acyl nitrite, sodium perborate, peracid (e.g., m-chloroperbenzoic acid, peracetic acid etc.) etc.), in a few minutes, at −78° C. to Also, in the case of the oxidation from sulfide group to sulfone group, for example, it can be carried out in an organic solvent (e.g., methylene chloride, chloroform, benzene, hexane, t-butyl alcohol etc.), in the presence of an excess amount of oxidizing agent (e.g., hydrogen peroxide, sodium periodate, potassium pemanganate, sodium perborate, potassium hydrogen peroxosulfate, peracid (e.g., m-chloroperbenzoic acid, pracetic acid etc.) etc.), in a few hours, at −78° C.~40° C.

(c) For the compounds of the formula (I), those in which E is —NR$^{10}$—, i.e., the compounds of the formula (I-C)

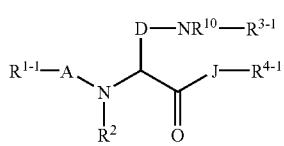
(I-C)

(wherein all the symbols are the same meanings as hereinbefore described.)
may be prepared by the reaction of a compound of formula (VIII)

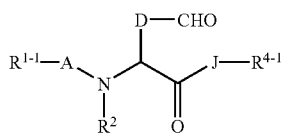
(VIII)

(wherein all the symbols are the same meanings as hereinbefore described.)
with a compound of formula (IX)

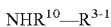
NHR$^{10}$—$R^{3-1}$ (IX)

(wherein all the symbols are the same meanings as hereinbefore described.).

The reaction of a compound of formula (VIII) with a compound of formula (IX) is known per se, and may be carried out, for example, in an organic solvent (e.g., methanol, ethanol etc.), using reducing agent (e.g., sodium cyanoborohydride, sodium borohydride etc.), in the presence or absence of pH modulator (e.g., acetic acid etc.), at 0° C.~40° C.

(d) For the compounds of the formula (I), those in which E is —SO$_2$NR$^{11}$—, i.e., the compounds of the formula (I-D)

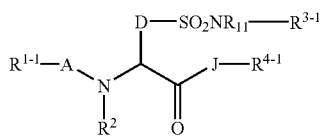
(I-D)

(wherein all the symbols are the same meanings as hereinbefore described.) may be prepared by the reaction of a compound of formula (X)

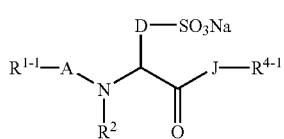
(X)

(wherein all the symbols are the same meanings hereinbefore described.)
with a compound of formula (XI)

 (XI)

(wherein all the symbols are the same meanings as hereinbefore described.).

The reaction of a compound of formula (X) with a compound of formula (XI) is known per se, and may be carried out, for example, by reacting a compound of formula (X) with an acid halide (e.g., oxalyl chloride, thionyl chloride, sulfulyl chloride etc.) in an organic solvent (chloroform, methylene chloride, diethyl ether, tetrahydrofuran etc.) in the presence of base (e.g., triphenylphosphine etc.) at −20° C. to the reflux temperature, and then by reacting the compound thus obtained with a compound of formula (XI) in the presence of a tertiary amine (e.g., pyridine, triethylamine, diethylaniline, diethylaminopyridine etc.), in an organic solvent (e.g., chloroform, methylene chloride, diethyl ether, tetrahydrofuran etc.), at 0° C.~40° C.

(e) For the compounds of the formula (I), those in which E is —NR$^{12}$SO$_2$—, i.e., the compounds of the formula (I-E)

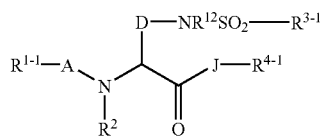 (I-E)

(wherein all the symbols are the same meanings as hereinbefore described.)
may be prepared by the reaction of a compound of formula (XII)

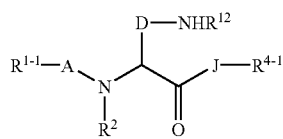 (XII)

(wherein all the symbols are the same meanings as hereinbefore described.)
with a compound of formula (XIII)

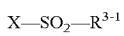 (XIII)

(wherein X is halogen, and the other symbol is the same meaning as hereinbefore described.).

The reaction of a compound of formula (XII) with a compound of formula (XIII) may be carried out, for example, in organic solvent (e.g., chloroform, methylene chloride, diethyl ether, tetrahydrofuran etc.), in the presence of a tertiary amine (e.g., pyridine, triethylamine, dimethylaniline, dimethylaminopyridine etc.), at 0° C.~40° C.

(f) For the compounds of the formula (I), those in which A is —CO— or —SO$_2$—, i.e., the compounds of the formula (I-F)

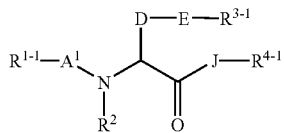 (I-F)

(wherein A$^1$ is —CO— or —SO$_2$— and the other symbols are the same meanings as hereinbefore described.)
may be prepared by amidation or sulfonamidation of a compound of formula (XIV)

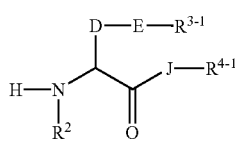 (XIV)

(wherein all the symbols are the same meanings as hereinbefore described.)
with a compound of formula (XV)

 (2)

(wherein A$^2$ is —COOH or —SO$_3$H, and the other symbol is the same meaning as hereinbefore described.).

Sulfonamidation is known per se, and can be carried out, for example, by reacting a sulfonic acid with an acid halide (e.g., oxalyl chloride, thionyl chloride, phosphorus pentachloride, phosphorus trichloride etc.) in an inert organic solvent (e.g., chloroform, methylene chloride, diethyl ether, tetrahydrofuran etc.) or without a solvent at −20° C. to the reflux temperature, and then by reacting the sulfonyl halide obtained with a tertiary amine (e.g., pyridine, triethylamine, dimethylaniline, dimethylaminopyridine etc.) in an inert organic solvent (e.g., chloroform, methylene chloride, diethyl ether, tetrahydrofuran etc.) at 0° C.~40° C.

Also, amidation may be carried out by the same method as hereinbefore described.

(g) For the compounds of the formula (I), those in which A is bond, R$^1$ is C1–4 alkyl substituted by phenyl, C3–8 cycloalkyl, or hetero ring, i.e., the compounds of the formula (I-G)

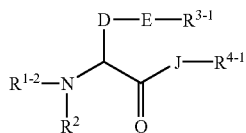 (I-G)

(wherein R$^{1\text{-}2}$ is C1–4 alkyl substituted by phenyl, C3–8 cycloalkyl, or hetero ring (when amino group exists as a substituent of each ring, it may be protected, if necessary.), and the other symbols are the same meanings as hereinbefore described.)
may be prepared by the reaction of a compound of formula (XIV)

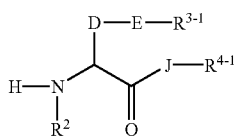 (XIV)

(wherein all the symbols are the same meanings as hereinbefore described.) with a compound of formula (XVI)

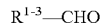 (XVI)

(wherein $R^{1-3}$ is phenyl, C3–8 cycloalkyl, hetero ring, or C1–3 alkyl substituted by phenyl, C3–8 cycloalkyl or hetero ring (when amino group exists as a substituent of each ring, it may be protected, if necessary.)).

This reaction can be carried out by the same method in the reaction of a compound of formula (VIII) with a compound of formula (IX), as hereinbefore described.

(h) For the compounds of the formula (I), those in which $R^1$ is hetero ring, or C1–4 alkyl substituted by hetero ring, and a substituent of such a hetero ring is C2–5 acyl or C1–4 alkoxycarbonyl, i.e., the compounds of the formula (I-H)

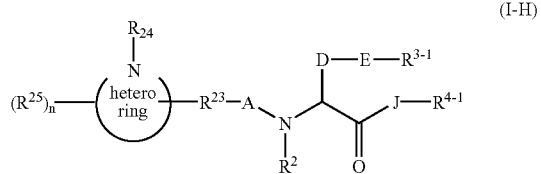 (I-H)

(wherein $R^{23}$ is bond or C1–4 alkylene, $R^{24}$ is C1–4 alkoxycarbonyl or C2–5 acyl, $R^{25}$ is C1–4 alkyl, C1–4 alkoxy, phenyl, phenoxy, benzyloxy, —$SR^5$, halogen, nitro or —$NR^6R^7$, n is 0~2,

is the same meaning as hereinbefore described for hetero ring in $R^1$, provided that it contains at least one nitrogen atom. Also, when amino group exists in a substituent represented by $R^{25}$, it may be protected, if necessary, and the other symbols are the same meanings as hereinbefore described.)

may be prepared by the amidation of a compound of formula (XVII)

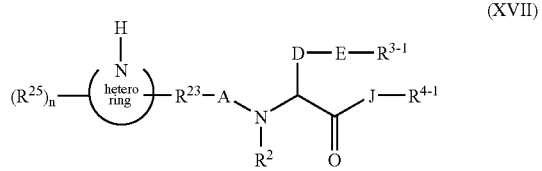 (XVII)

(wherein all the symbols are the same meanings as hereinbefore described.)

with a compound of formula (XVIII)

 (XVIII)

(wherein $R^{24}$ is the same meaning as hereinbefore described.)

The amidation can be carried out by the same method as hereinbefore described.

(i) In the compounds of the formula (I), the compounds of formula (I-I)

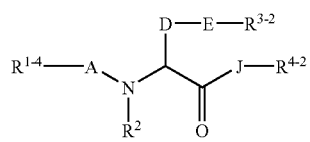 (I-I)

(wherein $R^{1-4}$, $R^{3-2}$ and $R^{4-2}$ are the same meanings as hereinbefore described for $R^1$, $R^3$, $R^4$, respectively, provided that at least one of $R^{1-4}$, $R^{3-2}$ and $R^{1-2}$ is a group containing —COOH, hydroxy or amino group, and the other symbols are the same meanings as hereinbefore described.)

may be prepared by the deprotection under alkaline conditions, the deprotection under acidic conditions and/ or hydrogenolysis of the above compound of formulae (I-A), (I-A-1), (I-B), (I-C), (I-D), (I-E), (I-F), (I-G) or (I-H).

The deprotection under alkaline conditions is known per se, and may be carried out, for example, in an organic solvent (e.g., methanol, tetrahydrofuran, dioxane etc.), using an alkali metal hydroxide (e.g., sodium hydroxide, potassium hydroxide, lithium hydroxide etc.), an alkaline earth metal hydroxide (e.g., calcium hydroxide etc.) or a carbonate (e.g., sodium carbonate, potassium carbonate etc.), an aqueous solution thereof or a mixture thereof at 0° C.~40° C.

The deprotection under acidic conditions is known per se, and may be carried out, for example, in an organic solvent (e.g., methylene chloride, chloroform, dioxane, ethyl acetate, anisole etc.) or without a solvent, using an organic acid (e.g., trifluoroacetic acid, methanesulfonic acid, trimethylsilyl iodide etc.), or an inorganic acid (e.g., hydrogen chloride etc.) or a mixture thereof (e.g hydrobromoacetic acid etc.) at 0° C.~90° C.

The hydrogenolysis is known per se, and may be carried out, for example, in an organic solvent (e.g., tetrahydrofuran, dioxane, diethyl ether, ethyl acetate, methanol, ethanol etc.), in the presence of a catalyst (e.g., palladium carbon, palladium, palladium hydroxide, palladium acetate, palladium black, platinum black, nickel, Raney-nickel etc.), at ordinary or elevated pressure under an atmosphere hydrogen gas, at 0° C.~80° C.

It should be easily understood by those skilled in the art that the carboxy or hydroxy protecting group are not only t-butyl group or benzyl group but any group which can be easily and selectively eliminated can be used in the present invention. For example, a protecting group described in Protective Groups in Organic Synthesis (T. W. Greene, Wiley, New York (1991)) may be used. The amino protecting group are not only benzyloxycarbonyl group or t-butoxycarbonyl group but any group which can be easily and selectively eliminated can be used in the present invention. The proposed compounds of the present invention may be easily prepared using those protecting groups.

The compounds of formulae (II), (III), (IV), (V), (VI), (VII), (VIII), (IX), (X), (XI), (XII), (XIII), (XIV), (XV), (XVI), (XVII) or (XVIII) are known per se or may be prepared by methods known per se or methods described in Example, but do not limit the present invention.

For example, the compounds of formula (X) may be prepared by the methods described in Liebigs Ann. Chem, 776–783, 1979.

For example, the compounds of formula (XII) may be prepared by the methods described in J. Org. Chem, Vol. 44, No. 10, 1979.

For example, for the compounds of formula (XIV), those in which E is —O—, —S—, —SO—, —SO$_2$—, i.e., the compound of formula (XIV'), and for the compounds of formula (XVII), those in which E is —O—, —S—, —SO—, —SO$_2$— i.e., the compounds of formula (XVII') may be prepared by the method described in the following Scheme 1 and Scheme 2.

(in each Scheme, $E^5$ is —O—, —S—, —SO—, or —SO$_2$—, Boc is t-butoxycarbonyl, (Boc)$_2$O is di-t-butyldicarbonate, $R^{26}$ is bond or C1–3 alkylene, and the other symbols are the same meanings as hereinbefore described.)

The reactions described in the above-mentioned Schemes may be carried out by known methods. In the above-mentioned Schemes, compounds used for starting materials are may be known per se or may be easily prepared by known methods.

In the present invention, the other starting materials and each reagent are known per se or may be prepared by known methods.

In each reaction in the present specification, products may be purified by a conventional manner. For example, it may

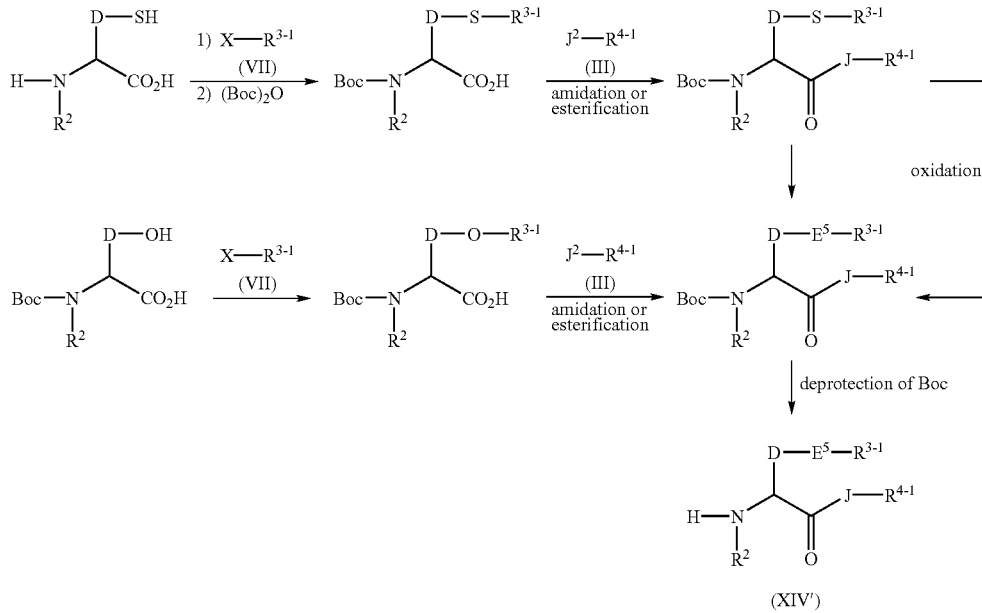

Scheme 1

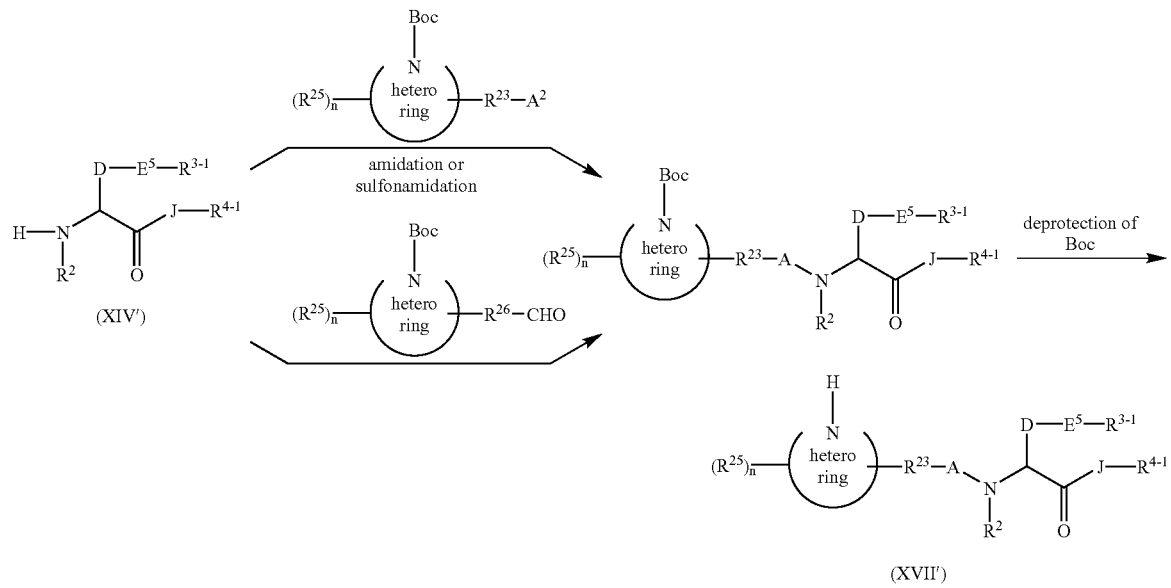

Scheme 2 be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

[Pharmacological Activity]

It has been confirmed that the compounds of the present invention of the formula (I) possess an inhibitory action on N-type calcium channel according to the following experiment.

Determination of Inhibitory Activity on N-Type Calcium Channel:

Cell line was differentiated according to the method described in FEBS Letters, 235, 178–182, 1988. The cell was loaded with fluorescent reagent, Fura-2•AM (at the final concentration of 10 μM), at 37° C. for 30 minutes and suspended in Krebs-buffer containing HEPES (25 mM) to obtain the cell suspension. The obtained cell suspension was incubated in the presence or absence of the compounds of the present invention with nifedipine for 5 minutes. The cell was depolarized by adding potassium chloride solution (at the final concentration of 80 mM) thereto and then a fluorescence intensity at the emission wavelength of 500 nm excited by the UV of 340 nm and 380 nm alternately was measured using the intracellular calcium analyzer (Nippon Bunko Co., CAF-110). The inhibitory activity of the compound of the present invention (at the final concentration of 3 μM) on calcium influx into the cell was calculated from the difference in changing the fluorescence intensity at peak (ΔR) according to the following equation.

$$\text{Inhibitory activity of the compound of the present invention (3 μM) on calcium influx (\%)} = \left\{1 - \frac{\text{Mean of } \Delta R \text{ in case of solution in the presence of the compound of the present invention}}{\text{Mean of } \Delta R \text{ in case of solution in the absence of the compound of the present invention}}\right\} \times 100$$

The results were shown in Table 41.

TABLE 41

| Example No. | Inhibitory activity on Ca influx (%) |
|---|---|
| 2 | 75 |
| 2 (29) | 75 |
| 2 (80) | 87 |
| 2 (86) | 83 |
| 6 (22) | 79 |
| 6 (27) | 72 |
| 6 (44) | 86 |
| 6 (68) | 73 |
| 9 (13) | 88 |

From the results of an experiment using the patch-clamp technique described in Pflüngers Archives, 391, 85–100, 1981, the compounds of the present invention at the concentration of 10 μM showed clearly an inhibitory action on flux of barium ion (calcium current) passed through an N-type calcium channel. The cells used in this experiment had been incubated according to the method described in FEBS Letters, 235, 178–182, 1988.

[Toxicity]

The toxicity of the compounds of the present invention are very low and therefore, it may be considered that the compounds of the present invention are safe for pharmaceutical use.

[Application for Pharmaceuticals]

The compounds of the formula (I) possess an inhibitory action on N-type calcium channel, so they are useful as agent for the prevention and/or treatment of cerebral infarct, transient ischemic attack, encephalomyelopathy after cardiac operation, spinal angiopathy, hypertension with stress, neurosis or epilepsy etc. or agent for the treatment of pain (for example, acute pain, chronic pain, pain after operation, cancer pain, neuralgia, pain caused by infection etc.).

For the purpose above described, the compounds of the general formula (I), of the present invention, non-toxic salts thereof, acid addition salts thereof and hydrates thereof may be normally administered systematically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules.

Capsules contain hard capsules and soft capsules.

In such compositions, one or more of the active compound(s) is or are, admixed with at least one inert diluent such as lactose, mannitol, glucose, hydroxypropyl cellulose, microcrystalline cellulose, starch, polyinylpyrrolidone, magnesium metasilicate aluminate. The compositions may also comprise, as is normal practice, additional substances other than inert diluents: e.g. lubricating agents such as magnesium stearate, disintegrating agents such as cellulose calcium glycolate, and assisting agents for dissolving such as glutamic acid, asparaginic acid. The tablets or pills may, if desired, be coated with film of gastric or enteric material such as sugar, gelatin, hydroxypropyl cellulose or hydroxypropyl cellulose phthalate etc., or be coated with two or more films. And further, coating may include containment within capsules of absorbable materials such as gelatin.

Liquid compositions for oral administration include pharmaceutically-acceptable emulsions, solutions, syrups and elixirs etc. In such liquid compositions, one or more of the active compound(s) is or are comprised in inert diluent(s) commonly used in the art (for example, purified water, ethanol etc.). Besides inert diluents, such compositions may also comprise adjuvants such as wetting agents, suspending agents, sweetening agents, flavouring agents, perfuming agents and preserving agents.

Other compositions for oral administration include spray compositions which may be prepared by known methods and which comprise one or more of the active compound(s). Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. Nos. 2,868,691 or 3,095,355 may be used.

Injections for parenteral administration include sterile aqueous or non-aqueous solutions, suspensions and emulsions. Aqueous solutions or suspensions include distilled water for injection and physiological salt solution. Non-aqueous solutions or suspensions include propylene glycol, polyethylene glycol, plant oil such as olive oil, alcohol such as ethanol, POLYSOLBATE80 (registered trade mark) etc. Such compositions may comprise additional diluents: e.g. preserving agents, wetting agents, emulsifying agents, dispersing agents, stabilizing agent (for example, lactose), assisting agents such as assisting agents for dissolving (for example, glutamic acid, asparaginic acid). They may be sterilized for example, by filtration through a bacteria-retaining filter, by incorporation of sterilizing agents in the compositions or by irradiation. They also may be manufactured in the form of sterile solid compositions and which can be dissolved in sterile water or some other sterile diluents for injection immediately before used.

Other compositions for parenteral administration include liquids for external use, and endemic liniments, ointment, suppositories and pessaries which comprise one or more of the active compound(s) and may be prepared by know methods.

REFERENCE EXAMPLE AND EXAMPLE

The following Reference Examples and Examples illustrate the present invention, but do not limit the present invention.

The solvents in the parentheses show the developing or eluting solvents and the ratios of the solvents used are by volume in chromatographic separations and TLC.

NMR in the parentheses show measured solvents.

Reference Example 1

(2S)-3-cyclohexylmethoxy-2-t-butoxycarbonylaminopropanoic acid

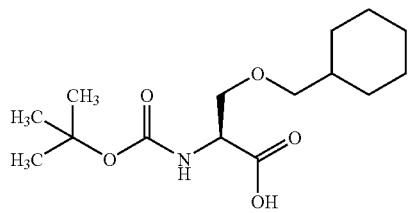

Undercooling with ice, sodium hydride (60%, 3.95 g) was added to a solution of (2S)-3-hydroxy-2-t-butoxycarbonylaminopropanoic acid (10.11 g) in dimethylformamide (200 ml, hereinafter abbreviated as DMF). The mixture was stirred for 30 minutes at 0° C. Under cooling with ice, (bromomethyl)cyclohexane (9.0 ml) was added dropwise to the reaction mixture and tetrabutylammonium iodide (910 mg) was added thereto. The mixture was stirred for 23 hours at room temperature. Further, (bromomethyl) cyclohexane (2.1 ml) was added dropwise to the reaction mixture. The mixture was stirred for 4 hours. (Bromomethyl)cyclohexane (2.1 ml) was added dropwise to reaciton mixture again. The mixture was stirred for 25 hours at room temperature. The reaction mixture was concentrated and the residue was diluted with 1N hydrochloric acid and extracted with ethyl acetate. The extract was washed with water and saturated aqueous sodium chloride, successively, dried over anhydrous magnesium sulfate. The organic layer was concentrated and the residue was purified by silica gel column chromatography (chloroform:methanol=97:3) to give the title compound (2.52 g) having the following physical data.

TLC: Rf 0.21 (chloroform:methanol=9:1); NMR (CDCl$_3$): δ 5.59–5.40 (1H, m), 4.46–4.27 (1H, m), 3.89–3.76 (1H, m), 3.64 (1H, dd, J=9.4, 4.6 Hz), 3.27 (2H, d, J=6.2 Hz), 1.79–0.79 (20H, m).

Reference Example 2

(2R)-3-cyclohexylmethylthio-2-t-butoxycarbonylaminopropanoic acid

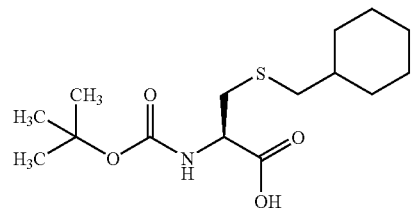

To a solution of L-cysteine (133 mg) in ethanol (10 ml), 2N aqueous solution of sodium hydroxide (1.1 ml) and (bromomethyl)cyclohexane (0.17 ml) were added. The mixture was stirred for 2.5 hours at room temperature. Two normal aqueous solution of sodium hydroxide (0.6 ml) and di-tert-butyl dicarbonate (0.28 ml) were added to the reaction mixture. The mixture was stirred for 1 hour. Ethanol was removed by evaporation from the reaction mixture and it was acidified by adding 1N hydrochloric acid and extraced with ethyl acetate. The extract was washed with saturated aqueous sodium chloride, dried over anhydrous magnesium sulfate. The organic layer was concentrated and the residue was purified by silica gel column chromatography (chloroform:methanol=19:1) to give the title compound (135 mg) having the following physical data.

TLC: Rf 0.21 (ethyl acetate: acetic acid:water=9:1:1); NMR (CDCl$_3$): δ 4.42–4.28 (1H, m), 3.01 (1H, dd, J=14.2, 5.2 Hz), 2.92 (1H, dd, J=14.2, 3.4 Hz), 2.45 (2H, d, J=7.0 Hz), 1.91–0.81 (20H, m).

Example 1

(2S)-3-cycolpentyloxycarbonyl-2-t-butoxycarbonylaminopropanoic acid.benzyl ester

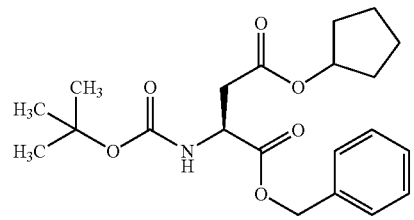

To a solution of (3S)-3-benzyloxycarbonyl-3-t-butoxycarbonylaminopropanoic acid (3.22 g), cyclopentanol (1.73 g) and dimethylaminopyridine (127 mg) in methylene chloride (20 ml), 1-ethyl-3-(3-dimethylaminopropyl)carbodiimide hydrochloric acid salt (3.83 g, hereinafter abbreviated as EDC-HCl) was added. The mixture was stirred for 2 hours at room temperature. One normal hydrochloric acid was added to the reaction mixture. The mixture was extracted with methylene chloride. The extract was washed with saturated aqueous sodium chloride, dried over anhydrous magnesium sulfate. The organic layer was concentrated and the residue was purified by silica gel column chromatography (hexane:ethyl acetate= 9:1) to give the compound of the present invention (4.19 g) having thefollowing physical data.

TLC: Rf 0.42 (hexane:ethyl acetate=4:1); NMR (CDCl$_3$): δ 7.34 (5H, s), 5.50 (1H, d, J=8.3 Hz), 5.25–5.11 (3H, m), 4.64–4.56 (1H, m), 2.97 (1H, dd, J=5.1, 16.9 Hz), 2.77 (1H, dd, J=4.8, 16.9 Hz), 1.88–1.54 (8H, m), 1.43 (9H, s).

Example 1(1)~Example 1(20)

By the reaction of the corresponding carboxylic acid derivatives with the corresponding alcohol derivatives or amine derivatives by the same desired procedure as Example 1, the following compounds of the present invention were obtained.

Example 1(1)

(2S)-3-benzyloxycarbonyl-2-t-butoxycarbonylaminopropanoic acid.cyclohexyl ester

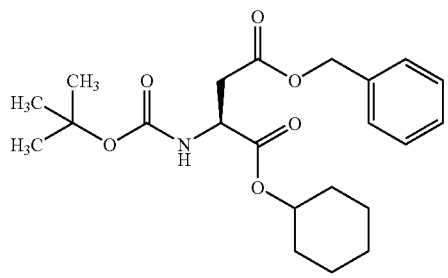

TLC: Rf 0.45 (hexane:ethyl acetate=4:1); 7.35 (5H, s), 5.50 (1H, d, J=7.5 Hz), 5.12 (2H, s), 4.86–4.73 (1H, m), 4.58–4.49 (1H, m), 3.04 (1H, dd, J=4.5, 16.8 Hz), 2.86 (1H, dd, J=4.8, 16.8 Hz), 1.86–1.58 (4H, m), 1.55–1.18 (15H, m).

Example 1(2)

(2S)-3-benzyloxycarbonyl-2-t-butoxycarbonylaminopropanoic acid.cyclopentyl ester

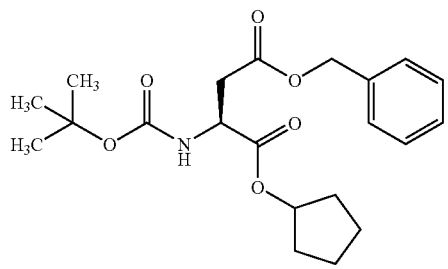

TLC: Rf 0.42 (hexane:ethyl acetate=4:1); NMR (CDCl$_3$): δ 7.35 (5H, s), 5.97 (1H, d, J=7.8 Hz), 5.22–5.15 (1H, m), 5.12 (2H, s), 4.56–4.47 (1H, m), 3.02 (1H, dd, J=4.8, 16.9 Hz), 2.84 (1H, dd, J=4.8, 16.9 Hz), 1.88–1.49 (8H, m), 1.44 (9H, s).

Example 1(3)

(2R)-3-benxyloxycarbonyl-2-t-butoxycarbonylaminopropanoic acid.cyclohexyl ester

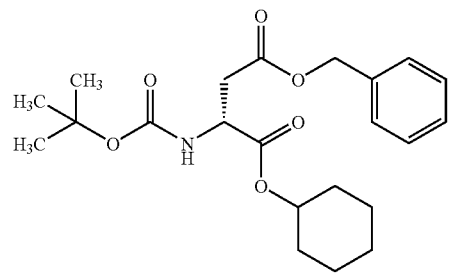

TLC: Rf 0.45 (hexane:ethyl acetate=4:1); 7.35 (5H, s), 5.50 (1H, d, J=7.5 Hz), 5.12 (2H, s), 4.86–4.73 (1H, m), 4.58–4.49 (1H, m), 3.04 (1H, dd, J=4.5, 16.8 Hz), 2.86 (1H, dd, J=4.8, 16.8 Hz), 1.86–1.58 (4H, m), 1.55–1.18 (15H, m).

Example 1(4)

(2R)-3-benzyloxycarbonyl-2-t-butoxycarbonylaminopropanoic acid.cyclopentyl ester

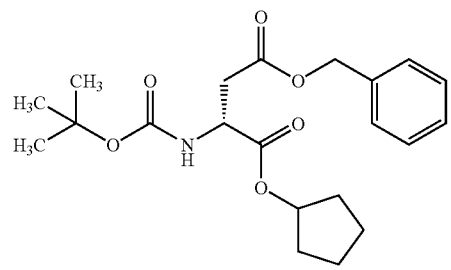

TLC: Rf 0.42 (hexane:ethyl acetate=4:1); NMR (CDCl$_3$): δ 7.34 (5H, s), 5.51 (1H, d, J=7.6 Hz), 5.22–5.15 (1H, m), 5.12 (2H, s), 4.57–4.47 (1H, m), 3.01 (1H, dd, J=4.8, 16.8 Hz), 2.84 (1H, dd, J=4.8, 16.8 Hz), 1.86–1.50 (8H, m), 1.44 (9H, s).

Example 1(5)

(2R)-3-cyclopentyloxycarbonyl-2-t-butoxycarbonylaminopropanoic acid.benzyl ester

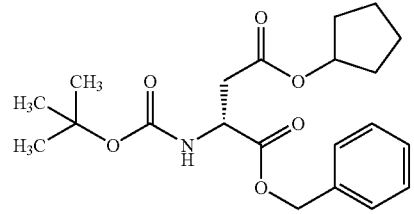

TLC: Rf 0.30 (hexane:ethyl acetate=6:1); NMR (CDCl₃): δ 7.40–7.30 (5H, m), 5.50 (1H, bd, J=9.0 Hz), 5.20 (1H, d, J=12 Hz), 5.18 (1H, d, J=12 Hz), 5.20–5.07 (1H, m), 4.65–4.50 (1H, m), 2.93 (1H, dd, J=18, 5 Hz), 2.78 (1H, dd, J=18, 5 Hz), 1.80–1.48 (8H, m), 1.44 (9H, s).

Example 1(6)

(2S)-4-cyclopentyloxycarbonyl-2-t-butoxycarbonylaminobutanoic acid.benzyl ester

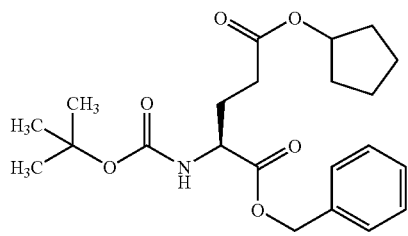

TLC: Rf 0.26 (hexane:ethyl acetate=5:1); NMR (CDCl₃): δ 7.40–7.30 (5H, m), 5.24–5.08 (4H, m), 4.43–4.25 (1H, m), 2.40–1.50 (12H, m), 1.43 (9H, s).

Example 1(7)

(2R)-4-cyclohexyloxycarbonyl-2-t-butoxycarbonylaminobutanoic acid.benzyl ester

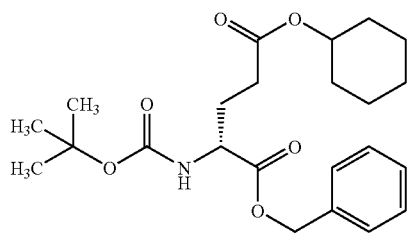

TLC: Rf 0.46 (hexane:ethyl acetate=4:1); NMR (CDCl₃): δ 7.35 (5H, s), 5.20 (1H, d, J=2.4 Hz), 5.13 (1H, d, J=9.2 Hz), 4.79–4.67 (1H, m), 4.41–4.31 (1H, m), 2.44–2.30 (2H, m), 2.24–2.08 (1H, m), 2.04–1.66 (5H, m), 1.61–1.25 (15H, m).

Example 1(8)

(2R)-4-cyclopentyloxycarbonyl-2-t-butoxycarbonylaminobutanoic acid.benzyl ester

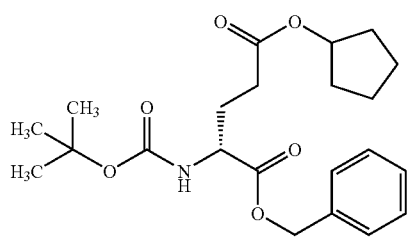

TLC: Rf 0.42 (hexane:ethyl acetate=4:1); NMR (CDCl₃): δ 7.35 (5H, s), 5.23–5.08 (4H, m), 4.40–4.29 (1H, m), 2.43–2.28 (2H, m), 2.23–2.03 (1H, m), 2.02–1.49 (9H, m), 1.42 (9H, s).

Example 1(9)

(2S)-4-benzyloxycarbonyl-2-t-butoxycarbonylaminobutanoic acid.cyclohexyl ester

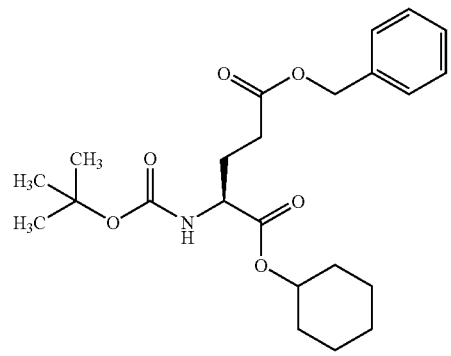

TLC: Rf 0.51 (hexane:ethyl acetate=4:1); NMR (CDCl₃): δ 7.34 (5H, s), 5.18–5.04 (3H, m), 4.85–4.74 (1H, m), 4.37–4.24 (1H, m), 2.59–1.25 (23H, m).

Example 1(10)

(2S)-4-benzyloxycarbonyl-2-t-butoxycarbonylaminobutanoic acid.cyclopentyl ester

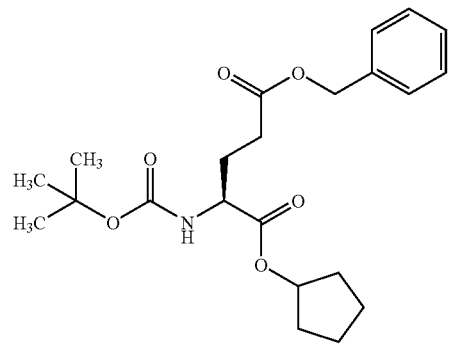

TLC: Rf 0.50 (hexane:ethyl acetate=4:1); NMR (CDCl₃): δ 7.36 (5H, s), 5.25–5.11 (4H, m), 4.37–4.15 (1H, m), 2.58–1.34 (21H, m).

Example 1(11)

(2R)-4-benzyloxycarbonyl-2-t-butoxycarbonylaminobutanoic acid.cyclohexyl ester

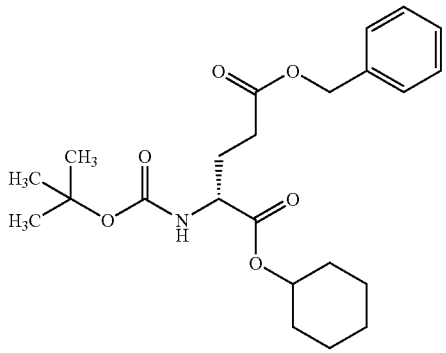

TLC: Rf 0.51 (hexane:ethyl acetate=4:1); NMR (CDCl$_3$): δ 7.36 (5H, s), 5.13 (2H, s), 5.14–5.04 (1H, m), 4.88–4.73 (1H, m), 4.39–4.22 (1H, m), 2.58–1.24 (23H, m).

Example 1(12)

(2R)-4-benzyloxycarbonyl-2-t-butoxycarbonylaminobutanoic acid.cyclopentyl ester

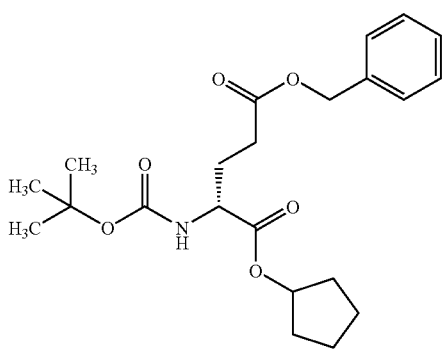

NMR (CDCl$_3$): δ 7.35 (5H, s), 5.25–5.03 (4H, m), 4.37–4.13 (1H, m), 2.59–1.37 (21H, m).

Example 1(13)

(2S)-3-cyclohexylcarbomoyl-2-t-butoxycarbonylaminopropanoic acid.benzyl ester

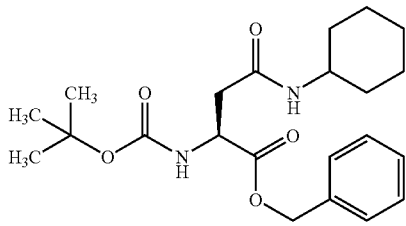

TLC: Rf 0.29 (hexane:ethyl acetate=2:1); NMR (CDCl$_3$): δ 7.43–7.25 (5H, m), 5.81 (1H, bd, J=9 Hz), 5.50 (1H, bd, J=9 Hz), 5.21 (1H, d, J=10 Hz), 5.16 (1H, d, J=10 Hz), 4.59–4.46 (1H, m), 3.81–3.60 (1H, m), 2.83 (1H, dd, J=16, 5 Hz), 2.68 (1H, dd, J=16, 5 Hz), 1.95–0.94 (10H, m), 1.42 (9H, s).

Example 1(14)

(2S)-3-cyclopentylcarbamoyl-2-t-butoxycarbonylaminopropanoic acid.benzyl ester

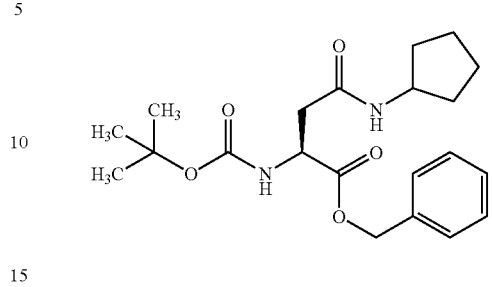

TLC: Rf 0.26 (hexane:ethyl acetate=2:1); NMR (CDCl$_3$): δ 7.43–7.25 (5H, m), 5.90–5.74 (1H, m), 5.73–5.55 (1H, m), 5.21 (1H, d, J=12 Hz), 5.16 (1H, d, J=12 Hz), 4.60–4.46 (1H, m), 4.24–4.05 (1H, m) 2.82 (1H, dd, J=16, 5 Hz), 2.68 (1H, dd, J=16, 5 Hz), 2.08–1.19 (8H, m), 1.42 (9H, s).

Example 1(15)

(2S)-4-(pyrrolidin-1-ylcarbonyl)-2-t-butoxycarbonylaminobutanoic acid.benzyl ester

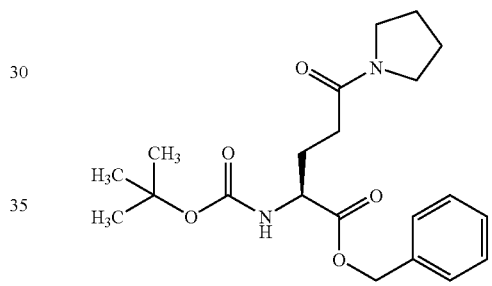

TLC: Rf 0.33 (hexane:ethyl acetate=1:1); NMR (CDCl$_3$): δ 7.40–7.30 (5H, m), 5.60–5.45 (1H, m), 5.21 (1H, d, J=12 Hz), 5.14 (1H, d, J=12 Hz), 4.40–4.23 (1H, m), 3.44 (2H, t, J=7 Hz), 3.27 (2H, t, J=7 Hz), 2.37–1.65 (8H, m), 1.44 (9H, s).

Example 1(16)

(2S)-3-cyclopentyloxycarbonyl-2-(N-t-butoxycarbonyl-N-methylamino)-propanoic acid.4-nitrobenzyl ester

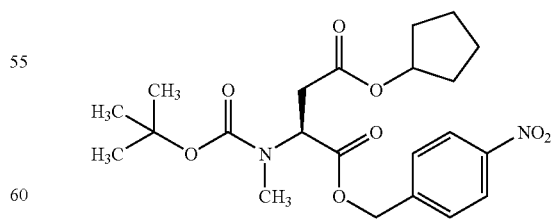

TLC: Rf 0.49 (ethyl acetate:hexane=1:2); NMR (CDCl$_3$): δ 8.25–8.18 (2H, m), 7.51 (2H, d, J=8.8 Hz), 5.30–5.11 (3H, m), 4.82–4.60 (1H, m), 3.17–2.66 (5H, m), 1.98–1.33 (17H, m).

Example 1(17)

(2S)-3-cyclohexyloxycarbonyl-2-(N-t-butoxycarbonyl-N-amino)propanoic acid.4-nitrobenzyl ester

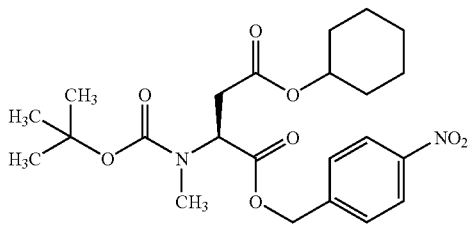

TLC: Rf 0.38 (ethyl acetate:hexane=1:2); NMR (CDCl$_3$): δ 8.28–8.15 (2H, m), 7.51 (2H, d, J=8.8 Hz), 5.38–5.14 (2H, m), 4.85–4.62 (2H, m), 3.18–3.01 (1H, m), 2.98–2.69 (4H, m), 1.94–1.16 (19H, m).

Example 1(18)

(2S)-3-cuyclobutyloxycarbonyl-2-t-butoxycarbonylaminopropanoic acid.benzyl ester

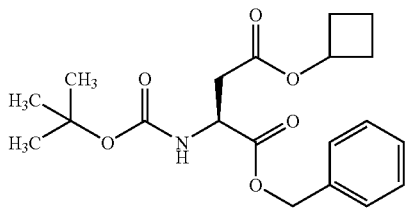

TLC: Rf 0.59 (hexane:ethyl acetate=2:1); NMR (CDCl$_3$): δ 7.36–7.31 (5H, m), 5.50 (1H, d, J=8.0 Hz), 5.22 (1H, d, J=12.4 Hz), 5.14 (1H, d, J=12.4 Hz), 5.01–4.86 (1H, m), 4.65–4.56 (1H, m), 2.99 (1H, dd, J=16.4, 6.0 Hz), 2.78 (1H, dd, J=16.4, 4.8 Hz), 2.39–2.21 (2H, m), 2.12–1.50 (4H, m), 1.43 (9H, s).

Example 1(19)

(2S)-3-(adamantan-2-yloxycarbonyl)-2-t-butoxycarbonylaminopropanoic acid.benzyl ester

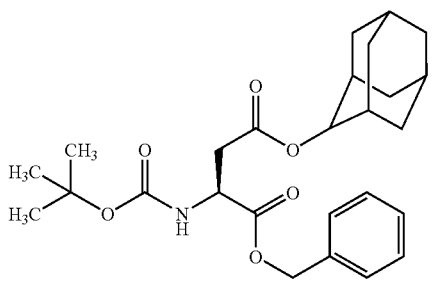

TLC: Rf 0.46 (hexane:ethyl acetate=4:1); NMR (CDCl$_3$): δ 7.34 (5H, s), 5.54 (1H, d, J=8.8 Hz), 5.22 (1H, d, J=12.2 Hz), 5.13 (1H, d, J=12.2 Hz), 4.93–4.87 (1H, br), 4.66–4.57 (1H, m), 3.04 (1H, dd, J=4.4, 16.8 Hz), 2.85 (1H, dd, J=4.6, 16.8 Hz), 2.01–1.65 (12H, m), 1.60–1.46 (2H, m), 1.43 (9H, s).

Example 1(20)

(2S)-3(adamantan-1-yloxycarbonyl)-2-t-butoxycarbonylaminopropanoic acid.benzyl ester

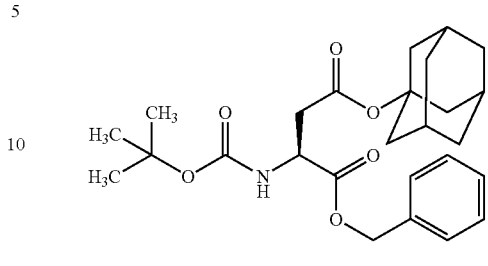

TLC: Rf 0.46 (hexane:ethyl acetate=4:1); NMR (CDCl$_3$): δ 7.34 (5H, s), 5.50 (1H, d, J=8.6 Hz), 5.23 (1H, d, J=12.4 Hz), 5.13 (1H, d, J=12.4 Hz), 4.60–4.52 (1H, m), 2.93 (1H, dd, J=4.6, 16.8 Hz), 2.71 (1H, dd, J=4.8, 16.8 Hz), 2.19–2.08 (3H, br), 2.02 (6H, d, J=3.0 Hz), 1.63 (6H, s), 1.44 (9H, s).

Reference Example 3

(2S)-3-cyclopentyloxycarbonyl-2-t-butoxycarbonylaminopropanoic acid

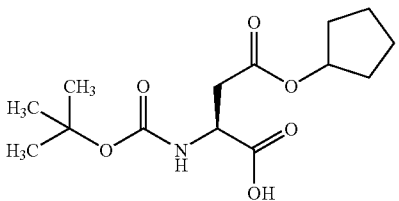

Under argon atmosphere, the compound prepared in Example 1 (4.19 g) was stirred in ethyl acetate (25 ml) and palladium carbon (5%, 500 mg) was added thereto. The mixture was stirred for 13 hours at room temperature under hydrogen atmosphere. The reaction mixture was filtered through Celite. The filtrate was concentrated to give the title compound (2.98 g) having the following physical data.

TLC: Rf 0.53 (chloroform:methanol=9:1); NMR (CDCl$_3$): δ 5.54 (1H, d, J=8.1 Hz), 5.24–5.17 (1H, m), 4.63–4.55 (1H, m), 2.97 (1H, dd, J=4.8, 17.1 Hz), 2.79 (1H, dd, J=4.8, 17.1 Hz), 1.87–1.55 (8H, m), 1.45 (9H, s).

Example 2

(2S)-N-(4-methoxybenzyl)-3-cyclohexylmethoxy-2-t-butoxycarbonylamino-propanamide

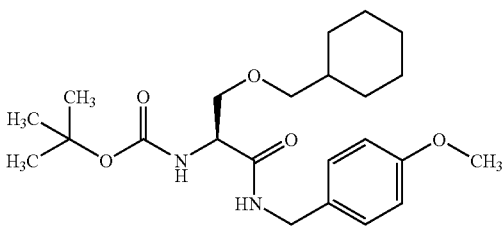

The compound prepared in Reference Example 1 (90 mg), dimethylaminopyridine (6 mg) and 4-methoxybenzylamine (43 mg) were dissolved in methylene chloride, and EDC-HCl (122 mg) was added thereto. The mixture was stirred for 12 hours at room temperature. The reaction mixture was concentrated. The residue was purified by silica gel column chromatography (hexane:ethyl acetate=3:1) to give the compound of the present invention (84 mg) having the following physical data.

TLC: Rf 0.20 (hexane:ethyl acetate=3:1); NMR (CDCl₃): δ 7.19 (2H, d, J=8.2 Hz), 6.85 (2H, d, J=8.2 Hz), 6.80–6.66 (1H, br), 5.52–5.26 (1H, br), 4.44 (1H, dd, J=5.2, 15.0 Hz), 4.36 (1H, dd, J=5.8, 15.0 Hz), 4.30–4.15 (1H, br), 3.89–3.79 (4H, m), 3.44 (1H, dd, J=7.0, 9.2 Hz), 3.27 (1H, dd, J=6.1, 9.3 Hz), 3.20 (1H, dd, J=6.1, 9.3 Hz), 1.94 (5H, m), 1.44 (9H, s), 1.34–1.04 (4H, m), 0.96–0.74 (2H, m).

Example 2(1)~Example 2(119)

By the reaction of the compounds prepared in Reference Example 1, Reference Example 2, Reference Example 3, or the carboxylic acid derivatives (obtained by the same desired procedure as Reference Example 3, using the compounds prepared in Example 1(1)~Example 1(20)) or the corresponding carboxylic acids derivatives thereof with the corresponding alcohol derivatives or amine derivatives by the same desired procedure as Example 2, the following compounds of the present invention were obtained.

Example 2(1)

(2S)-4-cyclohexyloxycarbonyl-2-t-butoxycarbonylaminobutanoic acid.4-nitrobenzyl ester

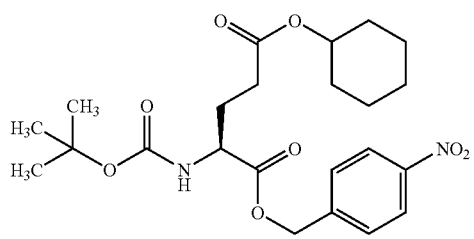

TLC: Rf 0.37 (hexane:ethyl acetate=4:1); NMR (CDCl₃): δ 8.23 (2H, d, J=8.8 Hz), 7.53 (2H, d, J=8.8 Hz), 5.27 (2H, s), 5.12 (1H, d, J=8.6 Hz), 4.80–4.69 (1H, m), 4.44–4.33 (1H, m), 2.43–2.36 (2H, m), 2.31–1.20 (21H. m).

Example 2(2)

(2S)-3-cyclohexyloxycarbonyl-2-t-butoxycarbonylaminopropanoic acid.4-fluorobenzyl ester

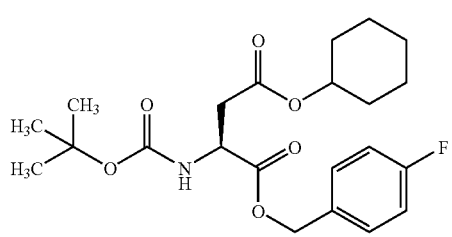

TLC: Rf 0.36 (hexane:ethyl acetate=4:1); NMR (CDCl₃): δ 7.36–7.29 (2H, m), 7.08–6.99 (2H, m), 5.48 (1H, d, J=2.3 Hz), 5.17 (1H, d, J=2.4 Hz), 5.09 (1H, d, J=12.4 Hz), 4.80–4.65 (1H, m), 4.65–4.52 (1H, m), 2.99 (1H, dd, J=4.5, 16.8 Hz), 2.78 (1H, dd, J=4.8, 16.8 Hz), 1.87–1.47 (6H, m), 1.43 (9H, s), 1.40–1.20 (4H, m).

Example 2(3)

(2R)-3-cyclohexyloxycarbonyl-2-t-butoxycarbonylaminopropanoic acic.4-fluorobenzyl ester

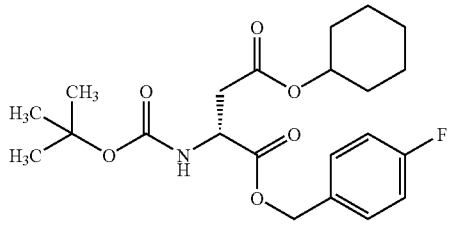

TLC: Rf 0.46 (ethyl acetate:hexane=1:4); NMR (CDCl₃): δ 7.36–7.29 (2H, m), 7.08–6.99 (2H, m), 5.49 (1H, d, J=8.5 Hz), 5.19 (1H, d, J=12.2 Hz), 5.09 (1H, d, J=12.2 Hz), 4.73–4.57 (2H, m), 2.98 (1H, dd, J=16.8, 4.8 Hz), 2.78 (1H, dd, J=16.8, 4.7 Hz), 1.80–1.24 (19H, m).

Example 2(4)

(2S)-3-cyclohexyloxycarbonyl-2-t-butoxycarbonylaminopropanoic acid.4-methoxybenzyl ester

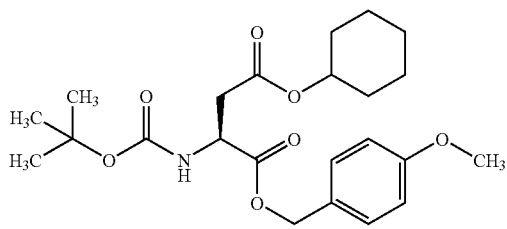

TLC: Rf 0.39 (hexane:ethyl acetate=4:1); NMR (CDCl₃): δ 7.27 (2H, d, J=8.6 Hz), 6.87 (2H, d, J=8.6 Hz), 5.52–5.42 (1H, m), 5.15 (1H, d, J=12.0 Hz), 5.07 (1H, d, J=12.0 Hz), 4.75–4.64 (1H, m), 4.62–4.50 (1H, m), 3.81 (3H, s), 2.98 (1H, dd, J=4.4, 16.8 Hz), 2.76 (1H, dd, J=5.0, 16.8 Hz), 1.90–1.52 (6H, m), 1.43 (9H, s), 1.40–1.22 (4H, m).

Example 2(5)

(2R)-3-cyclohexyloxycarbonyl-2-t-butoxycarbonylaminopropanoic acid.4-methoxybenzyl ester

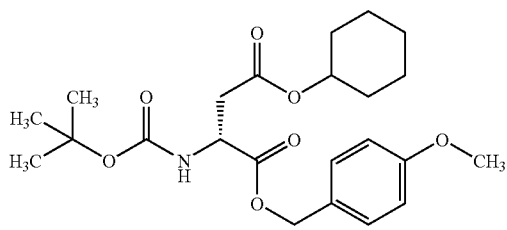

TLC: Rf 0.31 (ethyl acetate:hexane=1:4); NMR (CDCl₃): δ 7.27 (2H, d, J=8.5 Hz), 6.87 (2H, d, J=8.5 Hz), 5.48 (1H, d, J=10.4 Hz), 5.15 (1H, d, J=12.0 Hz), 5.07 (1H, d, J=12.0 Hz), 4.73–4.55 (2H, m), 3.81 (3H, s), 2.98 (1H, dd, J=16.8, 4.8 Hz), 2.77 (1H, dd, J=16.8, 4.6 Hz), 1.82–1.09 (19H, m).

Example 2(6)

(2S)-3-cyclohexyloxycarbonyl-2-benzyloxycarbonylaminopropanoic acid.4-nitrobenzyl ester

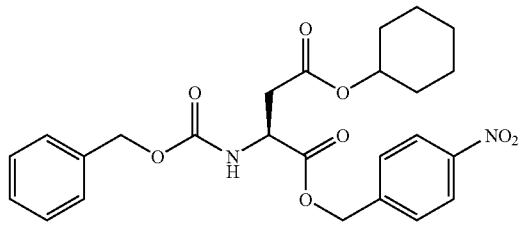

TLC: Rf 0.17 (ethyl acetate:hexane=1:4); NMR (CDCl$_3$): δ 8.20 (2H, d, J=8.5 Hz), 7.48 (2H, d, J=8.5 Hz), 7.35 (5H, s), 5.78 (1H, d, J=8.8 Hz), 5.33–5.19 (2H, m), 5.13 (2H, s), 4.76–4.67 (2H, m), 3.06 (1H, dd, J=17.2, 4.4 Hz), 2.83 (1H, dd, J=17.2, 4.4 Hz), 1.75–1.22 (10H, m).

Example 2(7)

(2S)-3-cyclohexyloxycarbonyl-2-t-butoxycarbonylaminopropanoic acid.4-nitrophenethyl ester

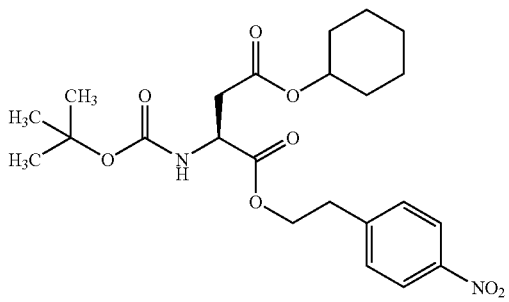

TLC: Rf 0.44 (hexane:ethyl acetate=3:1); NMR (CDCl$_3$): δ 8.18 (2H, d, J=8.2 Hz), 7.39 (2H, d, J=8.2 Hz), 5.43 (1H, d, J=9.6 Hz), 4.78–4.61 (1H, m), 4.60–4.46 (1H, m), 4.40 (2H, t, J=6.6 Hz), 3.07 (2H, t, J=6.6 Hz), 2.94 (1H, dd, J=4.8, 17.1 Hz), 2.76 (1H, dd, J=4.6, 17.1 Hz), 1.88–1.48 (6H, m), 1.44 (9H, s), 1.41–1.22 (4H, m).

Example 2(8)

(2S)-N-benzyl-3-cyclohexyloxycarbonyl-2-t-butoxycarbonylamino-propanamide

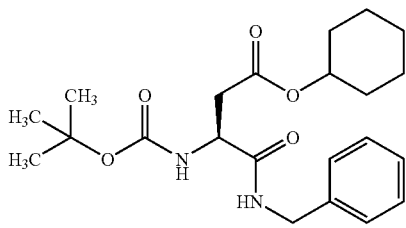

TLC: Rf 0.37 (hexane:ethyl acetate=3:1); NMR (CDCl$_3$): δ 7.38–7.21 (5H, m), 6.88–6.72 (1H, br), 5.75–5.58 (1H, m), 4.82–4.68 (1H, m), 4.58–4.38 (3H, m), 3.02 (1H, dd, J=4.6, 17.0 Hz), 2.70 (1H, dd, J=6.4, 17.0 Hz), 1.91–1.47 (6H, m), 1.43 (9H, s), 1.40–1.23 (4H, m).

Example 2(9)

(2S)-3-cyclopentyloxycarbonyl-2-t-butoxycarbonylaminopropanoic acid.4-methoxybenzyl ester

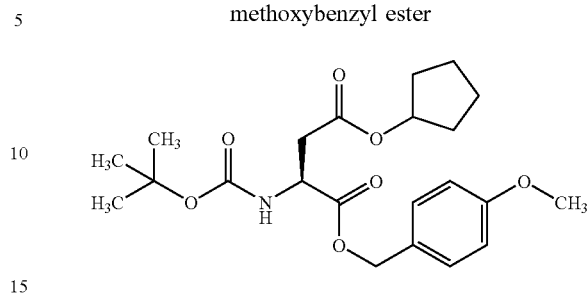

TLC: Rf 0.34 (hexane:ethyl acetate=4:1); NMR (CDCl$_3$): δ 7.27 (2H, d, J=8.6 Hz), 6.88 (2H, d, J=8.6 Hz), 5.48 (1H, d, J=8.8 Hz), 5.18–5.04 (3H, m), 4.60–4.51 (1H, m), 3.81 (3H, s), 2.96 (1H, dd, J=4.8, 17.0 Hz), 2.76 (1H, dd, J=4.8, 16.8 Hz), 1.83–1.54 (8H, m), 1.43 (9H, s).

Example 2(10)

(2S)-3-(4-methoxybenzyloxycarbonyl)-2-t-butoxycarbonylaminopropanoic acid.cyclohexyl ester

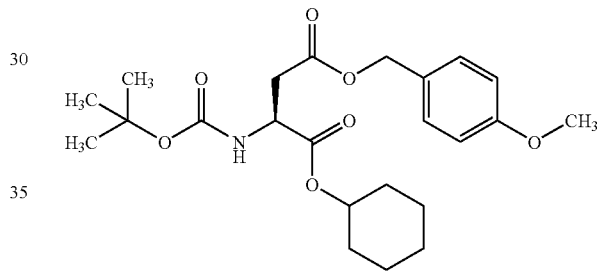

TLC: Rf 0.39 (hexane:ethyl acetate=4:1); NMR (CDCl$_3$): δ 7.28 (2H, d, J=8.6 Hz), 6.88 (2H, d, J=8.6 Hz), 5.48 (1H, d, J=8.6 Hz), 5.05 (2H, s), 4.84–4.72 (1H, m), 4.57–4.47 (1H, m), 3.81 (3H, s), 3.02 (1H, dd, J=4.4, 16.8 Hz), 2.82 (1H, dd, J=4.8, 16.8 Hz), 1.85–1.60 (4H, m), 1.56–1.27 (15H, m).

Example 2(11)

(2S)-3-(4-nitrobenzyloxycarbonyl)-2-t-butoxycarbonylaminopropanoic acid.cyclohexyl ester

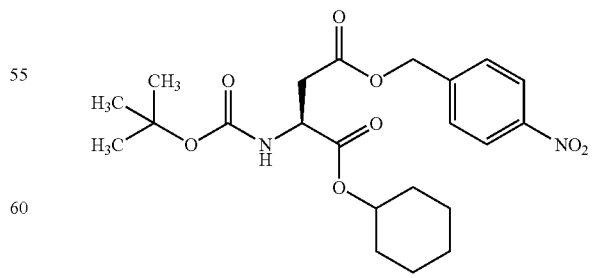

TLC: Rf 0.18 (hexane:ethyl acetate=4:1); NMR (CDCl$_3$): δ 8.23 (2H, d, J=8.8 Hz), 7.52 (2H, d, J=8.8 Hz), 5.48 (1H, d, J=8.0 Hz), 5.22 (2H, s), 4.86–4.74 (1H, m), 4.60–4.52

(1H, m), 3.07 (1H, dd, J=4.6, 16.8 Hz), 2.92 (1H, dd, J=5.0, 16.8 Hz), 1.88–1.58 (4H, m), 1.56–1.20 (15H, m).

Example 2(12)

(2S)-3-(4-methoxybenzyloxycarbonyl)-2-t-butoxycarbonylaminopropanoic acid.cyclopentyl ester

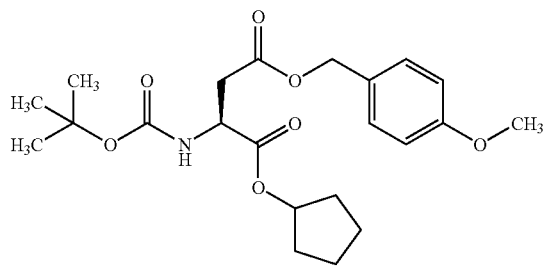

TLC: Rf 0.24 (hexane:ethyl acetate=4:1); NMR (CDCl$_3$): δ 7.28 (2H, d, J=8.8 Hz), 6.88 (2H, d, J=8.8 Hz), 5.47 (1H, d, J=8.4 Hz), 5.21–5.16 (1H, m), 5.05 (2H, s), 4.54–4.45 (1H, m), 3.81 (3H, s), 2.98 (1H, dd, J=4.8, 16.8 Hz), 2.76 (1H, dd, J=4.6, 16.8 Hz), 1.88–1.51 (8H, m), 1.44 (9H, s).

Example 2(13)

(2S)-3-(4-nitrobenzyloxycarbonyl)-2-t-butoxycarbonylaminopropanoic acid.cyclopentyl ester

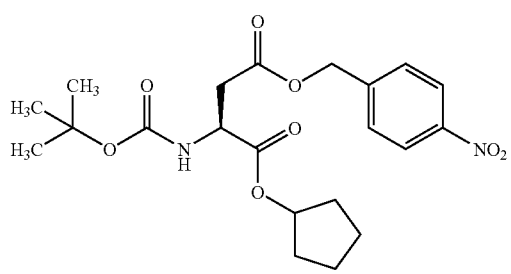

TLC: Rf 0.15 (hexane:ethyl acetate=4:1); NMR (CDCl$_3$): δ 8.23 (2H, d, J=8.8 Hz), 7.51 (2H, d, J=8.8 Hz), 5.44 (1H, d, J=8.4 Hz), 5.22–5.17 (3H, m), 4.59–4.50 (1H, m), 3.04 (1H, dd, J=4.8, 16.8 Hz), 2.92 (1H, dd, J=5.0, 16.8 Hz), 1.94–1.52 (8H, m), 1.44 (9H, s).

Example 2(14)

(2R)-3-(4-methoxybenzyloxycarbonyl)-2-t-butoxycarbonylaminopropanoic acid.cyclohexyl ester

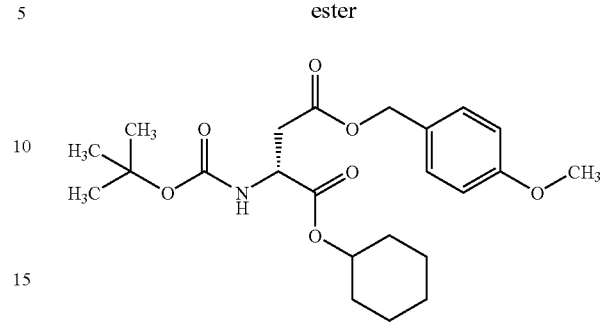

TLC: Rf 0.39 (hexane:ethyl acetate=4:1); NMR (CDCl$_3$): δ 7.28 (2H, d, J=8.6 Hz), 6.88 (2H, d, J=8.6 Hz), 5.48 (1H, d, J=8.6 Hz), 5.05 (2H, s), 4.84–4.72 (1H, m), 4.57–4.47 (1H, m), 3.81 (3H, s), 3.02 (1H, dd, J=4.4, 16.8 Hz), 2.82 (1H, dd, J=4.8, 16.8 Hz), 1.85–1.60 (4H, m), 1.56–1.27 (15H, m).

Example 2(15)

(2R)-3-(4-nitrobenzyloxycarbonyl)-2-t-butoxycarbonylaminopropanoic acid.cyclohexyl ester

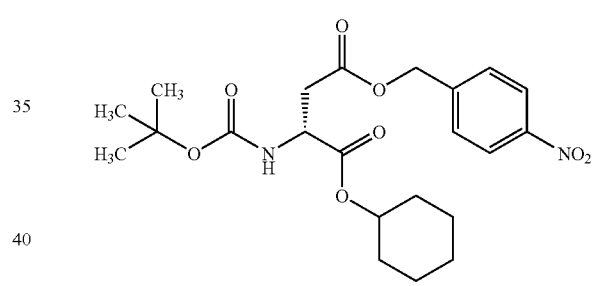

TLC: Rf 0.18 (hexane:ethyl acetate=4:1); NMR (CDCl$_3$): δ 8.23 (2H, d, J=8.8 Hz), 7.52 (2H, d, J=8.8 Hz), 5.48 (1H, d, J=8.0 Hz), 5.22 (2H, s), 4.86–4.74 (1H, m), 4.60–4.52 (1H, m), 3.07 (1H, dd, J=4.6, 16.8 Hz), 2.92 (1H, dd, J=5.0, 16.8 Hz), 1.88–1.58 (4H, m), 1.56–1.20 (15H, m).

Example 2(16)

(2R)-3-(4-methoxybenzyloxycarbonyl)-2-t-butoxycarbonylaminopropanoic acid.cyclopentyl ester

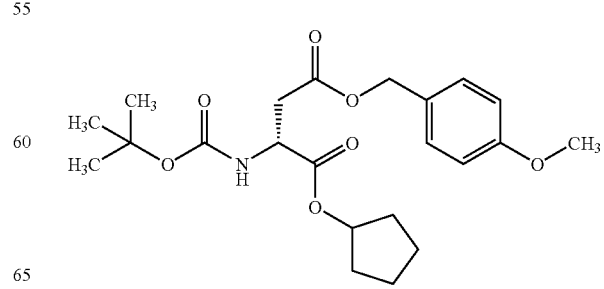

TLC: Rf 0.24 (hexane:ethyl acetate=4:1); NMR (CDCl₃): δ 7.28 (2H, d, J=8.8 Hz), 6.88 (2H, d, J=8.8 Hz), 5.47 (1H, d, J=8.4 Hz), 5.21–5.16 (1H, m), 5.05 (2H, s), 4.54–4.45 (1H, m), 3.81 (3H, s), 2.98 (1H, dd, J=4.8, 16.8 Hz), 2.76 (1H, dd, J=4.6, 16.8 Hz), 1.88–1.51 (8H, m), 1.44 (9H, s).

Example 2(17)

(2R)-3-(4-nitrobenzyloxycarbonyl)-2-t-butoxycarbonylaminopropanoic acid.cyclopentyl ester

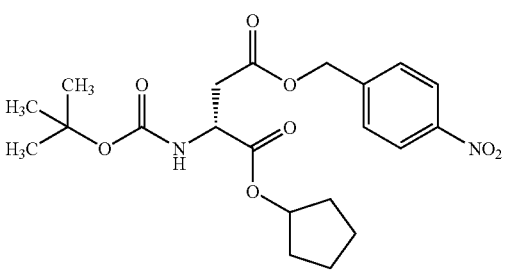

TLC: Rf 0.15(hexane:ethyl acetate=4:1); NMR (CDCl₃): δ 8.23 (2H, d, J=8.8 Hz), 7.51 (2H, d, J=8.8 Hz), 5.44 (1H, d, J=8.4 Hz), 5.22–5.17 (3H, m), 4.59–4.50 (1H, m), 3.04 (1H, dd, J=4.8, 16.8 Hz), 2.92 (1H, dd, J=5.0, 16.8 Hz), 1.94–1.52 (8H, m), 1.44 (9H, s).

Example 2(18)

(2R)-3-cyclopentyloxycarbonyl-2-t-butoxycarbonylaminopropanoic acid.4-methoxybenzyl ester

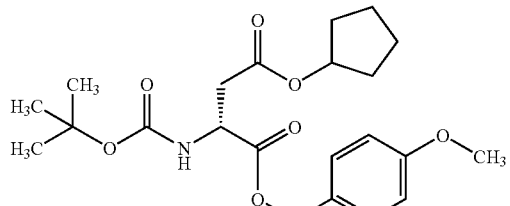

TLC: Rf 0.20 (ethyl acetate:hexane=1:5); NMR (CDCl₃): δ 7.27 (2H, d, J=9 Hz), 6.88 (2H, d, J=9 Hz), 5.48 (1H, d, J=8 Hz), 5.20–5.03 (3H, m), 4.63–4.48 (1H, m), 3.81 (3H, s), 2.93 (1H, dd, J=18, 5 Hz), 2.77 (1H, dd, J=18, 5 Hz), 1.90–1.48 (8H, m), 1.43 (9H, s).

Example 2(19)

(2S)-4-cyclohexyloxycarbonyl-2-t-butoxycarbonylaminobutanoic acid.4-methoxybenzyl ester

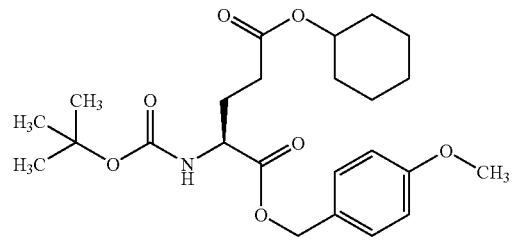

TLC: Rf 0.33 (ethyl acetate:hexane=1:4); NMR (CDCl₃): δ 7.22 (2H, d, J=9 Hz), 6.81 (2H, d, J=9 Hz), 5.12–4.95 (3H, m), 4.75–4.59 (1H, m), 4.33–4.15 (1H, m), 3.74 (3H, s), 2.40–1.05 (14H, m), 1.35 (9H, s).

Example 2(20)

(2S)-4-cyclopentyloxycarbonyl-2-t-butoxycarbonylaminobutanoic acid.4-methoxybenzyl ester

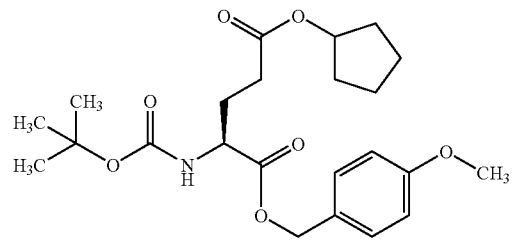

TLC: Rf 0.17 (ethyl acetate:hexane=1:5); NMR (CDCl₃): δ 7.29 (2H, d, J=9 Hz), 6.88 (2H, d, J=9 Hz), 5.20–5.03 (4H, m), 4.40–4.23 (1H, m), 3.81 (3H, s), 2.40–1.48 (12H, m), 1.42 (9H, s).

Example 2(21)

(2S)-4-cyclopentyloxycarbonyl-2-t-butoxycarbonylaminobutanoic acid.4-nitrobenzyl ester

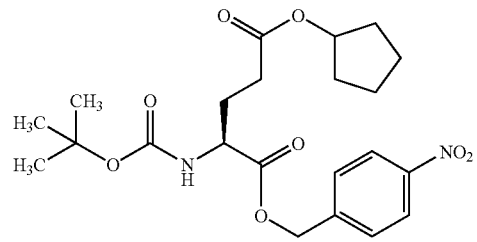

TLC: Rf 0.16 (ethyl acetate:hexane=1:4); NMR (CDCl₃): δ 8.23 (2H, d, J=9 Hz) 7.53 (2H, d, J=9 Hz), 5.27 (2H, s), 5.21–5.05 (2H, m) 4.47–4.28 (1H, m) 2.46–1.49 (12H, m), 1.44 (9H, s).

Example 2(22)

(2R)-4-cyclohexyloxycarbonyl-2-t-butoxycarbonylaminobutanoic acid.4-methoxybenzyl ester

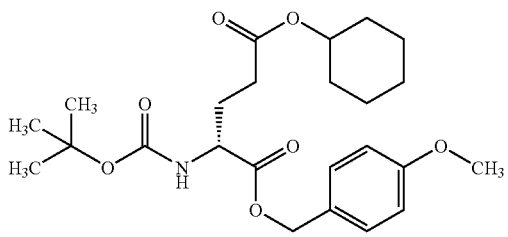

TLC: Rf 0.33 (hexane:ethyl acetate=4:1); NMR (CDCl₃): δ 7.29 (2H, d, J=8.8 Hz), 6.88 (2H, d, J=8.8 Hz), 5.17–5.04 (3H, m), 4.79–4.69 (1H, m), 4.39–4.25 (1H, m), 3.81 (3H, s), 2.43–2.29 (2H, m), 2.24–2.05 (1H, m), 2.03–1.53 (7H, m), 1.51–1.27 (13H, m).

Example 2(23)

(2R)-4-cyclohexyloxycarbonyl-2-t-butoxycarbonylaminobutanoic acid.4-nitrobenzyl ester

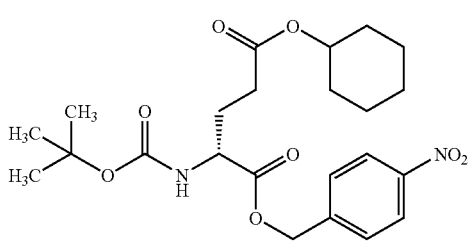

TLC: Rf 0.26 (hexane:ethyl acetate=4:1); NMR (CDCl₃): δ 8.23 (2H, d, J=8.8 Hz), 7.53 (2H, d, J=8.8 Hz), 5.29 (2H, s), 5.12 (1H, d, J=9.0 Hz), 4.81–4.69 (1H, m), 4.45–4.34 (1H, m), 2.48–2.35 (2H, m), 2.30–2.11 (1H, m), 2.07–1.53 (7H, m), 1.51–1.28 (13H, m).

Example 2(24)

(2R)-4-cyclopentyloxycarbonyl-2-t-butoxycarbonylaminobutanoic acid.4-methoxybenzyl ester

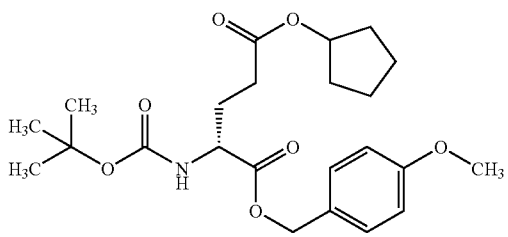

TLC: Rf 0.34 (hexane:ethyl acetate=4:1); NMR (CDCl₃): δ 7.29 (2H, d, J=8.8 Hz), 6.88 (2H, d, J=8.8 Hz), 5.19–5.04 (4H, m), 4.37–4.26 (1H, m), 3.81 (3H, S), 2.44–2.27 (2H, m), 2.23–2.04 (1H, m), 2.00–1.57 (9H, m), 1.43 (9H, s).

Example 2(25)

(2R)-4-cyclopentyloxycarbonyl-2-t-butoxycarbonylaminobutanoic acid.4-nitrobenzyl ester

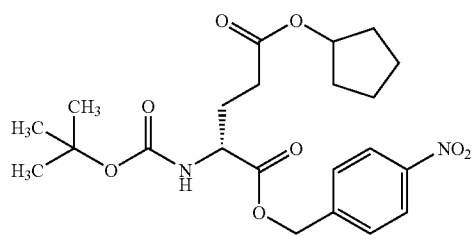

TLC: Rf 0.21 (hexane:ethyl acetate=4:1); NMR (CDCl₃): δ 8.23 (2H, d, J=8.8 Hz), 7.53 (2H, d, J=8.8 Hz), 5.27 (2H, s), 5.20–5.09 (2H, m), 4.43–4.33 (1H, m), 2.50–2.33 (2H, m), 2.28–2.10 (1H, m), 2.06–1.52 (9H, m), 1.43 (9H, s).

Example 2(26)

(2S)-4-(4-methoxybenzyloxycarbonyl)-2-t-butoxycarbonylaminobutanoic acid.cyclohexyl ester

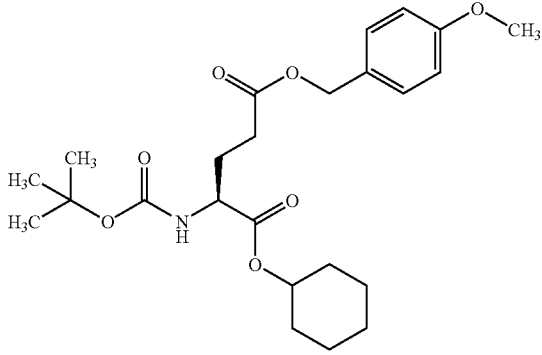

TLC: Rf 0.29 (ethyl acetate:hexane=1:4); NMR (CDCl₃): δ 7.34–7.20 (2H, m), 6.94–6.81 (2H, m), 5.12–5.00 (1H, m), 5.05 (2H, s), 4.84–4.74 (1H, m), 4.36–4.20 (1H, m), 3.81 (3H, s), 2.47–1.22 (23H, m).

Example 2(27)

(2S)-4-(4-nitrobenzyloxycarbonyl)-2-t-butoxycarbonylaminobutanoic acid.cyclohexyl ester

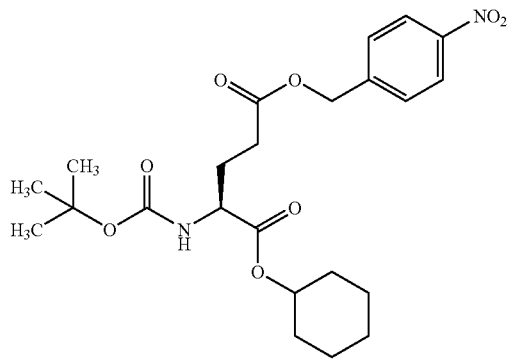

TLC: Rf 0.27 (ethyl acetate:hexane=1:4); NMR (CDCl$_3$): δ 8.29–8.18 (2H, m), 7.56–7.46 (2H m), 7.52 (2H, d, J=8.8 Hz), 5.30–5.05 (3H, m), 4.86–4.75 (1H, m), 4.37–4.25 (1H, m), 2.64–2.38 (2H, m), 2.33–2.13 (1H, m), 2.06–1.17 (20H, m).

Example 2(28)

(2S)-4-(4-methoxybenzyloxycarbonyl)-2-t-butoxycarbonylaminobutanoic acid.cyclopentyl ester

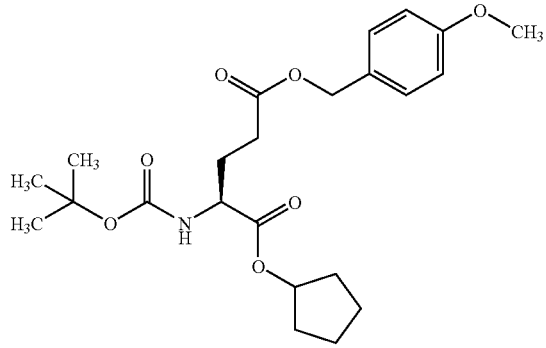

TLC: Rf 0.29 (ethyl acetate:hexane=1:4); NMR (CDCl$_3$): δ 7.28 (2H, d, J=11.2 Hz), 6.89 (2H, d, J=11.2 Hz), 5.24–5.20 (1H, m), 5.13–5.01 (1H, m), 5.05 (2H, s), 4.31–4.21 (1H, m), 3.81 (3H, s), 2.47–1.59 (12H, m), 1.43 (9H, s).

Example 2(29)

(2S)-4-(4-nitrobenzyloxycarbonyl)-2-t-butoxycarbonylaminobutanoic acid.cyclopentyl ester

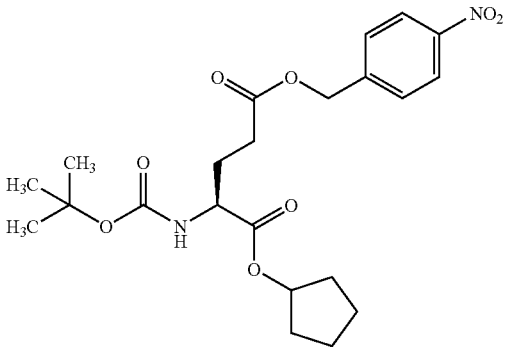

TLC: Rf 0.20 (ethyl acetate:hexane=1:4); NMR (CDCl$_3$): δ 8.28–8.18 (2H, m), 7.76–7.46 (2H, m), 5.25–5.06 (2H, m), 5.22 (2H, s), 4.35–4.24 (1H, m), 2.55–2.47 (2H, m), 2.40–1.53 (10H, m), 1.44 (9H, s).

Example 2(30)

(2R)-4-(4-methoxybenzyloxycarbonyl)-2-t-butoxycarbonylaminobutanoic acid.cyclohexyl ester TLC: Rf 0.42 (ethyl acetate:hexane=1:4); NMR (CDCl$_3$): δ 7.33–7.23 (2H, m), 6.93–6.84 (2H, m), 5.12–5.00 (1H, m), 5.05 (2H, s), 4.84–4.74 (1H, m), 4.36–4.20 (1H, m), 3.81 (3H, s), 2.47–1.22 (23H, m).

Example 2(31)

(2R)-4-(4-nitrobenzyloxycarbonyl)-2-t-butoxycarbonylaminobutanoic acid.cyclohexyl ester

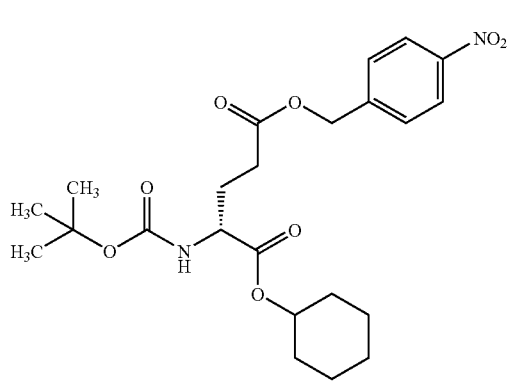

TLC: Rf 0.27 (ethyl acetate:hexane=1:4); NMR (CDCl$_3$): δ 8.26–8.18 (2H, m), 7.56–7.46 (2H, m), 5.22 (2H, s), 5.15–5.06 (1H, m), 4.86–4.75 (1H, m), 4.37–4.25 (1H, m), 2.56–1.20 (23H, m).

Example 2(32)

(2R)-4-(4-methoxybenzyloxycarbonyl)-2-t-butoxycarbonylaminobutanoic acid.cyclopentyl ester

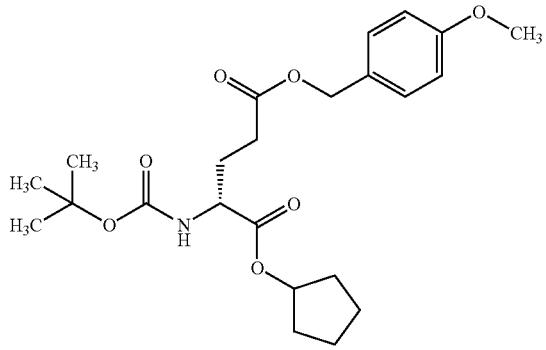

TLC: Rf 0.29 (ethyl acetate:hexane=1:4); NMR (CDCl$_3$): δ 7.33–7.24 (2H, m), 7.28 (2H, d, J=11.2 Hz), 6.93–6.84 (2H, m), 6.89 (2H, d, J=11.2 Hz), 5.24–5.03 (2H, m), 5.05 (2H, S), 4.31–4.21 (1H, m), 3.81 (3H, s), 2.47–1.59 (12H, m), 1.43 (9H, s).

Example 2(33)

(2R)-4-(4-nitrobenzyloxycarbonyl)-2-t-butoxycarbonylaminobutanoic acid.cyclopentyl ester

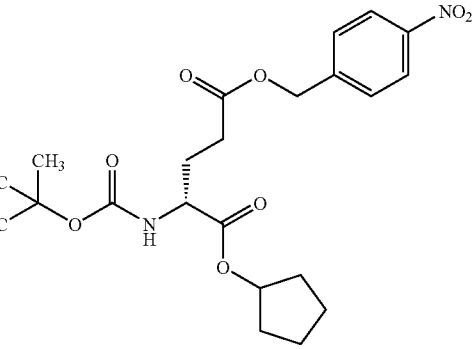

TLC: Rf 0.24 (ethyl acetate:hexane=1:4); NMR (CDCl$_3$): δ 8.25–8.18 (2H, m), 7.55–7.47 (2H, m), 5.25–5.06 (2H, m), 5.22 (2H, s), 4.35–4.24 (1H, m), 2.55–2.47 (2H, m), 2.31–1.53 (10H, m), 1.44 (9H, s).

Example 2(34)

(2S)-N-(4-methoxybenzyl)-3-cyclohexyloxycarbonyl-2-t-butoxycarbonylamino-propanamide

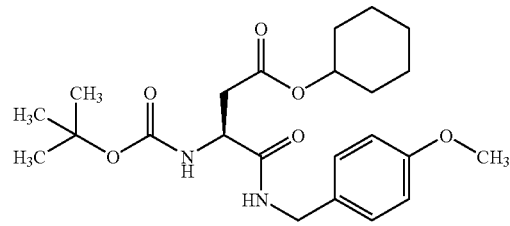

TLC: Rf 0.18 (ethyl acetate:hexane=1:3); NMR (CDCl$_3$): δ 7.18 (2H, d, J=9 Hz), 6.85 (2H, d, J=9 Hz), 6.85–6.67 (1H, m), 5.80–5.58 (1H, m), 4.83–4.67 (1H, m), 4.60–4.40 (1H, m), 4.43–4.25 (2H, m), 3.79 (3H, s), 2.98 (1H, dd, J=18, 5 Hz), 2.68 (1H, dd, J=18, 5 Hz), 1.95–1.60 (5H, m), 1.60–1.10 (5H, m), 1.42 (9H, s).

Example 2(35)

(2S)-3-cyclohexylcarbomoyl-2-t-butoxycarbonylaminopropanoic acid.4-methoxybenzyl ester

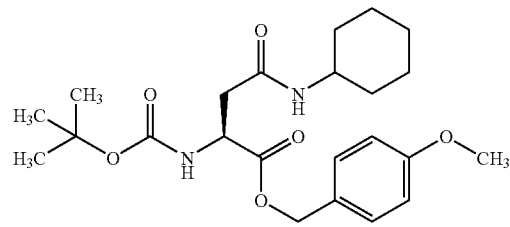

TLC: Rf 0.31 (ethyl acetate:hexane=1:3); NMR (CDCl₃): δ 7.28 (2H, d, J=9 Hz), 6.87 (2H, d, J=9 Hz), 5.85–5.70 (1H, m), 5.53–5.35 (1H, m), 5.14 (1H, d, J=12 Hz), 5.10 (1H, d, J=12 Hz), 4.55–4.43 (1H, m), 3.80 (3H, s), 3.78–3.58 (1H, m), 2.81 (1H, dd, J=15, 5 Hz), 2.66 (1H, dd, J=15, 5 Hz), 1.95–1.48 (5H, m), 1.48–0.94 (5H, m), 1.42 (9H, s).

Example 2(36)

(2S)-N-(4-methoxybenzyl)-3-cyclohexylcarbamoyl-2-t-butoxycarbonylamino-propanamide

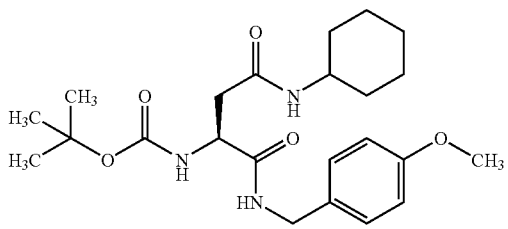

TLC: Rf 0.19 (ethyl acetate:hexane=1:3); NMR (CDCl₃): δ 7.25–7.10 (1H, m), 7.17 (2H, d, J=9 Hz), 6.84 (2H, d, J=9 Hz), 6.33–6.15 (1H, m), 5.87–5.70 (1H, m), 4.53–4.40 (1H, m), 4.36 (2H, d, J=6 Hz), 3.79 (3H, s), 3.78–3.58 (1H, m), 2.84 (1H, dd, J=15, 5 Hz), 2.51 (1H, dd, J=15, 5 Hz), 1.94–1.50 (5H, m), 1.50–0.97 (5H, m), 1.42 (9H, s).

Example 2(37)

(2S)-N-(4-methoxybenzyl)-3-cyclohexyloxycarbonyl-2-t-butoxycarbonylamino-propanamide

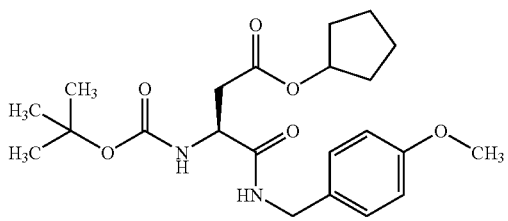

TLC: Rf 0.21 (ethyl acetate:hexane=1:3); NMR (CDCl₃): δ 7.18 (2H, d, J=9 Hz), 6.85 (2H, d, J=9 Hz), 6.80–6.70 (1H, m), 5.78–5.62 (1H, m), 5.23–5.08 (1H, m), 4.59–4.23 (3H, m), 3.80 (3H, s), 2.96 (1H, dd, J=18, 5 Hz), 2.65 (1H, dd, J=18, 8 Hz), 1.93–1.48 (8H, m), 1.42 (9H, s).

Example 2(38)

(2S)-3-cyclopentylcarbamoyl-2-t-butoxycarbonylaminopropanoic acid.4-methoxybenzyl ester

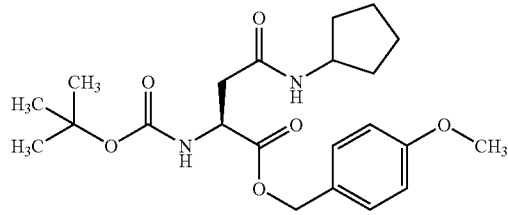

TLC: Rf 0.46 (ethyl acetate:hexane=1:1); NMR (CDCl₃): δ 7.28 (2H, d, J=9 Hz), 6.87 (2H, d, J=9 Hz), 5.83–5.73 (1H, m), 5.64–5.47 (1H, m), 5.14 (1H, d, J=12 Hz), 5.09 (1H, d, J=12 Hz), 4.56–4.40 (1H, m), 4.21–4.04 (1H, m), 3.81 (3H, s), 2.79 (1H, dd, J=15, 5 Hz), 2.65 (1H, dd, J=15, 5 Hz), 2.05–1.84 (2H, m), 1.75–1.48 (4H, m), 1.46–1.17 (2H, m), 1.42 (9H, s).

Example 2(39)

(2S)-N-(4-methoxybenzyl)-3-cyclopentylcarbamoyl-2-t-butoxycarbonylamino-propanamide

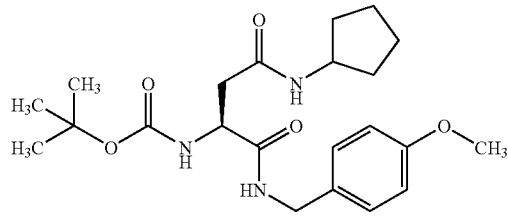

TLC: Rf 0.33 (methanol:methylene chloride=1:19); NMR (CDCl₃): δ 7.23–7.10 (1H, m), 7.17 (2H, d, J=9 Hz), 6.84 (2H, d, J=9 Hz), 6.32–6.15 (1H, m), 6.00–5.82 (1H, m), 4.51–4.31 (3H, m), 4.20–4.03 (1H, m), 3.79 (3H, s), 2.83 (1H, dd, J=15, 5 Hz), 2.50 (1H, dd, J=15, 8 Hz), 2.05–1.80 (2H, m), 1.75–1.46 (4H, m), 1.46–1.23 (2H, m), 1.42 (9H, s).

Example 2(40)

(2S)-3-cyclopentyloxycarbonyl-2-t-butoxycarbonylaminopropanoic acid.2-pyridylmethyl ester

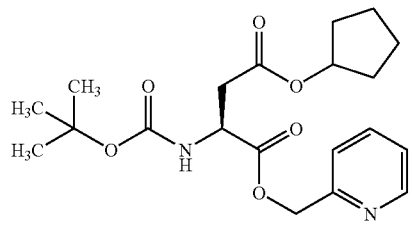

TLC: Rf 0.41 (hexane:ethyl acetate=2:1); NMR (CDCl₃): δ 8.58 (1H, d, J=4.6 Hz), 7.74–7.66 (1H, m), 7.37 (1H, d, J=7.8 Hz), 7.23 (1H, dd, J=4.6, 7.8 Hz), 5.55 (1H, d, J=8.8 Hz), 5.31 (2H, s), 5.20–5.12 (1H, m), 4.72–4.62 (1H, m), 3.02 (1H, dd, J=4.8, 16.8 Hz), 2.81 (1H, dd, J=4.8, 16.8 Hz), 1.84–1.56 (8H, m), 1.44 (9H, s).

Example 2(41)

(2S)-3-cyclopentyloxycarbonyl-2-t-butoxycarbonylaminopropanoic acid.4-t-butylbenzyl ester

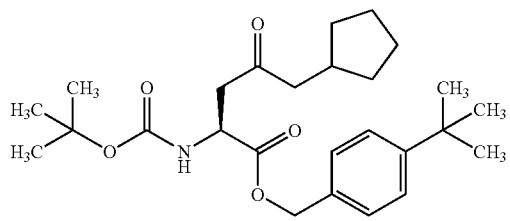

TLC: Rf 0.45 (hexane:ethyl acetate=6:1); NMR (CDCl$_3$): δ 7.38 (2H, d, J=8.6 Hz), 7.27 (2H, d, J=8.6 Hz), 5.49 (1H, d, J=8.6 Hz), 5.21–5.08 (3H, m), 4.62–4.53 (1H, m), 2.96 (1H, dd, J=4.8, 16.8 Hz), 2.77 (1H, dd, J=4.8, 16.8 Hz), 1.76–1.52 (8H, m), 1.43 (9H, s), 1.32 (9H, s).

Example 2(42)

(2S)-3-cyclopentyloxycarbonyl-2-t-butoxycarbonylaminopropanoic acid.2-methoxybenzyl ester

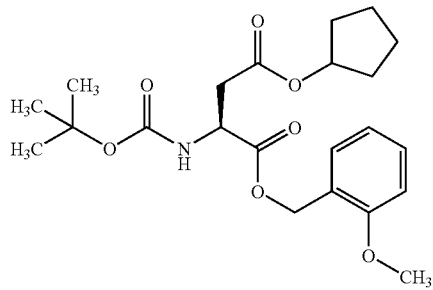

TLC: Rf 0.32 (hexane:ethyl acetate=4:1); NMR (CDCl$_3$): δ 7.34–7.26 (2H, m), 6.95 (1H, d, J=6.6 Hz), 6.86 (1H, d, J=8.4 Hz), 5.50 (1H, d, J=8.8 Hz), 5.23 (2H, s), 5.18–5.10 (1H, m), 4.65–4.56 (1H, m), 3.83 (3H, s), 2.96 (1H, dd, J=4.8, 16.8 Hz), 2.87 (1H, dd, J=4.8, 16.8 Hz), 1.84–1.45 (8H, m), 1.44 (9H, s).

Example 2(43)

(2S)-3-cyclopentyloxycarbonyl-2-t-butoxycarbonylaminopropanoic acid.3-methoxybenzyl ester

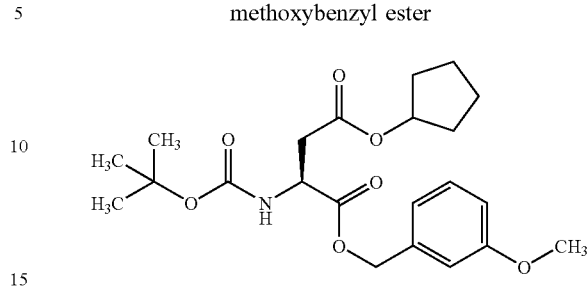

TLC: Rf 0.32 (hexane:ethyl acetate=4:1); NMR (CDCl$_3$): δ 7.31–7.23 (1H, m), 6.93–6.84 (3H, m), 5.50 (1H, d, J=8.8 Hz), 5.22–5.08 (3H, m), 4.64–4.54 (1H, m), 3.81 (3H, s), 2.97 (1H, dd, J=4.8, 16.8 Hz), 2.77 (1H, dd, J=4.8, 16.8 Hz), 1.86–1.50 (8H, m), 1.44 (9H, s).

Example 2(44)

(2S)-3-cyclopentyloxycarbonyl-2-t-butoxycarbonylaminopropanoic acid.3-pyridylmethyl ester

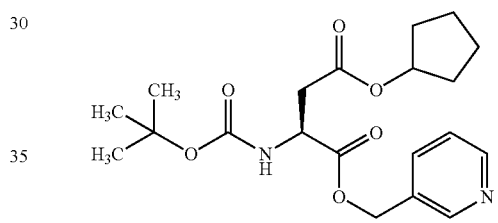

TLC: Rf 0.36 (hexane:ethyl acetate=1:1); NMR (CDCl$_3$): δ 8.60–8.57 (2H, m), 7.69 (1H, d, J=7.6 Hz), 7.33–7.27 (1H, m), 5.50 (1H, d, J=9.4 Hz), 5.28–5.10 (3H, m), 4.64–4.54 (1H, m), 2.97 (1H, dd, J=4.8, 17.0 Hz), 2.77 (1H, dd, J=4.8, 17.0 Hz), 1.86–1.49 (8H, m), 1.43 (9H, s).

Example 2(45)

(2S)-3-cyclopentyloxycarbonyl-2-t-butoxycarbonylaminopropanoic acid.4-pyridylmethyl ester

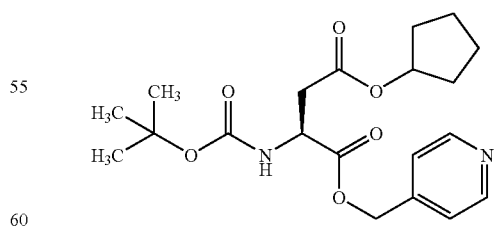

TLC: Rf 0.29 (hexane:ethyl acetate=1:1); NMR (CDCl$_3$): δ 8.60 (2H, d, J=6.0 Hz), 7.25 (2H, d, J=6.0 Hz), 5.54 (1H, d, J=8.8 Hz), 5.28–5.12 (3H, m), 4.70–4.61 (1H, m), 3.02 (1H, dd, J=4.8, 16.8 Hz), 2.80 (1H, dd, J=4.8, 16.8 Hz), 1.87–1.52 (8H, m), 1.45 (9H, s).

Example 2(46)

(2S)-3-cyclopentyloxycarbonyl-2-t-butoxycarbonylaminopropanoic acid.4-chlorobenzyl ester

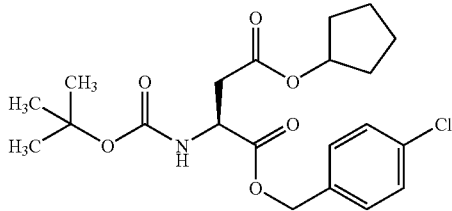

TLC: Rf 0.26 (hexane:ethyl acetate=6:1); NMR (CDCl$_3$): δ 7.33 (2H, d, J=8.8 Hz), 7.27 (2H, d, J=8.8 Hz), 5.49 (1H, d, J=8.0 Hz), 5.22–5.06 (3H, m), 4.63–4.54 (1H, m), 2.96 (1H, dd, J=4.6, 16.8 Hz), 2.76 (1H, dd, J=4.6, 16.8 Hz), 1.83–1.53 (8H, m), 1.44 (9H, s).

Example 2(47)

(2S)-3-cyclopentyloxycarbonyl-2-t-butoxycarbonylaminopropanoic acid.4-bromobenzyl ester

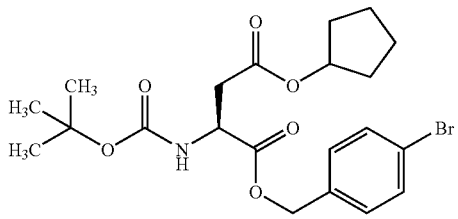

TLC: Rf 0.25 (hexane:ethyl acetate=6:1); NMR (CDCl$_3$): δ 7.48 (2H, d, J=8.6 Hz), 7.21 (2H, d, J=8.6 Hz), 5.49 (1H, d, J=8.4 Hz), 5.20–5.04 (3H, m), 4.63–4.54 (1H, m), 2.96 (1H, dd, J=4.6, 17.0 Hz), 2.76 (1H, dd, J=4.6, 17.0 Hz), 1.83–1.52 (8H, m), 1.43 (9H, s).

Example 2(48)

(2S)-4-(pyrrolidin-1-ylcarbonyl)-2-t-butoxycarbonylaminobutanoic acid.4-methoxybenzyl ester

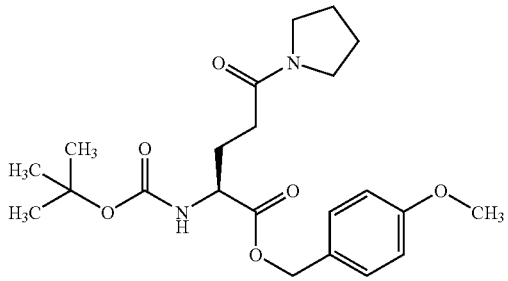

TLC: Rf 0.33 (methylene chloride:methanol=19:1); NMR (CDCl$_3$): δ 7.30 (2H, d, J=9 Hz), 6.87 (2H, d, J=9 Hz), 5.58–5.40 (1H, m), 5.15 (1H, d, J=13 Hz), 5.06 (1H, d, J=13 Hz), 4.38–4.20 (1H, m), 3.81 (3H, s), 3.48–3.38 (2H, m), 3.32–3.20 (2H, m), 2.16–1.78 (8H, m), 1.42 (9H, s).

Example 2(49)

(2S)-3-cyclohexylcarbonyloxy-2-t-butoxycarbonylaminopropanoic acid.4-methoxybenzyl ester

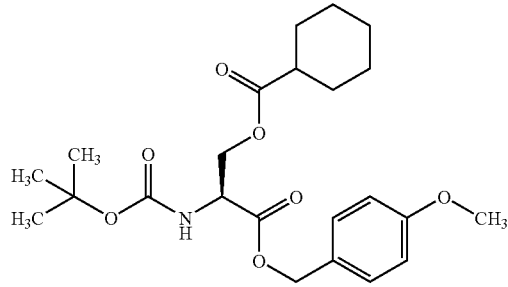

TLC: Rf 0.25 (ethyl acetate:hexane=1:5); NMR (CDCl$_3$): δ 7.29 (2H, d, J=9 Hz), 6.88 (2H, d, J=9 Hz), 5.28 (1H, d, J=8 Hz), 5.14 (1H, d, J=12 Hz), 5.09 (1H, d, J=12 Hz), 4.64–4.52 (1H, m), 4.45 (1H, dd, J=11, 4 Hz), 4.26 (1H, dd, J=11, 4 Hz), 3.81 (3H, s), 2.27–2.10 (1H, m), 1.89–1.53 (5H, m), 1.53–1.05 (5H, m), 1.44 (9H, s).

Example 2(50)

(2S)-3-cyclopentyloxycarbonyl-2-(N-methyl-N-t-butoxycarbonylamino)-propanoic acid.4-methoxybenzyl ester

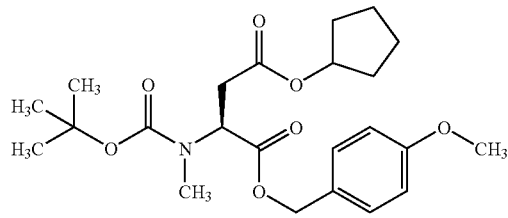

TLC: Rf 0.65 (ethyl acetate:hexane=1:2); NMR (CDCl$_3$): δ 7.31–7.25 (2H, m), 6.91–6.83 (2H, m), 5.23–5.01 (3H, m), 4.86–4.55 (1H, m), 3.81 (3H, s), 3.03 (1H, dd, J=16.2, 6.4 Hz), 2.91–2.83 (2H, m), 2.71 (1H, dd, J=16.2, 7.8 Hz), 1.96–1.52 (8H, m), 1.43–1.38 (9H, m).

Example 2(51)

(2S)-3-cyclohexyloxycarbonyl-2-(N-methyl-N-t-butoxycarbonylamino)-propanoic acid.4-methoxybenzyl ester

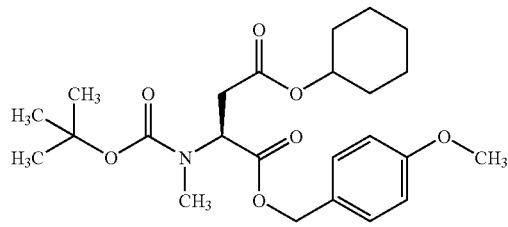

TLC: Rf 0.75 (ethyl acetate:hexane=1:2); NMR (CDCl$_3$): δ 7.27(2H, d, J=8.6 Hz), 6.87 (2H, d, J=8.6 Hz), 5.18–5.01 (2H, m), 4.88–4.55 (2H, m), 3.81 (3H, s), 3.05 (1H, dd, J=16.4, 6.4 Hz), 2.91–2.83 (3H, m), 2.74 (1H, dd, J=16.4, 8.4 Hz), 1.89–1.16 (19H, m).

Example 2(52)

(2R)-3-cyclohexylmethoxy-2-t-butoxycarbonylaminopropanoic acid.4-methoxybenzyl ester

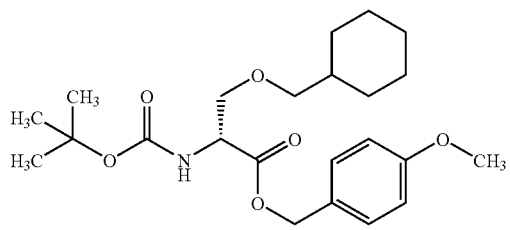

TLC: Rf 0.18 (ethyl acetate:hexane=1:8); NMR (CDCl$_3$): δ 7.32–7.25 (2H, m), 6.92–6.85 (2H, m), 5.36 (1H, br. d, J=8.8 Hz), 5.18 (1H, d, J=12.0 Hz), 5.06 (1H, d, J=12.0 Hz), 4.48–4.34 (1H, m), 3.81–3.76 (4H, m), 3.60 (1H, dd, J=9.8, 3.2 Hz), 3.19 (1H, dd, J=9.4, 6.6 Hz), 3.09 (1H, dd, J=9.4, 6.4 Hz), 1.74–1.13 (19H, m).

Example 2(53)

(2S)-3-cyclohexylmethoxy-2-t-butoxycarbonylaminopropanoic acid.4-methoxybenzyl ester

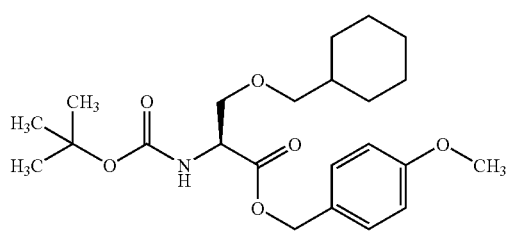

TLC: Rf 0.18 (ethyl acetate:hexane=1:8); NMR (CDCl$_3$): δ 7.32–7.25 (2H, m), 6.92–6.85 (2H, m), 5.36 (1H, br. d, J=8.8 Hz), 5.18 (1H, d, J=12.0 Hz), 5.06 (1H, d, J=12.0 Hz), 4.48–4.34 (1H, m), 3.81–3.76 (4H, m), 3.60 (1H, dd, J=9.8, 3.2 Hz), 3.19 (1H, dd, J=9.4, 6.6 Hz), 3.09 (1H, dd, J=9.4, 6.4 Hz), 1.74–1.13 (19H, m).

Example 2(54)

(2S)-3-cyclohexyloxycarbonyl-2-t-butoxycarbonylaminopropanoic acid.4-methoxyphenethyl ester TLC: Rf 0.60 (ethyl acetate:hexane=1:2); NMR (CDCl$_3$): δ 7.17–7.09 (2H, m), 6.88–6.80 (2H, m), 5.45 (1H. br. d, J=8.8 Hz), 4.78–4.65 (1H, m), 4.59–4.49 (1H, m), 4.40–4.22 (2H, m), 3.79 (3H, s), 2.99–2.85 (3H, m), 2.76 (1H, dd, J=17.0, 4.6 Hz), 1.86–1.24 (19H, m).

Example 2(55)

(2S)-3-cyclohexyloxycarbonyl-2-t-butoxycarbonylaminopropanoic acid.3-(4-methoxyphenyl)propyl ester TLC: Rf 0.67 (ethyl acetate:hexane=1:2); NMR (CDCl$_3$): δ 7.13–7.05 (2H, m), 6.86–6.79 (2H, m), 5.49 (1H, br. d, J=8.6 Hz), 4.81–4.70 (1H, m), 4.60–4.51 (1H, m), 4.24–4.04 (2H, m), 3.79 (3H, s), 2.98 (1H, dd, J=16.6, 4.6 Hz), 2.79 (1H, dd, J=16.6, 4.8 Hz), 2.62 (2H, t, J=7.4 Hz), 2.00–1.16 (21H, m).

Example 2(56)

(2S)-3-cyclohexyloxycarbonyl-2-t-butoxycarbonylaminopropanoic acid.furan-2-ylmethyl ester

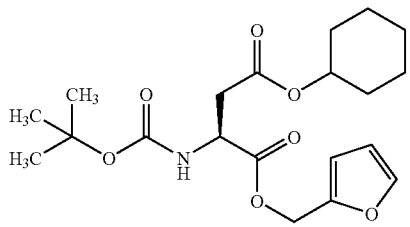

TLC: Rf 0.63 (ethyl acetate:hexane=1:2); NMR (CDCl$_3$): δ 7.42–7.40 (1H, m), 6.41 (1H, d, J=3.2 Hz), 6.35 (1H, dd, J=3.2, 2.0 Hz), 5.46 (1H, d, J=8.6 Hz), 5.12 (2H, s), 4.81–4.67 (1H, m), 4.62–4.53 (1H, m), 2.96 (1H, dd, J=16.8, 4.8 Hz), 2.77 (1H, dd, J=16.8, 5.0 Hz), 1.86–1.16 (19H, m).

Example 2(57)

(2S)-3-cyclohexyloxycarbonyl-2-t-butoxycarbonylaminopropanoic acid.thiophen-2-ylmethyl ester

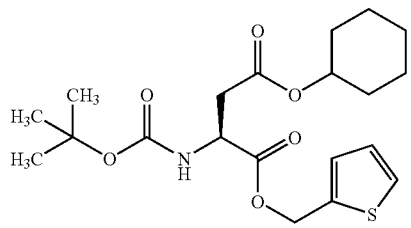

TLC: Rf 0.62 (ethyl acetate:hexane=1:2); NMR (CDCl$_3$): δ 7.32 (1H, dd, J=5.0, 1.4 Hz), 7.10–7.08 (1H, m), 6.98 (1H, dd, J=5.0, 3.2), 5.48 (1H, d, J=8.4 Hz), 5.37 (1H, d, J=12.8 Hz), 5.28 (1H, d, J=12.8 Hz), 4.76–4.66 (1H, m), 4.62–4.53 (1H, m), 2.97 (1H, dd, J=17.2, 4.8 Hz), 2.78 (1H, dd, J=17.2, 4.6 Hz), 1.86–1.22 (19H, m).

Example 2(58)

(2S)-3-cyclohexyloxycarbonyl-2-t-butoxycarbonylaminopanioc acid.4-(4-methoxyphenyl)butyl ester

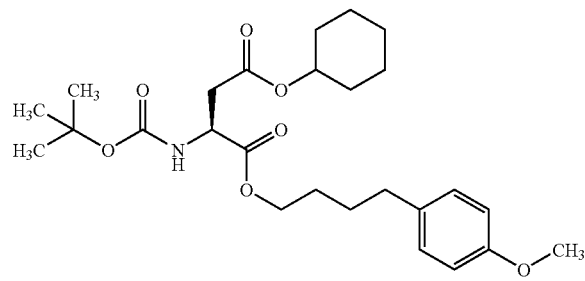

TLC: Rf 0.63 (ethyl acetate:hexane=1:2); NMR (CDCl$_3$): δ 7.12–7.05 (2H, m), 6.86–6.79 (2H, m), 5.47 (1H, d, J=8.8 Hz), 4.79–4.68 (1H, m), 4.58–4.49 (1H, m), 4.18–4.12 (2H, m), 2.96 (1H, dd, J=17.2, 4.0 Hz), 2.78 (1H, dd, J=17.2, 4.8 Hz), 2.61–2.54 (2H, m), 1.89–1.16 (23H, m).

Example 2(59)

(2S)-3-cyclohexyloxycarbonyl-2-t-butoxycarbonylaminopropanoic acid.cyclohexyl ester

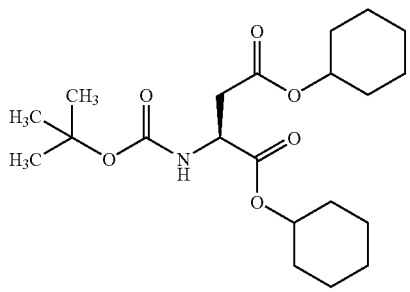

TLC: Rf 0.82 (ethyl acetate:hexane=1:2); NMR (CDCl$_3$): δ 5.48 (1H, d, J=8.4 Hz), 4.88–4.70 (2H, m), 4.56–4.47 (1H, m), 2.97 (1H, dd, J=16.6, 4.0 Hz), 2.78 (1H, dd, J=16.6, 4.8 Hz), 1.90–1.18 (29H, m).

Example 2(60)

(2S)-3-cyclohexyloxycarbonyl-2-t-butoxycarbonylaminopropanoic acid.methyl ester

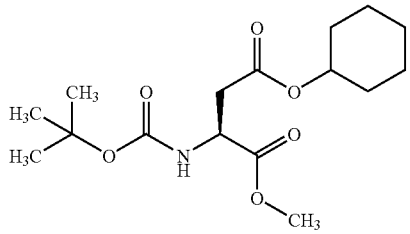

TLC: Rf 0.55 (ethyl acetate:hexane=1:2); NMR (CDCl$_3$): δ 5.47 (1H, d, J=8.0 Hz), 4.82–4.71 (1H, m), 4.62–4.53 (1H, m), 3.76 (3H, s), 2.97 (1H, dd, J=16.8, 4.6 Hz), 2.78 (1H, dd, J=16.8, 5.0 Hz), 1.90–1.18 (19H, m).

Example 2(61)

(2S)-N-(4-methoxyphenyl)-3-cyclohexyloxycarbonyl-2-t-butoxycarbonylamino-propanamide

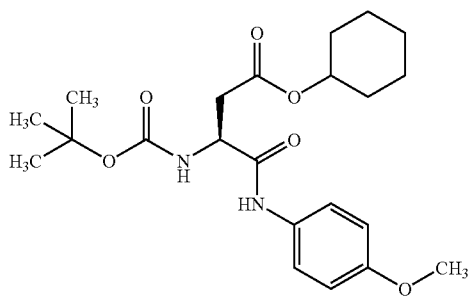

TLC: Rf 0.51 (ethyl acetate:hexane=1:2); NMR (CDCl$_3$): δ 8.41 (1H, br. s), 7.45–7.37 (2H, m), 6.89–6.81 (2H, m), 5.80 (1H, d, J=7.0 Hz), 4.84–4.73 (1H, m), 4.66–4.57 (1H, m), 3.79 (3H, s), 3.01 (1H, dd, J=16.8, 4.4 Hz), 2.73 (1H, dd, J=16.8, 7.0 Hz), 1.86–1.16 (19H, m).

Example 2(62)

(2S)-3-cyclobutyloxycarbonyl-2-t-butoxycarbonylaminopropanoic acid.4-methoxybenzyl ester

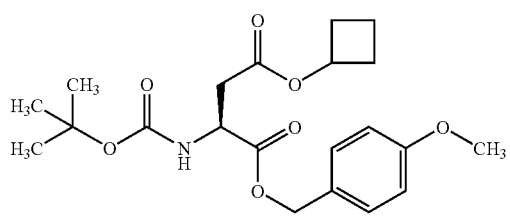

TLC: Rf 0.57 (ethyl acetate:hexane=1:2); NMR (CDCl$_3$): δ 7.31–7.24 (2H, m), 6.92–6.85 (2H, m), 5.48 (1H, d, J=9.0 Hz), 5.15 (1H, d, J=11.8 Hz), 5.07 (1H, d, J=11.8 Hz), 5.01–4.86 (1H, m), 4.62–4.52 (1H, m), 3.81 (3H, s), 2.96 (1H, dd, J=17.2, 5.2 Hz), 2.76 (1H, dd, J=17.2, 4.8 Hz), 2.37–2.22 (2H, m), 2.12–1.43 (13H, m).

Example 2(63)

(2S)-3-cyclohexyloxycarbonyl-2-t-butoxycarbonylaminopropanoic acid.diphenylmethyl ester

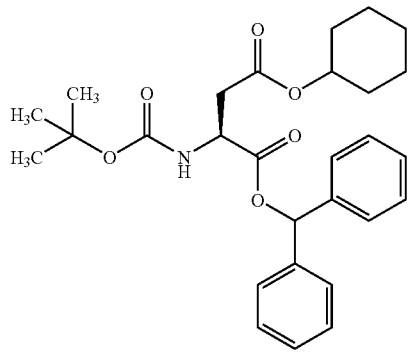

TLC: Rf 0.33 (ethyl acetate:hexane=1:5); NMR (CDCl$_3$): δ 7.45–7.18 (10H, m), 6.90 (1H, s), 5.56 (1H, d, J=8 Hz), 4.75–4.58 (2H, m), 3.03 (1H, dd, J=18, 5 Hz), 2.83 (1H, dd, J=18, 5 Hz), 1.80–1.08 (10H, m), 1.43 (9H, s).

Example 2(64)

(2S)-N-((1S)-2-phenyl-1-benzyloxycarbonylethyl)-3-cyclohexyloxycarbonyl-2-t-butoxycarbonylaminopropanamide

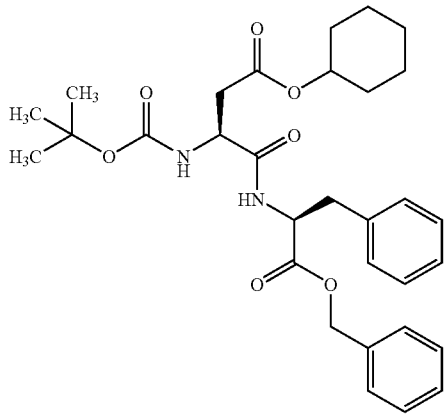

TLC: Rf 0.53 (ethyl acetate:hexane=1:2); NMR (CDCl$_3$): δ 7.39–7.19 (8H, m), 7.08–7.03 (2H, m), 6.97 (1H, d, J=8.4 Hz), 5.61 (1H, d, J=8.4 Hz), 5.14 (1H, d, J=12.4 Hz), 5.08 (1H, d, J=12.4 Hz), 4.90–4.69 (2H, m), 4.56–4.42 (1H, m), 3.10 (2H, d, J=6.0 Hz), 2.93 (1H, dd, J=17.2, 4.6 Hz), 2.62 (1H, dd, J=17.2, 6.2 Hz), 1.89–1.18 (19H, m).

Example 2(65)

(2S)-N-((1S)-1-benzyloxycarbonylethyl)-3-cyclohexyloxycarbonyl-2-t-butoxycarbonylaminopropanamide

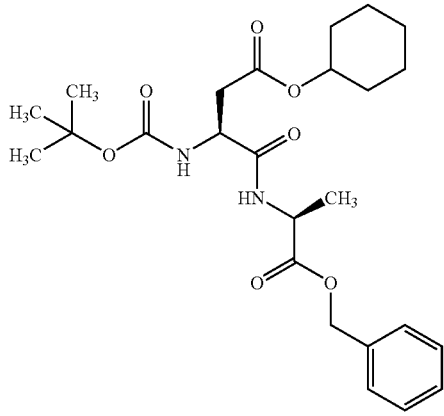

TLC: Rf 0.47 (ethyl acetate:hexane=1:2); NMR (CDCl$_3$): δ 7.41–7.31 (5H, m), 7.09 (1H, d, J=6.4 Hz), 5.67 (1H, d, J=7.8 Hz), 5.20 (1H, d, J=12.0 Hz), 5.13 (1H, d, J=12.0 Hz), 4.81–4.46 (3H, m), 2.96 (1H, dd, J=16.8, 4.4 Hz), 2.64 (1H, dd, J=16.8, 6.6), 1.92–1.18 (19H, m).

Example 2(66)

(2S)-3-benzyloxycarbonyl-2-t-butoxycarbonylaminopropanoic acid.4-methoxybenzyl ester

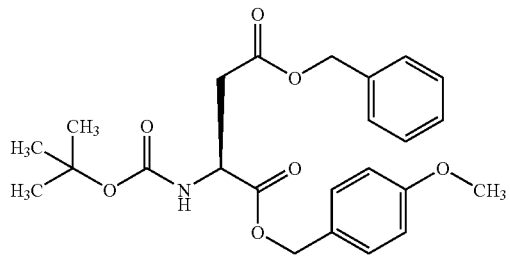

TLC: Rf 0.33 (ethyl acetate:hexane=1:3); NMR (CDCl$_3$): δ 7.40–7.27 (5H, m), 7.23 (2H, d, J=9 Hz), 6.85 (2H, d, J=9 Hz), 5.56–5.40 (1H, m), 5.07 (4H, s), 4.65–4.50 (1H, m), 3.80 (3H, s), 3.03 (1H, dd, J=18, 5 Hz), 2.85 (1H, dd, J=18, 5 Hz), 1.42 (9H, s).

Example 2(67)

(2S)-3-cycloheptyloxycarbonyl-2-t-butoxycarbonylaminopropanoic acid.4-methoxybenzyl ester

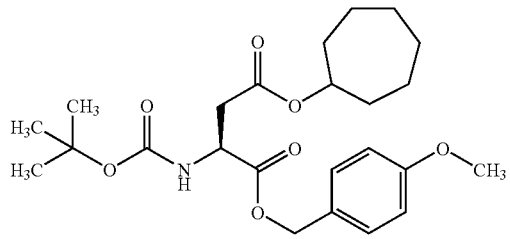

TLC: Rf 0.36 (hexane:ethyl acetate=4:1); NMR (CDCl$_3$): δ 7.27 (2H, d, J=8.4 Hz), 6.88 (2H, d, J=8.4 Hz), 5.48 (1H, d, J=8.4 Hz), 5.15 (1H, d, J=12.2 Hz), 5.07 (1H, d, J=12.2 Hz), 4.94–4.82 (1H, m), 4.61–4.52 (1H, m), 3.81 (3H, s), 2.95 (1H, dd, J=4.4, 16.8 Hz), 2.76 (1H, dd, J=4.8, 16.8 Hz), 1.90–1.75 (2H, m), 1.68–1.34 (19H, m).

Example 2(68)

(2S)-3-cyclooctyloxycarbonyl-2-t-butoxycarbonylaminopropanoic acid.4-methoxybenzyl ester

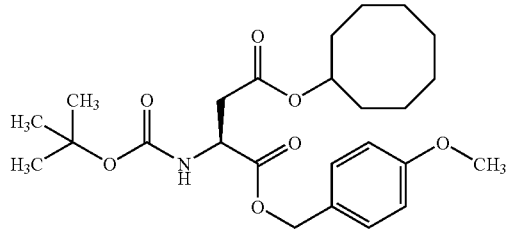

TLC: Rf 0.38 (hexane:ethyl acetate=4:1); NMR (CDCl$_3$): δ 7.27 (2H, d, J=8.4 Hz), 6.88 (2H, d, J=8.4 Hz), 5.49 (1H, d, J=8.4 Hz), 5.16 (1H, d, J=12.0 Hz), 5.07 (1H, d, J=12.0 Hz), 4.96–4.84 (1H, m), 4.61–4.52 (1H, m), 3.81 (3H, s), 2.94 (1H, dd, J=4.4, 16.8 Hz), 2.75 (1H, dd, J=4.8, 16.8 Hz), 1.75–1.46 (14H, m), 1.43 (9H, s).

Example 2(69)

(2S)-3-(adamantan-2-yloxycarbonyl)-2-t-butoxycarbonylaminopropanoic acid.4-methoxybenzyl ester

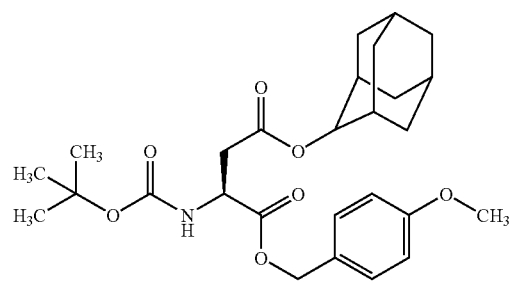

TLC: Rf 0.43 (hexane:ethyl acetate=4:1); NMR (CDCl$_3$): δ 7.27 (2H, d, J=8.6 Hz), 6.87 (2H, d, J=8.6 Hz), 5.51 (1H, d, J=8.4 Hz), 5.16 (1H, d, J=12.0 Hz), 5.06 (1H, d, J=12.0 Hz), 4.92–4.87 (1H, br), 4.63–4.54 (1H, m), 3.81 (3H, s), 3.01 (1H, dd, J=4.6, 16.8 Hz), 2.83 (1H, dd, J=4.8, 16.8 Hz), 2.01–1.67 (12H, m), 1.58–1.45 (2H, m), 1.43 (9H, s).

Example 2(70)

(2S)-3-(adamantan-1-yloxycarbonyl)-2-t-butoxycarbonylaminopropanoic acid.4-methoxybenzyl ester

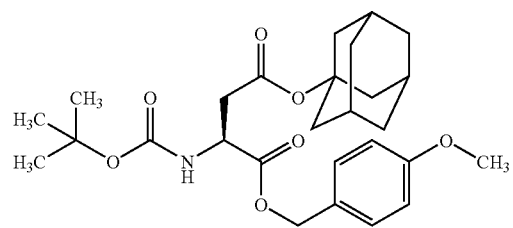

TLC: Rf 0.42 (hexane:ethyl acetate=4:1); NMR (CDCl$_3$): δ 7.29 (2H, d, J=8.6 Hz), 6.87 (2H, d, J=8.6 Hz), 5.49 (1H, d, J=8.4 Hz), 5.17 (1H, d, J=11.9 Hz), 5.05 (1H, d, J=11.9 Hz), 4.57–4.48 (1H, m), 3.80 (3H, s), 2.90 (1H, dd, J=4.4, 16.8 Hz), 2.69 (1H, dd, J=4.8, 16.8 Hz), 2.18–2.07 (3H, br), 2.01 (6H, d, J=3.0 Hz), 1.63 (6H, t, J=3.0 Hz), 1.44 (9H, s).

Example 2(71)

(2S, 3R)-3-cyclohexylcarbonyloxy-2-t-butoxycarbonylaminobutanoic acid.4-methoxybenzyl ester

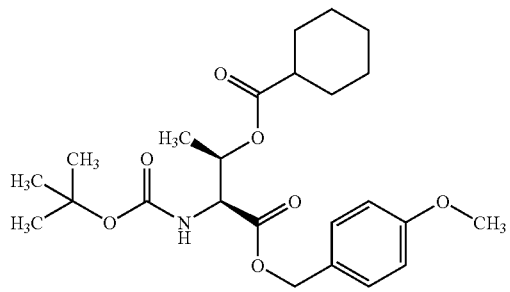

TLC: Rf 0.35 (ethyl acetate:hexane=1:5); NMR (CDCl$_3$): δ 7.29 (2H, d, J=9 Hz), 6.88 (2H, d, J=9 Hz), 5.46–5.30 (1H, m), 5.17 (1H, d, J=10 Hz), 5.06 (1H, d, J=13 Hz), 5.04 (1H, d, J=13 Hz), 4.44 (1H, dd, J=10, 2 Hz), 3.81 (3H, s), 2.20–2.00 (1H, m), 1.85–1.50 (5H, m), 1.46 (9H, s), 1.40–1.00 (5H, m), 1.25 (3H, d, J=6 Hz).

Example 2(72)

(2S)-N-((1S)-1-(4-methoxybenzyloxycarbonyl)ethyl)-3-cyclohexyloxycarbonyl-2-benzyloxycarbonylaminopropanamide

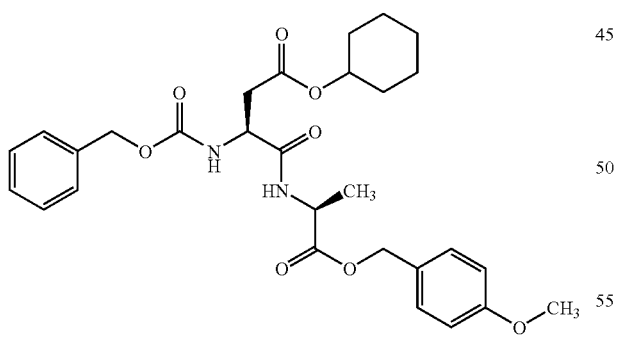

TLC: Rf 0.31 (ethyl acetate:hexane=1:2); NMR (CDCl$_3$): δ 7.39–7.24 (7H, m), 7.03 (1H, d, J=7.2 Hz), 6.92–6.85 (2H, m), 5.91 (1H, d, J=7.8 Hz), 5.16–5.03 (4H, m), 4.82–4.69 (1H, m), 4.64–4.47 (2H, m), 3.81 (3H, s), 2.99 (1H, dd, J=17.2, 4.0 Hz), 2.65 (1H, dd, J=17.2, 6.4 Hz), 1.84–1.18 (13H, m).

Example 2(73)

(2S)-N-((1S)-2-phenyl-1-(4-methoxybenzyloxycarbonyl)ethyl)-3-cyclohexyl-oxycarbonyl-2-benzyloxycarbonylaminopropanamide

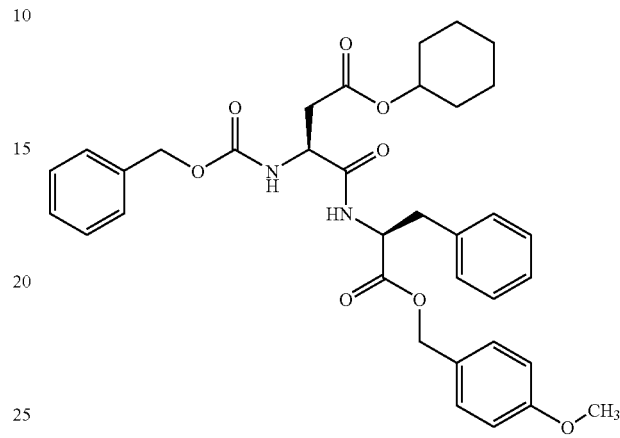

TLC: Rf 0.36 (ethyl acetate:hexane=1:2); NMR (CDCl$_3$): δ 7.38–7.33 (5H, m), 7.25–7.16 (5H, m), 7.05–6.84 (5H, m), 5.87 (1H, d, J=8.2 Hz), 5.15–4.98 (4H, m), 4.86–4.67 (2H, m), 4.59–4.50 (1H, m), 3.82 (3H, s), 3.06 (2H, d, J=6.0 Hz), 2.94 (1H, dd, J=17.2, 4.4 Hz), 2.62 (1H, dd, J=17.2, 6.6 Hz), 1.84–1.18 (10H, m).

Example 2(74)

(3S)-3-t-butoxycarbonylamino-3-(1,2,3,4-tetrahydroquinolin-1-ylcarbonyl)-propanoic acid.cyclohexyl ester

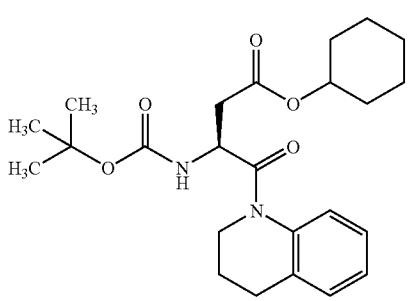

TLC: Rf 0.48 (ethyl acetate:hexane=1:2); NMR (DMSO-d$_6$): 7.50–7.05 (5H, m), 4.97 (1H, dd, J=15.4, 7.0 Hz), 4.67–4.52 (1H, m), 3.83–3.50 (2H, m), 2.70–2.38 (4H, m), 1.94–1.80 (2H, m), 1.75–1.18 (19H, m).

Example 2(75)

(3S)-3t-butoxycarbonylamino-3-(1,2,3,4-tetrahydroisoquinolin-2-yl-carbonyl)propanoic acid.cyclohexyl ester

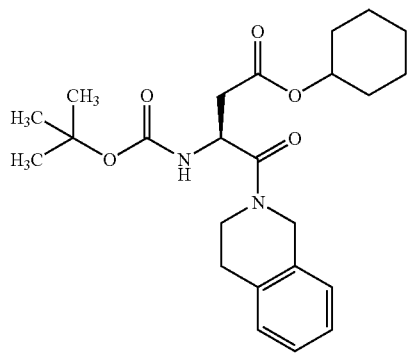

TLC: Rf 0.42 (ethyl acetate:hexane=1:2); NMR (CDCl$_3$): δ 7.23–7.11 (4H, m), 5.42 (1H, d, J=9.2 Hz), 5.14–5.03 (1H, m), 4.88–4.58 (3H, m), 4.02–3.71 (2H, m), 2.97–2.55 (4H, m), 1.92–1.08 (19H, m).

Example 2(76)

(2S)-N-methyl-N-(1,1-dimethyl-2-phenylethyl)-3-cyclohexyloxycarbonyl-2-t-butoxycarbonylaminopropanamide

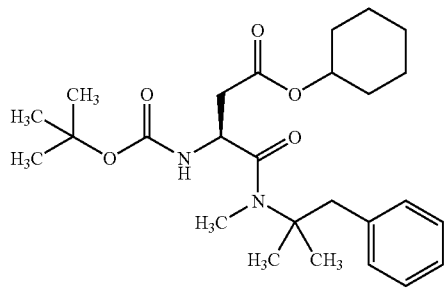

TLC: Rf 0.56 (ethyl acetate:hexane=1:2); NMR (CDCl$_3$): δ 7.31–7.09 (5H, m), 5.39 (1H, d, J=9.2 Hz), 4.99–4.88 (1H, m), 4.81–4.71 (1H, m), 3.35 (1H, d, J=13.2 Hz), 3.00 (1H, d, J=13.2 Hz), 2.73 (1H, dd, J=15.4, 6.6 Hz), 2.65 (3H, s), 2.54 (1H, dd, J=15.4, 6.6 Hz), 1.93–1.19 (25H, m).

Example 2(77)

(2S)-6-cyclohexylcarbonylamino-2-t-butoxycarbonylaminohexanoid acid.4-methoxybenzyl ester

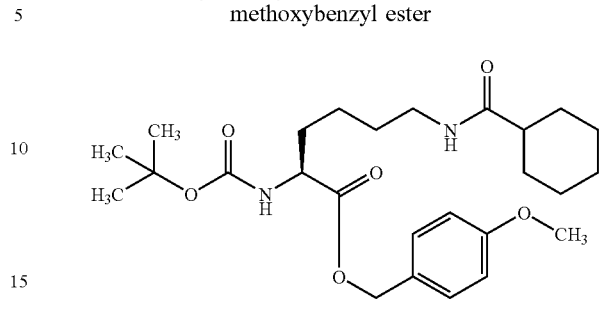

TLC: Rf 0.37 (ethyl acetate:hexane=1:1); NMR (CDCl$_3$): δ 7.32–7.25 (2H, m), 6.93–6.85 (2H, m), 5.55–5.44 (1H, m), 5.17–5.03 (3H, m), 4.35–4.21 (1H, m), 3.81 (3H, s), 3.23–3.14 (2H, m), 2.08–1.96 (1H, m), 1.88–1.18 (25H, m).

Example 2(78)

(2R)-3-(4-methoxybenzylthio)-2-t-butoxycarbonylaminopropanoic acid.cyclohexyl ester

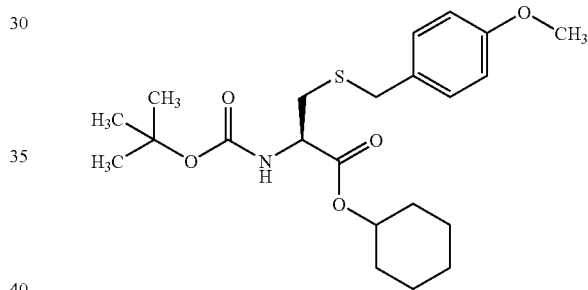

TLC: Rf 0.70 (ethyl acetate:hexane=1:2); NMR (CDCl$_3$): δ 7.28–7.19 (2H, m), 6.88–6.81 (2H, m), 5.29 (1H, d, J=7.4 Hz), 4.90–4.77 (1H, m), 4.54–4.44 (1H, m), 3.79 (3H, s), 3.70 (2H, s), 2.89 (1H, dd, J=14.0, 4.4 Hz), 2.79 (1H, dd, J=14.0, 6.0 Hz), 1.92–1.18 (19H, m).

Example 2(79)

(2R)-N-(4-methoxybenzyl)-3-(4-methoxybenzylthio)-2-t-butoxycarbonyl-aminopropanamide

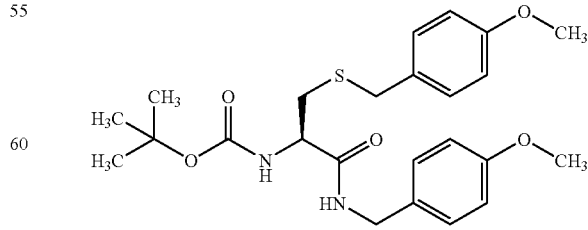

TLC: Rf 0.28 (ethyl acetate:hexane=1:2); NMR (CDCl$_3$): δ 7.26–7.16 (4H, m), 6.89–6.78 (4H, m), 6.53–6.41 (1H, m), 5.26 (1H, d, J=7.4 Hz), 4.38 (2H, d, J=5.4 Hz), 4.27–4.18 (1H, m), 3.79 (3H, s), 3.78 (3H, s), 3.68 (2H, s), 2.91 (1H, dd, J=14.0, 5.4 Hz), 2.74 (1H, dd, J=14.0, 6.8 Hz), 1.43 (9H, s).

Example 2(80)

(2R)-N-(4-methoxybenzyl)-3-cyclohexylmethylthio-2-t-butoxycarbonylamino-propanamide

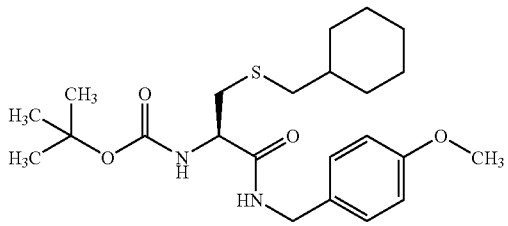

TLC: Rf 0.48 (ethyl acetate:hexane=1:2); NMR (CDCl₃): δ 7.25–7.18 (2H, m), 6.89–6.84 (2H, m), 6.68–6.60 (1H, m), 5.36 (1H, d, J=7.0 Hz), 4.39 (2H, d, J=5.6 Hz), 4.28–4.18 (1H, m), 3.80 (3H, s), 2.98 (1H, dd, J=14.0, 5.8 Hz), 2.82 (1H, dd, J=14.0, 7.0 Hz), 2.46 (1H, dd, J=12.8, 7.0 Hz), 2.39 (1H, dd, J=12.8, 6.6 Hz), 1.83–0.82 (20H, m).

Example 2(81)

(2S)-N-(4-methoxybenzyl)-3-benzyloxy-2-t-butoxycarbonylaminopropanamide

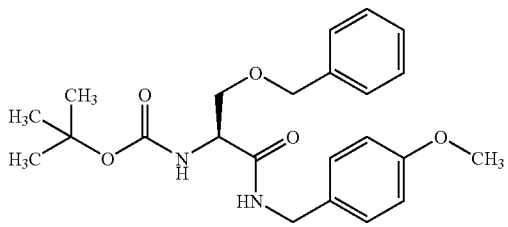

TLC: Rf 0.26 (ethyl acetate:hexane=1:2); NMR (CDCl₃): δ 7.38–7.12 (7H, m), 6.84–6.77 (2H, m), 6.69–6.61 (1H, m), 5.44–5.34 (1H, m), 4.56 (1H, d, J=11.4 Hz), 4.47 (1H, d, J=11.4 Hz), 4.39 (2H, d, J=5.8 Hz), 4.34–4.24 (1H, m), 3.95 (1H, dd, J=9.2, 3.8 Hz), 3.78 (3H, s), 3.59 (1H, dd, J=9.2, 6.6 Hz), 1.43 (9H, s).

Example 2(82)

(2S)-N-(4-dimethylaminobenzyl)-3-cyclohexylmethoxy-2-t-butoxycarbonyl-aminopropanamide

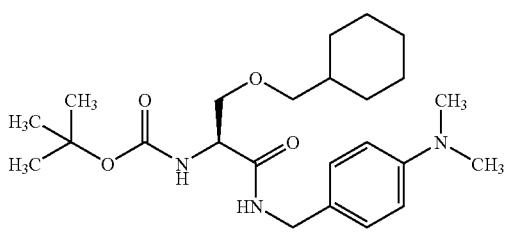

TLC: Rf 0.42 (ethyl acetate:hexane=1:2); NMR (CDCl₃): δ 7.18–7.11 (2H, m), 6.72–6.56 (3H, m), 5.46–5.30 (1H, m), 4.41 (1H, dd, J=14.2, 5.4 Hz), 4.30 (1H, dd, J=14.2, 5.2 Hz), 4.29–4.15 (1H, m), 3.82 (1H, dd, J=9.2, 3.6 Hz), 3.47 (1H, dd, J=9.2, 6.8), 3.31–3.16 (2H, m), 2.93 (6H, s), 1.75–0.74 (20H, m).

Example 2(83)

(2R)-N-(4-methoxybenzyl)-3-cyclohexylmethoxy-2-t-butoxycarbonylamino-propanamide

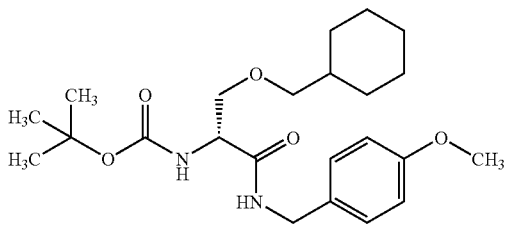

TLC: Rf 0.18 (ethyl acetate:hexane=1:2); NMR (CDCl₃): δ 7.23–7.16 (2H, m), 6.89–6.82 (2H, m), 6.78–6.68 (1H, m), 5.46–5.28 (1H, m), 4.45 (1H, dd, J=14.2, 5.4 Hz), 4.35 (1H, dd, J=14.2, 5.6 Hz), 4.28–4.16 (1H, m), 3.86–3.79 (4H, m), 3.47 (1H, dd, J=9.2, 7.0 Hz), 3.27 (1H, dd, J=8.8, 6.4 Hz), 3.20 (1H, dd, J=8.8, 6.2 Hz), 1.75–0.74 (20H, m).

Example 2(84)

(2S)-N-methyl-N-(4-methoxybenzyl)-3-cyclohexylmethoxy-2-t-butoxycarbonyl-aminopropanamide

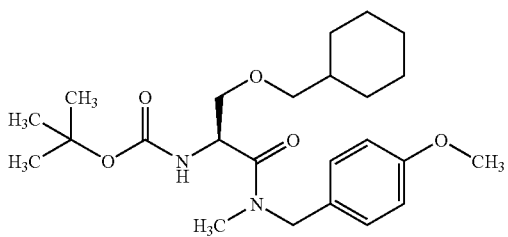

TLC: Rf 0.56 (ethyl acetate:hexane=1:2); NMR (CDCl₃): δ 7.21–7.13 (2H, m), 6.89–6.80 (2H, m), 5.47–5.38 (1H, m), 5.00–4.70 (2H, m), 4.45 (0.3H, d, J=16.6 Hz), 4.30 (0.7H, d, J=14.4 Hz), 3.79 (3H, s), 3.66–3.47 (2H, m), 3.22–3.14 (2H, m), 3.01 (2.1H, s), 2.89 (0.9H, s), 1.74–0.74 (20H, m).

Example 2(85)

(2RS)-N-(4-methoxybenzyl)-4-cyclohexylmethoxy-2-t-butoxycarbonylamino-butanamide

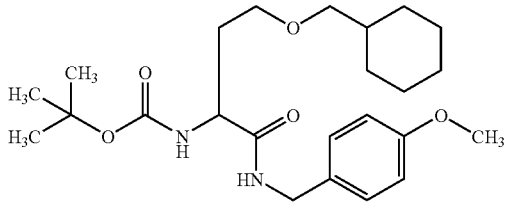

TLC: Rf 0.24 (ethyl acetate:hexane=1:2); NMR (CDCl₃): δ 7.20 (2H, d, J=9 Hz), 6.86 (2H, d, J=9 Hz), 6.83–6.68 (1H, m), 6.00–5.85 (1H, m), 4.39 (2H, d, J=6 Hz), 4.37–4.17 (1H, m), 3.80 (3H, s), 3.62–3.43 (2H, m), 3.13 (2H, d, J=6 Hz), 2.16–1.97 (2H, m), 1.80–1.00 (9H, m), 1.42 (9H, s), 1.00–0.70 (2H, m).

Example 2(86)

(2S)-N-(4-nitrobenzyl)-3-cyclohexylmethoxy-2-t-butoxycarbonylamino-propanamide

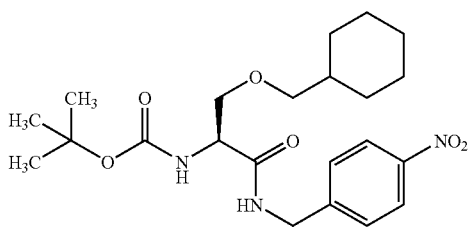

TLC: Rf 0.28 (ethyl acetate:hexane=1:2); NMR (CDCl$_3$): δ 8.22–8.14 (2H, m), 7.48–7.41 (2H, m), 7.02–6.94 (1H, m), 5.37 (1H, d, J=6.4 Hz), 4.64 (1H, dd, J=13.2, 5.8 Hz), 4.53 (1H, dd, J=13.2, 6.2 Hz), 4.34–4.22 (1H, m), 3.87 (1H, dd, J=9.2, 3.6 Hz), 3.52 (1H , dd, J=9.2, 6.6 Hz), 3.30 (1H, dd, J=9.2, 6.2 Hz), 3.24 (1H, dd, J=9.2, 6.0 Hz), 1.77–0.78 (20H, m).

Example 2(87)

(2S)-N-(4-methoxybenzyl)-3-(2-cyclohexenyloxy)-2-t-butoxycarbonylamino-propanamide

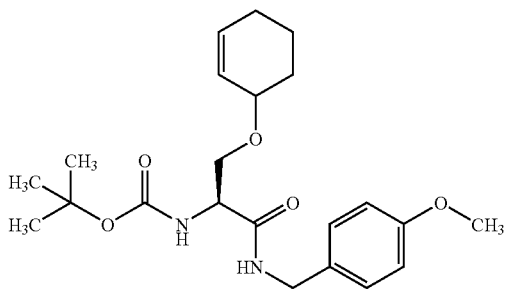

TLC: Rf 0.26 (ethyl acetate:hexane=1:2); NMR (CDCl$_3$): δ 7.20 (2H, d, J=9 Hz), 6.84 (2H, d, J=9 Hz), 6.84–6.59 (1H, m), 5.90–5.78 (1H, m), 5.74–5.60 (1H, m), 5.52–5.34 (1H, m), 4.41 (2H, d, J=6 Hz) 4.30–4.15 (1H, m), 4.00–3.83 (2H, m), 3.79 (3H, s), 3.64–3.48 (1H, m), 2.05–1.90 (2H, m), 1.90–1.35 (4H, m), 1.43 (9H, S).

Example 2(88)

(2S)-N-(4-methoxybenzyl)-3-cyclohexyloxy-2-t-butoxycarbonylamino-propanamide

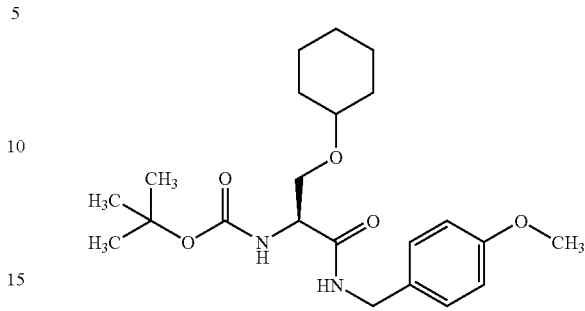

TLC: Rf 0.28 (ethyl acetate:hexane=1:2); NMR (CDCl$_3$): δ 7.20 (2H, d, J=9 Hz), 6.85 (2H, d, J=9 Hz), 6.85–6.70 (1H, m), 5.50–5.30 (1H, m), 4.41 (2H, d, J=6 Hz), 4.26–4.14 (1H, m), 3.88 (1H, dd, J=9, 14 Hz), 3.80 (3H, s), 3.50 (1H, dd, J=9, 7 Hz), 3.36–3.20 (1H, m), 1.90–1.05 (10H, m), 1.44 (9H, s).

Example 2(89)

(2S)-N-(4-methoxybenzyl)-3-cyclohexylmethylthio-2-t-butoxycarbonylamino-propanamide

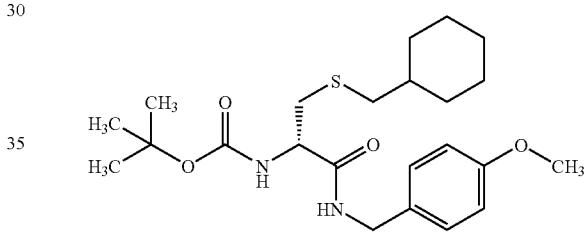

TLC: Rf 0.43 (ethyl acetate:hexane=1:2); NMR (CDCl$_3$): δ 7.25–7.18 (2H, m), 6.90–6.82 (2H, m), 6.68–6.58 (1H, m), 5.35 (1H, d, J=7.4 Hz), 4.40 (2H, d, J=6.0 Hz), 4.28–4.18 (1H, m), 3.80 (3H, s), 2.99 (1H, dd, J=13.6, 5.6 Hz), 2.82 (1H, dd, J=13.6, 7.0 Hz), 2.48 (1H, dd, J=12.8, 7.0), 2.39 (1H, dd, J=12.8, 6.6 Hz), 1.86–0.80 (20H, m).

Example 2(90)

(2R)-N-(4-methoxybenzyl)-3-cyclopentylmethylthio-2-t-butoxycarbonylamino-propanamide

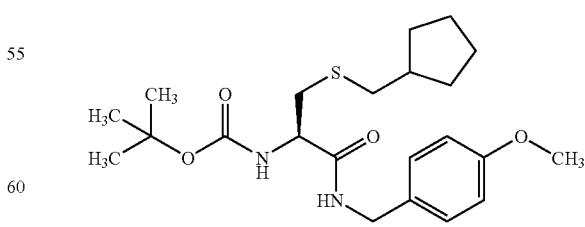

TLC: Rf 0.36 (ethyl acetate:hexane=1:2); NMR (CDCl$_3$): δ 7.25–7.18 (2H, m), 6.89–6.82 (2H, m), 6.68–6.59 (1H, m), 5.36 (1H, d, J=7.4 Hz), 4.39 (2H, d, J=5.6 Hz), 4.29–4.19 (1H, m), 3.80 (3H, s), 3.00 (1H, dd, J=13.6, 5.4 Hz), 2.84

(1H, dd, J=13.6, 6.6 Hz), 2.54 (2H, d, J=7.4 Hz), 2.10–1.95 (1H, m), 1.91–1.08 (17H, m).

Example 2(91)

(2S)-N-(4-methoxybenzyl)-3-cyclopentylmethoxy-2-t-butoxycarbonylamino-propanamide

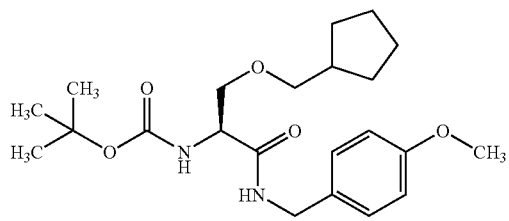

TLC: Rf 0.33 (ethyl acetate:hexane=1:2); NMR (CDCl$_3$): δ 7.25–7.16 (2H, m), 7.01–6.82 (2H, m), 6.81–6.69 (1H, m), 5.42 (1H, d, J=5.8 Hz), 4.44 (1H, dd, J=15.4, 6.0 Hz), 4.37 (1H, dd, J=15.4, 5.8 Hz), 4.29–4.18 (1H, m), 3.84 (1H, dd, J=9.2, 3.8 Hz), 3.80 (3H, s), 3.50 (1H, dd, J=9.2, 7.0 Hz), 3.37 (1H, dd, J=16.8, 7.4 Hz), 3.28 (1H, dd, J=16.8, 6.8 Hz), 2.14–1.99 (1H, m), 1.75–0.83 (17H, m).

Example 2(92)

(2S)-N-(4-methoxybenzyl)-3-cyclohexylcarbonylamino-2-t-butoxycarbonyl-aminopropanamide

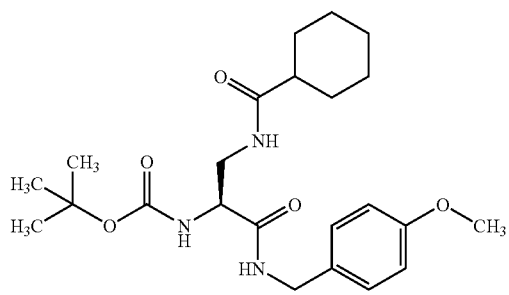

TLC: Rf 0.20 (ethyl acetate:hexane=1:1); NMR (CDCl$_3$+ CD$_3$OD): δ 7.22–7.14 (2H, m), 6.87–6.80 (2H, m), 4.40 (1H, d, J=14.8 Hz), 4.29 (1H, d, J=14.8 Hz), 4.25–4.20 (1H m), 3.78 (3H, s), 3.72–3.48 (2H, m), 2.09–1.97 (1H, m), 1.86–1.16 (19H, m).

Example 2(93)

(2S)-N-(4-methoxybenzyl)-4-(2-cyclohexenyloxy)-2-t-butoxycarbonylamino-butanamide

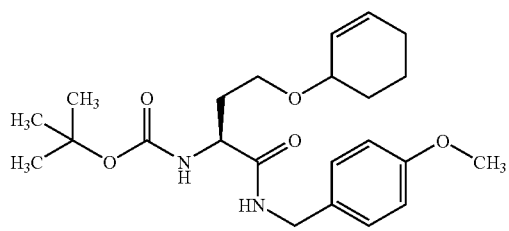

TLC: Rf 0.19 (ethyl acetate:hexane=1:2); NMR (CDCl$_3$): δ 7.24–7.15 (2H, m), 6.94–6.78 (3H, m), 5.94–5.74 (2H, m), 5.72–5.60 (1H, m), 4.50–4.15 (3H, m), 3.82–3.52 (3H, m), 3.80 (3H, s), 2.13–1.90 (4H, m), 1.80–1.35 (4H, m), 1.42 (9H, s).

Example 2(94)

(2S)-N-(4-methoxybenzyl)-4-cyclohexyloxy-2-t-butoxycarbonylamino-butanamide

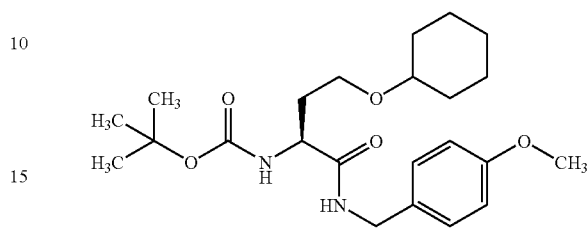

TLC: Rf 0.21 (ethyl acetate:hexane=1:2); NMR (CDCl$_3$): δ 7.25–7.15 (2H, m), 7.00–6.80 (3H, m), 6.03–5.88 (1H, m), 4.52–4.15 (3H, m), 3.80 (3H, s), 3.71–3.42 (2H, m), 3.26–3.08 (1H, m), 2.10–1.95 (2H, m), 1.85–1.05 (10H, m), 1.42 (9H, s).

Example 2(95)

(2S)-N-(4-methoxybenzyl)-3-cyclopentylmethylthio-2-t-butoxycarbonylamino-propanamide

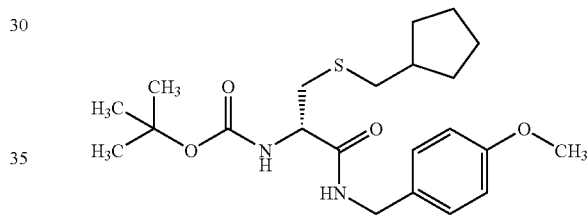

TLC: Rf 0.53 (ethyl acetate:chloroform=15:100); NMR (CDCl$_3$): δ 7.25–7.18 (2H, m), 6.90–6.82 (2H, m), 6.64 (1H, t, J=6.0 Hz), 5.36 (1H, d, J=7.2 Hz), 4.39 (2H, d, J=6.0 Hz), 4.29–4.19 (1H, m), 3.80 (3H, s), 3.00 (1H, dd, J=14.0, 5.4 Hz), 2.84 (1H, dd, J=14.0, 7.0 Hz), 2.54 (2H, d, J=7.0 Hz), 2.13–1.91 (1H, m), 1.90–1.08 (17H, m).

Example 2(96)

(2R)-N-(4-nitrobenzyl)-3-cyclohexylmethoxy-2-t-butoxycarbonylamino-propanamide

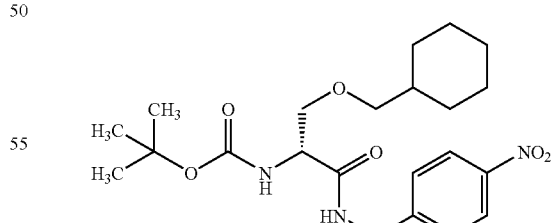

TLC: Rf 0.21 (ethyl acetate:hexane=1:2); NMR (CDCl$_3$): δ 8.21–8.14 (2H, m), 7.48–7.41 (2H, m), 7.03 (1H, t, J=5.8 Hz), 5.39 (1H, d, J=6.2 Hz), 4.63 (1H, dd, J=16.2, 5.8 Hz), 4.53 (1H, dd, J=16.2, 6.2 Hz), 4.36–4.22 (1H, m), 3.87 (1H, dd, J=9.0, 3.6 Hz), 3.53 (1H, dd, J=9.2, 6.6 Hz), 3.30 (1H, dd, J=9.2, 6.2 Hz), 3.24 (1H, dd, J=9.2, 6.2 Hz), 1.79–0.76 (20H, m).

Example 2(97)

(2R)-N-(4-nitrobenzyl)-3-cyclohexylmethylthio-2-t-butoxycarbonylamino-propanamide

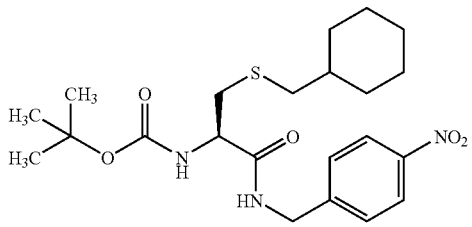

TLC: Rf 0.40 (ethyl acetate:hexane=1:2); NMR (CDCl$_3$): δ 8.19–8.14 (2H, m), 7.48–7.43 (2H, m), 7.12 (1H, t, J=6.0 Hz), 5.44 (1H, d, J=7.2 Hz), 4.66–4.47 (2H, m), 4.36–4.25 (1H, m), 2.98 (1H, dd, J=13.8, 5.8 Hz), 2.86 (1H, dd, J=13.8, 6.6 Hz), 2.56–2.33 (2H, m), 1.95–0.71 (20H, m).

Example 2(98)

(2R)-N-(furan-2-ylmethyl)-3-cyclohexylmethylthio-2-t-butoxycarbonylamino-propanamide

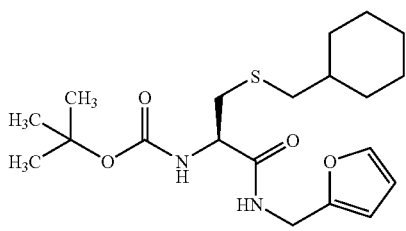

TLC: Rf 0.60 (ethyl acetate:hexane=1:2); NMR (CDCl$_3$): δ 7.37–7.34 (1H, m), 6.76–6.71 (1H, m), 6.33 (1H, dd, J=5.0, 1.8 Hz), 6.26–6.23 (1H, m), 5.35 (1H, d, J=7.2 Hz), 4.51 (1H, dd, J=15.4, 5.4 Hz), 4.40 (1H, dd, J=5.4, 5.4 Hz), 4.28–4.18 (1H, m), 2.98 (1H, dd, J=13.8, 5.4 Hz), 2.81 (1H, dd, J=13.8, 7.0 Hz), 2.45 (1H, dd, J=12.6, 7.0 Hz), 2.39 (1H, dd, J=12.6, 6.6 Hz), 1.88–0.78 (20H, m).

Example 2(99)

(2R)-N-(4-dimethylaminobenzyl)-3-cyclohexylmethylthio-2-t-butoxycarbonyl-aminopropanamide

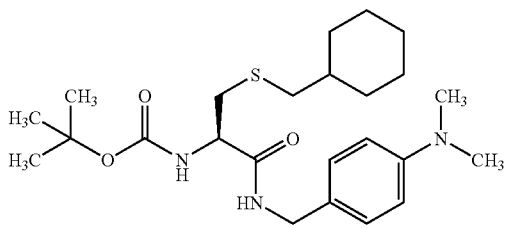

TLC: Rf 0.43 (ethyl acetate:hexane=1:2); NMR (CDCl$_3$): δ 7.20–7.12 (2H, m), 6.73–6.67 (2H, m), 6.55–6.51 (1H, m), 5.35 (1H, d, J=7.4 Hz), 4.44–4.17 (3H, m), 2.98 (1H, dd, J=13.8, 5.4 Hz), 2.94 (6H, s), 2.82 (1H, dd, J=13.8, 7.0 Hz), 2.51–2.34 (2H, m), 1.88–0.79 (20H, m).

Example 2(100)

(2R)-2-t-butoxycarbonylamino-3-cyclohexylmethylthiopropanoic acid.4-methoxybenzyl ester

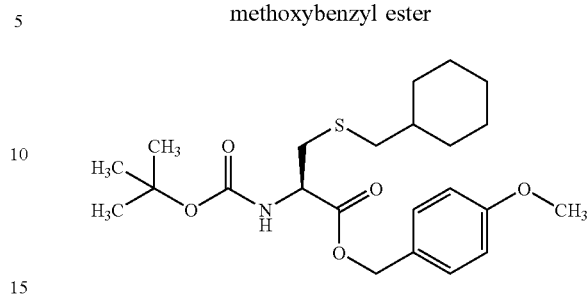

TLC: Rf 0.68 (ethyl acetate:hexane=1:2); NMR (CDCl$_3$): δ 7.34–7.25 (2H, m), 6.92–6.85 (2H, m), 5.36 (1H, d, J=8.0 Hz), 5.16 (1H, d, J=11.6 Hz), 5.08 (1H, d, J=11.6 Hz), 4.57–4.48 (1H, m), 3.81 (3H, s), 2.93 (2H, d, J=4.8 Hz), 2.35 (2H, d, J=7.0 Hz), 1.85–0.75 (20H, m).

Example 2(101)

(2R)-N-(4-methoxycyclohexylmethyl)-2-t-butoxycarbonylamino-3-cyclohexyl-methylthiopropanamide

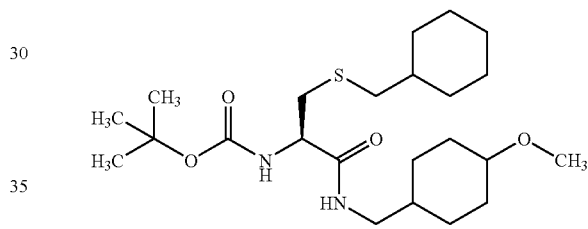

(The relative configuration of cyclohexyl ring substituted by methoxy group is not determined, but the above compound is a single compound. This compound is the isomer of the compound prepared in Example 2(102).)

TLC: Rf 0.40 (ethyl acetate:hexane=1:2); NMR (CDCl$_3$): δ 6.47 (1H, t, J=6.0 Hz), 5.37 (1H, d, J=7.4 Hz), 4.22–4.12 (1H, m), 3.46–3.36 (1H, m), 3.29 (3K, s), 3.17–3.09 (2H, m), 2.95 (1H, dd, J=13.6, 5.6 Hz), 2.78 (1H, dd, J=13.6, 6.8 Hz), 2.54–2.38 (2H, m), 2.00–0.81 (29H, m).

Example 2(102)

(2R)-N-(4-methoxycyclohexylmethyl)-2-t-butoxycarbonylamino-3-cyclohexyl-methylthiopropanamide

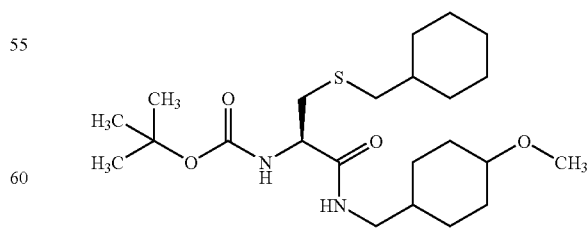

(The relative configuration of cyclohexyl ring substituted by methoxy group is not determined, but the above compound is a single compound. This compound is the isomer of the compound prepared in Example 2(101).)

TLC: Rf 0.30 (ethyl acetate:hexane=1:2); NMR (CDCl₃): δ 6.46 (1H, t, J=5.6 Hz), 5.36 (1H, d, J=7.0 Hz), 4.22–4.12 (1H, m), 3.34 (3H, s), 3.17–2.91 (4H, m), 2.79 (1H, dd, J=13.8, 7.0 Hz), 2.54–2.38 (2H, m), 2.15–2.01 (2H, m), 1.89–0.82 (27H, m).

Example 2(103)

(2R)-N-(4-phenoxybenzyl)-2-t-butoxycarbonylamino-3-cyclohexylmethyl-thiopropanamide

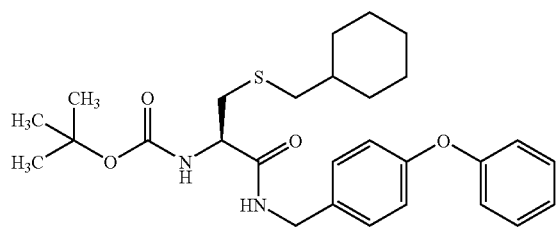

NMR (CDCl₃): δ 7.39–7.22 (m, 4H), 7.15–7.06 (m, 1H), 7.03–6.93 (m, 4H), 6.70 (t, J=5.3 Hz, 1H), 5.35 (d, J=6.8 Hz, 1H), 4.44 (d, J=6.0 Hz, 2H), 4.30–4.20 (m, 1H), 2.99 (dd, J=14.0, 5.6 Hz, 1H), 2.83 (dd, J=14.0, 7.0 Hz, 1H), 2.52–2.36 (m, 2H), 1.88–0.79 (m, 20H).

Example 2(104)

(2R)-N-((1S)-1-(4-nitrophenyl)ethyl)-2-t-butoxycarbonylamino-3-cyclohexyl-methylthiopropanamide

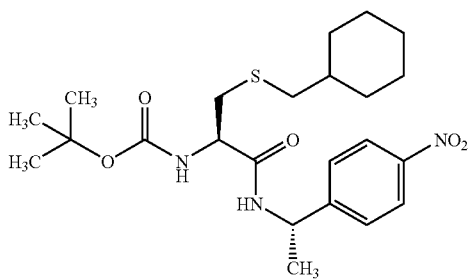

TLC: Rf 0.46 (ethyl acetate:hexane=1:2); NMR (CDCl₃): δ 8.25–8.15 (2H, m), 7.54–7.45 (2H, m), 6.84 (1H, d, J=7 Hz), 5.36 (1H, d, J=7 Hz), 5.15 (1H, quintet, J=7 Hz), 4.21 (1H, td, J=7, 5 Hz), 2.93 (1H, dd, J=14, 5 Hz), 2.79 (1H, dd, J=14, 7 Hz), 2.44 (2H, d, J=7 Hz), 1.88–0.78 (11H, m), 1.52 (3H, d, J=7 Hz), 1.46 (9H, s).

Example 2(105)

(2R)-N-((1R)-1-(4-nitrophenyl)ethyl)-2-t-butoxycarbonylamino-3-cyclohexyl-methylthiopropanamide

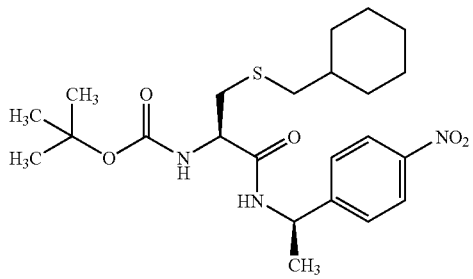

TLC: Rf 0.47 (ethyl acetate:hexane=1:2); NMR (CDCl₃): δ 8.22–8.15 (2H, m), 7.51–7.44 (2H, m), 6.89 (1H, d, J=7.8 Hz), 5.32 (1H, d, J=7.0 Hz), 5.21–5.06 (1H, m), 4.27–4.17 (1H, m), 2.95 (1H, dd, J=14.0, 5.8 Hz), 2.80 (1H, dd, J=14.0, 7.0 Hz), 2.44 (1H, dd, J=12.4, 6.8 Hz), 2.38 (1H, dd, J=12.4, 6.6 Hz), 1.88–0.80 (23H, m).

Example 2(106)

(2R)-N-methyl-N-(4-nitrobenzyl)-2-t-butoxycarbonylamino-3-cyclohexyl-methylthiopropanamide

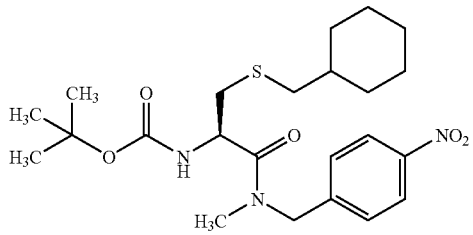

TLC: Rf 0.37 (ethyl acetate:hexane=1:2); NMR (CDCl₃): δ 8.25–8.16 (2H, m), 7.48–7.41 (2H, m), 5.38–5.25 (1H, m), 4.95–4.60 (3H, m), 3.14 (2.33H, s), 2.98 (0.67H, s), 2.96–2.66 (2H, m), 2.46 (1.56H, d, J=6.6 Hz), 2.33 (0.44H, d, J=6.6 Hz), 1.88–0.81 (20H, m).

Example 2(107)

(2R)-N-(1-(4-methoxyphenyl)-1-methylethyl)-2-t-butoxycarbonylamino-3-cyclohexylmethylthiopropanamide

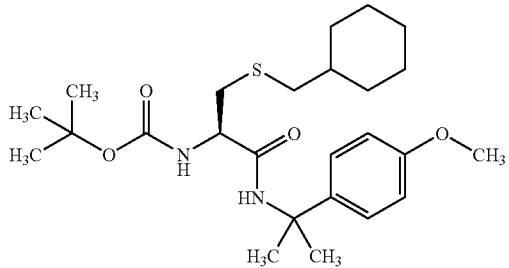

TLC: Rf 0.21 (ethyl acetate:hexane=1:5); NMR (CDCl₃): δ 7.37–7.26 (2H, m), 6.89–6.79 (2H, m), 6.70 (1H, bs), 5.36

(1H, d, J=8 Hz), 4.11 (1H, td, J=7, 5 Hz), 3.80 (3H, s), 2.91 (1H, dd, J=14, 5 Hz), 2.75 (1H, dd, J=14, 7 Hz), 2.47 (2H, d, J=7 Hz), 1.90–0.80 (11H, m), 1.70 (3H, s), 1.69 (3H, s), 1.47 (9H, s).

Example 2(108)

(2R)-N-(1-methyl-1-(4-nitrophenyl)ethyl)-2-t-butoxycarbonylamino-3-cyclohexylmethylthiopropanamide

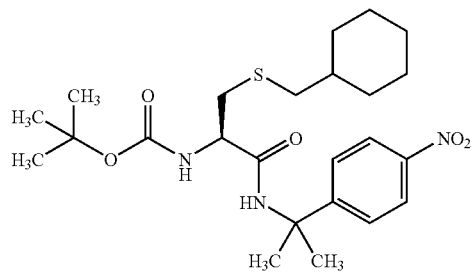

TLC: Rf 0.34 (ethyl acetate:hexane=1:3); NMR (CDCl$_3$): δ 8.22–8.12 (2H, m), 7.60–7.49 (2H, m), 6.89 (1H, bs), 5.31 (1H, d, J=8 Hz), 4.14 (1H, td, J=7, 5 Hz), 2.90 (1H, dd, J=14, 5 Hz), 2.75 (1H, dd, J=14, 7 Hz), 2.47 (2H, d, J=7 Hz), 1.90–0.80 (11H, m), 1.71 (3H, s), 1.70 (3H, s), 1.50 (9H, s).

Example 2(109)

(2S)-N-((1R)-1-(4-nitrophenyl)ethyl)-2-t-butoxycarbonylamino-3-cyclohexyl-methylthiopropanamide

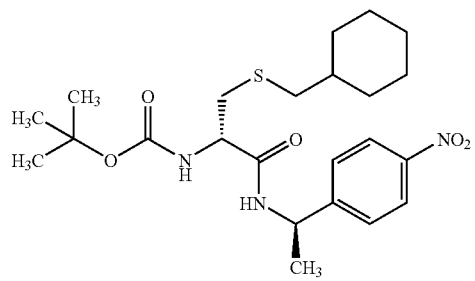

TLC: Rf 0.37 (ethyl acetate:hexane=1:2); NMR (CDCl$_3$): δ 8.23–8.16 (2H, m), 7.53–7.46 (2H, m), 6.83 (1H, d, J=7.4 Hz), 5.36 (1H, d, J=7.4 Hz), 5.22–5.08 (1H, m), 4.25–4.16 (1H, m), 2.94 (1H, dd, J=13.6, 5.6 Hz) 2.78 (1H, dd, J=13.6, 7.0 Hz), 2.44 (2H, d, J=6.8 Hz), 1.88–0.80 (23H, m).

Example 2(110)

(2R)-N-methyl-N-(4-methoxybenzyl)-2-t-butoxycarbonylamino-3-cyclohexyl-methylthiopropanamide

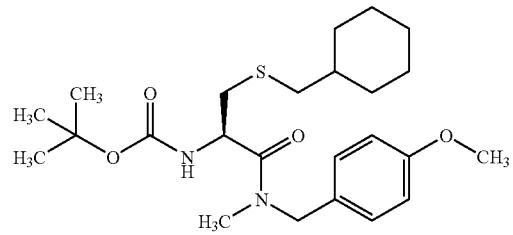

TLC: Rf 0.44 (ethyl acetate:hexane=1:2);

Example 2(111)

(2R)-N-(4-methoxybenzyl)-3-cyclohexylmethylthio-2-(N'-methyl-N'-(t-butoxy-carbonyl)amino) propanamide

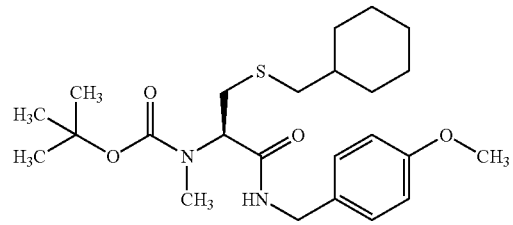

TLC: Rf 0.71 (hexane:ethyl acetate=1:1);

Example 2(112)

(2R)-N-(4-benzyloxybenzyl)-2-t-butoxycarbonylamino-3-cyclohexyl-methylthiopropanamide

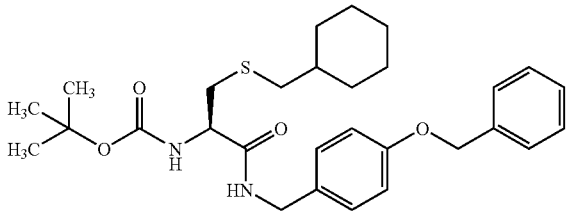

TLC: Rf 0.54 (ethyl acetate:hexane=1:2); NMR (CDCl$_3$): δ 7.46–7.15 (m, 7H), 6.98–6.88 (m, 2H), 6.64 (t, J=6.0 Hz, 1H), 5.35 (d, J=6.6 Hz, 1H), 5.05 (s, 2H), 4.39 (d, J=5.4 Hz, 2H), 4.28–4.18 (m, 1H), 2.98 (dd, J=3.8, 5.8 Hz, 1H), 2.82 (dd, J=13.8, 7.0 Hz, 1H), 2.42 (d, J=7.8 Hz, 2H), 1.88–0.76 (m, 20H).

Example 2(113)

(2R)-N-(3-benzyloxy-4-methoxybenzyl)-2-t-butoxycarbonylamino-3-cyclohexylmethylthiopropanamide

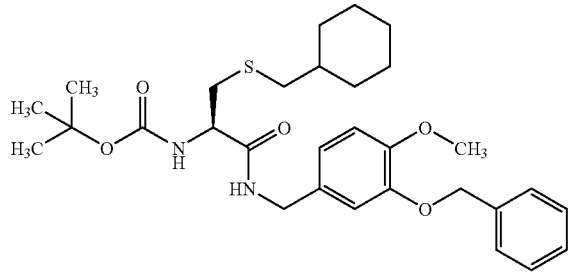

TLC: Rf 0.33 (hexane:ethyl acetate=2:1); NMR (CDCl$_3$): δ 7.47–7.30 (m, 5H), 6.86–6.84 (m, 3H), 6.60 (t, J=6.0 Hz, 1H) 5.31 (d, J=6.8 Hz, 1H), 5.14 (s, 2H), 4.35 (d, J=6.0 Hz, 2H), 4.26–4.16 (m, 1H), 3.87 (s, 3H), 2.96 (dd, J=13.6, 5.6 Hz, 1H), 2.80 (dd, J=13.6, 6.6 Hz, 1H), 2.50–2.34 (m, 2H), 1.85–1.57 (m, 5H), 1.53–1.35 (m, 10H), 1.33–0.78 (m, 5H).

Example 2(114)

N-((1R)-2-cyclohexylmethylthio-1-(4-phenylpiperazin-1-ylcarbonyl)ethyl)-carbamide acid.t-butyl ester

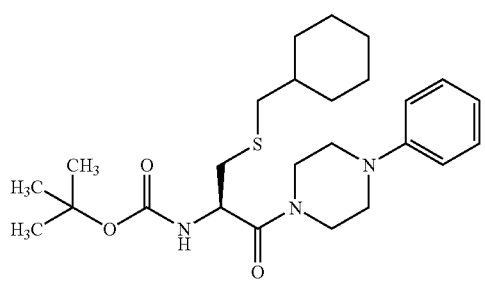

TLC: Rf 0.49 (ethyl acetate:hexane=1:2); NMR (CDCl$_3$): δ 7.33–7.25 (m, 2H), 6.95–6.89 (m, 3H), 5.41 (d, J=8.7 Hz, 1H), 4.86–4.78 (m, 1H), 3.82–3.76 (m, 4H), 3.26–3.17 (m, 4H), 2.87 (dd, J=13.5, 7.5 Hz, 1H), 2.76 (dd, J=13.5, 6.0 Hz, 1H), 2.44 (d, J=6.9 Hz, 2H), 1.84–0.86 (m, 20H).

Example 2(115)

(2R)-N-(2-phenoxypyridin-5-yl)-2-t-butoxycarbonylamino-3-cyclohexyl-methylthiopropanamide

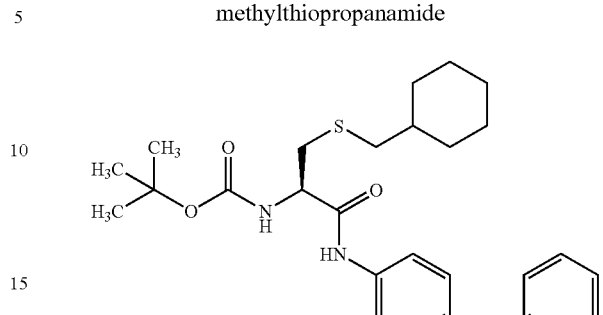

TLC: Rf 0.56 (ethyl acetate:hexane=1:2); NMR (CDCl$_3$): δ 8.53 (br. s, 1H), 8.20 (d, J=3.0 Hz, 1H), 8.07 (dd, J=9.0, 2.8 Hz 1H), 7.44–7.34 (m, 2H), 7.22–7.09 (m, 3H), 6.89 (d, J=9.2 Hz, 1H), 5.47 (d, J=7.2 Hz, 1H), 4.42–4.32 (m, 1H), 3.04 (dd, J=13.8, 6.2 Hz, 1H), 2.88 (dd, J=13.8, 7.0 Hz, 1H), 2.48 (d, J=6.6 Hz, 2H), 1.90–0.79 (m, 20H).

Example 2(116)

(2R)-N-(2-phenoxypyridin-5-ylmethyl)-2-t-butoxycarbonylamino-3-cyclohexyl-methylthiopropanamide

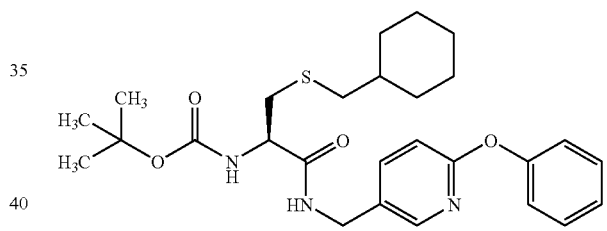

TLC: Rf 0.59 (ethyl acetate:hexane=1:1); NMR (CDCl$_3$): δ 8.11–8.07 (m, 1H), 7.66 (dd, J=8.4, 2.2 Hz, 1H), 7.46–7.35 (m, 2H), 7.25–7.08 (m, 4H), 6.87 (d, J=8.4 Hz, 1H), 6.82–6.74 (m, 1H), 5.34 (d, J=7.2 Hz, 1H), 4.42 (d, J=6.4 Hz, 2H), 4.29–4.19 (m, 1H), 2.97 (dd, J=13.6, 5.6 Hz, 1H), 2.82 (dd, J=13.6, 6.6 Hz, 1H), 2.42 (d, J=6.6 Hz, 2H), 1.88–0.78 (m, 20H).

Example 2(117)

(2R)-N-(4-(morpholin-4-yl)benzyl)-2-t-butoxycarbonylamino-3-cyclohexyl-methylthiopropanamide

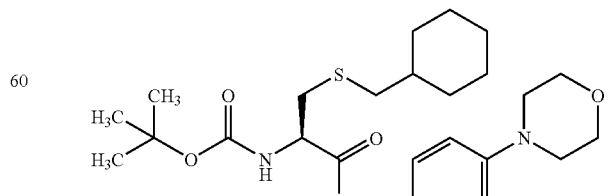

TLC: Rf 0.41 (ethyl acetate:hexane=1:1); NMR (CDCl$_3$): δ 7.23–7.18 (m, 2H), 6.89–6.84 (m, 2H), 6.60 (t, J=5.1 Hz, 1H), 5.35 (d, J=7.8 Hz, 1H), 4.38 (d, J=5.7 Hz, 2H), 4.26–4.20 (m, 1H), 3.88–3.84 (m, 4H), 3.16–3.12 (m, 4H), 2.98 (dd, J=13.8, 5.7 Hz, 1H), 2.82 (dd, J=13.8, 6.9 Hz, 1H), 2.45 (dd, J=12.6, 6.6 Hz, 1H), 2.40 (dd, J=12.6, 6.9 Hz, 1H), 1.85–0.82 (m, 20H).

Example 2(118)

(2R)-N-(1-phenylpiperidin-4-yl)-2-t-butoxycarbonylamino-3-cyclohexyl-methylthiopropanamide

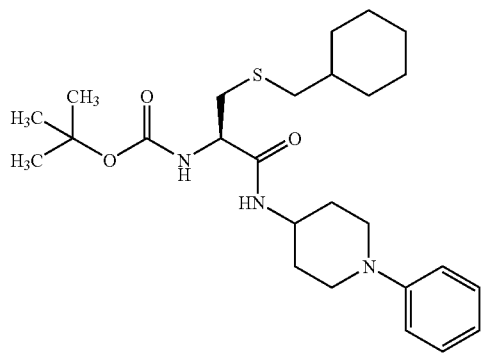

TLC: Rf 0.42 (hexane:ethyl acetate=2:1); NMR (CDCl$_3$): δ 7.29–7.22 (m, 2H), 6.95–6.92 (m, 2H), 6.88–6.82 (m, 1H), 6.37 (d, J=7.5 Hz, 1H), 5.36 (d, J=6.6 Hz, 1H), 4.20–4.13 (m, 1H), 4.01–3.88 (m, 1H), 3.63–3.56 (m, 2H), 2.99–2.86 (m, 3H), 2.78 (dd, J=13.5, 6.9 Hz, 1H), 2.48 (dd, J=12.6, 6.9 Hz, 1H), 2.45 (dd, J=12.6, 6.6 Hz, 1H), 2.08–1.98 (m, 2H), 1.87–1.78 (br, 2H), 1.76–1.54 (m, 5H), 1.52–1.38 (m, 10H), 1.31–1.06 (m, 3H), 1.00–0.86 (m, 2H).

Example 2(119)

(2R)-N-(1-methylpiperidin-4-yl)-2-t-butoxycarbonylamino-3-cyclohexyl-methylthiopropanamide

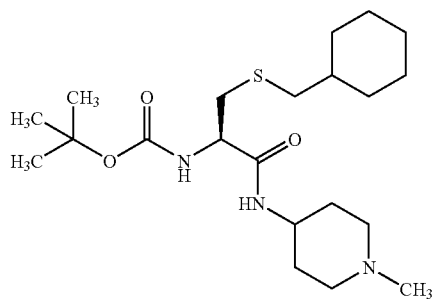

TLC: Rf 0.41 (chloroform:methanol=9:1); NMR (CDCl$_3$): δ 6.41 (d, J=6.9 Hz, 1H), 5.36 (d, J=6.6 Hz, 1H), 4.19–4.12 (m, 1H), 3.88–3.75 (m, 1H), 2.97–2.75 (m, 4H), 2.51–2.40 (m, 2H), 2.36 (s, 3H), 2.31–2.21 (m, 2H), 1.99–1.88 (m, 2H), 1.86–1.56 (m, 7H), 1.53–1.59 (m, 10H), 1.30–0.86 (m, 5H).

Example 3~Example 3(1)

By the same desired procedure as Reference Example 3, using the compounds prepared in Example 2(64) and Example 2(65), the following compounds of the present invention were obtained.

Example 3

(2S)-N-((1S)-1-carboxy-2-phenylethyl)-3-cyclohexyloxycarbonyl-2-t-butoxy-carbonylaminopropanamide

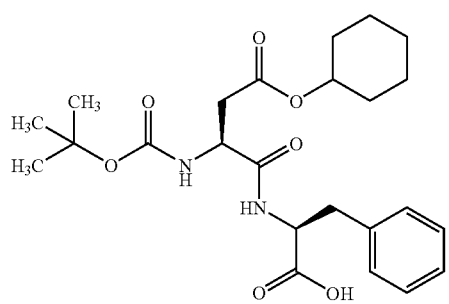

TLC: Rf 0.51 (chloroform:methanol=9:1); NMR (CDCl$_3$): δ 7.35–7.17 (5H, m), 7.04 (1H, d, J=7.8 Hz), 6.90–6.10 (1H, br. s), 5.64 (1H, d, J=8.0 Hz), 4.86–4.69 (2H, m), 4.61–4.42 (1H, m), 3.18 (1H, dd, J=13.8, 5.4 Hz), 3.07 (1H, dd, J=13.8, 6.2 Hz), 2.86 (1H, dd, J=17.0, 5.0 Hz), 2.64 (1H, dd, J=17.0, 6.2 Hz), 1.88–1.18 (19H, m).

Example 3(1)

(2S)-N-((1S)-1-carboxyethyl)-3-cyclohexyloxycarbonyl-2-t-butoxycarbonyl-aminopropanamide

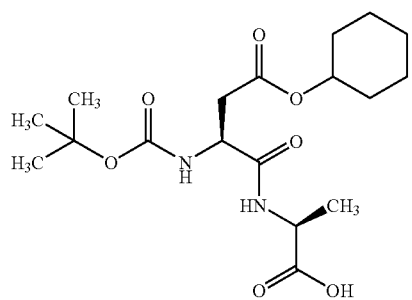

TLC: Rf 0.46 (chloroform:methanol=9:1); NMR (CDCl$_3$): δ 7.20 (1H, d, J=6.0 Hz), 6.50–6.00 (1H, br. s), 5.74 (1H, d, J=8.4 Hz), 4.85–4.69 (1H, m), 4.66–4.47 (2H, m), 2.93 (1H, dd, J=17.0, 5.2 Hz), 2.69 (1H, dd, J=17.0, 6.0 Hz), 1.92–1.20 (22H, m).

Example 4~Example 4(1)

By the reaction of the compounds prepared in Example 3 and Example 3(1) with alcohol derivatives by the same desired procedure as Example 2, the following compounds of the present invention were obtained.

Example 4

(2S)-N-((1S)-1-(4-methoxybenzyloxycarbonyl)ethyl)-3-cyclohexyloxycarbonyl-2-t-butoxycarbonylaminopropanamide

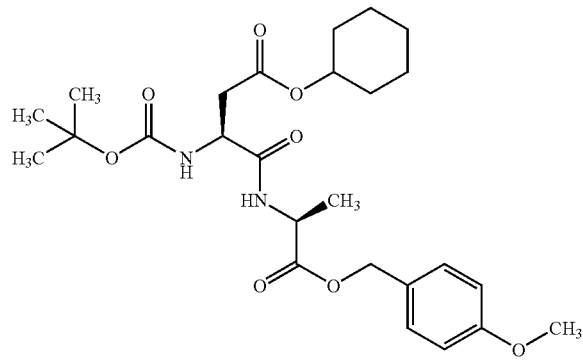

TLC:Rf 0.34 (ethyl acetate:hexane=1:2); NMR (CDCl$_3$): δ 7.31–7.24 (2H, m), 7.07 (1H, d, J=7.0 Hz), 6.92–6.85 (2H, m), 5.66 (1H, d, J=8.2 Hz), 5.13 (1H, d, J=12.2 Hz), 5.06 (1H, d, J=12.2 Hz), 4.84–4.70 (1H, m), 4.62–4.46 (2H, m), 3.81 (3H, s), 2.96 (1H, dd, J=16.8, 4.4 Hz), 2.64 (1H, dd, J=16.8, 6.4 Hz), 1.92–1.24 (22H, m).

Example 4(1)

(2S)-N-((1S)-2-phenyl-1-(4-methoxybenzyloxycarbonyl)ethyl)-3-cyclohexyl-oxycarbonyl-2-t-butoxycarbonylaminopropanamide

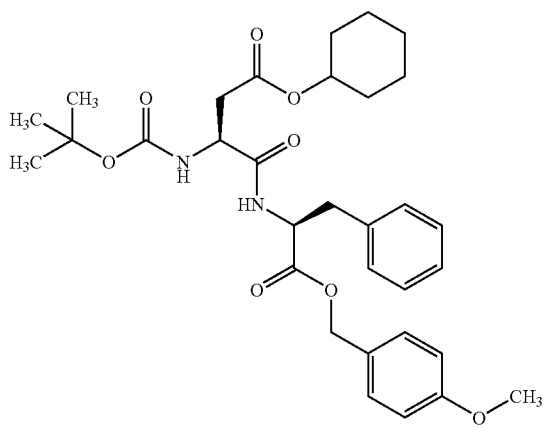

TLC: Rf 0.42 (ethyl acetate:hexane=1:2); NMR (CDCl$_3$): δ 7.26–7.19 (5H, m), 7.06–7.01 (2H, m), 6.97 (1H, d, J=8.0 Hz), 6.91–6.84 (2H, m), 5.61 (1H, d, J=7.8 Hz), 5.09 (1H, d, J=12.0 Hz), 5.01 (1H, d, J=12.0 Hz), 4.86–4.69 (2H, m), 4.56–4.40 (1H, m), 3.82 (3H, s), 3.08 (1H, d, J=5.8 Hz), 2.93 (1H, dd, J=17.0, 4.4 Hz), 2.62 (1H, dd, J=17.0, 6.2 Hz), 1.90–1.18 (19H, m).

Reference Example 4

(2S)-N-(4-methoxybenzyl)-3-cyclohexylmethoxy-2-aminopropanamide.hydrochloride

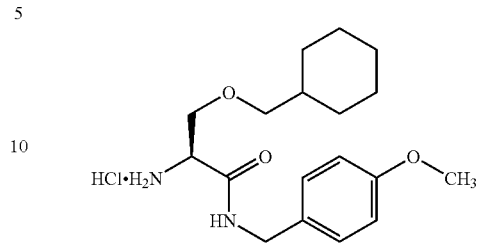

Under cooling with ice, a solution of 4N solution of hydrogen chloride in dioxane (12 ml) was added dropwise to the compound prepared in Example 2 (1180 mg). The solution was warmed to room temperature and stirred for 1 hour. The reaction mixture was concentrated to give the title compound (920 mg) having the following physical data.

TLC: Rf 0.78 (chloroform:methanol=9:1); NMR (CD$_3$OD): δ 7.26–7.19 (2H, m), 6.91–6.83 (2H, m), 4.43 (1H, d, J=14.6 Hz), 4.28 (1H, d, J=14.6 Hz), 4.03 (1H, dd, J=5.8, 4.0 Hz), 3.83–3.66 (5H, m), 3.35–3.20 (2H, m), 1.75–0.81 (11H, m).

Example 5

(2S)-N-(4-methoxybenzyl)-3-cyclohexylmethoxy-2-benzoylaminoprpanamide

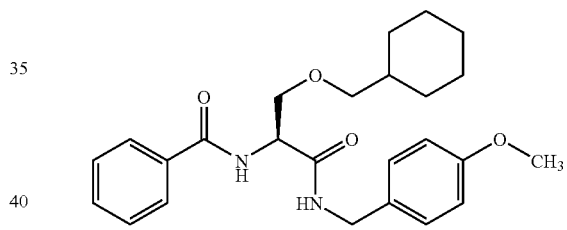

Benzoyl chloride (0.04 ml) was added dropwise to a solution of the compound prepared in Reference Example 4 (95 mg) and pyridine (0.07 ml) in methylene chloride (2 ml). The mixture was stirred for 1 hour at room temperature. The reaction mixture was diluted with methylene chloride and washed with 1N hydrochloric acid, water and saturated aqueous sodium chloride, successively, dried over anhydrous magnesium sulfate. The organic layer was concentrated and the residue was purified by silica gel column chromatography (hexane:ethyl acetate=2:1) to give the compound of the present invention (90 mg) having the following physical data.

TLC: Rf 0.21 (ethyl acetate:hexane=1:2); NMR (CDCl$_3$): δ 7.86–7.80 (2H, m), 7.56–7.39 (3H, m), 7.27–7.18 (3H, m), 6.93–6.83 (3H, m), 4.70 (1H, ddd, J=8.8, 6.4, 4.2 Hz), 4.47 (1H, dd, J=14.8, 5.6 Hz), 4.39 (1H, dd, J=14.8, 5.6 Hz), 3.95 (1H, dd, J=9.0, 4.2 Hz), 3.80 (3H, s), 3.50 (1H, t, J=8.4 Hz), 3.36 (1H, dd, J=9.0, 6.2 Hz), 3.24 (1H, dd, J=9.0, 6.2 Hz), 1.77–0.71 (11H, m).

Example 6~Example 6(86)

By the same desired procedure as Reference Example 4→Example 5, using the compounds prepared in Example 2, Example 2(4), Example 2(9), Example 2(80), Example 2(83), Example 2(100)~Example 2(119), Example 3 and Example 3(1), the following compounds of the present invention were obtained.

Also, (−)-3-t-butoxycarbonylthiazolidin-2-ylcarboxylic acid was used for the preparation of the compound of Example 6(60).

(+)-3-t-butoxycarbonylthiazolidin-2-ylcarboxylic acid was used for the preparation of the compound of Example 6(61).

(+)-3-t-butoxycarbonylthiazolidin-2-ylcarboxylic acid was used for the preparation of the compound of Example 6(63).

Example 6

(2S)-3-cyclopentyloxycarbonyl-2-methylcarbonylaminopropanoic acid.4-methoxybenzyl ester

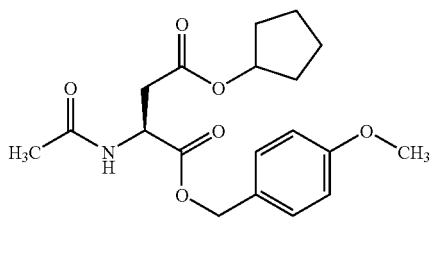

TLC: Rf 0.27 (ethyl acetate:hexane=1:1); NMR (CDCl$_3$): δ 7.29–7.23 (2H, m), 6.92–6.84 (2H, m), 6.50 (1H, br. d, J=7.0 Hz), 5.19–5.05 (3H, m), 4.88–4.80 (1H, m), 3.81 (3H, s), 2.97 (1H, dd, J=17.2, 4.4 Hz), 2.78 (1H, dd, J=17.2, 4.4 Hz), 2.02 (3H, s), 1.92–1.46 (8H, m).

Example 6(1)

(2S)-3-cyclopentyloxycarbonyl-2-benzoylaminopropanoic acid.4-methoxybenzyl ester

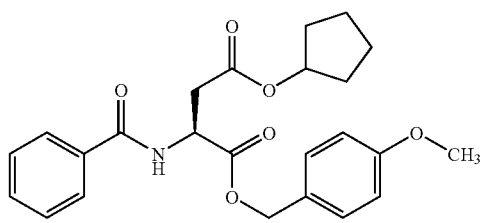

TLC: Rf 0.54 (ethyl acetate:hexane=1:1); NMR (CDCl$_3$): δ 7.82–7.77 (2H, m), 7.56–7.38 (3H, m), 7.32–7.21 (3H, m), 6.91–6.84 (2H, m), 5.18–5.01 (4H, m), 3.81 (3H, s), 3.08 (1H, dd, J=17.0, 4.2 Hz), 2.91 (1H, dd, J=17.0, 4.6 Hz), 1.92–1.49 (8H, m).

Example 6(2)

(2S)-3-cyclopentyloxycarbonyl-2-pivalocyaminopropanoic acid.4-methoxybenzyl ester

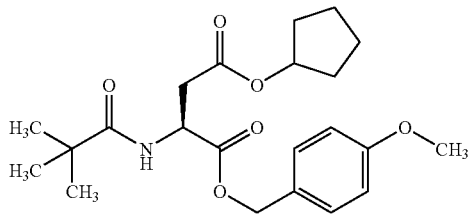

TLC: Rf 0.53 (ethyl acetate:hexane=1:1); NMR (CDCl$_3$): δ 7.29–7.23 (2H, m), 6.91–6.85 (2H, m), 6.71 (1H, br. d, J=8.2 Hz), 5.18–5.04 (3H, m), 4.86–4.77 (1H, m), 3.81 (3H, s), 2.98 (1H, dd, J=17.2, 4.4 Hz), 2.77 (1H, dd, J=17.2, 4.4 Hz), 1.94–1.45 (8H, m), 1.19(9H, s).

Example 6(3)

(2S)-3-cyclopentyloxycarbonyl-2-cinnamoylaminopropanoic acid.4-methoxybenzyl ester

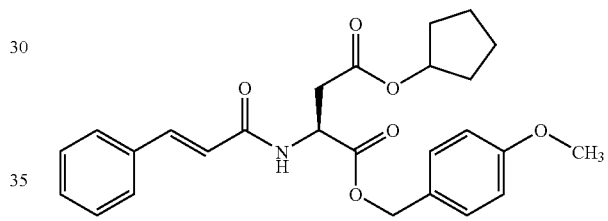

TLC: Rf 0.56 (ethyl acetate:hexane=1:1); NMR (CDCl$_3$). 7.63 (1H, d, J=15.6 Hz), 7.53–7.46 (2H, m), 7.40–7.33 (3H, m), 7.32–7.25 (2H, m), 6.92–6.84 (2H, m), 6.68 (1H, br. d, J=8.0 Hz), 6.44 (1H, d, J=15.6 Hz), 5.22–5.08 (3H, m), 5.03–4.94 (1H, m), 3.80 (3H, s), 3.05 (1H, dd, J=17.4, 4.4 Hz), 2.87 (1H, dd, J=17.4, 4.4 Hz), 1.93–1.44 (8H, m).

Example 6(4)

(2S)-3-cyclopentyloxycarbonyl-2-valerylaminopropanoic acid.4-methoxybenzyl ester

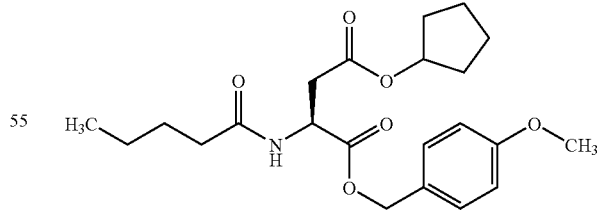

TLC: Rf 0.50 (ethyl acetate:hexane=1:1); NMR (CDCl$_3$): δ 7.30–7.23 (2H, m), 6.92–6.84 (2H, m), 6.47 (1H, d, J=8.3 Hz), 5.16 (1H, d, J=12.0 Hz), 5.08 (1H, d, J=12.0 Hz), 4.90–4.81 (1H, m), 3.81 (3H, s), 2.98 (1H, dd, J=17.0, 4.3 Hz), 2.77 (1H, dd, J=17.0, 4.5 Hz), 2.22 (2H, t, J=7.4 Hz), 1.92–1.46 (10H, m), 1.42–1.24 (2H, m), 0.98 (3H, t, J=8.0 Hz).

Example 6(5)

(2S)-3-cyclopentyloxycarbonyl-2-(octylcarbonylamino)propanoic acid.4-methoxybenzyl ester

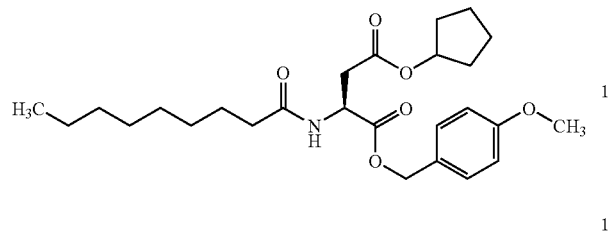

TLC: Rf 0.62 (ethyl acetate:hexane=1:1); NMR (CDCl$_3$): δ 7.30–7.23 (2H, m), 6.91–6.84 (2H, m), 6.46 (1H, d, J=7.6 Hz), 5.18–5.04 (3H, m), 4.89–4.81 (1H, m), 3.81 (3H, s), 2.98 (1H, dd, J=17.2, 4.2 Hz), 2.77 (1H, dd, J=17.2, 4.4 Hz), 2.21 (2H, t, J=7.0 Hz), 1.92–1.46 (8H, m), 1.38–1.15 (12H, m), 0.88 (3H, t, J=7.2 Hz).

Example 6(6)

(2S)-3-cyclopentyloxycarbonyl-2-mesylaminopropanoic acid.4-methoxybenzyl ester

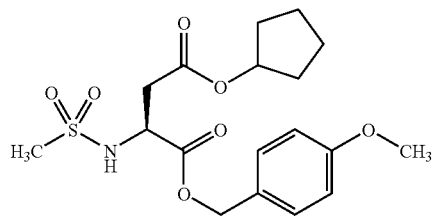

TLC: Rf 0.54 (ethyl acetate:hexane=1:1); NMR (CDCl$_3$): δ 7.31–7.24 (2H, m), 6.92–6.85 (2H, m), 5.48 (1H, d, J=9.2 Hz), 5.22–5.05 (3H, m), 4.41–4.32 (1H, m), 3.81 (3H, s), 3.00 (1H, dd, J=17.4, 4.6 Hz), 2.99 (3H, s), 2.80 (1H, dd, J=17.4, 4.4 Hz), 1.94–1.46 (8H, m).

Example 6(7)

(2S)-3-cyclopentyloxycarbonyl-2-phenylsulfonylaminopropanoic acid.4-methoxybenzyl ester

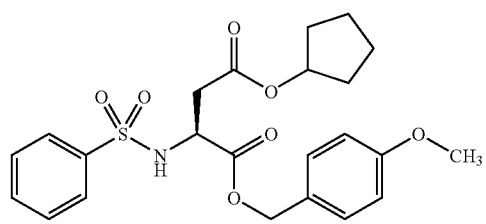

TLC: Rf 0.69 (ethyl acetate:hexane=1:1); NMR (CDCl$_3$): δ 7.87–7.82 (2H, m), 7.60–7.41 (3H, m), 7.16–7.10 (2H, m), 6.89–6.81 (2H, m), 5.69 (1H, d, J=8.3 Hz), 5.13–5.03 (1H, m), 4.94 (3H, s), 4.21–4.12 (1H, m), 3.81 (3H, s), 2.92 (1H, dd, J=17.0, 4.3 Hz), 2.77 (1H, dd, J=17.0, 4.8 Hz), 1.93–1.44 (8H, m).

Example 6(8)

(2S)-3-cyclopentyloxycarbonyl-2-(butylsulfonylamino)propanoic acid.4-methoxybenzyl ester

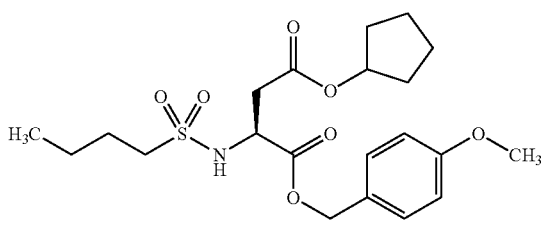

TLC: Rf 0.60 (ethyl acetate:hexane=1:2); NMR (CDCl$_3$): δ 7.31–7.22 (2H, m), 6.92–6.83 (2H, m), 5.36 (1H, d, J=9.0 Hz), 5.21–5.05 (3H, m), 4.39–4.30 (1H, m), 3.79 (3H, s), 3.06–2.93 (3H, m), 2.79 (1H, dd, J=17.2, 4.4 Hz), 1.92–1.24 (12H, m), 0.91 (3H, t, J=7.2 Hz).

Example 6(9)

(2S)-3-cyclopentyloxycarbonyl-2-(octylsulfonylamino)propanoic acid.4-methoxybenzyl ester

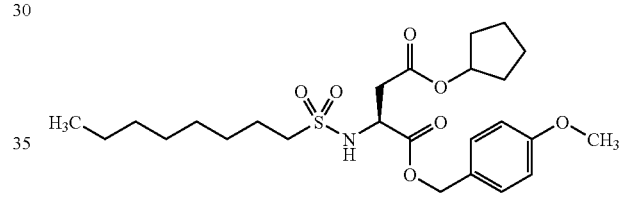

TLC: Rf 0.55 (ethyl acetate:hexane=1:2); NMR (CDCl$_3$): δ 7.31–7.23 (2H, m), 6.92–6.73 (2H, m), 6.88 (2H, d, J=8.8 Hz), 5.35 (1H, d, J=10.0 Hz), 5.21–5.05 (3H, m), 4.39–4.30 (1H, m), 3.81 (3H, s), 3.03–2.93 (3H, m), 2.79 (1H, dd, J=17.2, 4.4 Hz), 1.87–1.27 (20H, m), 0.89 (3H, t, J=6.8 Hz).

Example 6(10)

(2S)-3-cyclopentyloxycarbonyl-2-((E)-styrylsulfonylamino)propanoic acid.4-methoxybenzyl ester

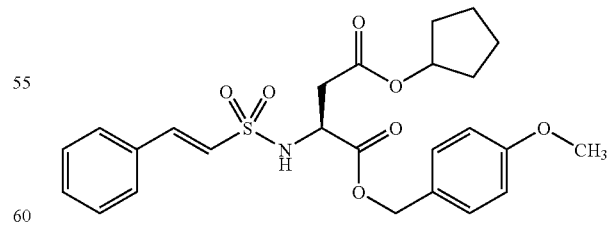

TLC: Rf 0.38 (ethyl acetate:hexane=1:2); NMR (CDCl$_3$): δ 7.49–7.41 (6H, m), 7.17 (2H, d, J=8.8 Hz), 6.82–6.71 (3H, m), 5.55 (1H, d, J=8.6 Hz), 5.15–5.00 (3H, m), 4.26–4.17 (1H, m), 3.78 (3H, s), 3.01 (1H, dd, J=17.2, 4.4 Hz), 2.84 (1H, dd, J=17.2, 4.4 Hz), 1.89–1.44 (8H, m).

Example 6(11)

(2S)-3-cyclopentyloxycarbonyl-2-benzyloxycarbonylaminopropanoic acid.4-methoxybenzyl ester

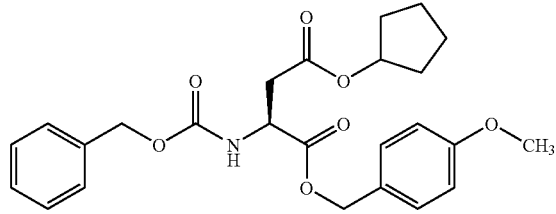

TLC: Rf 0.67 (ethyl acetate:hexane=1:2); NMR (CDCl$_3$): δ 7.39–7.23 (7H, m), 6.91–6.82 (2H, m), 5.74 (1H, d, J=9.2 Hz), 5.17–5.04 (5H, m), 4.67–4.58 (1H, m), 3.80 (3H, s), 2.97 (1H, dd, J=17.0, 4.6 Hz), 2.78 (1H, dd, J=17.0, 4.8 Hz), 1.88–1.46 (8H, m).

Example 6(12)

(2S)-3-cyclohexyloxycarbonyl-2-benzoylaminopropanoic acid.4-methoxybenzyl ester

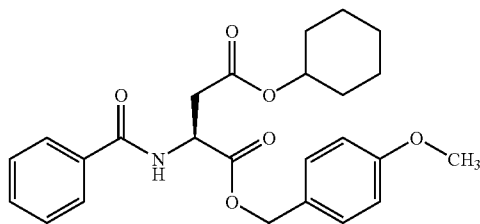

TLC: Rf 0.42 (ethyl acetate:hexane=1:2); NMR (CDCl$_3$): δ 7.83–7.76 (2H, m), 7.52–7.39 (3H, m), 7.32–7.21 (3H, m), 6.91–6.83 (2H, m), 5.21 (1H, d, J=12.0 Hz), 5.11 (1H, d, J=12.0 Hz), 5.10–5.02 (1H, m), 4.77–4.64 (1H, m), 3.81 (3H, s), 3.11 (1H, dd, J=17.0, 4.2 Hz), 2.93 (1H, dd, J=17.0, 4.6 Hz), 1.84–1.16 (10H, m).

Example 6(13)

(2S)-3-cyclohexyloxycarbonyl-2-(4-fluorobenzoylamino)propanoic acid.4-methoxybenzyl ester

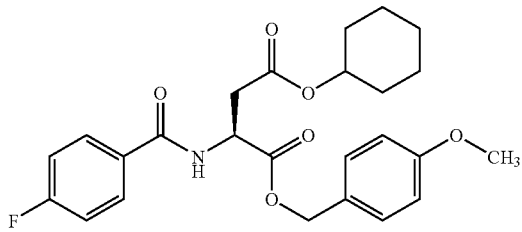

TLC: Rf 0.37 (ethyl acetate:hexane=1:2); NMR (CDCl$_3$): δ 7.86–7.76 (2H, m), 7.32–7.06 (5H, m), 6.91–6.84 (2H, m), 5.20 (1H, d, J=1.8 Hz), 5.11 (1H, d, J=11.8 Hz), 5.08–4.99 (1H, m), 4.77–4.63 (1H, m), 3.81 (3H, s), 3.10 (1H, dd, J=17.2, 5.0 Hz), 2.91 (1H, dd, J=17.2, 5.0 Hz), 1.84–1.13 (10H, m).

Example 6(14)

(2S)-3-cyclohexyloxycarbonyl-2-(4-methoxybenzoyl)propanoic acid.4-methoxybenzyl ester

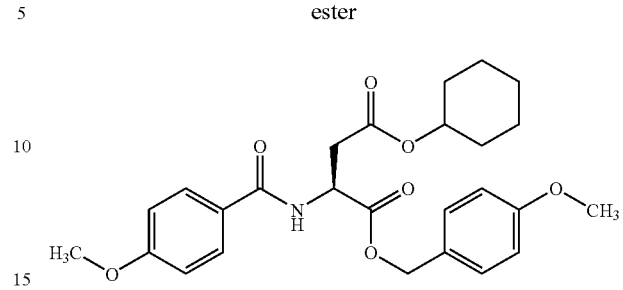

TLC: Rf 0.32 (ethyl acetate:hexane=1:2); NMR (CDCl$_3$): δ 7.80–7.73 (2H, m), 7.31–7.15 (2H, m), 7.13 (1H, d, J=7.8 Hz), 6.96–6.85 (4H, m), 5.20 (1H, d, J=12.0 Hz), 5.13 (1H, d, J=12.0 Hz), 5.08–5.00 (1H, m), 4.77–4.63 (1H, m), 3.85 (3H, s), 3.81 (3H, s), 3.09 (1H, dd, J=17.2, 4.4 Hz), 2.91 (1H, dd, J=17.2, 4.4 Hz), 1.84–1.09 (10H, m).

Example 6(15)

(2S)-3-cyclohexyloxycarbonyl-2-(4-phenylbenzoylamino)propanoic acid.4-methoxybenzyl ester

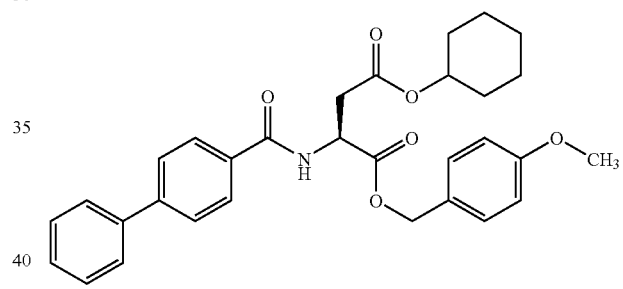

TLC: Rf 0.42 (ethyl acetate:hexane=1:2); NMR (CDCl$_3$): δ 7.91–7.84 (2H, m), 7.69–7.58 (4H, m), 7.52–7.25 (6H, m), 6.92–6.85 (2H, m), 5.22 (1H, d, J=12.0 Hz), 5.11 (1H, d, J=12.0 Hz), 5.13–5.04 (1H, m), 4.80–4.64 (1H, m), 3.81 (3H, s), 3.12 (1H, dd, J=17.2, 4.2 Hz), 2.94 (1H, dd, J=17.2, 4.6 Hz), 1.84–1.14 (10H, m).

Example 6(16)

(2S)-3-cyclohexyloxycarbonyl-2-(4-nitrobenzoylamino)propanoic acid.4-methoxybenzyl ester

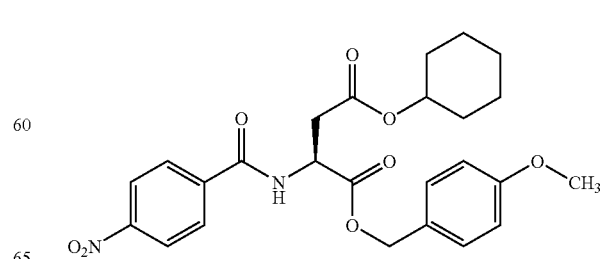

TLC: Rf 0.36 (ethyl acetate:hexane=1:2); NMR (CDCl₃): δ 8.32–8.26 (2H, m), 7.99–7.92 (2H, m), 7.36 (1H, br. d, J=7.8 Hz), 7.32–7.25 (2H, m), 6.92–6.85 (2H, m), 5.22 (1H, d, J=12.0 Hz), 5.12 (1H, d, J=12.0 Hz), 5.08–5.00 (1H, m), 4.78–4.63 (1H, m), 3.81 (3H, s), 3.13 (1H, dd, J=17.2, 4.2 Hz), 2.93 (1H, dd, J=17.2, 4.4 Hz), 1.84–1.14 (10H, m).

Example 6(17)

(2S)-3-cyclohexyloxycarbonyl-2-(4-acetylbenzoylamino)propanoic acid.4-methoxybenzyl ester

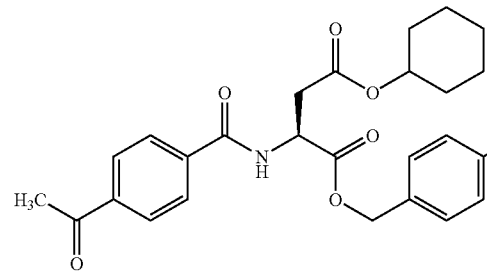

TLC: Rf 0.24 (ethyl acetate:hexane=1:2); NMR (CDCl₃): δ 8.05–7.98 (2H, m), 7.90–7.85 (2H, m), 7.33–7.25 (3H, m), 6.92–6.84 (2H, m), 5.21 (1H, d, J=11.8 Hz), 5.12 (1H, d, J=11.8 Hz), 5.09–5.01 (1H, m), 4.78–4.64 (1H, m), 3.81 (3H, s), 3.12 (1H, dd, J=17.0, 4.2 Hz), 2.93 (1H, dd, J=17.0, 4.6 Hz), 2.64 (3H, s), 1.84–1.18 (10H, m).

Example 6(18)

(2S)-3-cyclohexyloxycarbonyl-2-(4-methylthiobenzoylamino)propanoic acid.4-methoxybenzyl ester

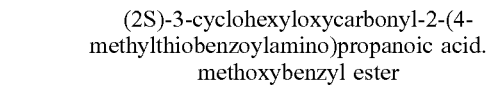

TLC: Rf 0.37 (ethyl acetate:hexane=1:2); NMR (CDCl₃): δ 7.75–7.68 (2H, m), 7.30–7.22 (4H, m), 7.18 (1H, br. d, J=7.8 Hz), 6.91–6.84 (2H, m), 5.20 (1H, d, J=11.8 Hz), 5.11 (1H, d, J=11.8 Hz), 5.08–5.00 (1H, m), 4.78–4.62 (1H, m), 3.81 (3H, s), 3.10 (1H, dd, J=17.2, 4.4 Hz), 2.91 (1H, dd, J=17.2, 4.6 Hz), 2.51 (3H, s), 1.84–1.12 (10H, m).

Example 6(19)

(2S)-3-cyclohexyloxycarbonyl-2-(4-dimethylaminobenzoylamino)propanoic acid.4-methoxybenzyl ester

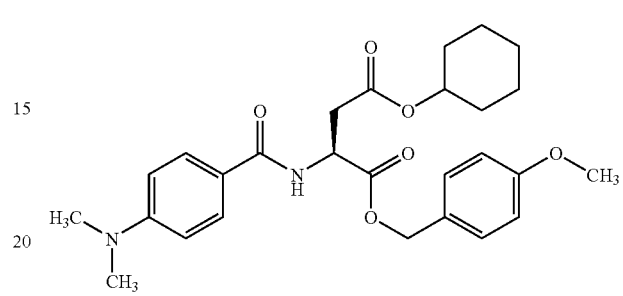

TLC: Rf 0.24 (ethyl acetate:hexane=1:2); NMR (CDCl₃): δ 7.74–7.66 (2H, m), 7.32–7.25 (2H, m), 7.04 (1H, br. d, J=7.4 Hz), 6.91–6.83 (2H, m), 6.69–6.63 (2H, m), 5.19 (1H, d, J=12.2 Hz), 5.11 (1H, d, J=12.2 Hz), 5.10–5.02 (1H, m), 4.78–4.64 (1H, m), 3.81 (3H, s), 3.09 (1H, dd, J=17.0, 4.4 Hz), 3.02 (6H, s) 2.91 (1H, dd, J=17.0, 4.6 Hz), 1.84–1.16 (10H, m).

Example 6(20)

(2S)-N-((1S)-1-carboxyethyl)-3-cyclohexyloxycarbonyl-2-benzyloxycarbonyl-aminopopanamide

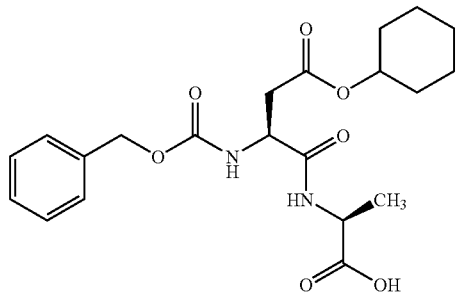

TLC: Rf 0.48 (chloroform:methanol=8:2); NMR (CDCl₃+CD₃OD): δ 7.52 (1H, d, J=6.2 Hz), 7.37–7.28 (5H, m), 6.36 (1H, d, J=9.2 Hz), 5.15 (1H, d, J=12.2 Hz), 5.07 (1H, d, J=112.2 Hz), 4.79–4.52 (2H, m), 4.42–4.29 (1H, m), 2.87 (1H, dd, J=16.8, 6.2 Hz), 2.74 (1H, dd, J=16.8, 5.8 Hz), 1.82–1.08 (13H, m).

Example 6(21)

(2S)-N-((1S)-2-phenyl-1-carboxyethyl)-3-cyclohexyloxycarbonyl-2-benzyloxycarbonylaminopropanamide. dicyclohexylamine salt

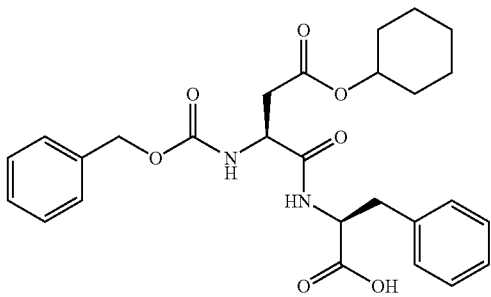

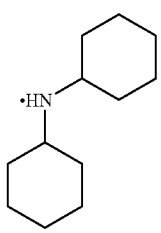

TLC: Rf 0.46 (chloroform:methanol=8:2); NMR (CDCl₃+CD₃OD): δ 7.37–7.28 (5H, m), 7.19–7.12 (5H, m), 5.13 (1H, d, J=12.0 Hz), 5.01 (1H, d, J=12.0 Hz), 4.79–4.64 (1H, m), 4.61–4.40 (2H, m), 3.26–2.66 (6H, m), 2.06–1.08 (30H, m).

Example 6(22)

(2S)-N-(4-methoxybenzyl)-3-cyclohexylmethoxy-2-phenylsulfonylamino-propanamide

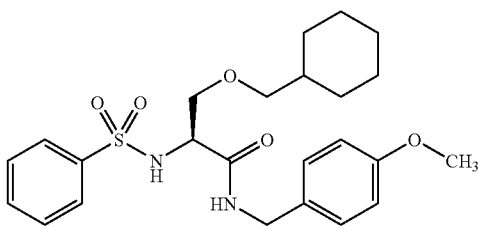

TLC: Rf 0.31 (ethyl acetate:hexane=1:2); NMR (CDCl₃): δ 7.91–7.85 (2H, m), 7.66–7.48 (3H, m), 7.16–7.09 (2H, m), 7.00–6.95 (1H, m), 6.88–6.80 (2H, m), 5.67–5.64 (1H, m), 4.36 (1H, dd, J=14.6, 5.6 Hz), 4.27 (1H, dd, J=14.6, 5.4 Hz), 3.82–3.70 (5H, m), 3.29–3.21 (1H, m), 3.16 (1H, dd, J=9.0, 6.2 Hz), 3.04 (1H, dd, J=9.0, 6.6 Hz), 1.72–0.64 (11H, m).

Example 6(23)

(2S)-N-(4-methoxybenzyl)-3-cyclohexylmethoxy-2-pivaloylaminopropanamide

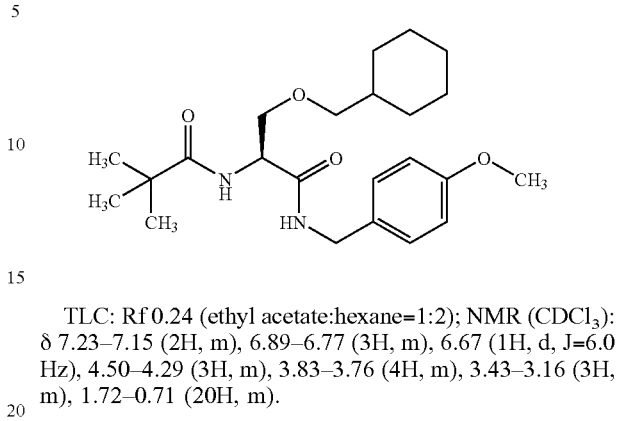

TLC: Rf 0.24 (ethyl acetate:hexane=1:2); NMR (CDCl₃): δ 7.23–7.15 (2H, m), 6.89–6.77 (3H, m), 6.67 (1H, d, J=6.0 Hz), 4.50–4.29 (3H, m), 3.83–3.76 (4H, m), 3.43–3.16 (3H, m), 1.72–0.71 (20H, m).

Example 6(24)

(2S)-N-(4-methoxybenzyl)-3-cyclohexylmethoxy-2-(4-methoxybenzoylamino)-propanamide

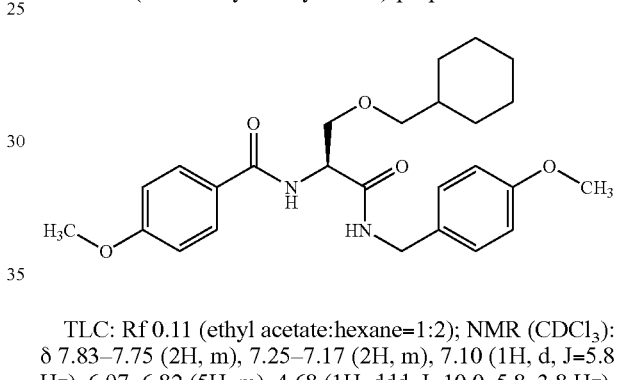

TLC: Rf 0.11 (ethyl acetate:hexane=1:2); NMR (CDCl₃): δ 7.83–7.75 (2H, m), 7.25–7.17 (2H, m), 7.10 (1H, d, J=5.8 Hz), 6.97–6.82 (5H, m), 4.68 (1H, ddd, J=10.0, 5.8, 3.8 Hz), 4.42 (2H, d, J=5.4 Hz), 3.95 (1H, dd, J=9.2, 4.0 Hz), 3.86 (3H, s), 3.80 (3H, s), 3.49 (1H, t, J=9.2 Hz), 3.36 (1H, dd, J=9.2, 6.2 Hz), 3.24 (1H, dd, J=9.2, 6.6 Hz), 1.76–0.74 (11H, m).

Example 6(25)

(2S)-N-(4-methoxybenzyl)-3-cyclohexylmethoxy-2-(4-nitrobenzoylamino)-propanamide

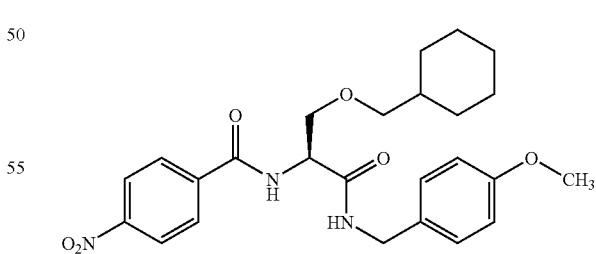

TLC: Rf 0.26 (ethyl acetate:hexane=1:2); NMR (CDCl₃): δ 8.33–8.26 (2H, m), 8.01–7.94 (2H, m), 7.38 (1H, d, J=5.8 Hz), 7.25–7.18 (2H, m), 6.95–6.83 (3H, m), 4.67 (1H, ddd, J=9.6, 5.8, 4.0 Hz), 4.48 (1H, dd, J=14.6, 5.8 Hz), 4.38 (1H, dd, J=14.6, 5.4 Hz), 3.92 (1H, dd, J=9.2, 4.4 Hz), 3.80 (3H, s), 3.49 (1H, t, J=9.2 Hz), 3.37 (1H, dd, J=9.6, 6.2 Hz), 3.24 (1H, dd, J=9.6, 6.6 Hz), 1.74–0.70 (11H, m).

Example 6(26)

(2S)-N-(4-methoxybenzyl)-3-cyclohexylmethoxy-2-(12-methyltridecylcarbonyl-amino)propanamide

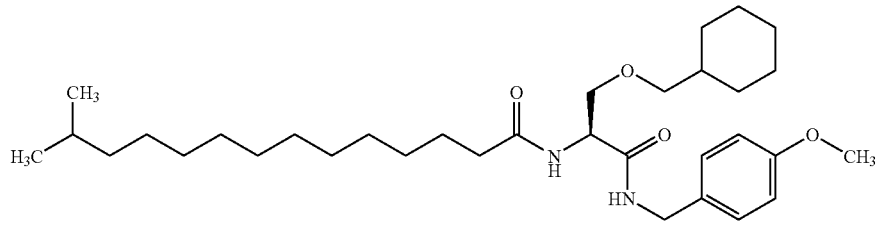

TLC: Rf 0.60 (ethyl acetate:hexane=1:1); NMR (CDCl$_3$): δ 7.23–7.15 (2H, m), 6.89–6.82 (2H, m), 6.81–6.70 (1H, m), 6.41 (1H, d, J=6.2 Hz), 4.50 (1H, ddd, J=8.4, 6.6, 4.4 Hz), 4.39 (2H, d, J=6.2 Hz), 3.86–3.73 (4H, m), 3.39 (1H, t, J=8.8 Hz), 3.30 (1H, dd, J=9.4, 6.0 Hz), 3.19 (1H, dd, J=9.4, 6.2 Hz), 2.22 (1H, t, J=7.0 Hz), 1.74–0.70 (38H, m).

Example 6(27)

(2S)-N-(4-methoxybenzyl)-3-cyclohexylmethoxy-2-cyclohexylcarbonylamino-propanamide

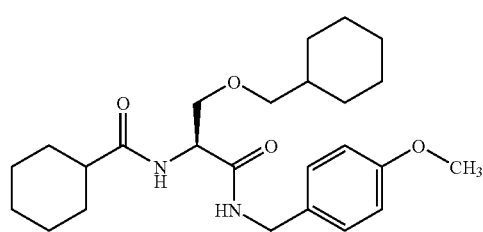

TLC: Rf 0.48 (ethyl acetate:hexane=1:1); NMR (CDCl$_3$): δ 7.22–7.15 (2H, m), 6.89–6.73 (3H, m), 6.43 (1H, d, J=6.4 Hz), 4.48 (1H, ddd, J=8.2, 6.4, 4.2 Hz), 4.46–4.29 (2H, m), 3.82–3.73 (4H, m), 3.38 (1H, t, J=8.4 Hz), 3.31 (1H, dd, J=9.2, 6.4 Hz), 3.20 (1H, dd, J=9.2, 6.2 Hz), 2.14 (1H, tt, J=11.6, 4.0 Hz), 1.94–0.71 (21H, m).

Example 6(28)

(2S)-N-(4-methoxybenzyl)-3-cyclohexylmethoxy-2-(4-methoxyphenylsulfonyl-amino)propanamide

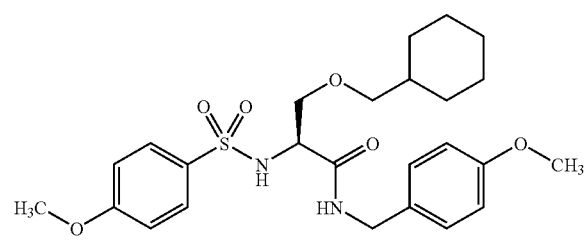

TLC: Rf 0.21 (ethyl acetate:hexane=1:2); NMR (CDCl$_3$): δ 7.83–7.76 (2H, m), 7.16–7.09 (2H, m), 7.05–6.94 (3H, m), 6.88–6.80 (2H, m), 5.55 (1H, d, J=5.4 Hz), 4.38 (1H, dd, J=14.6, 5.8 Hz), 4.28 (1H, dd, J=14.6, 5.6 Hz), 3.88 (3H, s), 3.82–3.67 (5H, m), 3.26 (1H, dd, J=8.8, 6.4 Hz), 3.17 (1H, dd, J=9.2, 6.2 Hz), 3.05 (1H, dd, J=9.2, 6.2 Hz), 1.74–0.79 (11H, m).

Example 6(29)

(2S)-N-(4-methoxybenzyl)-3-cyclohexylmethoxy-2-cyclohexylsulfonylamino-propanamide

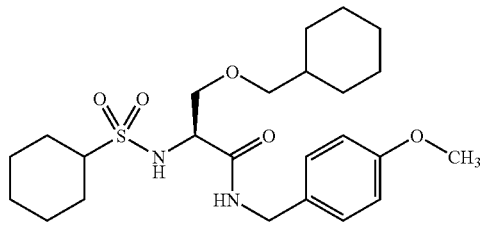

TLC: Rf 0.24 (ethyl acetate:hexane=1:2); NMR (CDCl$_3$): δ 7.23–7.16 (2H, m), 7.01 (1H, t, J=4.8 Hz), 6.90–6.82 (2H, m), 5.23 (1H, d, J=6.6 Hz), 4.40 (2H, d, J=5.8 Hz), 4.06–3.97 (1H, m), 3.85 (1H, dd, J=9.2, 4.0 Hz), 3.80 (3H, s), 3.55 (1H, dd, J=9.2, 7.2 Hz), 3.28 (1H, dd, J=9.2, 6.6 Hz), 3.20 (1H, dd, J=9.2, 6.2 Hz), 2.90 (1H, tt, J=11.8, 3.2 Hz), 2.28–2.08 (2H, m), 1.93–1.82 (2H, m), 1.76–1.04 (15H, m), 0.94–0.70 (2H, m).

Example 6(30)

(2R)-N-(4-methoxybenzyl)3-cyclohexylmethylthio-2-cyclopentylcarbonyl-aminopropanamide

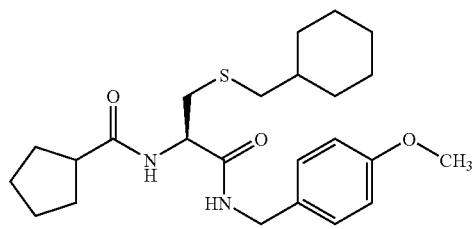

TLC: Rf 0.19 (ethyl acetate:hexane=1:2); NMR (CDCl$_3$): δ 7.24–7.05 (3H, m), 6.87–6.80 (2H, m), 6.59 (1H, d, J=7.0 Hz), 4.62–4.52 (1H, m), 4.39 (1H, dd, J=15.0, 5.8 Hz), 4.31 (1H, dd, J=15.0, 5.4 Hz), 3.78 (3H, s), 2.93 (1H, dd, J=13.4, 5.4 Hz), 2.79 (1H, dd, J=13.4, 7.4 Hz), 2.66–2.50 (1H, m), 2.45 (2H, d, J=7.0 Hz), 1.95–0.78 (19H, m).

Example 6(31)

(2R)-N-(4-methoxybenzyl)-3-cyclohexylmethylthio-2-cyclohexylcarbonyl-aminopropanamide

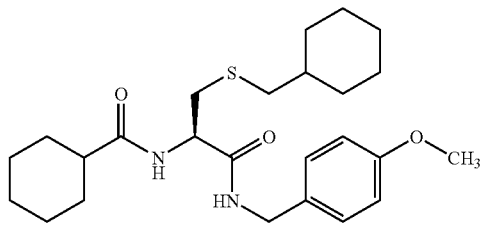

TLC: Rf 0.27 (ethyl acetate:hexane=1:2); NMR (CDCl$_3$): δ 7.24–7.16 (2H, m), 6.89–6.78 (3H, m), 6.46 (1H, d, J=6.8 Hz), 4.52–4.42 (1H, m), 4.38 (2H, d, J=5.8 Hz), 3.79 (3H, S), 2.95 (1H, dd, J=13.6, 5.0 Hz), 2.74 (1H, dd, J=13.6, 8.0 Hz), 2.47 (2H, d, J=7.0 Hz), 2.20–2.05 (1H, m), 1.92–0.82 (21H, m).

Example 6(32)

(2R)-N-(4-methoxybenzyl)-3-cyclohexylmethylthio-2-cyclobutylcarbonylamino-propanamide

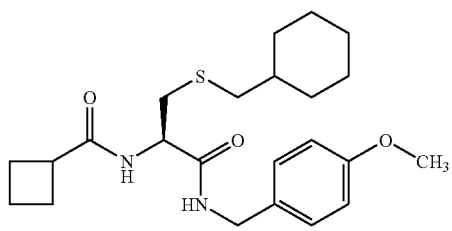

TLC: Rf 0.15 (hexane:ethyl acetate=2:1); NMR (CDCl$_3$): δ 7.20 (2H, d, J=8.6 Hz), 6.86 (2H, d, J=8.6 Hz), 6.80–6.72 (1H, br), 6.35 (1H, d, J=7.0 Hz), 4.52–4.38 (3H, m), 3.80 (3H, s), 3.09–2.91 (2H, m), 2.73 (1H, dd, J=8.0, 14.0 Hz), 2.48 (2H, d, J=6.6 Hz), 2.38–2.07 (4H, m), 2.06–1.32 (8H, m), 1.27–1.08 (3H, m), 1.03–0.89 (2H, m).

Example 6(33)

(2R)-N-(4-methoxybenzyl)-3-cyclohexylmethylthio-2-cycloheptylcarbonyl-aminopropanamide

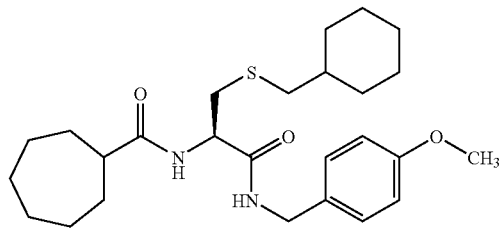

TLC: Rf 0.30 (hexane:ethyl acetate=2:1); NMR (CDCl$_3$): δ 7.20 (2H, d, J-8.6 Hz), 6.86 (2H, d, J=8.6 Hz), 6.80–6.74 (1H, br), 6.37 (1H, d, J=7.0 Hz), 4.50–4.37 (3H, m), 3.80 (3H, s), 2.95 (1H, dd, J=5.6, 14.0 Hz), 2.74 (1H, dd, J-8.0,14.0 Hz), 2.47 (2H, d, J=6.6 Hz), 2.35–2.20 (11H, m), 1.95–1.33 (18H, m), 1.30–1.08 (3H, m), 1.03–0.90 (2H, m).

Example 6(34)

(2R)-N-(4-methoxybenzyl)-3-cyclohexylmethylthio-2-(4-methoxycyclohexyl-carbonylamino) propanamide

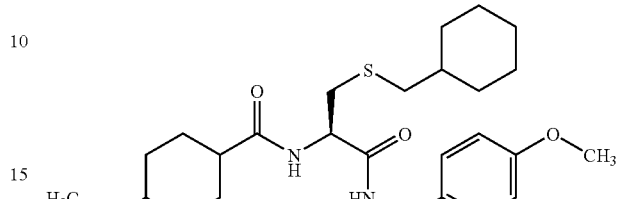

(The relative configuration of cyclohexyl ring substituted by methoxy group is not determined, but the above compound is a single compound. This compound is the isomer of the compound prepared in Example 6(35).) less polar TLC: Rf 0.46 (hexane:ethyl acetate=1:1); NMR (CDCl$_3$): δ 7.20 (2H, d, J=8.8 Hz), 6.86 (2H, d, J=8.8 Hz), 6.82–6.79 (1H, br), 6.49 (1H, d, J=7.0 Hz), 4.51–4.37 (3H, m), 3.80 (3H, s), 3.46–3.39 (1H, m), 3.29 (3H, s), 2.95 (1H, dd, J=5.6, 14.0 Hz), 2.73 (1H, dd, J=8.0, 14.0 Hz), 2.47 (2H, d, J=6.6 Hz), 2.28–2.13 (1H, m), 2.00–1.59 (12H, m), 1.51–0.93 (7H, m).

Example 6(35)

(2R)-N-(4-methoxybenzyl)-3-cyclohexylmethylthio-2-(4-methoxycyclohexyl-carbonylamino) propanamide

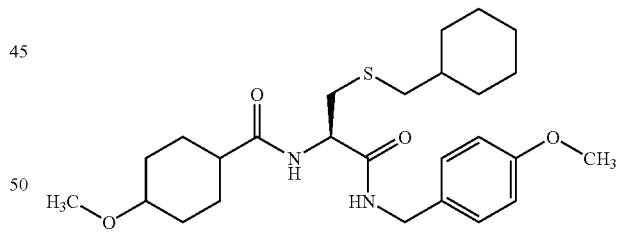

(The relative configuration of cyclohexyl ring substituted by methoxy group is not determined, but the above compound is a single compound. This compound is the isomer of the compound prepared in Example 6(34).) more polar TLC: Rf 0.33 (hexane:ethyl acetate=1:1); NMR (CDCl$_3$): δ 7.20 (2H, d, J=8.8 Hz), 6.86 (2H, d, J=8.8 Hz), 6.77 (1H, t, J=5.8 Hz), 6.48 (1H, d, J=7.0 Hz), 4.50–4.37 (3H, m), 3.80 (3H, s), 3.35 (3H, s), 3.12 (1H, tt, J=4.2, 10.6 Hz), 2.94 (1H, dd, J=5.1, 13.9 Hz), 2.72 (1H, dd, J=8.1, 13.9 Hz), 2.47 (2H, d, J=6.6 Hz), 2.17–2.03 (3H, m), 2.00–1.57 (8H, m), 1.51–0.93 (9H, m).

Example 6(36)

(2R)-N-(4-methoxybenzyl)-3-cyclohexylmethylthio-2-((2RS)-3-t-butoxy-carbonylthiazolidin-2-ylcarbonylamino)propanamide

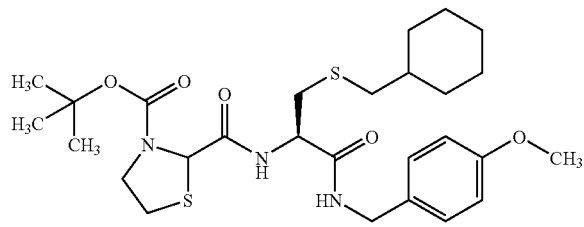

TLC: Rf 0.29 (ethyl acetate:hexane=2:3); NMR (CD$_3$OD): δ 7.23 (2H, d, J=9 Hz), 6.85 (2H, d, J=9 Hz), 5.23 (1H, bs), 4.56–4.44 (1H, m), 4.44–4.22 (2H, m), 4.00–3.84 (1H, m), 3.81–3.63 (1H, m), 3.77 (3H, s), 3.40–2.65 (4H, m), 2.42 (2H, d, J=7 Hz), 1.91–1.58 (6H, m), 1.58–1.10 (3H, m), 1.45 and 1.40 (9H, s), 1.05–0.80 (2H, m).

Example 6(37)

(2R)-N-(4-methoxybenzyl)-3-cyclohexylmethylthio-2-(2-methylpropylcarbonyl-amino)propanamide

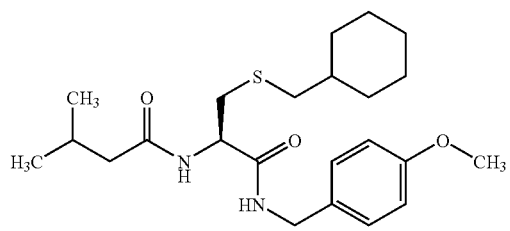

TLC: Rf 0.36 (ethyl acetate:hexane=2:3); NMR (CD$_3$OD): δ 7.26–7.16 (2H, m), 6.91–6.76 (3H, m), 6.43 (1H, d, J=8 Hz), 4.50 (1H, td, J=8, 5 Hz), 4.38 (2H, d, J=6 Hz), 3.80 (3H, s), 2.95 (1H, dd, J=14, 6 Hz), 2.76 (1H, dd, J=14, 8 Hz), 2.47 (2H, d, J=7 Hz), 2.20–1.95 (3H, m), 1.89–1.56 (6H, m), 1.56–1.05 (3H, m), 1.05–0.78 (2H, m), 0.94 (3H, d, J=7 Hz), 0.93 (3H, d, J=7 Hz).

Example 6(38)

(2R)-N-(4-methoxybenzyl)-3-cyclohexylmethylthio-2-(2-methylpropyloxy-carbonylamino)propanamide

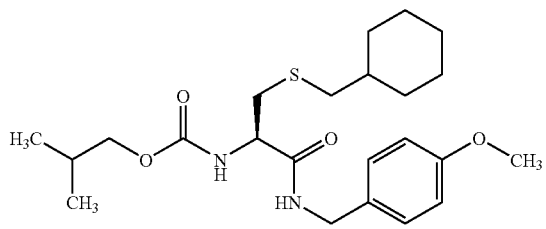

TLC: Rf 0.53 (ethyl acetate:hexane=2:3); NMR (CDCl$_3$): δ 7.26–7.15 (2H, m), 6.92–6.80 (2H, m), 6.75–6.58 (1H, m), 5.58 (1H, d, J=8 Hz), 4.40 (2H, d, J=6 Hz), 4.27 (1H, td, J=8, 5 Hz), 3.85 (2H, d, J=7 Hz), 3.80 (3H, s), 2.99 (1H, dd, J=14, 5 Hz), 2.82 (1H, dd, J=14, 8 Hz), 2.44 (2H, d, J=7 Hz), 2.02–1.55 (6H, m), 1.55–1.03 (4H, m), 1.03–0.77 (2H, m), 0.92 (6H, d, J=7 Hz).

Example 6(39)

(2R)-N-(4-methoxybenzyl)-3-cyclohexylmethylthio-2-(1-(t-butoxycarbonyl)-piperidin-4-ylcarbonylamino)propanamide

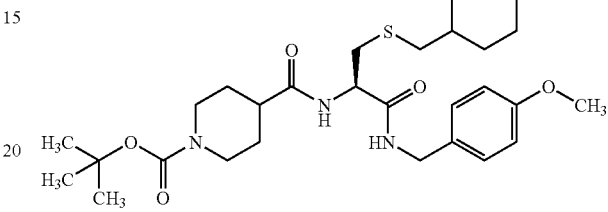

TLC: Rf 0.17 (hexane:ethyl acetate=2:1); NMR (CDCl$_3$): δ 7.20 (2H, d, J=8.2 Hz), 6.87 (2H, d, J=8.2 Hz), 6.79–6.73 (1H, br), 6.54 (1H, d, J=7.2 Hz), 4.50–4.38 (3H, m), 4.16–4.10 (2H, br), 3.80 (3H, s), 2.93 (1H, dd, J=4.9, 13.7 Hz), 2.81–2.67 (3H, m), 2.48 (2H, d, J=7.0 Hz), 2.29 (1H, tt, J=4.0, 11.8 Hz), 1.83–1.57 (9H, m), 1.46 (9H, s), 1.36–0.84 (6H, m).

Example 6(40)

(2R)-N-(4-methoxybenzyl)-3-cyclohexylmethylthio-2-(4-(t-butoxycarbonyl-amino)cyclohexylcarbonylamino)propanamide

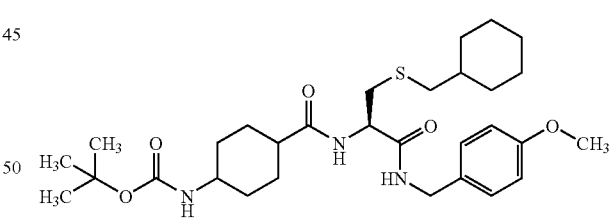

(The relative configuration of cyclohexyl ring substituted by t-butoxycarbonylamino group is not determined, but the above compound is a single compound. This compound is the isomer of the compound prepared in Example 6(41).)

TLC: Rf 0.27 (hexane:ethyl acetate=1:1); NMR (CDCl$_3$): δ 7.20 (2H, d, J=8.8 Hz), 6.94–6.82 (3H, m), 6.61 (1H, d, J=6.8 Hz), 4.71 (1H, d, J=8.0 Hz), 4.54–4.44 (1H, m), 4.38 (2H, d, J=5.4 Hz), 3.79–3.65 (4H, m), 2.92 (1H, dd, J=5.4, 13.8 Hz), 2.75 (1H, dd, J=8.0, 13.8 Hz), 2.47 (2H, d, J=6.6 Hz), 2.30–2.15 (1H, br), 1.92–1.53 (13H, m), 1.44 (9H, s), 1.26–1.08 (4H, m), 1.00–0.83 (2H, m).

Example 6(41)

(2R)-N-(4-methoxybenzyl)-3-cyclohexylmethylthio-2-(4-(t-butoxycarbonyl-amino)cyclohexylcarbonylamino)propanamide

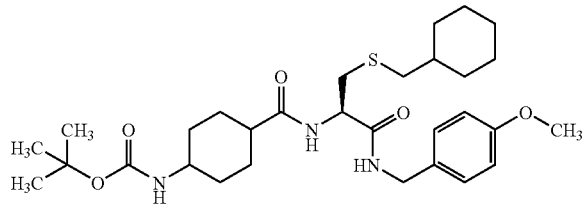

(The relative configuration of cyclohexyl ring substituted by t-butoxycarbonylamino group is not determined, but the above compound is a single compound. This compound is the isomer of the compound prepared in Example 6(40).)

TLC: Rf 0.27 (hexane:ethyl acetate=1:1); NMR (CDCl$_3$): δ 7.20 (2H, d, J=8.8 Hz), 6.86 (2H, d, J=8.8 Hz), 6.78–6.73 (1H, br), 6.48 (1H, d, J=6.6 Hz), 4.49–4.37 (4H, m), 3.80 (3H, s), 3.51–3.30 (1H, br), 2.93 (1H, dd, J=5.1, 13.9 Hz), 2.72 (1H, dd, J=8.1, 13.9 Hz), 2.48 (2H, d, J=6.6 Hz), 2.14–1.53 (14H, m), 1.44 (9H, s), 1.27–1.07 (4H, m), 1.00–0.83 (2H, m).

Example 6(42)

(2R)-N-(4-methoxybenzyl)-3-cyclohexylmethylthio-2-(tetrahydrofuran-2-ylcarbonylamino)propanamide

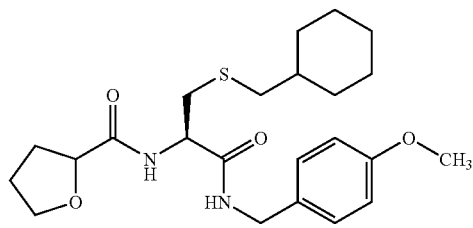

TLC: Rf 0.27 (hexane:ethyl acetate=2:1); NMR (DMSO-d$_6$): δ 7.43 (1H, t, J=10.6 Hz), 7.20 (2H, d, J=8.8 Hz), 6.85 (2H, d, J=8.8 Hz), 6.80–6.71 (1H, br), 4.55–4.31 (4H, m), 4.05–3.83 (2H, m), 3.79 (3H, s), 3.00–2.74 (2H, m), 2.45 (2H, t, J=6.6 Hz), 2.36–1.62 (9H, m), 1.51–1.07 (4H, m), 1.03–0.90 (2H, m).

Example 6(43)

(2R)-N-(4-methoxybenzyl)-3-cyclohexylmethoxy-2-cyclohexylcarbonyl-aminopropanamide

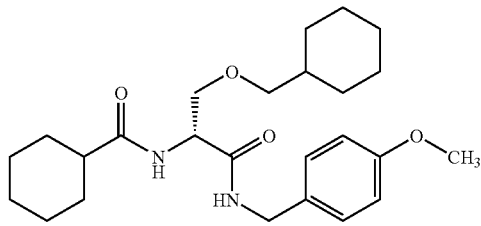

TLC: Rf 0.31 (ethyl acetate:hexane=2:3); NMR (CDCl$_3$): δ 7.25–7.14 (2H, m), 6.93–6.72 (3H, m), 6.43 (1H, d, J=6 Hz), 4.49 (1H, ddd, J=8, 6, 4 Hz), 4.43–4.28 (2H, m), 3.84–3.73 (1H, m), 3.80 (3H, s), 3.45–3.33 (1H, m), 3.29 (1H, dd, J=9, 5 Hz), 3.21 (1H, dd, J=9, 6 Hz), 2.24–2.06 (1H, m), 1.95–0.70 (21H, m).

Example 6(44)

(2R)-N-(4-methoxybenzyl)-3-cyclohexylmethylthio-2-((4R)-3-t-butoxycarbonyl-thiazolidin-4-ylcarbonylamino)propanamide

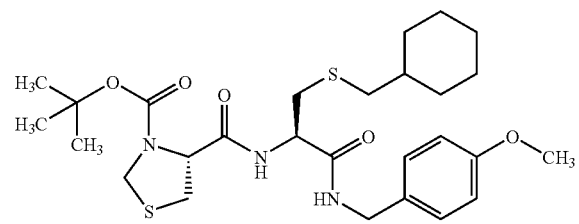

TLC: Rf 0.29 (ethyl acetate:hexane=2:3); NMR (CD$_3$OD): δ 7.27–7.17 (2H, m), 6.90–6.80 (2H, m), 4.67–4.43 (4H, m), 4.32 (1H, d, J=15 Hz), 4.30 (1H, d, J=15 Hz), 3.76 (3H, s), 3.42–3.30 (1H, m), 3.12 (1H, dd, J=12, 5 Hz), 3.00–2.70 (2H, m), 2.41 (2H, d, J=6 Hz), 1.90–0.78 (11H, m), 1.45 (9H, s).

Example 6(45)

(2R)-N-(4-methoxybenzyl)-3-cyclohexylmethylthio-2-((2S)-1-t-butoxycarbonyl-pyrrolidin-2-ylcarbonylamino)propanamide

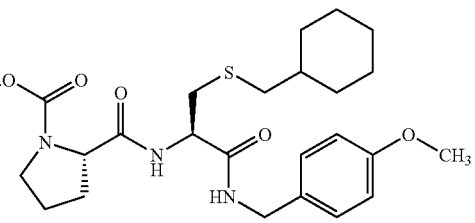

TLC: Rf 0.38 (ethyl acetate:chloroform=1:4); NMR (DMSO-d$_6$): δ 8.03–7.97 (1H, m), 7.57 (1H, d, J=8.8 Hz), 7.18 (2H, d, J=8.8 Hz), 6.85 (2H, d, J=8.8 Hz), 4.45–4.40 (1H, m), 4.21 (2H, d, J=7.5 Hz), 4.15–4.12 (1H, m), 3.73 (3H, s), 3.40–3.30 (2H, m), 2.85 (1H, dd, J=15.0, 8.7 Hz), 2.76 (1H, dd, J=15.0, 6.3 Hz), 2.42 (2H, d, J=3.0 Hz), 2.11–2.03 (1H, m), 1.88–1.72 (4H, m), 1.69–1.58 (3H, m), 1.45–1.33 (2H, m), 1.26–1.10 (3H, m), 0.98–0.92 (2H, m).

Example 6(46)

(2R)-N-(4-methoxybenzyl)-3-cyclohexylmethylthio-2-(thiazol-4-ylcarbonyl-amino)propanamide

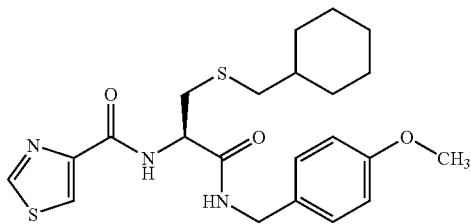

TLC: Rf 0.38 (ethyl acetate:hexane=1:1); NMR (CDCl$_3$): δ 8.77 (1H, d, J=1.8 Hz), 8.18 (1H, d, J=7.8 Hz), 8.12 (1H, d, J=1.8 Hz), 7.25–7.18 (2H, m), 6.88–6.81 (3H, m), 4.78–4.68 (1H, m), 4.51–4.33 (2H, m), 3.79 (3H, s), 3.16 (1H, dd, J=14.0, 5.6 Hz), 2.92 (1H, dd, J=14.0, 7.4 Hz), 2.57–2.41 (2H, m), 1.88–0.80 (11H, m).

Example 6(47)

(2R)-N-((1R)-1-(4-nitrophenyl)ethyl)-3-cyclohexylmethylthio-2-((4R)-3-t-butoxycarbonylthiazolidin-4-ylcarbonylamino)propanamide

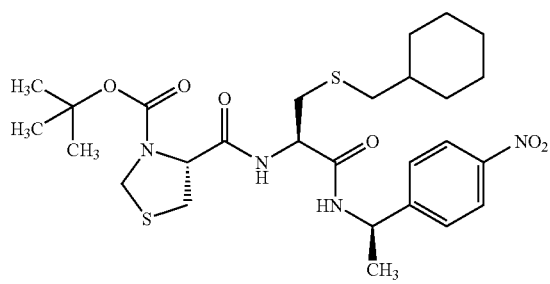

TLC: Rf 0.67 (ethyl acetate:hexane=1:1); NMR (CDCl$_3$): δ 8.19–8.12 (2H, m), 7.58–7.32 (3H, m), 7.12 (1H, d, J=8.0 Hz), 5.20–5.06 (1H, m), 4.67–4.46 (4H, m), 3.40–3.15 (3H, m), 2.75 (1H, dd, J=13.6, 5.8 Hz) 2.38–2.14 (2H, m), 1.80–0.64 (23H, m).

Example 6(48)

(2S)-N-((1R)-1-(4-nitrophenyl)ethyl)-3-cyclohexylmethylthio-2-((4R)-3-t-butoxycarbonylthiazolidin-4-ylcarbonylamino)propanamide

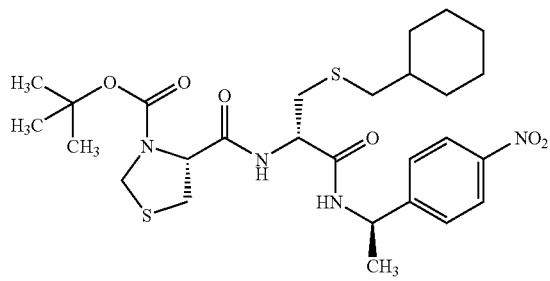

TLC: Rf 0.61 (ethyl acetate:hexane=1:1); NMR (CDCl$_3$): δ 8.21–8.14 (2H, m), 7.58–7.30 (3H, m), 7.05 (1H, d, J=7.4 Hz), 5.19–5.05 (1H, m), 4.65–4.47 (4H, m), 3.37–3.06 (3H, m), 2.79(1H, dd, J=13.8, 6.2 Hz) 2.50 (1H, dd, J=12.4, 6.6 Hz), 2.40 (1H, dd, J=12.4, 7.0 Hz), 1.90–0.78 ((23H, m).

Example 6(49)

(2R)-N-(4-methoxybenzyl)-3-cyclohexylmethylthio-2-(2-t-butoxycarbonyl-aminothiazol-4-ylcarbonylamino)propanamide

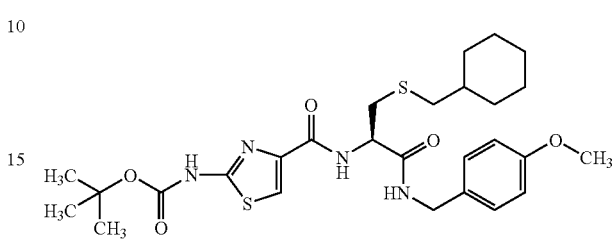

TLC: Rf 0.28 (ethyl acetate:hexane=2:3); NMR (CDCl$_3$): δ 8.09 (1H, bs), 7.91 (1H, bd, J=8 Hz), 7.66 (1H, s), 7.25–7.15 (2H, m), 6.89–6.78 (3H, m), 4.66 (1H, td, J=8, 6), 4.50–4.28 (2H, m), 3.80 (3H, s), 3.07 (1H, dd, J=14, 6 Hz), 2.91 (1H, dd, J=14, 8 Hz), 2.48 (2H, d, J=7 Hz), 1.90–0.78 (11H, m), 1.56 (9H, s).

Example 6(50)

(2R)-N-(4-methoxybenzyl)-3-cyclohexylmethylthio-2-((4S)-3-t-butoxycarbonyl-thiazolidin-4-ylcarbonylamino)propanamide

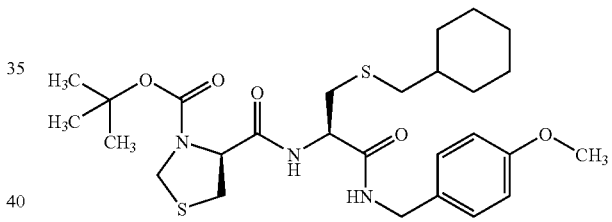

TLC: Rf 0.34 (ethyl acetate:hexane=2:3); NMR (CD$_3$OD) δ 7.27–7.17 (2H, m), 6.90–6.80 (2H, m), 4.66–4.43 (4H, m), 4.40–4.23 (2H, m), 3.78 (3H, s), 3.43–3.30 (1H, m), 3.16 (1H, dd, J=12, 6 Hz), 3.08–2.75 (1H, m), 2.78 (1H, dd, J=14, 7 Hz), 2.41 (2H, d, J=7 Hz), 1.90–0.80 (11H, m), 1.43 (9H, s).

Example 6(51)

(2R)-N-(4-nitrobenzyl)-3-cyclohexylmethylthio-2-((4R)-3-t-butoxycarbonyl-thiazolidin-4-ylcarbonylamino)propanamide

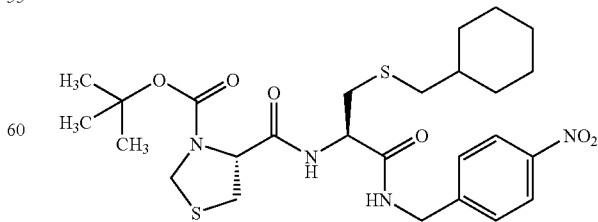

TLC: Rf 0.36 (ethyl acetate:hexane=1:1); NMR (CD$_3$OD) δ 8.25–8.15 (2H, m), 7.61–7.51 (2H, m), 4.70–4.41 (6H, m), 3.45–3.32 (1H, m), 3.22–3.08 (1H, m), 3.04–2.72 (2H, m), 2.45 (2H, d, J=7 Hz), 1.91–0.80 (11H, m), 1.45 (9H, s).

Example 6(52)

(2R)-N-(4-nitrobenzyl)-3-cyclohexylmethylthio-2-((2RS)-3-t-butoxycarbonyl-thiazolidin-2-ylcarbonylamino)propanamide

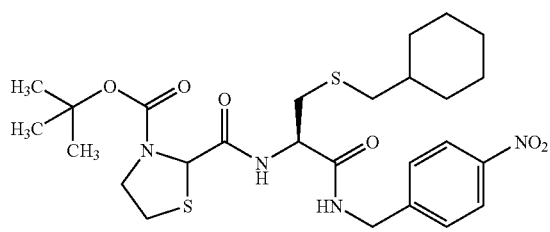

TLC: Rf 0.38 (ethyl acetate:hexane=1:1); NMR (CD$_3$OD): δ 8.23–8.14 (2H, m), 7.61–7.49 (2H, m), 5.22 (1H, bs), 4.62–4.42 (3H, m), 4.00–3.87 (1H, m), 3.80–3.64 (1H, m), 3.33–2.70 (4H, m), 2.45 (2H, d, J=7 Hz), 1.91–0.80 (11H, m), 1.45 and 1.40 (9H, s).

Example 6(53)

(2R)-N-(4-nitrobenzyl)-3-cyclohexylmethylthio-2-((4R)-3-methylthiazolidin-4-ylcarbonylamino)propanamide

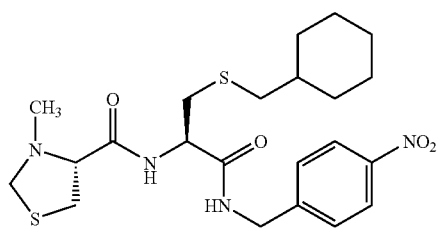

TLC: Rf 0.32 (ethyl acetate:hexane=1:1); NMR (CDCl$_3$): δ 8.23–8.16 (2H, m), 7.89 (1H, d, J=7.4 Hz), 7.49–7.42 (2H, m), 7.20–7.09 (1H, m), 4.61 (1H, dd, J=15.6, 6.2 Hz), 4.50 (1H, dd, J=15.6, 5.8 Hz), 4.51–4.40 (1H, m) 4.18 (1H, d, J=9.8 Hz), 3.89 (1H, dd, J=9.8, 1.0 Hz), 3.79 (1H, dd, J=7.4, 2.6 Hz), 3.52 (1H, dd, J=1.0, 2.6 Hz), 3.13 (1H, dd, J=11.0, 7.4 Hz), 2.98–2.80 (2H, m), 2.47 (3H, s), 2.45 (2H, d, J=7.4 Hz), 1.88–0.80 (11H, m).

Example 6(54)

(2R)-N-(4-dimethylaminobenzyl)-3-cyclohexylmethylthio-2-((4R)-3-t-butoxy-carbonylthiazolidin-4-ylcarbonylamino)propanamide

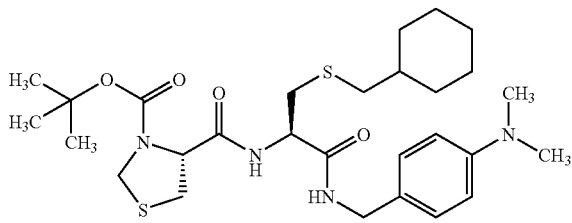

TLC: Rf 0.35 (ethyl acetate:hexane=2:3); NMR (CD$_3$OD): δ 7.20–7.10 (2H, m), 6.77–6.67 (2H, m), 4.67–4.43 (4H, m), 4.29 (1H, d, J=6 Hz), 4.28 (1H, d, J=6 Hz), 3.41–3.30 (1H, m), 3.12 (1H, dd, J=12, 5 Hz), 3.00–2.65 (8H, m), 2.41 (2H, d, J=7 Hz), 1.88–0.80 (11H, m), 1.45 (9H, s).

Example 6(55)

(2R)-N-(4-dimethylaminobenzyl)-3-cyclohexylmethylthio-2-((2RS)-3-t-butoxy-carbonylthiazolidin-2-ylcarbonylamino)propanamide

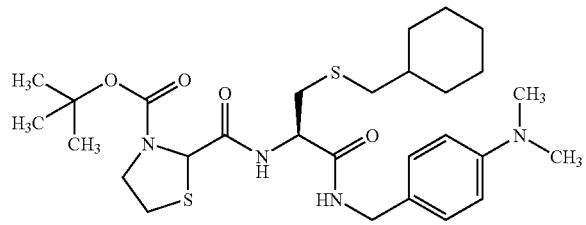

TLC: Rf 0.29 (ethyl acetate:hexane=2:3); NMR (CD$_3$OD): δ 7.20–7.10 (2H, m), 6.77–6.67 (2H, m), 5.23 (1H, bs), 4.55–4.43 (1H, m), 4.40–4.16 (2H, m), 4.00–3.84 (1H, m), 3.79–3.63 (1H, m), 3.30–2.66 (10H, m), 2.42 (2H, d, J=7 Hz), 1.90–0.80 (11H, m), 1.45 and 1.42 (9H, s).

Example 6(56)

(2R)-N-(4-nitrobenzyl)-3-cyclohexylmethylthio-2-(1-t-butoxycarbonylimidazol-4-ylcarbonylamino)propanamide

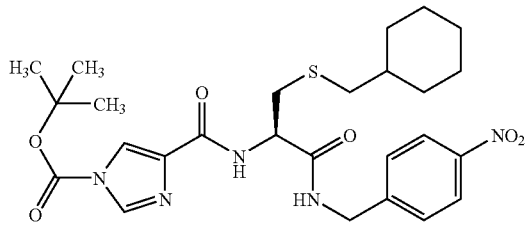

TLC: Rf 0.48 (methylene chloride:ethyl acetate=4:1); NMR (CDCl$_3$): δ 8.17 (2H, d, J=8.8 Hz), 8.03 (1H, d, J=1.4 Hz), 7.98 (1H, d, J=1.4 Hz), 7.85 (1H, d, J=7.4 Hz), 7.45 (2H, d, J=8.8 Hz), 7.10 (1H, t, J=6.2 Hz), 4.78–4.68 (1H, m), 4.57 (2H, d, J=6.2 Hz), 3.12 (1H, dd, J=5.8, 13.6 Hz), 2.96 (1H, dd, J=7.0, 13.6 Hz), 2.50 (2H, d, J=6.6 Hz), 1.88–1.36 (15H, m), 1.30–0.90 (5H, m).

Example 6(57)

(2R)-N-(4-nitrobenzyl)-3-cyclohexylmethylthio-2-((4R)-2,2-dimethylthiazolidin-4-ylcarbonylamino)propanamide

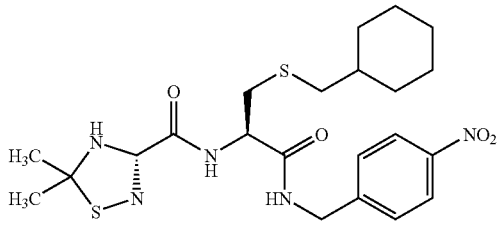

TLC: Rf 0.47 (ethyl acetate:hexane=2:1); NMR (CDCl₃): δ 8.24–8.17 (2H, m), 7.81 (1H, bd, J=8 Hz), 7.50–7.42 (2H, m), 7.09 (1H, bt, J=6 Hz), 4.68–4.45 (3H, m), 4.16 (1H, t, J=7 Hz), 3.45 (1H, dd, J=11, 8 Hz), 3.37 (1H, dd, J=11, 7 Hz), 2.97 (1H, dd, J=14, 5 Hz), 2.82 (1H, dd, J=14, 8 Hz), 2.62–2.35 (1H, b), 2.49 (2H, d, J=7 Hz), 1.88–0.78 (11H, m), 1.65 (3H, s), 1.57 (3H, s).

Example 6(58)

(2R)-N-(4-nitrobenzyl)-3-cyclohexylmethylthio-2-(thiophen-2-ylcarbonyl-amino)propanamide

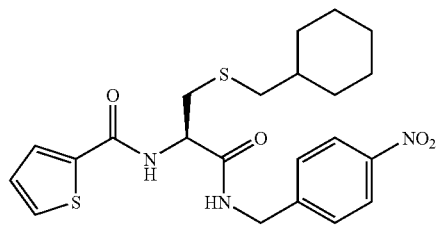

TLC: Rf 0.20 (hexane:ethyl acetate=2:1); NMR (CDCl₃): δ 8.18 (2H, d, J=8.8 Hz), 7.58–7.52 (2H, m), 7.47 (2H, d, J=8.8 Hz), 7.31–7.25 (1H, br), 7.11 (1H, dd, J=3.6, 5.2 Hz), 7.04, (1H, d, J=6.6 Hz), 4.77–4.49 (3H, m), 3.13 (1H, dd, J=5.2, 14.0 Hz), 2.87 (1H, dd, J=8.2, 14.0 Hz), 2.54 (2H, d, J=7.0 Hz), 1.88–1.37 (6H, m), 1.33–0.82 (5H, m).

Example 6(59)

(2R)-N-(4-nitrobenzyl)-3-cyclohexylmethylthio-2-(5-methyloxazol-2-ylcarbonyl-amino)propanamide

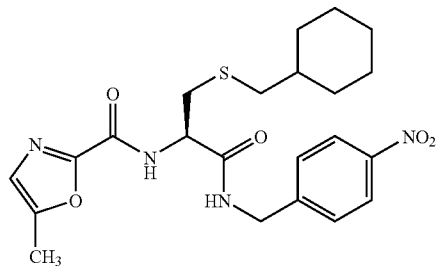

TLC: Rf 0.48 (methylene chloride:ethyl acetate=4:1); NMR (CDCl₃): δ 8.18 (2H, d, J=8.8 Hz), 7.81 (1H, d, J=7.4 Hz), 7.46 (2H, d, J=8.8 Hz), 7.06 (1H, t, J=5.4 Hz), 6.88 (1H, d, J=1.2 Hz), 4.75–4.49 (3H, m), 3.09 (1H, dd, J=5.8, 13.8 Hz), 2.90 (1H, dd, J=7.6, 13.8 Hz), 2.59–2.46 (2H, m), 2.41 (3H, d, J=1.2 Hz), 1.88–1.37 (6H, m), 1.34–0.81 (5H, m).

Example 6(60)

(2R)-N-(4-methoxybenzyl)-3-cyclohexylmethylthio-2-(3-t-butoxycarbonyl-thiazolidin-2-ylcarbonylamino)propanamide

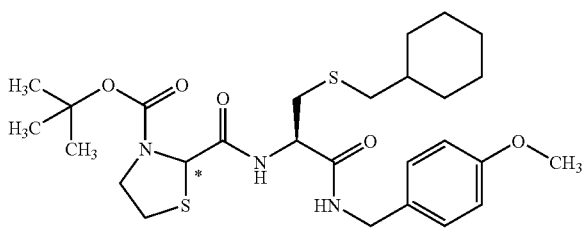

(The absolute configuration of * carbon is not determined, but the above compound is a single optical isomer.)

$[α]_D$=−40.4 (c 0.1, CHCl₃);

TLC: Rf 0.19 (hexane:ethyl acetate=2:1); NMR (CDCl₃): δ 7.21 (2H, d, J=8.4 Hz), 7.13–6.85 (2H, br), 6.84 (2H, d, J=8.4 Hz), 5.24 (1H, s), 4.57–4.46 (1H, m), 4.37 (2H, d, J=5.6 Hz), 3.90–3.80 (2H, m), 3.79 (3H, s), 3.22–3.03 (2H, m), 2.95 (1H, dt, J=5.2, 11.0 Hz), 2.81 (1H, dd, J=7.0, 14.0 Hz), 2.50–2.32 (2H, m), 1.85–1.56 (6H, m), 1.41 (9H, s), 1.30–0.77 (5H, m).

Example 6(61)

(2R)-N-(4-methoxybenzyl)-3-cyclohexylmethylthio-2-(3-t-butoxycarbonyl-thiazolidin-2-ylcarbonylamino)propanamide

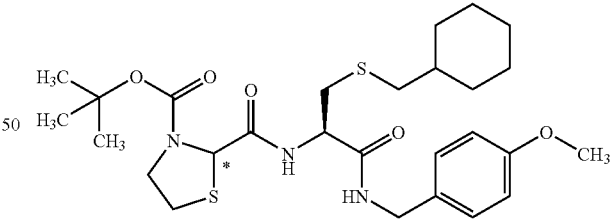

(The absolute configuration of * carbon is not determined, but the above compound is a single optical isomer.)

$[α]_D$=+22.0 (c 0.11, CHCl₃);

TLC: Rf 0.19 (hexane:ethyl acetate=2:1); NMR (CDCl₃): δ 7.43–7.25 (1H, br), 7.21 (2H, d, J=8.8 Hz), 6.90–6.78 (3H, m), 5.16 (1H, s), 4.61–4.20 (3H, m), 3.94–3.81 (2H, br), 3.79 (3H, s), 3.40–3.02 (2H, br), 2.96 (1H, dt, J=5.0, 11.0 Hz), 2.76 (1H, dd, J=7.0, 13.8 Hz), 2.50–2.31 (2H, m), 1.83–1.57 (6H, m), 1.42 (9H, s), 1.29–0.77 (5H, m).

Example 6(62)

(2R)-N-(4-dimethylaminobenzyl)-3-cyclohexylmethylthio-2-cyclohexyl-carbonylaminopropanamide

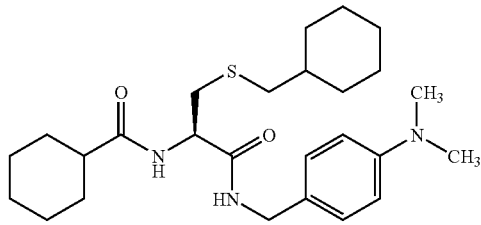

TLC: Rf 0.58 (ethyl acetate:hexane=1:1); NMR (CDCl$_3$): δ 7.17–7.13 (2H, m), 6.79–6.69 (3H, m), 6.51 (1H, d, J=6.6 Hz), 4.50–4.44 (1H, m), 4.34 (2H, d, J=5.4 Hz), 2.96–2.90 (7H, m), 2.74 (1H, dd, J=13.5, 8.1 Hz), 2.49 (1H, dd, J=12.9, 6.9 Hz), 2.44 (1H, dd, J=12.9, 6.6 Hz), 2.18–2.08 (1H, m), 1.98–0.83 (21H, m).

Example 6(63)

(2S)-N-(4-methoxybenzyl)-3-cyclohexylmethylthio-2-(3-t-butoxycarbonyl-thiazolidin-2-ylcarbonylamino)propanamide

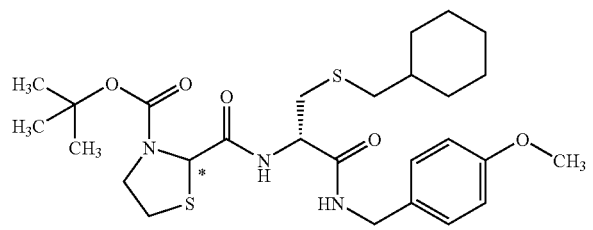

(The absolute configuration of * carbon is not determined, but the above compound is a single optical isomer.)
[α]$_D$=+31.11 (c 1.08, CHCl$_3$);
TLC: Rf 0.19 (ethyl acetate:hexane=1:2); NMR (CDCl$_3$): δ 7.21 (2H, d, J=8.7 Hz), 7.10–6.73 (4H, m), 5.24 (1H, s), 4.57–4.45 (1H, m), 4.38 (2H, d, J=5.4 Hz), 3.88–3.73 (5H, m), 3.20–3.11 (2H, m), 2.99–2.92 (1H, m), 2.79 (1H, dd, J=13.8, 7.2 Hz), 2.48–2.35 (2H, m), 1.83–1.58 (5H, m), 1.51–1.37 (10H, m), 1.28–1.05 (3H, m), 0.98–0.83 (2H, m).

Example 6(64)

(2S)-N-(4-methoxybenzyl)-3-cyclohexylmethylthio-2-((4S)-3-t-butoxycarbonyl-thiazolidin-4-ylcarbonylamino)propanamide

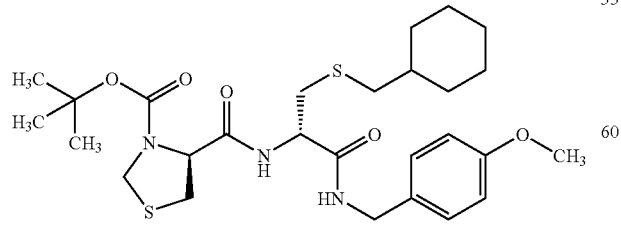

TLC: Rf 0.57 (ethyl acetate:hexane=1:1); NMR (CD$_3$OD): δ 7.25–7.18 (2H, m), 6.88–6.81 (2H, m), 4.65–4.45 (4H, m), 4.35 (1H, d, J=14:6 Hz), 4.26 (1H, d, J=14.6 Hz), 3.75 (3H, s), 3.35 (1H, dd, J=12.2, 7.4 Hz), 3.11 (1H, dd, J=12.2, 4.8 Hz), 2.98–2.72 (2H, m), 2.41 (2H, d, J=6.6 Hz), 1.88–0.80 (20H, m).

Example 6(65)

(2S)-N-(4-methoxybenzyl)-3-cyclohexylmethylthio-2-((4R)-3-t-butoxycarbonyl-thiazolidin-4-ylcarbonylamino)propanamide

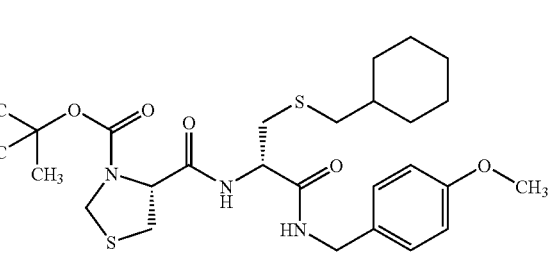

TLC: Rf 0.61 (ethyl acetate:hexane=1:1); NMR (CD$_3$OD): δ 7.25–7.17 (2H, m), 6.88–6.81 (2H, m), 4.64–4.44 (4H, m), 4.32 (2H, br. s), 3.75 (3H, s), 3.35 (1H, dd, J=12.2, 7.4 Hz), 3.13 (1H, dd, J=12.2, 5.4 Hz), 2.97 (1H, br. s), 2.76 (1H, dd, J=13.6, 8.4 Hz), 2.40 (2H, d, J=7.0 HZ), 1.88–0.80 (20H, m).

Example 6(66)

(2R)-N-methyl-N-(4-methoxybenzyl)-3-cyclohexylmethylthio-2-((4R)-3-t-butoxycarbonylthiazolidin-4-ylcarbonylamino)propanamide

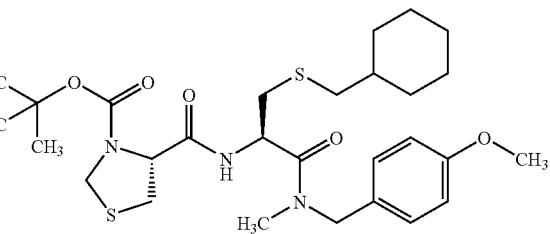

TLC: Rf 0.28 (ethyl acetate:hexane=1:2); NMR (CDCl$_3$): δ 7.24–7.02 (3H, m), 6.90–6.83 (2H, m), 5.16–5.06 (1H, m), 4.90–4.38 (5H, m), 3.80–3.79 (3H, m), 3.39–3.16 (2H, m), 3.03–2.69 (5H, m), 2.44–2.23 (2H, m), 1.85–0.76 (20H, m).

Example 6(67)

(2R)-N-(4-methoxybenzyl)-3-cyclohexylmethylthio-2-((4R)-N'-methyl-N'-(3-t-butoxycarbonylthiazolidin-4-ylcarbonyl)amino)propanamide

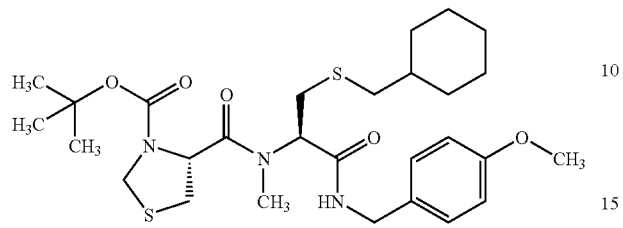

TLC: Rf 0.37 (ethyl acetate:hexane=1:2); NMR (CD₃OD): δ 7.23–7.17 (2H, m), 6.86–6.82 (2H, m), 5.18–5.00 (2H, m), 4.70–4.66 (1H, m), 4.49–4.18 (3H, m), 3.76 and 3.75 (3H, s), 3.54–2.68 (7H, m), 2.47–2.43 (2H, m), 1.90–1.60 (5H, m), 1.50–1.05 (4H, m), 1.44 and 1.33 (9H, m), 1.05–0.87 (2H, m).

Example 6(68)

(2R)-N-(4-penoxybenzyl)-3-cyclohexylmethylthio-2-((4R)-3-t-butoxycarbonyl-thiazolidin-4-ylcarbonylamino)propanamide

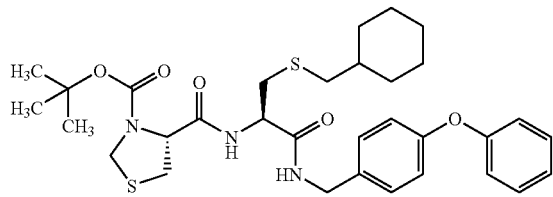

TLC: Rf 0.58 (ethyl acetate:hexane=1:11); NMR (CDCl₃): δ 7.36–7.23 (5H, m), 7.15–7.07 (2H, m), 7.01–6.91 (4H, m), 4.65–4.32 (6H, m), 3.33–3.13 (3H, m), 2.79 (1H, dd, J=14.1, 6.3 Hz), 2.45–2.30 (2H, m), 1.83–0.78 (20H, m).

Example 6(69)

(2R)-N-(4-methoxybenzyl)-3-cyclohexylmethylthio-2-((2RS,4R)-3-t-butoxy-carbonyl-2-(2-methylpropyl)thiazolidin-4-ylcarbonylamino)propanamide

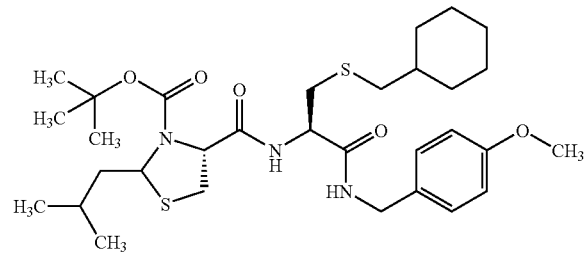

TLC: Rf 0.32 (ethyl acetate:hexane=1:2); NMR (CDCl₃): δ 7.40–7.19 (3H, m), 7.14 (1H, d, J=8 Hz), 6.86–6.80 (2H, m), 5.20–5.07 (1H, m), 4.64 (1H, t, J=7 Hz), 4.63–4.52 (1H, m), 4.43 (1H, dd, J=15, 6 Hz), 4.32 (1H, dd, J=15, 6 Hz), 3.78 (3H, s), 3.36–3.15 (3H, m), 2.78 (1H, dd, J=14, 6 Hz), 2.46–2.24 (2H, m), 1.91–1.53 (8H, m), 1.50–1.30 (10H, m), 1.30–1.03 (3H, m), 1.00–0.78 (8H, m).

Example 6(70)

(2R)-N-(4-methoxybenzyl)-3-cyclohexylmethylthio-2-(pyridin-3-ylcarbonyl-amino)propanamide

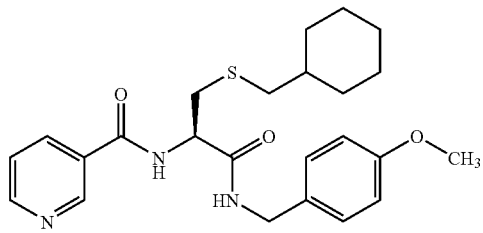

TLC: Rf 0.19 (ethyl acetate:hexane=3:1); NMR (CDCl₃): δ 9.04 (1H, dd, J=3, 1 Hz), 8.75 (1H, dd, J=5, 2 Hz), 8.10 (1H, ddd, J=8, 3, 2 Hz), 7.39 (1H, ddd, J=8, 5, 1 Hz), 7.43–7.36 (1H, m), 7.26–7.19 (2H, m), 6.97–6.90 (1H, m), 6.90–6.83 (2H, m), 4.72–4.63 (1H, m), 4.43 (1H, dd, J=15, 6 Hz), 4.42 (1H, dd, J=15, 6 Hz), 3.79 (3H, s), 3.09 (1H, dd, J=14, 5 Hz), 2.84 (1H, dd, J=14, 8 Hz), 2.54 (1H, dd, J=12, 7 Hz), 2.52 (2H, dd, J=12, 7 Hz), 1.86–1.59 (5H, m), 1.56–1.39 (1H, m), 1.30–1.03 (3H, m), 1.00–0.85 (2H, m).

Example 6(71)

(2R)-N-(4-benzyloxybenzyl)-3-cyclohexylmethylthio-2-((4R)-3-t-butoxy-carbonylthiazolidin-4-ylcarbonylamino)propanamide

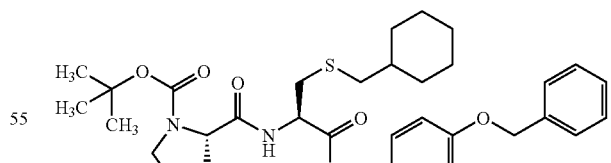

TLC: Rf 0.63 (ethyl acetate:hexane=1:1); NMR (CDCl₃): δ 7.44–7.18 (8H, m), 7.13 (1H, d, J=7.8 Hz), 6.93–6.88 (2H, m), 5.04 (2H, s), 4.65–4.21 (6H, m), 3.32–3.12 (3H, m), 2.78 (1H, dd, J=13.8, 6.3 Hz), 2.44–2.30 (2H, m), 1.80–0.78 (20H, m).

Example 6(72)

(2R)-N-(3-benzyloxy-4-methoxybenzyl)-3-cyclohexylmethylthio-2-((4R)-3-t-butoxycarbonylthiazolidin-4-ylcarbonylamino)propanamide

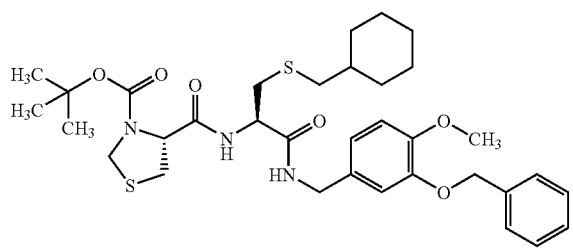

TLC: Rf 0.46 (hexane:ethyl acetate=1:1); NMR (CD₃OD): δ 7.47–7.25 (5H, m), 7.00 (1H, d, J=1.4 Hz), 6.92–6.83 (2H, m), 5.09 (2H, s), 4.63–4.42 (4H, m), 4.35 (1H, d, J=14.8 Hz), 4.24 (1H, d, J=14.8 Hz), 3.81 (3H, s), 3.41–3.30 (1H, m), 3.12 (1H, dd, J=5.0, 12.2 Hz), 3.00–2.71 (2H, br), 2.40 (2H, d, J=7.0 Hz), 1.89–1.59 (5H, m), 1.54–1.31 (10H, m), 1.29–1.08 (3H, m), 1.04–0.76 (2H, m).

Example 6(73)

(2R)-N-(4-methoxybenzyl)-3-cyclohexylmethylthio-2-(pyridin-4-ylcarbonyl-amino)propanamide

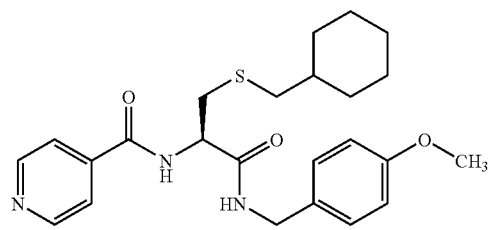

TLC: Rf 0.23 (ethyl acetate:methylene chloride=1:1); NMR (CDCl₃): δ 8.79–8.72 (2H, m), 7.66–7.61 (2H, m), 7.47 (1H, d, J=6 Hz), 7.26–7.19 (2H, m), 6.96–6.84 (3H, m), 4.69–4.61 (1H, m), 4.43 (1H, dd, J=15, 6 Hz), 4.42 (1H, dd, J=15, 6 Hz), 3.80 (3H, s), 3.08 (1H, dd, J=14, 5 Hz), 2.82 (1H, dd, J=14, 9 Hz), 2.54 (1H, dd, J=14, 7 Hz), 2.53 (2H, dd, J=14, 7 Hz), 1.86–1.75 (2H, m), 1.75–1.59 (3H, m), 1.55–1.39 (1H, m), 1.30–1.03 (3H, m), 1.03–0.85 (2H, m).

Example 6(74)

(2R)-N-(4-methoxybenzyl)-3-cyclohexylmethylthio-2-((2RS,4R)-3-t-butoxycarbonyl-2-phenylthiazolidin-4-ylcarbonylamino)propanamide

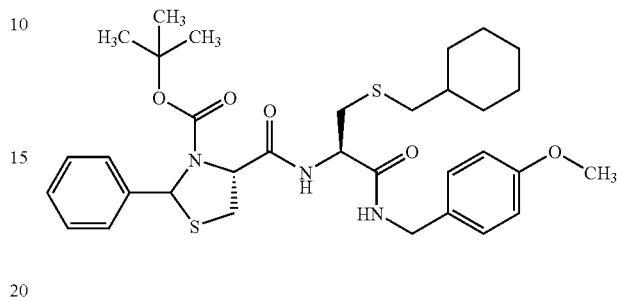

TLC: Rf 0.26 (ethyl acetate:hexane=2:3); NMR (CDCl₃): δ 7.53–7.20 (m, 9H), 6.85–6.79 (m, 2H), 5.99 (bs, 1H), 4.80 (dd, J=8, 5 Hz, 1H), 4.72–4.60 (b, 1H), 4.44 (dd, J=15, 6 Hz, 1H), 4.31 (dd, J=15, 6 Hz, 1H), 3.77 (s, 3H), 3.47 (dd, J=12, 5 Hz, 1H), 3.36 (dd, J=12, 8 Hz, 1H), 3.25–3.10 (b, 1H), 2.85–2.73 (m, 1H), 2.38 (dd, J=12, 6 Hz, 1H), 2.29 (dd, J=12, 8 Hz, 1H), 1.78–1.56 (m, 5H), 1.47–1.00 (m, 13H), 0.94–0.74 (m, 2H).

Example 6(75)

(4R)-N-((1R)-2-cyclohexylmethylthio-1-(4-phenylpiperazin-1-ylcarbonyl)ethyl)-3-t-butoxycarbonylthiazolidin-4-ylcarboxamide

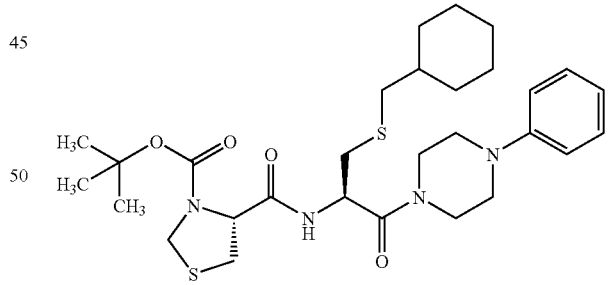

TLC: Rf 0.57 (ethyl acetate:hexane=1:1); NMR (CDCl₃): δ 7.32–7.26 (m, 2H), 7.20–7.05 (br. s, 1H), 6.95–6.89 (m, 2H), 5.14–5.07 (m, 1H), 4.80–4.58 (m, 2H), 4.40 (d, J=9.3 Hz, 1H), 3.88–3.66 (m, 4H), 3.38 (dd, J=11.7, 2.7 Hz 1H), 3.25–3.16 (m, 5H), 2.91 (dd, J=13.8, 7.2 Hz, 1H), 2.77 (dd, J=13.8, 5.7 Hz, 1H), 2.44 (d, J=6.6 Hz, 2H), 1.86–1.59 (m, 5H), 1.54–1.34 (m, 10H), 1.30–1.04 (m, 3H), 0.99–0.84 (m, 2H).

Example 6(76)

(2R)-N-(4-methoxybenzyl)-3-cyclohexylmethylthio-2-((3RS)-4-t-butoxy-carbonylthiomorpholin-3ylcarbonylamino)propanamide

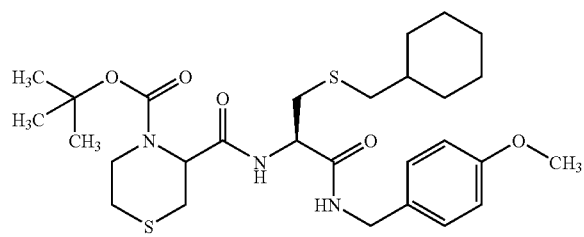

TLC: Rf 0.34 (ethyl acetate:hexane=2:3); NMR (CDCl$_3$): δ 7.26–7.18 (m, 2H), 7.06–6.82 (m, 4H), 5.00 (bs, 1H), 4.63–4.52 (m, 1H), 4.50–4.10 (m, 3H), 3.79 (s, 3H), 3.30–3.05 (m, 3H), 2.89–2.57 (m, 3H), 2.53–2.28 (m, 3H), 1.85–1.56 (m, 5H), 1.55–1.35 (m, 1 0H), 1.30–1.03 (m, 3H), 1.00–0.81 (m, 2H).

Example 6(77)

(2R)-N-(4-phenoxybenzyl)-3-cyclohexylmethylthio-2-((3RS)-4-t-butoxy-carbonylthiomorpholin-3-ylcarbonylamino)propanamide

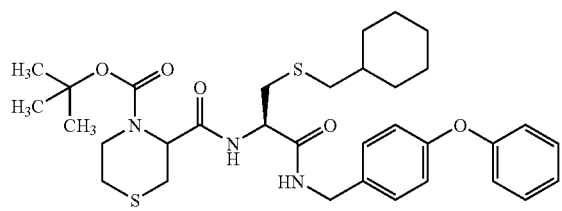

TLC: Rf 0.27 (ethyl acetate:hexane=1:2); NMR (CDCl$_3$): δ 7.37–7.29 (m, 2H), 7.29–7.22 (m, 2H), 7.14–7.07 (m, 1H), 7.05–6.90 (m, 6H), 5.06–4.93 (m, 11H), 4.65–4.10 (m, 4H), 3.35–3.00 (m, 3H), 2.91–2.57 (m, 3H), 2.55–2.30 (m, 3H), 1.84–1.56 (m, 5H), 1.56–1.35 (m, 10H), 1.30–1.03 (m, 3H), 1.00–0.83 (m, 2H).

Example 6(78)

(2R)-N-(2-phenoxypyride-5-yl)-3-cyclohexylmethylthio-2-((4R)-3-t-butoxy-carbonylthiazolidin-4-ylcarbonylamino)propanamide

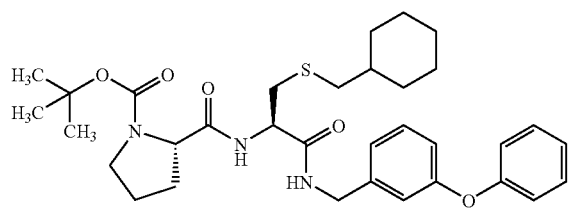

TLC: Rf 0.57 (ethyl acetate:hexane=1:1); NMR (CDCl$_3$): δ 8.93 (br. s, 1H), 8.49 (br. s, 1H), 8.20 (d, J=7.5 Hz, 1H), 7.42–7.35 (m, 2H), 7.24–7.08 (m, 4H), 6.86 (d, J=9.0 Hz, 1H), 4.80–4.70 (m, 1H), 4.66 (dd, J=7.2, 3.9 Hz, 1H), 4.60 (d, J=9.9 Hz, 1H), 4.55 (d, J=9.9 Hz, 1H), 3.41–3.27 (m, 3H), 2.84 (dd, J=13.8, 5.7 Hz, 1H), 2.48–2.33 (m, 2H), 1.82–1.58 (m, 5H), 1.54–1.35 (m, 10H), 1.28–1.02 (m, 3H), 0.96–0.78 (m, 2H).

Example 6(79)

(2R)-N-(4-methoxybenzyl)-3-cyclohexylmethylthio-2-((2RS)-4-t-butoxy-carbonylthiomorpholin-2-ylcarbonylamino)propanamide

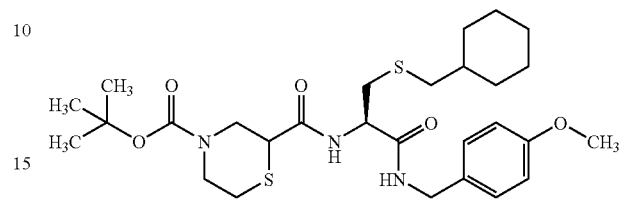

TLC: Rf 0.27 (ethyl acetate:hexane=2:3); NMR (CDCl$_3$): δ 7.65–7.30 (b, 1H), 7.24–7.18 (m, 2H), 6.90–6.83 (m, 2H), 6.77–6.67 (b, 1H), 4.51–4.04 (m, 4H), 3.92–3.46 (m, 3H), 3.80 (s, 3H), 3.40–3.29 (m, 1H), 3.03–2.92 (m, 1H), 2.90–2.67 (m, 2H), 2.60–2.49 (m, 1H), 2.49–2.42 (m, 2H), 1.94–1.55 (m, 5H), 1.53–1.33 (m, 10H), 1.30–1.04 (m, 3H), 1.00–0.83 (m, 2H).

Example 6(80)

(2R)-N-(4-methoxybenzyl)-3-cyclohexylmethylthio-2-((4RS)-3-t-butoxycarbonyl-1,3-perhydrothiazin-4-ylcarbonylamino)propanamide

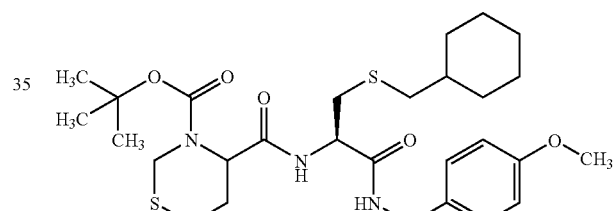

TLC: Rf 0.38 (ethyl acetate:hexane=2:3); NMR (CDCl$_3$): δ 7.24–7.17 (m, 2H), 7.04–6.93 and 6.79–6.68 (m, 2H), 6.90–6.82 (m, 2H), 4.86–4.20 (m, 6H), 3.79 (s, 3H), 3.04–2.70 (m, 3H), 2.66–2.37 (m, 4H), 2.07–1.85 (m, 1H), 1.85–1.55 (m, 5H), 1.53–1.33 (m, 10H), 1.30–1.04 (m, 3H), 1.00–0.83 (m, 2H).

Example 6(81)

(2R)-N-(2-phenoxypyridin-5-ylmethyl)-3-cyclohexylmethylthio-2-((4R)-3-t-butoxycarbonylthiazolidin-4-ylcarbonylamino)propanamide

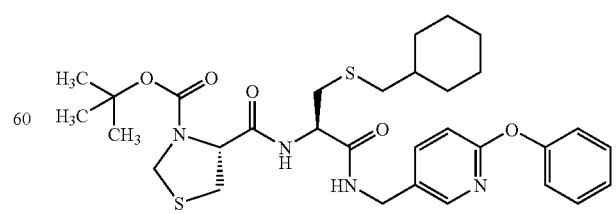

TLC: Rf 0.56 (ethyl acetate:hexane=2:1); NMR (CDCl$_3$): δ 8.11 (d, J=2.4 Hz, 1H), 7.68 (dd, J=8.4, 2.4 Hz, 1H), 7.50–7.35 (m, 3H), 7.22–7.16 (m, 1H), 7.14–7.08 (m, 3H), 6.84 (d, J=8.4 Hz, 1H), 4.68–4.31 (m, 6H), 3.35–3.20 (m, 3H), 2.78 (dd, J=13.8, 6.0, 1H), 2.44–2.28 (m, 2H), 1.82–1.60 (m, 5H), 1.51–1.36 (m, 10H), 1.32–1.08 (m, 3H), 0.98–0.80 (m, 2H).

Example 6(82)

(2R)-N-(4-(morpholin-4-yl)benzyl)-3-cyclohexylmethylthio-2-((4R)-3-t-butoxy-carbonylthiazolidin-4-ylcarbonylamino)propanamide

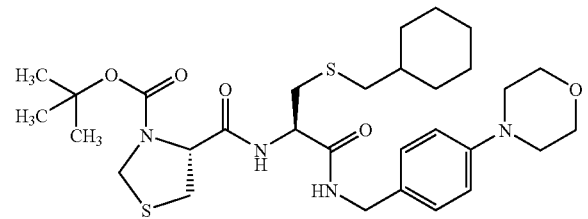

TLC: Rf 0.34 (ethyl acetate:hexane=1:1); NMR (CDCl$_3$): δ 7.20 (d, J=8.7 Hz, 1H), 7.17–7.12 (m, 2H), 6.84 (d, J=8.7 Hz, 2H), 4.64 (dd, J=6.6, 4.2 Hz, 1H), 4.58 (br. s, 2H), 4.44 (d, J=9.3 Hz, 1H), 4.41–4.28 (m, 2H), 3.87–3.84 (m, 4H), 3.31 (dd, J=12.3, 3.9, 1H), 3.26 (dd, J=12.3,6.6 Hz, 1H), 3.20 (br. s, 1H), 3.19–3.11 (m, 4H), 2.78 (dd, J=13.5, 6.3 Hz, 1H), 2.44–2.28 (m, 2H), 1.82–1.60 (m, 5H), 1.5–1.34 (m, 10H), 1.31–1.04 (m, 3H), 0.96–0.80 (m, 2H).

Example 6(83)

(2R)-N-(4-Phenoxybenzyl)-3cyclohexylmethylthio-2-((4RS)-3-t-butoxycarbonyl-1,3-perhydrothiazin-4-ylcarbonylamino)propanamide

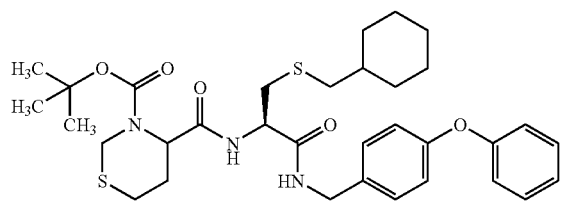

TLC: Rf 0.33 ethyl acetate:hexane=1:2); NMR (CD$_3$OD) δ 7.37–7.25 (m, 4H), 7.13–7.06 (m, 1H), 6.99–6.89 (m, 4H), 4.94–4.30 (m, 6H), 3.08–2.87 (m, 2H), 2.87–2.76 (m, 1H), 2.68–2.50 (m, 1H), 2.50–2.30 (m, 3H), 2.08–1.76 (m, 3H), 1.76–1.60 (m, 3H), 1.60–1.35 (m, 10H), 1.35–1.07 (m, 3H), 1.03–0.85 (m, 2H).

Example 6(84)

(2R)-N-(1-phenylpiperidin-4-yl)-3-cyclohexylmethylthio-2-((4R)-3-t-butoxy-carbonylthiazolidin-4-ylcarbonylamino)propanamide

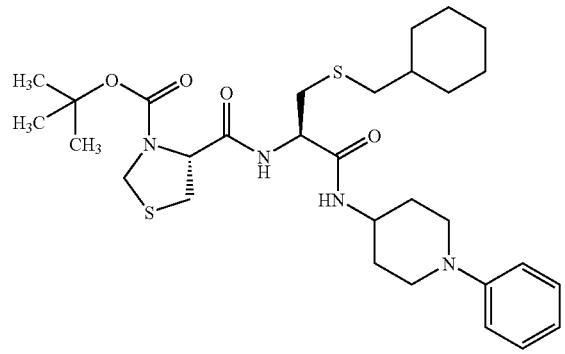

TLC: Rf 0.46 (hexane:ethyl acetate=1:1); NMR (CD$_3$OD): δ 7.24–7.18 (m, 2H), 6.97 (dd, J=8.7, 0.9 Hz, 2H), 6.81 (t, J=7.5 Hz, 1H), 4.65–4.56 (m, 2H), 4.50–4.45 (m, 2H), 3.86–3.76 (m, 1H), 3.68–3.57 (br, 2H), 3.43–3.32 (br, 1H), 3.16 (dd, J=12.0, 4.8 Hz, 1H), 2.94–2.77 (m, 4H), 2.46 (d, J=6.6 Hz, 2H), 2.00–1.79 (br, 4H), 1.78–1.59 (m, 5H), 1.52–1.38 (m, 10H), 1.33–1.09 (m, 3H), 1.01–0.89 (m, 2H).

Example 6(85)

(2R)-N-(4-methoxybenzyl)-3-cyclohexylmethylthio-2-((4R)-2-oxothiazolidin-4-ylcarbonylamino)propanamide

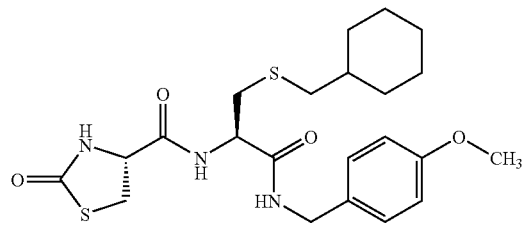

TLC: Rf 0.30 (ethyl acetate:hexane=2:1); NMR (CDCl$_3$): δ 7.72–7.58 (1H, m), 7.30–7.11 (3H, m), 7.11–6.96 (1H, m), 6.89–6.79 (2H, m), 4.59 (1H, q, J=7 Hz), 4.45–4.18 (3H, m), 3.78 (3H, s), 3.69 (1H, dd, J=11, 8 Hz), 3.57 (1H, dd, J=11, 5 Hz), 2.86 (2H, d, J=7 Hz), 2.43 (2H, d, J=7 Hz), 1.86–0.75 (11 Hz m).

Example 6(86)

(2R)-N-(1-methylpiperidin-4-yl)-3-cyclohexylmethylthio-2-((4R)-3-t-butoxycarbonylthiazolidin-4-ylcarbonylamino)propanamide

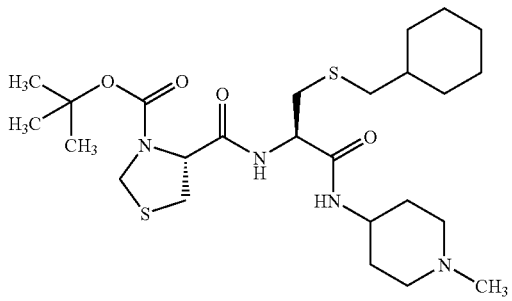

TLC: Rf 0.44 (chloroform:methanol=9:1); NMR (CD₃OD): δ 4.65–4.56 (m, 2H), 4.49–4.43 (m, 2H), 3.72–3.62 (m, 1H), 3.42–3.33 (m, 1H), 3.14 (dd, J=12.0, 4.8 Hz, 1H), 2.93–2.70 (br, 4H), 2.45 (d, J=6.9 Hz, 2H), 2.30 (s, 3H), 2.26–2.14 (br, 2H), 1.93–1.79 (br, 4H), 1.76–1.37 (m, 15H), 1.33–1.09 (m, 3H), 1.02–0.88 (m, 2H).

Example 7

(2R)-N-(4-methoxybenzyl)-3-cyclohexylmethylsulfonyl-2-t-butoxycarbonylaminopropanamide

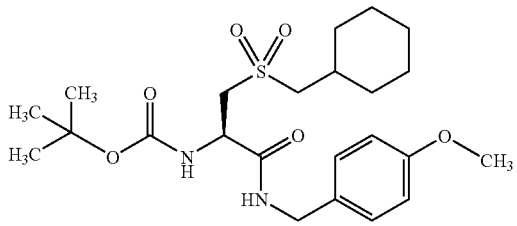

A solution of the compound prepared in Example 2(80) (147 mg) in methylene chloride (5 ml) was cooled to −78° C. and m-chloroperbenzoic acid (117 mg) was added thereto. The mixture was stirred for 70 minutes. The reaction mixture was warmed to room temperature with stirring for 3.5 hours. To the reaction mixture, m-chloroperbenzoic acid (10 mg) was added. The reaction mixture was stirred for 1 hour. The reaction mixture was diluted with chloroform, washed with saturated aqueous sodium hydrogencarbonate, saturated aqueous sodium thiosulfate and saturated aqueous sodium chloride, successively, dried over anhydrous magnesium sulfate. The organic layer was concentrated and the residue was purified by recrystallization (ethyl acetate) to give the compound of the present invention (101 mg) having the following physical data.

TLC: Rf 0.25 (ethyl acetate:hexane=1:2); NMR (CDCl₃): δ 7.24–7.17 (2H, m), 7.00 (1H, t, J=5.6 Hz), 6.89–6.82 (2H, m), 5.84 (1H, d, J=8.2 Hz), 4.66 (1H, dt, J=8.0, 5.0 Hz), 4.47 (1H, dd, J=15.0, 5.8 Hz), 4.31 (1H, dd, J=15.0, 5.6 Hz), 3.79 (3H, s), 3.70 (1H, dd, J=14.6, 5.0 Hz), 3.39 (1H, dd, J=14.6, 5.2 Hz), 3.09–2.91 (2H, m), 2.16–0.96 (20H, m).

Example 7(1)~7(4)

By the same desired procedure as Example 7, using the compounds prepared in Example 2(80), Example 2(90), Example 2(95) and Example 6(31), the following compounds of the present invention were obtained.

Example 7(1)

(2R)-N-(4-methoxybenzyl)-3-cyclohexylmethylsulfinyl-2-t-butoxycarbonylaminopropanamide

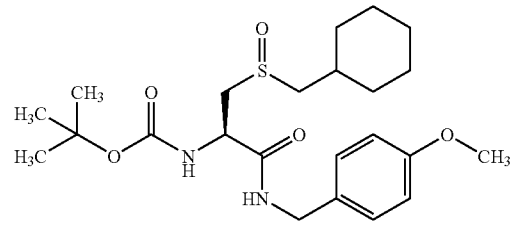

TLC: Rf 0.51 (methanol:chloroform=1:19); NMR (CDCl₃): δ 7.65 (0.33H, br.s), 7.37–7.17 (2.67H, m), 6.89–6.81 (2H, m), 6.39–6.27 (0.67H, m), 5.87 (0.33H, d, J=5.8 Hz), 4.80–4.60 (1H, m), 4.51–4.28 (2H, m), 3.79 (3H, s), 3.34–3.21 (1H, m), 3.01–2.86 (1H, m), 2.78–2.66 (1H, m); 2.55–2.45 (1H, m), 2.02–0.92 (20H, m).

Example 7(2)

(2R)-N-(4-methoxybenzyl)-3-cyclopentylmethylsulfonyl-2-t-butoxycarbonylaminopropanamide

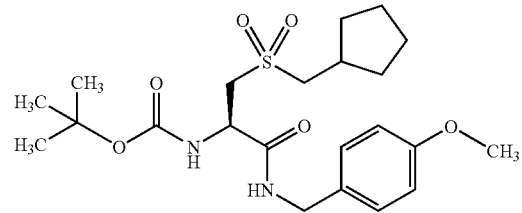

TLC: Rf 0.21 (ethyl acetate:hexane=1:2); NMR (CDCl₃): δ 7.25–7.18 (2H, m), 6.99 (1H, t, J=4.8 Hz), 6.90–6.82 (2H, m), 5.84 (1H, d, J=8.0 Hz), 4.71–4.62 (1H, m), 4.47 (1H, dd, J=14.6, 6.2 Hz), 4.32 (1H, dd, J=14.6, 5.4 Hz), 3.81–3.68 (4H, m), 3.40 (1H, dd, J=15.0, 5.2 Hz), 3.20 (1H, dd, J=14.2, 6.8 Hz), 3.11 (1H, dd, J=14.2, 6.8 Hz), 2.46–2.26 (1H, m), 2.05–1.91 (2H, m), 1.75–1.19 (15H, m).

Example 7(3)

(2R)-N-(4-methoxybenzyl)-3-cyclohexylmethylsulfonyl-2-cyclohexylcarbonylaminopropanamide

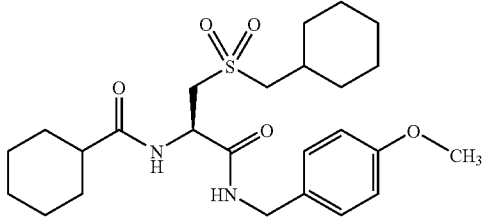

TLC: Rf 0.18 (chloroform: ethyl acetate=100:15); NMR (CDCl₃): δ 7.26–7.15 (3H, m), 6.93–6.82 (3H, m), 4.84 (1H, td, J=6.6, 4.4 Hz), 4.44 (1H, dd, J=14.6, 5.8 Hz), 4.31 (1H, dd, J=14.6, 5.4 Hz), 3.79 (3H, s), 3.63 (1H, dd, J=15.0, 4.4 Hz), 3.30 (1H, dd, J=15.0, 6.2 Hz), 3.17 (1H, dd, J=14.2, 6.6 Hz), 3.07 (1H, dd, J=14.2, 6.2 Hz), 2.24–1.00 (22H, m).

Example 7(4)

(2S)-N-(4-methoxybenzyl)-3-cyclopentylmethylsulfonyl-2-t-butoxycarbonyl-aminopropanamide

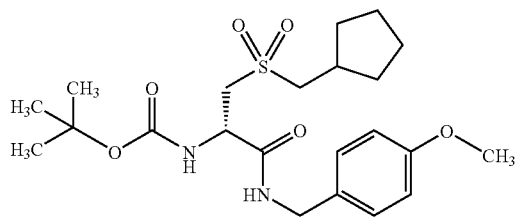

TLC: Rf 0.22 (ethyl acetate:hexane=1:2); NMR (CDCl₃): δ 7.25–7.17 (2H, m), 6.97 (1H, t, J=5.4 Hz), 6.90–6.82 (2H, m), 5.82 (1H, d, J=8.4 Hz), 4.71–4.62 (1H, m), 4.48 (1H, dd, J=14.8, 6.4 Hz), 4.32 (1H, dd, J=14.8, 5.4 Hz), 3.79–3.68 (4H, m), 3.39 (1H, dd, J=14.6, 5.0 Hz), 3.21 (1H, dd, J=14.2, 7.4 Hz), 3.11 (1H, dd, J=14.2, 7.0 Hz), 2.46–2.30 (1H, m), 2.05–1.91 (2H, m), 1.75–1.17 (15H, m);

Example 8~Example 8(12)

By the same desired procedure as Example 6, using the compounds prepared in Example 7 and Example 7(1), the following compounds of the present invention were obtained.

Also, (+)-3-t-butoxycarbonylthiazolidin-2-ylcarboxylic acid was used for the preparation of the compound of Example 8(8).

Example 8

(2R)-N-(4-methoxybenzyl)-3-cyclohexylmethylsulfonyl-2-(4-methoxy-cyclohexylcarbonylamino)propanamide

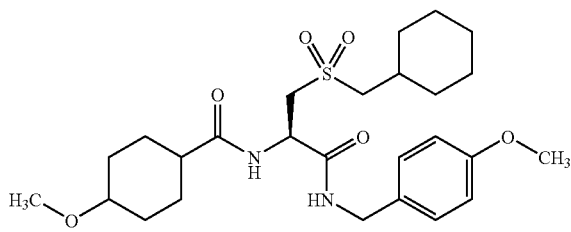

(The relative configuration of cyclohexyl ring substituted by methoxy group is not determined, but the above compound is a single compound. This compound is the isomer of the compound prepared in Example 8(1).) more polar TLC: Rf 0.68 (ethyl acetate); NMR (CDCl₃): δ 7.30–7.24 (1H, m), 7.22–7.15 (2H, m), 6.97 (1H, d, J=6.6 Hz), 6.89–6.82 (2H, m), 4.90–4.81 (1H, m), 4.42 (1H, dd, J=14.6, 5.8 Hz), 4.30 (1H, dd, J=14.6, 5.6 Hz), 3.79 (3H, s), 3.60 (1H, dd, J=15.0, 4.8 Hz), 3.45–3.26 (5H, m), 3.15(1H, dd, J=140, 6.2 Hz), 3.05(1H, dd, J=14.0, 6.2 Hz), 2.28–1.00 (20H, m).

Example 8(1)

(2R)-N-(4-methoxybenzyl)-3-cyclohexylmethylsulfonyl-2-(4-methoxy-cyclohexylcarbonylamino)propanamide

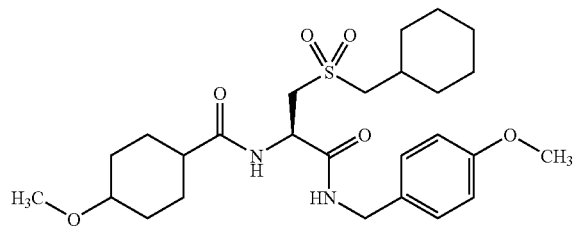

(The relative configuration of cyclohexyl ring substituted by methoxy group is not determined, but the above compound is a single compound. This compound is the isomer of the compound prepared in Example 8.) less polar TLC: Rf 0.59 (ethyl acetate); NMR (CDCl₃): δ 7.28–7.14 (3H, m), 6.94 (1H, d, J=7.0 Hz), 6.89–6.82 (2H, m), 4.91–4.82 (1H, m), 4.42 (1H, dd, J=14.6, 5.8 Hz), 4.30 (1H, dd, J=14.6, 5.4 Hz), 3.79 (3H, s), 3.60 (1H, dd, J=15.0, 4.8 Hz), 3.38–3.24 (4 H, m), 3.18–2.99 (3H, m), 2.21–1.00 (20H, m).

Example 8(2)

(2R)-N-(4-methoxybenzyl)-3-cyclohexylmehtylsulfonyl-2-cyclobutyl-carbonylaminopropanamide

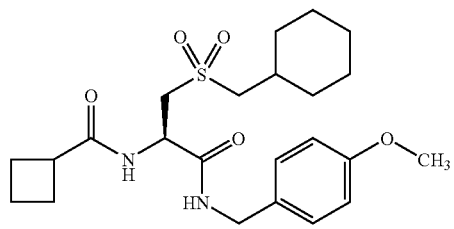

TLC: Rf 0.26 (ethyl acetate:hexane=1:1); NMR (CDCl₃): δ 7.30–7.15 (3H, m), 6.89–6.78 (3H, m), 4.89–4.80 (1H, m), 4.43 (1H, dd, J=14.6, 5.8 Hz), 4.31 (1H, dd, J=14.6, 5.6 Hz), 3.79 (3H, s), 3.62 (1H, dd, J=15.0, 4.2 Hz), 3.31 (1H, dd, J=15.0, 6.6 Hz), 3.23–2.98 (3H, m), 2.38–1.01 (17H, m).

Example 8(3)

(2R)-N-(4-methoxybenzyl)-3-cyclohexylmethylsulfonyl-2-(tetrahydrofuran-2-ylcarbonylamino)propanamide

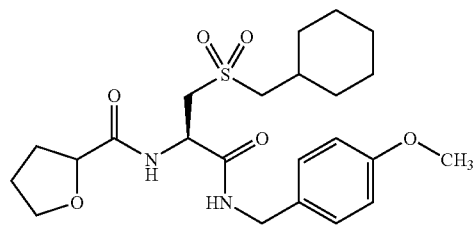

TLC: Rf 0.14 (ethyl acetate:hexane=1:1); NMR (CDCl₃): δ 7.82–7.77 (1H, m), 7.23–7.05 (3H, m), 6.89–6.82 (2H, m), 4.99–4.90 (0.5H, m), 4.85–4.75 (0.5H, m), 4.49–4.27 (3H, m), 4.09–3.79 (5H, m), 3.73–3.33 (2H, m), 3.21–2.94 (2H, m), 2.38–0.98 (15H, m).

Example 8(4)

(2R)-N-(4-methoxybenzyl)-3-cyclohexylmethylsulfonyl-2-cycloheptylcarbonyl-aminopropanamide

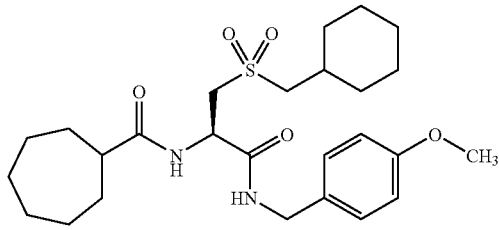

TLC: Rf 0.14 (ethyl acetate:hexane=1:2); NMR (CDCl$_3$): δ 7.26–7.15 (3H, m), 6.89–6.82 (3H, m), 4.88–4.79 (1H, m), 4.44 (1H, dd, J=14.8, 6.0 Hz), 4.30 (1H, dd, J=14.8, 5.6 Hz), 3.79 (3H, s), 3.61 (1H, dd, J=15.0, 4.4 Hz), 3.31 (1H, dd, J=15.0, 6.2 Hz), 3.17 (1H, dd, J=14.0, 6.2 Hz), 3.06 (1H, dd, J=14.0, 5.8 Hz), 2.38–1.00 (24H, m).

Example 8(5)

(2R)-N-(4-mrethoxybenzyl)-3-cyclohexylmethylsulfonyl-2-(tetrahydrofuran-3-ylcarbonylamino)propanamide

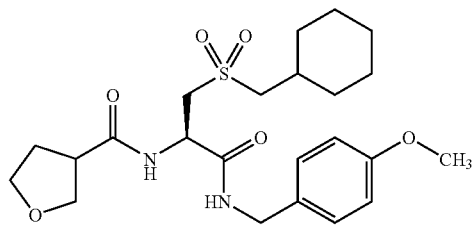

TLC: Rf 0.08 (ethyl acetate:hexane=1:1); NMR (CD$_3$OD): δ 7.25–7.15 (3H, m), 7.02 (1H, d, J=7.0 Hz), 6.90–6.82 (2H, m), 4.88–4.80 (1H, m), 4.43 (1H, dd, J=14.8, 6.0 Hz), 4.31 (1H, dd, J=14.8, 5.6 Hz), 4.01–3.73 (7H, m), 3.64–3.54 (1H, m), 3.39–3.27 (1H, m), 3.21–2.89 (3H, m), 2.20–1.00 (13H, m).

Example 8(6)

(2R)-N-(4-methoxybenzyl)-3-cyclohexylmethylsulfonyl-2-((2RS)-3-t-butoxy-carbonylthiazolidin-2-ylcarbonylamino)propanamide

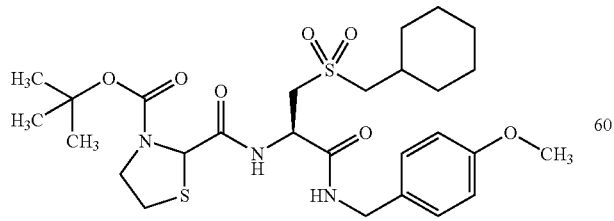

TLC: Rf 0.32 (ethyl acetate:hexane=1:1); NMR (CD$_3$OD): δ 7.23 (2H, d, J=9 Hz), 6.85 (2H, d, J=9 Hz), 5.20 (s) and 5.16 (bs) (1H), 4.97–4.84 (1H, m), 4.42–4.23 (2H, m), 4.02–3.85 (1H, m), 3.84–3.60 (2H, m), 3.77 (3H, s), 3.53–3.10 (2H, m), 3.08–2.90 (3H, m), 2.20–1.58 (6H, m), 1.44 and 1.40 (9H, s), 1.35–1.00 (5H, m).

Example 8(7)

(2R)-N-(4-methoxybenzyl)-3-cyclohexylmethylsulfonyl-2-((4R)-3-t-butoxy-carbonylthiazolidin-4-ylcarbonylamino)propanamide

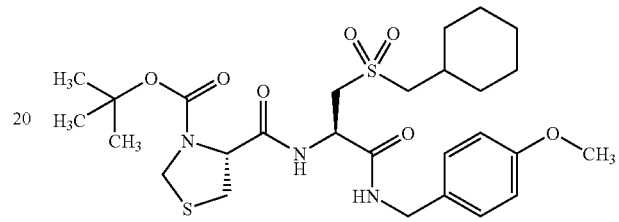

TLC: Rf 0.61 (methylene chloride:ethyl acetate=2:1); NMR (CDCl$_3$): δ 7.96 (1H, brs), 7.67 (1H, brs), 7.25–7.22 (2H, m), 6.84–6.82 (2H, m), 5.02–4.91 (1H, m), 4.62–4.42 (4H, m), 4.30 (1H, dd, J=14.4, 5.0 Hz), 4.06–3.92 (1H, m), 3.78 (3H, s), 3.34–3.15 (3H, m), 2.93–2.72 (2H, m), 2.10–1.59 (6H, m), 1.40 (9H, s), 1.50–0.85 (5H, m).

Example 8(8)

(2R)-N-(4-methoxybenzyl)-3-cyclohexylmethylsulfonyl-2-(3-t-butoxycarbonyl-thiazolidin-2-ylcarbonylamino)propanamide

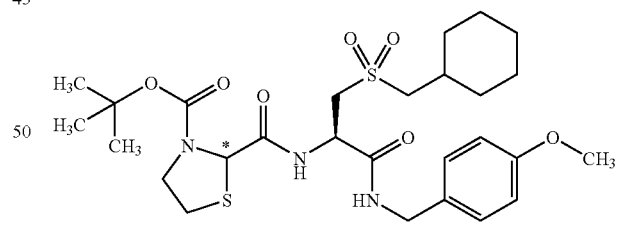

(The absolute configuration of * carbon is not determined, but the above compound is a single optical isomer.)

[α]$_D$=+1.23 (c 1.31, CHCl$_3$); TLC: Rf 0.63 (methylene chloride:ethyl acetate=2:1); NMR (CD$_3$OD): δ 7.23–7.18 (2H, m), 6.86–6.81 (2H, m), 5.16 (1H. br), 4.96–4.84 (1H, m), 4.40–4.23 (2H, m), 4.00–3.82 (1H, m), 3.80–3.50 (2H, m), 3.75 (3H, s), 3.50–3.10 (2H, m), 3.09–2.95 (1H, m), 3.00 (2H, d, J=6.2 Hz), 2.17–1.80 (3H, m), 1.80–1.55 (3H, m), 1.39 (9H, s), 1.42–1.00 (5H, m).

Example 8(9)

(2R)-N-(4-methoxybenzyl)-3-cyclohexylmethylsulfinyl-2-((4R)-3-t-butoxycarbonylthiazolidin-4-ylcarbonylamino)propanamide

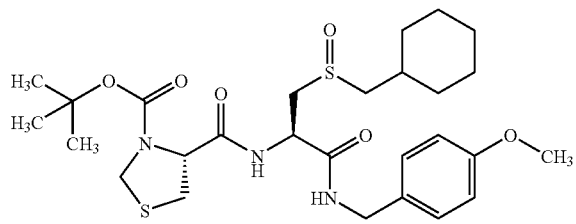

TLC: Rf 0.65 (chloroform:methanol=14:1); NMR (CD₃OD): δ 7.23–7.18 (2H, m), 6.87–6.83 (2H, m), 4.90–4.75 (1H, m), 4.63–4.45 (3H, m), 4.34–4.32 (2H, m), 3.76 (3H, s), 3.41–3.05 (4H, m), 2.84–2.59 (2H, m), 2.01–1.60 (6H, m), 1.43 and 1.42 (9H, s), 1.43–1.00 (5H, m).

Example 8(10)

(2R)-N-(4-methoxybenzyl)-3-cyclohexylmethylsulfonyl-2-(1-t-butoxycarbonylapiperidin-4-ylcarbonylamino)propanamide

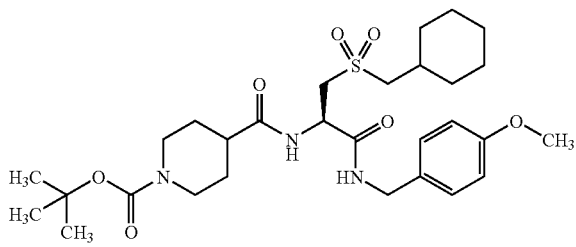

TLC: Rf 0.25 (ethyl acetate:chloroform=2:3); NMR (CDCl₃): δ 7.28–7.15 (3H, m), 6.97 (1H, d, J=6.6 Hz), 6.90–6.82 (2H, m), 4.88–4.79 (1H, m), 4.43 (1H, dd, J=14.2, 5.8 Hz), 4.31 (1H, dd, J=14.2, 5.4 Hz), 4.22–4.04 (2H, m), 3.79 (3H, s), 3.61 (1H, dd, J=15.2, 4.8 Hz), 3.30 (1H, dd, J=15.2, 6.6 Hz), 3.16 (1H, dd, J=14.4, 6.6 Hz), 3.06 (1H, dd, J=14.4, 6.2 Hz), 2.79–2.66 (2H, m), 2.39–1.00 (25H, m).

Example 8(11)

(2R)-N-(4-methoxybenzyl)-3-cyclohexylmethylsulfonyl-2-(4-t-butozycarbonylaminocyclohexylcarbonylamino)propanamide

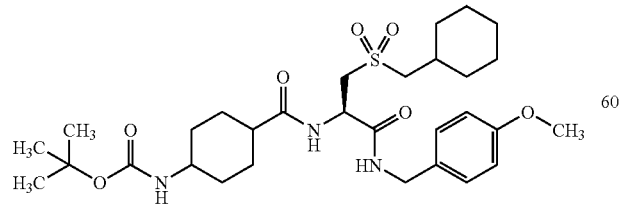

(The relative configuration of cyclohexyl ring substituted by t-butoxycarbonylamino group is not determined, but the above compound is a single compound. This compound is the isomer of the compound prepared in Example 8(12).)

TLC: Rf 0.17 (ethyl acetate:chloroform=3:7); NMR (CDCl₃): δ 7.27–7.15 (3H, m), 6.97 (1H, d, J=7.0 Hz), 6.90–6.82 (2H, m), 4.90–4.81 (1H, m), 4.67 (1H, d, J=7.6 Hz), 4.43 (1H, dd, J=14.6, 5.8 Hz), 4.31 (1H, dd, J=14.6, 6.0 Hz), 3.79–3.57 (5H, m), 3.32 (1H, dd, J=15.0, 6.2 Hz), 3.17 (1H, dd, J=14.2, 6.6 Hz), 3.05 (1H, dd, J=14.2, 6.2 Hz), 2.34–1.00 (29H, m).

Example 8(12)

(2R)-N-(4-methoxybenzyl)-3-cyclohexylmethylsulfonyl-2-(4-t-butoxycarbonylaminocyclohexylcarbonylamino)propanamide

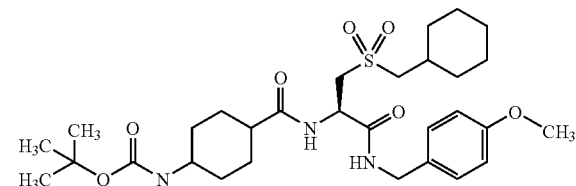

(The relative configuration of cyclohexyl ring substituted by t-butoxycarbonylamino group is not determined, but the above compound is a single compound. This compound is the isomer of the compound prepared in Example 8(11).)

TLC: Rf 0.17 (ethyl acetate:chloroform=3:7); NMR (CDCl₃): δ 7.28–7.14 (3H, m), 6.95 (1H, d, J=6.6 Hz), 6.89–6.82 (2H, m), 4.88–4.79 (1H, m), 4.47–4.24 (3H, m), 3.79 (3H, s), 3.60 (1H, dd, J=15.0, 4.8 Hz), 3.50–3.25 (2H, m), 3.15 (1H, dd, J=14.4, 6.4 Hz), 3.05 (1H, dd, J=14.4, 6.2 Hz), 2.18–0.96 (29H, m).

Example 9~Example 9(16)

By the same desired procedure as Reference Example 4, using the compounds prepared in Example 6(36), Example 6(39), Example 6(40), Example 6(41), Example 6(44), Example 6(47), Example 6(50)~Example 6(52), Example 6(54)~Example 6(56), Example 6(71), Example 6(72), Example 6(84) and Example 8(6), the following compounds of the present invention were obtained.

Example 9

(2R)-N-(4-methoxybenzyl)-3-cyclohexylmethylthio-2-((2RS)-thoazolidin-2-ylcarbonylamino)propanamide.hydrochloride

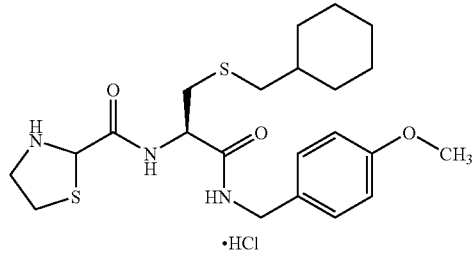

TLC: Rf 0.27 (methylene chloride:methanol=97:3); NMR (CD₃OD) δ 7.22 (2H, d, J=9 Hz), 6.85 (2H, d, J=9 Hz), 5.41 and 5.39 (1H, s), 4.55–4.44 (1H, m), 4.36–4.26 (2H, m), 3.85–3.70 (1H, m), 3.76 (3H, s), 3.70–3.52 (1H, m), 3.40–3.10 (2H, m), 3.00–2.84 (1H, m), 2.84–2.68 (1H, m), 2.46–2.38 (2H, m), 1.90–1.55 (5H, m), 1.55–1.08 (4H, m), 1.07–0.77 (2H, m).

Example 9(1)

(2R)-N-(4-methoxybenzyl)-3-cyclohexylmethylsulfonyl-2-((2RS)-thoazolidin-2-ylcarbonylamino)propanamide.hydrochloride

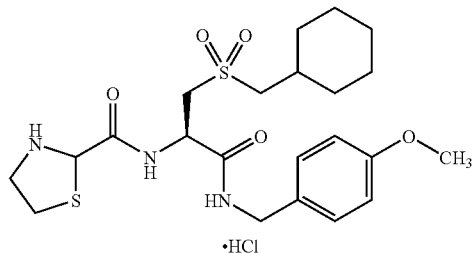

TLC: Rf 0.25 (methylene chloride:methanol=97:3); NMR (CD₃OD) δ 7.22 (2H, d, J=9 Hz), 6.86 (2H, d, J=9 Hz), 5.44 (s) and 5.37 (1H, s), 5.03–4.93 (1H, m), 4.42–4.22 (2H, m), 3.84–3.34 (4H, m), 3.77 (3H, s), 3.34–3.12 (2H, m), 3.05 (2H, d, J=6 Hz), 2.10–1.83 (3H, m), 1.83–1.58 (3H, m), 1.50–1.00 (5H, m).

Example 9(2)

(2R)-N-(4-methoxybenzyl)-3-cyclohexylmethylthio-2-(piperidin-4-ylcarbonylamino)propanamide.hydrochloride

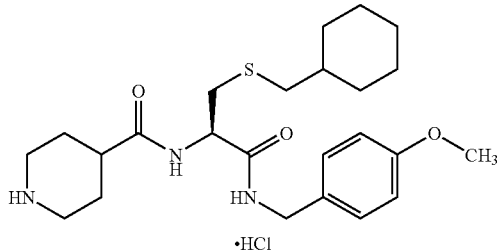

TLC: Rf 0.19 (chloroform:methanol=9:1); NMR (DMSO-d₆): δ 9.06–8.90 (1H. br), 8.74–8.52 (2H, m), 8.19 (1H, d, J=8.4 Hz), 7.18 (2H, d, J=8.8 Hz), 6.86 (2H, d, J=8.8 Hz), 4.48–4.37 (1H, m), 4.21 (2H, d, J=6.0 Hz), 3.73 (3H, s), 3.33–3.23 (2H, br), 2.96–2.76 (3H, m), 2.59 (1H, dd, J=8.8, 13.4 Hz), 2.55–2.43 (1H, m), 2.39 (2H, d, J=7.0 Hz), 1.94–1.52 (9H, m), 1.49–1.03 (4H, m), 0.99–0.77 (2H, m).

Example 9(3)

(2R)-N-(4-methoxybenzyl)-3-cyclohexylmethylthio-2-(4-aminocyclohexyl-carbonylamino)propanamide.hydrochloride

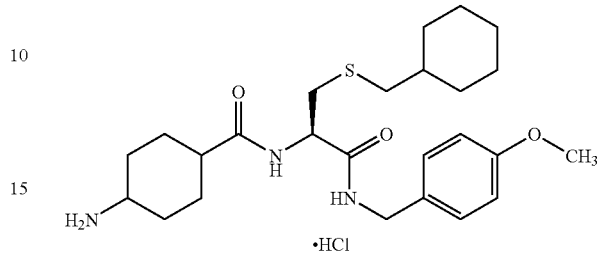

(The relative configuration of cyclohexyl ring substituted by amino group is not determined, but the above compound is a single compound. This compound is the isomer of the compound prepared in Example 9(4).)

TLC: Rf 0.16 (chloroform:methanol=9:1); NMR (DMSO-d₆): δ 8.49 (1H, d, J=6.0 Hz), 8.06–7.85 (4H, m), 7.18 (2H, d, J=8.8 Hz), 6.86 (2H, d, J=8.8 Hz), 4.47–4.36 (1H, m), 4.21 (2H, d, J=6.0 Hz), 3.73 (3H, s), 3.17–3.04 (1H, br), 2.82 (1H, dd, J=5.6, 13.4 Hz), 2.64 (1H—, dd, J=8.6, 13.4 Hz), 2.44–2.31 (3H, m), 1.99–1.49 (12H, m), 1.46–1.03 (5H, m), 0.98–0.76 (2H, m).

Example 9(4)

(2R)-N-(4-methoxybenzyl)-3-cyclohexylmethylthio-2-(4-aminocyclohexyl-carbonylamino)propanamide.hydrochloride

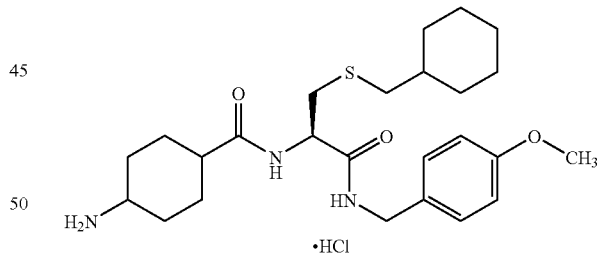

(The relative configuration of cyclohexyl ring substituted by amino group is not determined, but the above compound is a single compound. This compound is the isomer of the compound prepared in Example 9(3).)

TLC: Rf 0.11 (chloroform:methanol=9:1); NMR (DMSO-d₆): δ 8.53–8.47 (1H, br), 8.05–7.94 (4H, br), 7.17 (2H, d, J=8.4 Hz), 6.85 (2H, d, J=8.4 Hz), 4.45–4.35 (1H, br), 4.19 (2H, br), 3.72 (3H, s), 3.16 (1H, d, J=5.2 Hz), 3.04–2.88 (1H, br), 2.78 (1H, dd, J=5.8, 13.2 Hz), 2.59 (1H, dd, J=8.2, 13.2 Hz), 2.38 (2H, d, J=6.6 Hz), 2.35–2.08 (2H, br), 1.98–1.55 (8H, m), 1.49–1.02 (7H, m), 0.99–0.77 (2H, m).

Example 9(5)

(2R)-N-(4-methoxybenzyl)-3-cyclohexylmethylthio-2-((4R)-thiazolidin-4-ylcarbonylamino)propanamide.hydrochloride

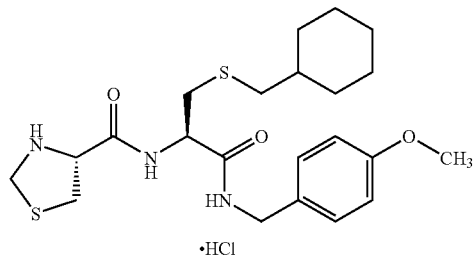

TLC: Rf 0.26 (methylene chloride:methanol=97:3); NMR (CD$_3$OD): δ 7.27–7.17 (2H, m), 6.93–6.80 (2H, m), 4.61–4.47 (2H, m), 4.41 (2H, s), 4.33 (1H, d, J=14 Hz), 4.31 (1H, d, J=14 Hz), 3.77 (3H, s), 3.55 (1H, dd, J=12, 7), 3.22 (1H, dd, J=12, 7 Hz), 2.92 (1H, dd, J=14, 7 Hz), 2.80 (1H, dd, J=14, 8 Hz), 2.43 (2H, d, J=6 Hz), 1.90–0.80 (11H, m).

Example 9(6)

(2R)-N-((1R)-1-(4-nitrophenyl)ethyl)-3-cyclohexylmethylthio-2-((4R)-thiazolidin-4-ylcarbonylamino)propanamide.hydrochloride

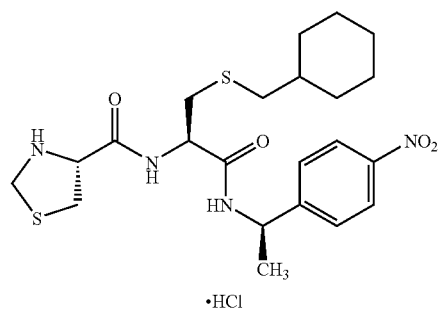

TLC: Rf 0.74 (methanol:chloroform=5:95); NMR (CD$_3$OD): δ 8.92 (1H, d, J=7.2 Hz), 8.21–8.14 (2H, m), 7.60–7.54 (2H, m), 5.12–4.98 (1H, m), 4.55 (2H, t, J=7.0 Hz), 4.44 (1H, d, J=10.2 Hz), 4.38 (1H, d, J=10.2 Hz) 3.51 (1H, dd, J=12.2, 7.4 Hz), 3.12 (1H, dd, J=12.2, 7.0 Hz), 2.94 (1H, dd, J=13.6, 6.6 Hz), 2.80 (1H, dd, J=13.4, 8.2 Hz), 2.50 (2H, d, J=6.6 Hz), 1.93–0.85 (14H, m).

Example 9(7)

(2R)-N-(4-methoxybenzyl)-3-cyclohexylmethylthio-2-((4S)-thiazolidin-4-ylcarbonylamino)propanamide.hydrochloride

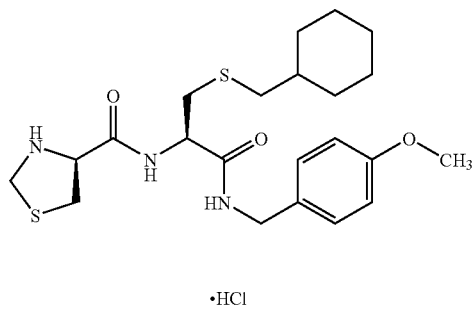

TLC: Rf 0.44 (methylene chloride:methanol=19:1); NMR (CD$_3$OD): δ 7.29–7.18 (2H, m), 6.91–6.81 (2H, m), 4.65–4.51 (2H, m), 4.44 (1H, d, J=11 Hz), 4.43 (1H, d, J=11 Hz), 4.32 (2H, m), 3.77 (3H, s), 3.59 (1H, dd, J=12, 8 Hz), 3.38–3.26 (1H, m), 2.97 (1H, dd, J=14, 5 Hz), 2.76 (1H, dd, J=14, 9 Hz), 2.42 (2H, d, J=7 Hz), 1.89–0.80 (11H, m).

Example 9(8)

(2R)-N-(4-nitrobenzyl)-3-cyclohexylmethylthio-2-((4R)-thiazolidin-4-ylcarbonylamino)propanamide.hydrochloride

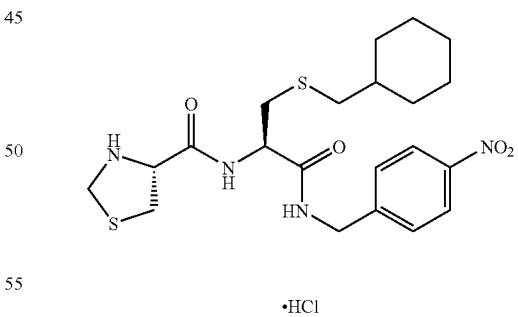

TLC: Rf 0.43 (methylene chloride:methanol=19:1); NMR (CD$_3$OD): δ 8.25–8.15 (2H, m), 7.62–7.50 (2H, m), 4.63–4.49 (4H, m), 4.43, (1H, d, J=10 Hz), 4.41 (1H, d, J=10 Hz), 3.56 (1H, dd, J=12, 7 Hz), 3.26 (1H, dd, J=12, 7 Hz), 2.96 (1H, dd, J=13, 7 Hz), 2.85 (1H, dd, J=13, 8 Hz), 2.46 (2H, d, J=7 Hz), 1.91–0.80 (11H, m).

Example 9(9)

(2R)-N-(4-nitrobenzyl)-3-cyclohexylmethylthio-2-((2RS)-thiazolidin-2-ylcarbonylamino)propanamide.hydrochloride

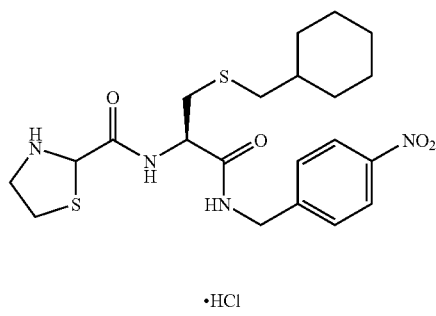

•HCl

TLC: Rf 0.41 (methylene chloride:methanol=19:1); NMR (DMSO-d$_6$): δ 9.10–8.93 (2H, m), 8.24–8.14 (2H, m), 7.62–7.52 (2H, m), 5.35 and 5.27 (1H, s), 4.58–4.39 (3H, m), 3.72–3.46 (2H, m), 3.28–3.03 (2H, m), 2.94–2.64 (2H, m), 2.44 (2H, d, J=7 Hz), 1.94–0.75 (11H, m).

Example 9(10)

(2R)-N-(4-nitrobenzyl)-3-cyclohexylmethylthio-2-(imidazol-4-ylcarbonylamino)propanamide.hydrochloride

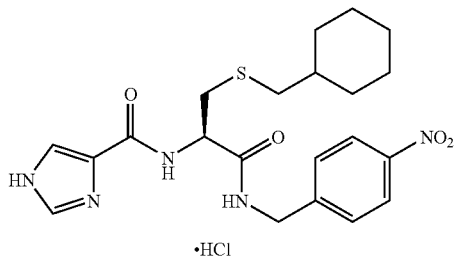

•HCl

TLC: Rf 0.31 (chloroform:methanol=9:1); NMR (DMSO-d$_6$): δ 9.10–9.01 (3H, m), 8.28 (1H, s), 8.18 (2H, d, J=8.8 Hz), 7.56 (2H, d, J=8.8 Hz), 4.73–4.61 (1H, m), 4.40 (2H, d, J=6.0 Hz), 2.98 (1H, dd, J=6.0, 13.6 Hz), 2.82 (1H, dd, J=8.4, 13.6 Hz), 2.45 (2H, d, J=7.0 Hz), 1.80–1.30 (6H, m), 1.28–0.78 (5H, m).

Example 9(11)

(2R)-N-(4-dimethylaminobenzyl)-3-cyclohexylmethylthio-2-((4R)-thiazolidin-4-ylcarbonylamino)propanamide.2hydrochloride

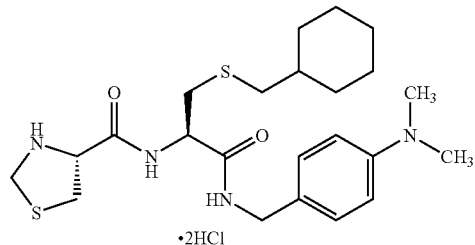

•2HCl

TLC: Rf 0.42 (methylene chloride:methanol=19:1); NMR (CD$_3$OD): δ 7.67–7.60 (2H, m), 7.60–7.50 (2H, m), 4.66–4.37 (6H, m), 3.59 (1H, dd, J=12, 8 Hz), 3.33–3.21 (1H, m), 3.28 (6H, s), 2.94 (1H, dd, J=16, 7 Hz), 2.84 (1H, dd, J=16, 8 Hz), 2.48 (2H, d, J=7 Hz), 1.93–0.83 (11H, m).

Example 9(12)

(2R)-N-(4-dimethylaminobenzyl)-3-cyclohexylmethylthio-2-((2RS)-thiazolidin-2-ylcarbonylamino)propanamide.2 hydrochloride

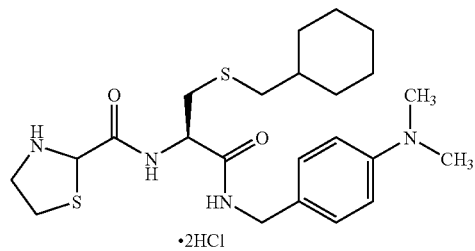

•2HCl

TLC: Rf 0.40 (methylene chloride:methanol=19:1); NMR (CD$_3$OD): δ 7.68–7.59 (2H, m), 7.59–7.51 (2H, m), 5.47 and 5.42 (1H, s), 4.59–4.43 (3H, m), 3.92–3.76 (1H, m), 3.72–3.68 (1H, m), 3.39–3.17 (2H, m), 3.29 (6H, m), 3.07–2.73 (2H, m), 2.47 (2H, d, J=7 Hz), 1.93–0.83 (11H, m).

Example 9(13)

(2R)-N-(4-phenoxybenzyl)-3-cyclohexylmethylthio-2-((4R)-thiazolidin-4-ylcarbonylamino)propanamide.hydrochloride

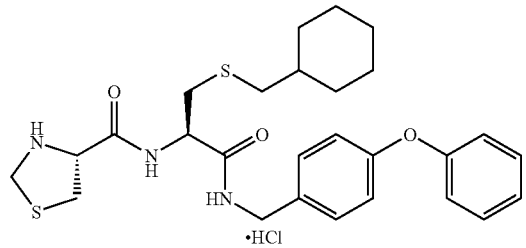

•HCl

TLC: Rf 0.65 (ethyl acetate); NMR (CD$_3$OD): δ 8.71 (1H, t, J=5.7 Hz), 7.36–7.28 (4H, m), 7.09 (1H, t, J=7.2 Hz), 6.96–6.89 (4H, m), 4.59–4.51 (2H, m), 4.44–4.30 (4H, m), 3.55 (1H, dd, J=11.7, 7.5 Hz), 3.24 (1H, dd, J=11.7, 6.9 Hz), 2.93 (1H, dd, J=13.5, 6.3 Hz), 2.81 (1H, dd, J=13.5, 7.5 Hz), 2.46 (1H, dd, J=12.6, 6.9 Hz), 2.42 (1H, dd, J=12.6, 6.6 Hz), 1.88–1.79 (2H, m), 1.74–1.61 (3H, m), 1.53–1.36 (1H, m), 1.31–1.08 (3H, m), 1.00–0.88 (2H, m).

Example 9(14)

(2R)-N-(4-benzyloxybenzyl)-3-cyclohexylmethylthio-2-((4R)-thiazolidin-4-ylcarbonylamino)propanamide.hydrochloride

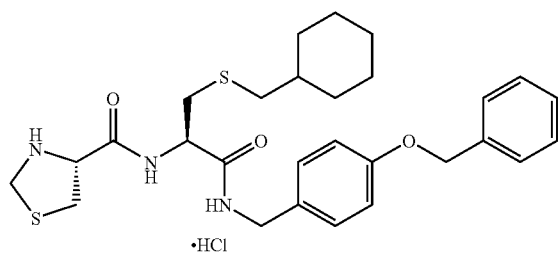

TLC: Rf 0.30 (ethyl acetate:hexane=1:1); NMR (CD$_3$OD): δ 8.81 (1H, d, J=8.1 Hz), 8.63 (1H, t, J=7.5 Hz), 7.43–7.19 (7H, m), 6.95–6.69 (2H, m), 5.05 (2H, s), 4.60–4.25 (6H, m), 3.56 (1H, dd, J=12.3, 7.5 Hz), 3.21 (1H, dd, J=12.3, 7.2 Hz), 2.91 (1H, dd, J=13.8, 6.6 Hz), 2.78 (1H, dd, J=13.8, 7.5 Hz), 2.44 (1H, dd, J=2.6, 6.9 Hz), 2.40 (1H, dd, J=12.6, 6.6 Hz), 1.86–0.83 (11H, m).

Example 9(15)

(2R)-N-(3-benzyloxy-4-methoxybenzyl)-3-cyclohexylmethylthio-2-((4R)-thiazolidin-4-ylcarbonylamino)propanamide.hydrochloride

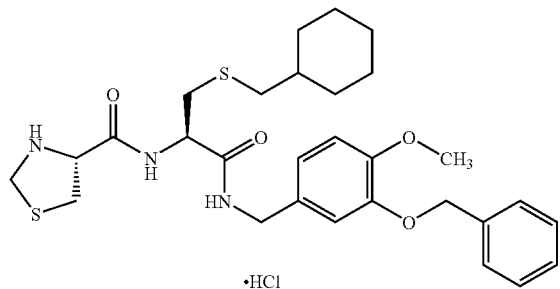

TLC: Rf 0.27 (hexane:ethyl acetate=1:1); NMR (CD$_3$OD): δ 7.47–7.26 (m, 5H), 7.00 (d, J=1.8 Hz, 1H), 6.91 (d, J=8.2 Hz, 1H), 6.88 (dd, J=8.2, 1.8 Hz, 1H), 5.08 (s, 2H), 4.60–4.48 (m, 2H), 4.39 (s, 2H), 4.36 (d, J=14.8 Hz, 1H), 4.23 (d, J=14.8 Hz, 1H), 3.82 (s, 3H), 3.56 (dd, J=12.2, 7.4 Hz, 1H), 3.22 (dd, J=12.2, 7.0 Hz, 1H), 2.91 (dd, J=13.8, 6.6 Hz, 1H), 2.77 (dd, J=13.8, 7.8 Hz, 1H), 2.42 (d, J=6.8 Hz, 2H), 1.85–1.56 (m, 5H), 1.54–0.80 (m, 6H).

Example 9(16)

(2R)-N-(1-phenylpiperidin-4-yl)-3-cyclohexylmethylthio-2-((4R)-thiazolidin-4-ylcarbonylamino)propanamide.2 hydrochloride

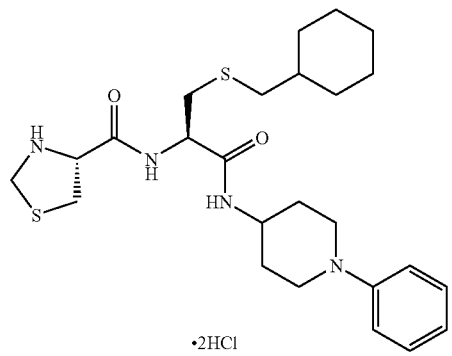

TLC: Rf 0.26 (hexane:ethyl acetate=1:1); NMR (CD$_3$OD): δ 7.80–7.76 (m, 2H), 7.65–7.54 (m, 3H), 4.63 (t, J=7.2 Hz, 1H), 4.54 (t, J=7.2 Hz, 1H), 4.45 (d, J=9.9 Hz, 1H), 4.42 (d, J=9.9 Hz, 1H), 4.20–4.10 (m, 1H), 3.87–3.70 (br, 4H), 3.61 (dd, J=12.0, 7.5 Hz, 1H), 3.29 (dd, J=0.12.0, 6.9 Hz, 1H), 2.95 (dd, J=13.2, 6.6 Hz, 1H), 2.83 (dd, J=13.2, 7.8 Hz, 1H), 2.57–2.46 (m, 2H), 2.32–2.14 (m, 4H), 1.90–1.81 (br, 2H), 1.77–1.63 (m, 3H), 1.54–1.40 (m, 1H), 1.36–1.10 (m, 3H), 1.03–0.91 (m, 2H).

Reference Example 5

Bis((2R)-2-(4-methoxybenzylcarbamoyl)-2-t-butoxycarbonylaminoethyl)-disulfide

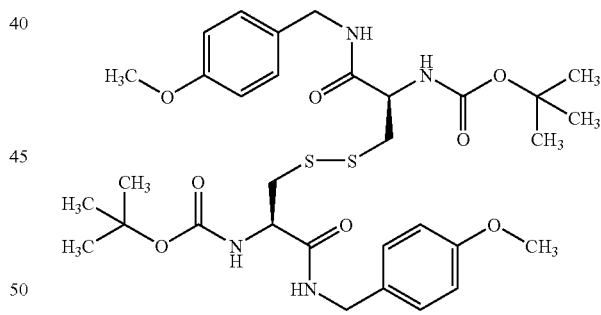

Bis((2R)-carboxy-2-t-butoxycarbonylaminoethyl) disulfide (5 g), 4-methoxybenzylamine (3.7 ml) and 1-hydroxybenzotriazole (3.84 g) were dissolved in a mixture of methylene chloride (50 ml) and DMF (10 ml). The solution was cooled with ice and EDC-HCl (5.45 g) was added thereto. The mixture was stirred for 12 hours. The reaction mixture was diluted with chloroform, washed with 1N hydrochloric acid, saturated aqueous sodium hydrogencarbonate and saturated aqueous sodium chloride, successively, dried over anhydrous magnesium sulfate. The organic layer was concentrated and the residue was washed with diehylether to give the title compound (8.15 g) having the following physical data.

TLC: Rf 0.16 (ethyl acetate:hexane=1:2); NMR (CDCl₃): 8.03 (2H, t, J=6.3 Hz), 7.23–7.15 (4H, m), 6.87–6.80 (4H, m), 5.54 (2H, d, J=9.6 Hz), 4.94–4.82 (2H, m), 4.46 (2H, dd, J=14.6, 6.2 Hz), 4.30 (2H, dd, J=14.6, 5.8 Hz), 3.78 (6H, s), 3.04–2.82 (4H, m), 1.26 (18H, s).

Reference Example 6

(2R)-N-(4-methoxybenzyl)-3-mercapto-2-t-butoxycarbonylaminopropanamide

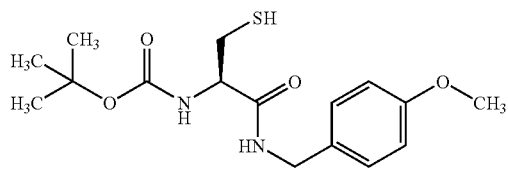

The compound prepared in Reference Example 5 (315 mg), tributylphosphine (103 mg) and acetic acid (15 drops) were dissolved in a mixture of dioxane (8 ml) and water (2 ml). The mixture was stirred for 3 days at room temperature. The reaction mixture was concentrated. The residue was purified by silica gel column chromatography (ethyl acetate:chloroform=1:19) to give the title compound (242 mg) having the following physical data.

TLC: Rf 0.47 (ethyl acetate:chloroform=1:4); NMR (CDCl₃): δ 7.24–7.16 (2H, m), 6.90–6.82 (2H, m), 6.70–6.51 (1H, m), 5.41 (1H, d, J=7.6 Hz), 4.49–4.29 (3H, m), 3.80 (3H, s), 3.14 (1H, ddd, J=14.0, 7.8, 4.4 Hz), 2.73 (1H, ddd, J=14.0, 10.2, 5.8 Hz), 1.59–1.50 (1H, m), 1.43 (9H, s).

Example 10

(2R)-N-(4-methoxybenzyl)-3-(tetrahydropyran-2-yl)methylthio-2-t-butoxycarbonylaminopropanamide

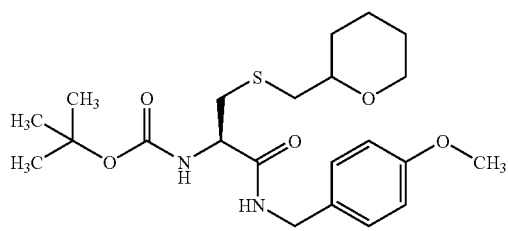

A solution of the compound prepared in Reference Example 6 (103 mg), 2-(bromomethyl)tetrahydropyran (0.05 ml) and potassium carbonate (168 mg) in DMF (5 ml) was degassed and stirred for 15 hours at room temperature. The reaction mixture was concentrated. The residue was diluted with 1N hydrochloric acid and extraced with ethyl acetate. The extract was washed with water and saturated aqueous sodium chloride, successively, dried over anhydrous magnesium sulfate. The organic layer was concentrated and the residue was purified by silica gel column chromatography (ethyl acetate:hexane=1:6) to give the compound of the present invention (68 mg) having the following physical data.

TLC: Rf 0.40 (ethyl acetate:chloroform=1:4); NMR (CDCl₃): δ 7.28–7.20 (2H, m), 7.09–6.95 (1H, m), 6.90–6.82 (2H, m), 5.88–5.78 (1H, m), 4.42–4.38 (2H, m), 4.32–4.20 (1H, m), 3.96–3.76 (4H, m), 3.52–3.18 (2H, m), 3.13–3.01 (1H, m), 2.84–2.51 (3H, m), 1.88–1.74 (1H, m), 1.65–1.08 (14H, m).

Example 10(1)~Example 10(11)

By the same desired procedure as Example 10, using the compound prepared in Reference Example 6, the following compounds of the present invention were obtained.

Example 10(1)

(2R)-N-(4-methoxybenzyl)-3-(bicyclo[2.2.1]heptan-2-ylmethylthio)-2-t-butoxycarbonylaminopropanamide

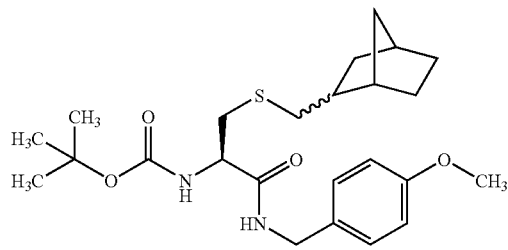

TLC: Rf 0.81 (ethyl acetate:chloroform=1:4); NMR (CDCl₃): δ 7.25–7.18 (2H, m), 6.90–6.82 (2H, m), 6.68–6.58 (1H, m), 535 (1H, d, J=6.6 Hz), 4.40 (2H, d, J=6.0 Hz), 4.29–4.19 (1H, m), 3.80 (3H, s), 3.05–2.94 (1H, m), 2.90–2.78 (1H, m), 2.65–2.25 (2H, m), 2.24–0.60 (20H, m).

Example 10(2)

(2R)-N-(4-methoxybenzyl)-3-(4-methoxycyclohexylmethylthio)-2-t-butoxycarbonylaminopropanamide

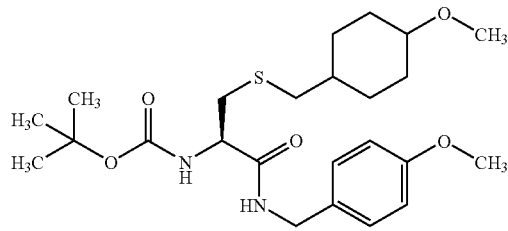

(The relative configuration of cyclohexyl ring substituted by methoxy group is not determined, but the above compound is a single compound. This compound is the isomer of the compound prepared in Example 10(3).) less polar TLC: Rf 0.41 (ethyl acetate:chloroform=1:4); NMR (CDCl₃): δ 7.25–7.17 (2H, m), 6.89–6.82 (2H, m), 6.62 (1H, t, J=5.4 Hz 5.34 (1H, d, J=7.2 Hz), 4.39 (2H, d, J=5.8 Hz), 4.28–4.18 (1H, m), 3.79 (3H, s), 3.44–3.37 (1H, m), 3.29 (3H, s), 2.99 (1H, dd, J=14.0, 6.0 Hz), 2.82 (1H, dd, J=14.0, 7.0 Hz), 2.53–2.37 (2H, m), 1.94–1.80 (2H, m), 1.68–1.20 (16H, m).

Example 10(3)

(2R)-N-(4-methoxybenzyl)-3-(4-methoxycyclohexylmethylthio)-2-t-butoxycarbonylaminopropanamide

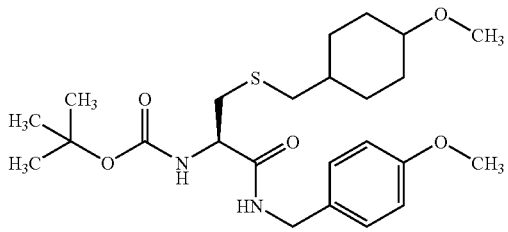

(The relative configuration of cyclohexyl ring substituted by methoxy group is not determined, but the above compound is a single compound. This compound is the isomer of the compound prepared in Example 10(2).) more polar TLC: Rf 0.38 (ethyl acetate:chloroform=1:4); NMR (CDCl$_3$): δ 7.25–7.17 (2H, m), 6.89–6.82 (2H, m), 6.62 (1H, t, J=5.0 Hz), 5.34 (1H, d, J=7.8 Hz), 4.39 (2H, d, J=5.8 Hz), 4.28–4.18 (1H, m), 3.80 (3H, s), 3.34 (3H, s), 3.14–2.93 (2H, m), 2.83 (1H, dd, J=13.8, 6.6 Hz), 2.47 (1H, dd, J=12.8, 7.0 Hz), 2.40 (1H, dd, J=12.8, 6.8 Hz), 2.13–1.98 (2H, m), 1.85–1.81 (2H, m), 1.54–0.84 (14H, m).

Example 10(4)

(2R)-N-(4-methoxybenzyl)-3-(1-methylpeperidin-2-ylmethylthio)-2-t-butoxycarbonylaminopropanamide

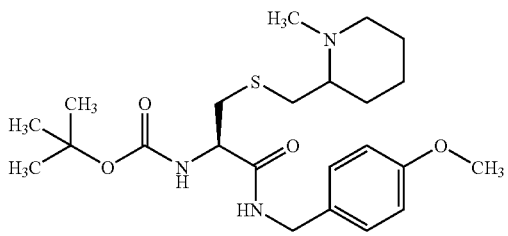

TLC: Rf 0.45 (methanol:chloroform=1:9); NMR (CDCl$_3$): δ 7.27–7.13 (2.5H, m), 6.89–6.74 (2.5H, m), 6.05 (0.5H, d, J=6.8Hz), 5.69 (0.5H, d, J=7.0 Hz), 4.49–4.15 (3H, m), 3.80 (3H, s), 3.15–1.18 (25H, m).

Example 10(5)

(2R)-N-(4-methoxybenzyl)-3-(pyridin-4-ylmethylthio)-2-t-butoxycarbonyl-aminopropanamide

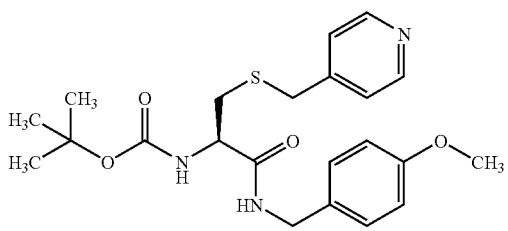

TLC: Rf 0.12 (ethyl acetate:chloroform=1:4); NMR (CDCl$_3$): δ 8.54–8.51 (2H, m), 7.27–7.17 (4H, m), 6.89–6.82 (2H, m), 6.58 (1H, t, J=5.4 Hz), 5.30 (1H, d, J=7.6 Hz), 4.39 (2H, d, J=5.4 Hz), 4.32–4.22 (1H, m), 3.79 (3H, s), 3.70 (1H, d, J=13.8 Hz), 3.62 (1H, d, J=13.8 Hz), 2.89 (1H, dd, J=14.0, 5.6 Hz), 2.76 (1H, dd, J=14.0, 6.6 Hz), 1.43 (9H, s).

Example 10(6)

(2R)-N-(4-methoxybenzyl)-3-(quinolin-2-ylmethylthio)-2-t-butoxycarbonyl-aminopropanamide

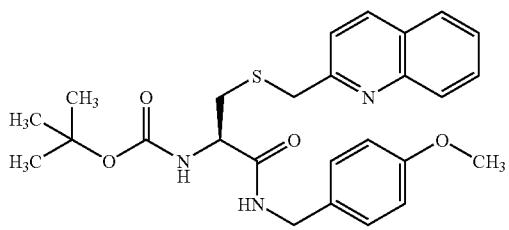

TLC: Rf 0.50 (ethyl acetate:chloroform=1:4); NMR (CDCl$_3$): δ 8.13 (1H, d, J=8.4 Hz), 7.94 (1H, d, J=8.2 Hz), 7.80 (1H, d J=8.0, 1.4 Hz), 7.68–7.43 (3H, m), 7.17–7.10 (2H, m), 7.05–6.90 (1H, m), 6.82–6.74 (2H, m), 6.19 (1H, d, J=7.8 Hz), 4.51–4.36 (2H, m), 4.30 (1H, dd, J=11.4, 5.4 Hz), 4.06 (2H, s), 3.78 (3H, s), 2.96 (1H, dd, J=14.4, 6.6 Hz), 2.79 (1H, dd, J=14.4, 5.8 Hz), 1.43 (9H, s).

Example 10(7)

(2R)-N-(4-methoxybenzyl)-3-(imidazol-4-ylmethylthio)-2-t-butoxycarbonyl-aminopropanamide

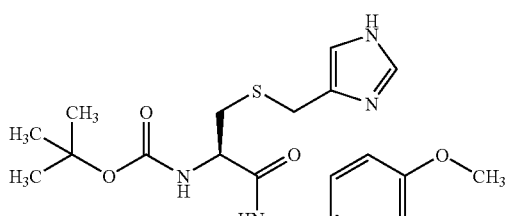

TLC: Rf 0.61 (methanol:chloroform=1:9); NMR (CDCl$_3$): δ 7.63 (1H, br. s), 7.34 (1H, s), 7.24–7.18 (2H, m), 6.90–6.81 (2H, m), 5.81 (1H, dd, J=7.6 Hz), 4.46–4.30 (3H, m), 3.82–3.66 (5H, m), 2.96 (1H, d, J=14.2, 5.4 Hz), 2.78 (1H, dd, J=14.2, 7.2 Hz), 1.44 (9H, s).

Example 10(8)

(2R)-N-(4-methoxybenzyl)-3-((1R,4R,5R)-bicyclo[2.2.1]hept-2-en-5-ylmethylthio)-2-t-butoxycarbonylaminopropanamide

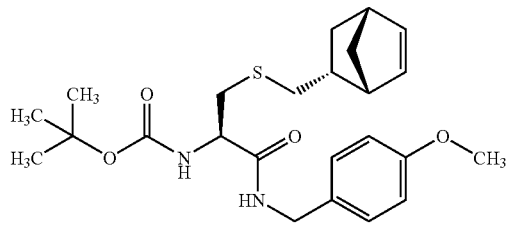

TLC: Rf 0.25 (ethyl acetate:chloroform=1:19); NMR (CDCl$_3$): δ 7.27–7.16 (2H, m), 6.92–6.82 (2H, m), 6.67–6.55 (1H, m), 6.17 (1H, dd, J=6, 3 Hz), 5.92 (1H, dd, J=6, 3 Hz), 5.33 (1H, d, J=7 Hz), 4.39 (2H, d, J=6 Hz), 4.29–4.16 (1H, m), 3.81 (3H, s), 2.98 (1H, dd, J=14, 6 Hz), 2.91–2.75 (3H, m), 2.38–2.14 (3H, m), 1.98–1.82 (1H, m), 1.55–1.38 (1H, m), 1.45 (9H, s), 1.29–1.21 (1H, m), 0.63–0.52 (1H, m).

Example 10(9)

(2R)-N-(4-methoxybenzyl)-3-((1S,4S,5S)-bicyclo[2.2.1]hept-2-en-5-ylmethylthio)-1-t-butoxycarbonylaminopropanamide

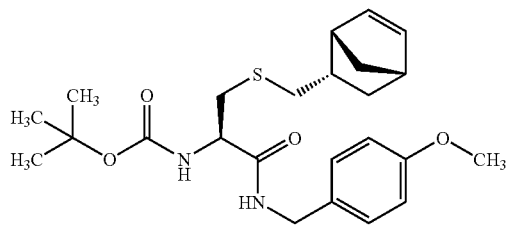

TLC: Rf 0.38 (ethyl acetate:hexane=1:2); NMR (CDCl$_3$): δ 7.27–7.17 (2H, m), 6.93–6.81 (2H, m), 6.70–6.55 (1H, m), 6.16 (1H, dd, J=6, 3 Hz), 5.94 (1H, dd, J=6, 3 Hz), 5.33 (1H, d, J=7 Hz), 4.39 (2H, d, J=6 Hz), 4.29–4.15 (1H, m), 3.81 (3H, s), 2.96 (1H, dd, J=14, 6 Hz), 2.92–2.74 (3H, m), 2.37–2.13 (3H, m), 1.97–1.82 (1H, m), 1.55–1.38 (1H, m), 1.44 (9H, s), 1.29–1.20 (1H, m), 0.63–0.51 (1H, m).

Example 10(10)

(2R)-N-(4-methoxybenzyl)-3-((1S,2R,4R)-bicyclo[2.2.1]heptan-2-ylmethylthio)-2-t-butoxycarbonylaminopropanamide

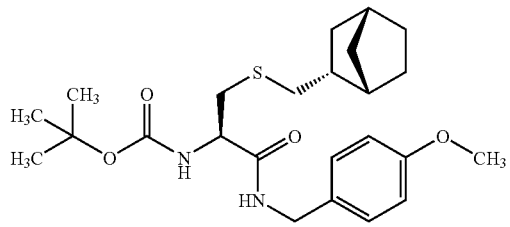

TLC: Rf 0.48 (ethyl acetate:hexane=1:2); NMR (CDCl$_3$): δ 7.27–7.17 (2H, m), 6.93–6.83 (2H, m), 6.71–6.57 (1H, m), 5.35 (1H, d, J=7 Hz), 4.40 (2H, d, J=6 Hz), 4.32–4.19 (1H, m), 3.81 (3H, s), 2.99 (1H, dd, J=14, 6 Hz), 2.86 (1H, dd, J=14, 7 Hz), 2.58 (1H, dd, J=12, 8 Hz), 2.55 (1H, dd, J=12, 8 Hz), 2.23–2.13 (2H, m), 2.13–1.88 (1H, m), 1.88–1.70 (1H, m), 1.64–1.18 (5H, m), 1.45 (9H, s), 1.16–1.01 (1H, m), 0.66 (1H, ddd, J=12, 5, 2 Hz).

Example 10(11)

(2R)-N-(4-methoxybenzyl)-3-((1R,2S,4S)-bicyclo[2.2.1]heptan-2-ylmethylthio)-2-t-butoxycarbonylaminopropanamide

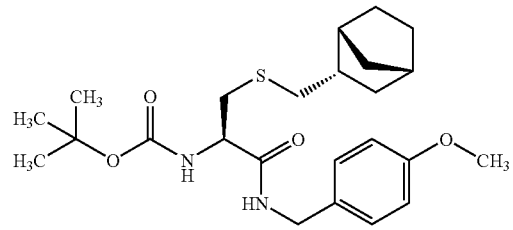

TLC: Rf 0.23 (ethyl acetate:hexane=1:3); NMR (CDCl$_3$): δ 7.27–7.16 (2H, m), 6.93–6.81 (2H, m), 6.73–6.57 (1H, m), 5.36 (1H, d, J=7 Hz), 4.40 (2H, d, J=6 Hz), 4.31–4.18 (1H, m), 3.81 (3H, s), 2.98 (1H, dd, J=14, 6 Hz), 2.87 (1H, dd, J=14, 7 Hz), 2.58 (1H, dd, J=12, 8 Hz), 2.55 (1H, dd, J=12, 8 Hz), 2.24–2.13 (2H, m), 2.10–1.88 (1H, m), 1.87–1.69 (1H, m), 1.60–1.20 (5H, m), 1.43 (9H, s), 1.16–1.01 (1H, m), 0.66 (1H, ddd, J=12, 5, 2 Hz).

Reference Example 7

(2S)-4-hydroxy-2-t-butoxycarbonylaminobutanoic acid.4-methoxybenzyl ester

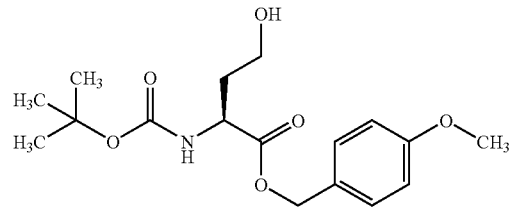

Under cooling with ice, isobutyl chloroformate (0.35 ml) was added dropwise to a solution of (2S)-3-carboxy-2-t-butoxycarbonylaminopropanoic acid.4-methoxybenzyl ester.dicyclohexylamine salt (1350 mg) and N-methylmorpholine (0.32 ml) in tetrahydrofuran (6 ml). The mixture was stirred for 45 minutes. The reaction mixture was filtered through Celite. Under cooling with ice, sodium borohydride (229 mg) was added to the filtrate and methanol (1.2 ml) was added dropwise thereto for 1 hour. One normal hydrochloric acid was added to the reaciton mixture. The mixture was extracted with ethyl acetate. The extract was washed with water and saturated aqueous sodium chloride, successively, and concentrated. The residue was purified by silica gel column chromatography (ethyl acetate hexane=1:2) to give the title compound (180 mg) having the following physical data.

TLC: Rf 0.42 (methanol:chloroform=1:9); NMR (CDCl$_3$): δ 7.30 (2H, d, J=8.7 Hz), 6.89 (2H, d, J=8.7 Hz), 5.38 (1H, brd, J=8.4 Hz), 5.13 (2H, s), 4.55–4.43,(1H, m), 3.82 (3H, s), 3.75–3.55 (2H, m), 3.24–3.05 (1H, m), 2.23–2.06 (1H, m), 1.69–1.56 (1H, m).

Reference Example 8

(2S)-3-formyl-2-t-butoxycarbonylaminopropanoic acid.4-methoxybenzyl ester

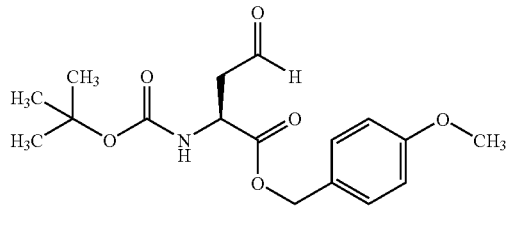

The compound prepared in Reference Example 7 (162 mg) and triethylamine (0.40 ml) were dissolved in a mixture of methylene chloride (4 ml) and dimethylsulfoxide (4 ml). Under cooling with ice, sulfur trioxide pyridine complex (228 mg) was added to the mixture. The mixture was warmed to room temperature. The reaction mixture was diluted with water and extracted with ethyl acetate. The extract was washed with 1N hydrochloric acid, water and saturated aqueous sodium chloride, successively, dried over anhydrous magnesium sulfate and concentrated. The obtained title compound (180 mg) was used for the next reaction without purification.

Example 11

(2S)-4-cyclopentylamino-2-t-butoxycarbonylaminobutanoic acid.4-methoxybenzyl ester

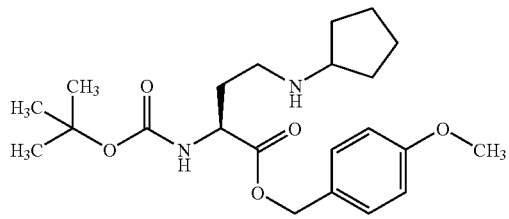

Under cooling with ice, sodium cyanoborohydride (74 mg) was added to a solution of the compound prepared in Reference Example 8 (180 mg), cyclopentylamine (0.10 ml) and acetic acid (0.04 ml) in methanol (5 ml). The mixture was stirred for 6.5 hours under cooling with ice and stirred for 12 hours at room temperature. The reaction mixture was diluted with water and methanol was distilled off under reduced pressure. The aqueous layer was extracted with ethyl acetate. The extract was washed with water and saturated aqueous sodium chloride, successively, dried over anhydrous magnesium sulfate. The organic layer was concentrated and the residue was purified by silica gel column chromatography (ethyl acetate:hexane=1:1) to give the compound of the present invention (35 mg) having the following physical data.

TLC: Rf 0.17 (methanol:chloroform=1:9); NMR (CD$_3$OD): δ 7.31 (2H, d, J=8.4 Hz), 6.89 (2H, d, J=8.4 Hz), 5.17 (1H, d J=11.8 Hz), 5.04 (1H, d, J=11.8 Hz), 4.26–4.14 (1H, m), 3.78 (3H, s), 3.27–3.12 (1H, m), 2.77 (2H, t, J=6.2 Hz), 2.12–1.49 (10H, m), 1.42 (9H, s).

Example 12

(2S)-N-(4-methoxybenzyl)-3-cyclohexylsulfonylamino-2-t-butoxycarbonyl-aminopropanamide

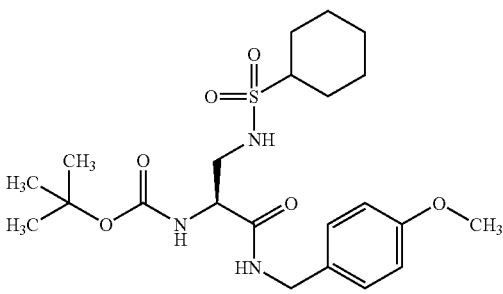

(2S)-N-(4-methoxybenzyl)-3-amino-2-t-butoxycarbonylaminopropanamide (98 mg) was dissolved in a mixture of pyridine (3 ml) and methylene chloride (5 ml). Under cooling with ice, cyclohexylsulfonyl chloride (166 mg) was added thereto and dimethylaminopyridine (3 mg) was added thereto. The mixture was stirred for 1 hour. The reaction mixture was diluted with water and extracted with ethyl acetate. The extract was washed with 1N hydrochloric acid, water and saturated aqueous sodium chloride, successively, dried over anhydrous magnesium sulfate. The organic layer was concentrated and the residue was purified by silica gel column chromatography (ethyl acetate:hexane= 1:2) to give the compound of the present invention (25 mg) having the following physical data.

TLC: Rf 0.43 (ethyl acetate:hexane=1:1); NMR (CDCl$_3$): δ 7.22–7.14 (2H, m), 7.12–7.00 (1H, m), 6.89–6.81 (2H, m), 5.75 (1H, d, J=7.2 Hz), 5.34–5.20 (1H, m), 4.46–4.21 (3H, m), 3.79 (3H, s), 3.60 (1H, dt, J=14.0, 4.8 Hz), 3.38 (1H, ddd, J=14.0, 8.6,4.2 Hz), 2.97–2.82 (1H, m), 2.24–1.08 (19H, m).

Reference Example 9

(2R)-2-t-butoxycarbonylamino-2-(4-methoxybenzylcarbomoyl)ethansulfonic. acid sodium salt

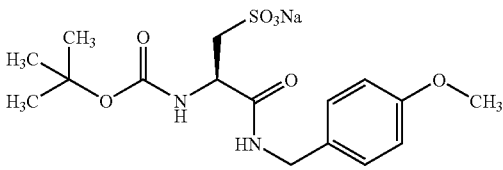

Under cooling with ice, dicyclohexylcarbodiimide (823 mg) was added to a solution of (2R)-2-t-butoxycarbonylamino-2-carboxyethansulfonic acid sodium salt (893 mg) and p-nitrophenol (470 mg) in DMF (15 ml). The mixture was stirred for 30 minutes. The reaction mixture was allowed to stand for 4 days at 5° C. Acetic acid was added to the reaction mixture for treating with an excess amount of-dicyclohexylcarbodiimide. The mixture was filtered. The filtrate was concentrated. Under cooling with ice, 4-methoxybenzylamine (0.40 ml) was added to a solution of the residue in DMF (10 ml). The mixture was stirred for 2 hours. The reaction mixture was concentrated. The residue was diluted with water. The aqueous layer was washed with ethyl acetate. The aqueous layer was concentrated under reduced pressure to give the compound of the present invention (610 mg) having the following physical data.

TLC: Rf 0.33 (methanol:chloroform=1:4); NMR (CD₃OD): δ 7.24–7.18 (2H, m), 6.87–6.81 (2H, m), 4.42–4.21 (3H, m), 3.75 (3H, s), 3.22–3.16 (2H, m), 1.41 (9H, s).

Example 13

(2R)-N-(4-methoxybenzyl)-3-cyclohexylsulfamoyl-2-t-butoxycarbonyl-aminopropanamide

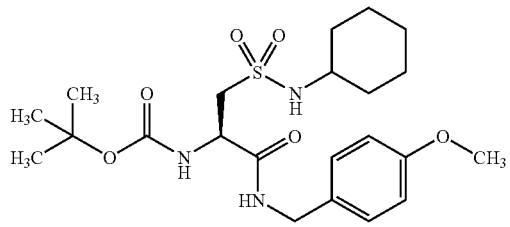

Under cooling with ice, sulfuryl chloride (0.045 ml) was added dropwise to a solution of triphenylphosphine (127 mg) in methylene chloride (1 ml). The mixture was stirred and allowed to warm to room temperature. A solution of the compound prepared in Reference Example 9 (100 mg) in methylene chloride (2 ml) was added to the reaction mixture. The mixture was stirred for 1 hour at room temperature. The mixture of cyclohexylamine (0.14 ml) and triethylamine (0.17 ml) was added to the reaction mixture. The mixture was stirred for 1 hour. The reaction mixture was diluted with saturated aqueous sodium hydrogencarbonate and extracted with chloroform. The extract was washed with 1N hydrochloric acid, water and saturated aqueous sodium chloride, successively, dried over anhydrous magnesium sulfate. The organic layer was concentrated and the residue was purified by silica gel column chromatography (ethyl acetate:hexane=1:2) to give the compound of the present invention (15 mg) having the following physical data.

TLC: Rf 0.56 (ethyl acetate:hexane=1:1); NMR (CDCl₃): δ 7.24–7.15 (2H, m), 6.90–6.81 (3H, m), 5.72 (1H, d, J=8.4 4.75 (1H, d, J=7.4 Hz), 4.69–4.60 (1H, m), 4.43 (1H, dd, J=14.0, 5.4 Hz), 4.33 (1H, dd, J=14.0, 5.8 Hz), 3.79 (3H, s), 3.60 (1H, dd, J=15.0, 6.2 Hz), 3.50 (1H, dd, J=15.0, 4.8 Hz), 3.38–3.19 (1H, m), 2.04–1.08 (19H, m).

Example 13(1)

(2R)-N-(4-methoxybenzyl)-3-(piperidin-1-ylsul (2R)-N-(4-methoxybenzyl)-3-(piperidin-1-ylsulfonyl)-2-t-butoxycarbonyl-aminopropanamide

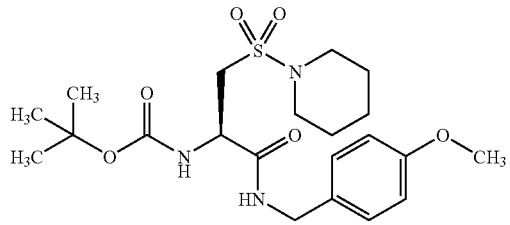

By the same desired procedure as Example 13, using the compound prepared in Reference Example 9, the compound of the present invention having the following physical data was obtained.

TLC: Rf 0.41 (ethyl acetate:hexane=1:1); NMR (CDCl₃): δ 7.25–7.17 (2H, m), 6.89–6.82 (3H, m), 5.64 (1H, d, J=7.4 Hz), 4.61–4.51 (1H, m), 4.45 (1H, dd, J=15.0, 6.2 Hz), 4.35 (1H, dd, J=15.0, 5.4 Hz), 3.79 (3H, s), 3.54 (1H, dd, J=13.2, 5.8 Hz), 3.39 (1H, dd, J=13.2, 5.4 Hz), 3.26–3.21 (4H, m), 1.75–1.50 (6H, m), 1.44 (9H, s).

Example 14

(2S)-3-cyclohexyloxycarbonyl-2-(N-benzyl-N-t-butoxycarbonylamino)-prpanoic acid.4-methoxybenzyl ester

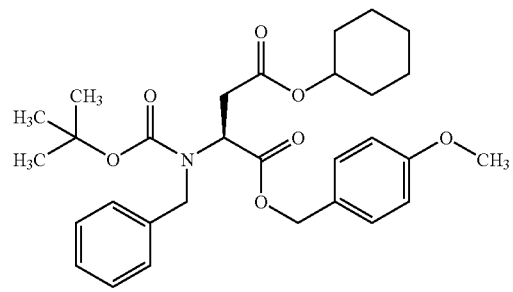

Under cooling with ice, sodium hydride (60%, 13 mg) was added to a solution of the compound prepared in Example 2(4) (122 mg) in DMF (3 ml). The mixture was stirred for 30 minutes at 0° C. Benzyl bromide (37 μl) was added to the reaction mixture. The mixture was stirred for 3 hours at 0° C. The reaction mixture was acidified by adding 1N hydrochloric acid, diluted with water and extracted with ethyl acetate. The extract was washed with water and saturated aqueous sodium chloride, successively, dried over anhydrous magnesium sulfate. The organic layer was concentrated and the residue was purified by silica gel column chromatography (ethyl acetate:hexane=1:8) to give the compound of the present invention (52 mg) having the following physical data.

TLC: Rf 0.44 (ethyl acetate:hexane=1:4); NMR (CDCl₃): δ 7.34–7.14 (7H, m), 6.89–6.82 (2H, m), 5.10–4.25 (6H, m), 3.81 (3H, s), 3.25–3.03 (1H, m), 2.72–2.46 (1H, m), 1.84–1.22 (19H, m).

Example 15

(2S)-3-cyclohexyloxycarbonyl-2-benzylaminopropanoic acid.4-methoxybenzyl ester

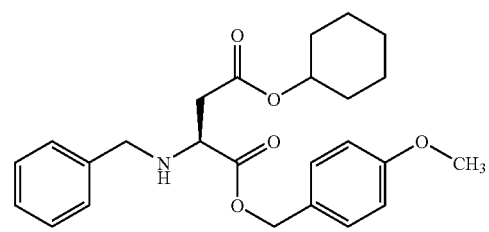

P-toluenesulfonic acid monohydrate (42 mg) was added to a solution of the compound prepared in Example 14 (115 mg) in diethylether (0.5 ml). The mixture was stirred for 19 hours at room temperature. The reaction mixture was washed with diethylether. The obtained cyrstal was dissolved in ethyl acetate, washed with saturated aqueous sodium hydrogencarbonate and saturated aqueous sodium chloride, successively, dried over anhydrous magnesium sulfate and concentrated to give the compound of the present invention (89 mg) having the following physical data.

TLC: Rf 0.63 (ethyl acetate:hexane=1:2); NMR (CDCl₃): δ 7.34–7.22 (7H, m), 6.93–6.85 (2H, m), 5.11 (2H, s), 4.80–4.66 (1H, m), 3.85 (1H, d, J=12.8 Hz), 3.81 (3H, s), 3.69 (1H, d, J=12.8 Hz), 3.68 (1H, dd, J=6.8, 6.2 Hz), 2.73 (1H, dd, J=15.8, 6.2 Hz), 2.63 (1H, dd, J=15.8, 6.8 Hz), 1.95 (1H, br. s), 1.84–1.19 (10H, m).

Example 16

(2R)-N-(4-phenoxybenzyl)-3-cyclohexylmethylthio-2-((4R)-thiazolidin-4-ylcarbonylamino)propanamide

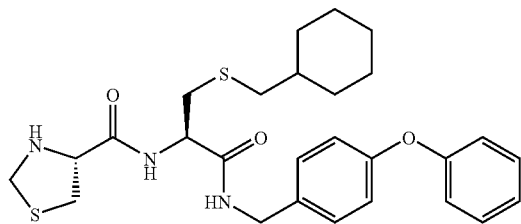

A solution of the compound prepared in Example 9(13) (107 mg) in ethyl acetate (10 ml) was washed with saturated aqueous sodium hydrogencarbonate (5 ml) and saturated aqueous sodium chloride, successively, dried over anhydrous magnesium sulfate and concentrated to give the compound of the present invention (96 mg) having the following physical data.

TLC: Rf 0.39 (ethyl acetate:hexane=1:1); NMR (CDCl₃): δ 7.88 (d, J=7.5 Hz, 1H), 7.37–7.30 (m, 2H), 7.25–7.21 (m, 2H), 7.14–7.08 (m, 1H), 7.02–6.94 (m, 4H), 6.84–6.80 (m, 1H), 4.49–4.36 (m, 3H), 4.26 (d, J=9.9 Hz, 1H), 4.19–4.15 (m, 1H), 4.05 (d, J=9.9 Hz, 1H), 3.42 (dd, J=11.1, 4.2 Hz, 1H), 3.10 (dd, J=11.1, 7.5 Hz, 1H), 2.93 (dd, J=13.8, 6.3 Hz, 2H), 2.83 (dd, J=13.8, 7.2 Hz, m), 2.45 (d, J=6.6 Hz, 2H), 1.86–1.58 (m, 5H), 1.51–1.36 (m, 1H), 1.29–1.05 (3H, m), 0.98–0.85 (m, 2H).

Example 16(1)

(2R)-N-(1-phenylpiperidin-4-yl)-3-cyclohexylmethylthio-2-((4R)-thiazolidin-4-ylcarbonylamino)prop

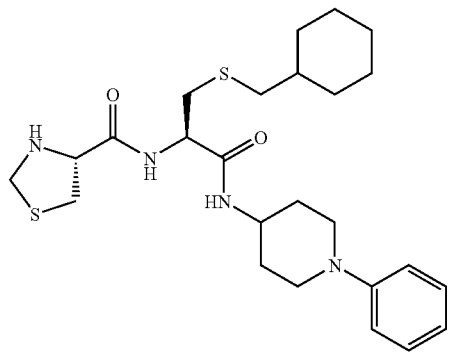

By the same desired procedure as Example 16, using the compound prepared in Example 9(16), the compound of the present invention having the following physical data was obtained.

TLC: Rf 0.26 (hexane:ethyl acetate=1:1); NMR (CDCl₃): δ 7.86 (d, J=7.5 Hz, 1H), 7.29–7.23 (m, 2H), 6.95–6.91 (m, 2H), 6.88–6.83 (m, 1H), 6.47 (d, J=8.1 Hz, 1H), 4.37 (dd, J=14.1, 7.5 Hz, 1H), 4.27 (d, J=9.9 Hz, 1H), 4.18 (dd, J=7.8, 4.2 Hz, 1H), 4.05 (d, J=9.9 Hz, 1H), 4.00–3.88 (m, 1H), 3.63–3.51 (m, 2H), 3.43 (dd, J=11.1, 4.2 Hz, 1H), 3.12 (dd, J=11.1, 7.8 Hz, 1H), 2.95–2.86 (m, 3H), 2.79 (dd, J=13.8, 7.5 Hz, 1H), 2.48 (d, J=6.9 Hz, 2H), 2.08–1.98 (m, 2H), 1.84–1.39 (m, 8H), 1.31–1.06 (m, 3H), 1.00–0.87 (m, 2H).

Example 17~Example 17(16)

By the same desired procedure as Example 9→Example 16, using the comounds prepared in Example 6(36), Example 6(44), Example 6(49), Example 6(60), Example 6(61), Example 6(69), Example 6(74)~Example 6(83) and Example 6(86), the following compounds of the present invention were obtained.

Example 17

(2R)-N-(4-methoxybenzyl)-3-cyclohexylmethylthio-2-((2RS)-thiazolidin-2-ylcarbonylamino)propanamide

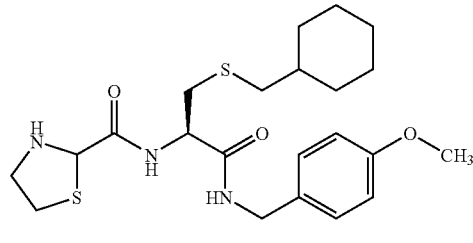

TLC: Rf 0.45 (methylene chloride:methanol=19:1); NMR (CD₃OD): δ 7.27–7.17 (2H, m), 6.92–6.82 (2H, m), 5.01 and 4.98 (1H, s) 4.49 and 4.48 (1H, t, J=7 Hz), 4.34 (1H, d, J=15 Hz), 4.28 (1H, d, J=15 Hz), 3.77 (3H, s), 3.48–3.02 (2H, m), 3.00–2.71 (4H, m), 2.41 and 2.39 (2H, d, J=7 Hz), 1.90–0.78 (11H, m).

Example 17(1)

(2R)-N-(4-methoxybenzyl)-3-cyclohexylmethylthio-2-((4R)-thiazolidin-4-ylcarbonylamino)propanamide

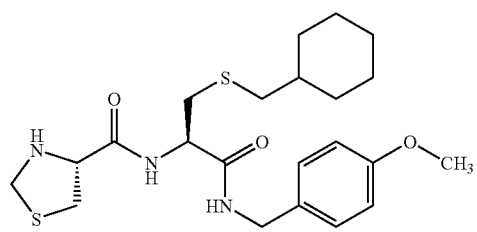

TLC: Rf 0.59 (methylene chloride:methanol=9:1); NMR (CDCl₃): δ 7.87 (1H, d, J=8 Hz), 7.25–7.18 (2H, m), 6.90–6.83 (2H, m), 6.78–6.70 (1H, m), 4.48–4.31 (3H, m), 4.30–4.21 (1H, m), 4.20–4.12 (1H, m), 4.10–4.00 (1H, m), 3.80 (3H, s), 3.41 (1H, dd, J=11, 4 Hz), 3.10 (1H, dd, J=11, 8 Hz), 2.92 (1H, dd, J=14, 6 Hz), 2.83 (1H, dd, J=14, 7 Hz), 2.50–2.38 (1H, b), 2.44 (2H, d, J=7 Hz), 1.85–1.55 (5H, m), 1.50–1.35 (1H, m), 1.31–1.03 (3H, m), 0.98–0.84 (2H, m).

Example 17(2)

(2R)-N-(4-methoxybenzyl)-3-cyclohexylmethylthio-2-(2-aminothiazol-4-ylcarbonylamino)propanamide

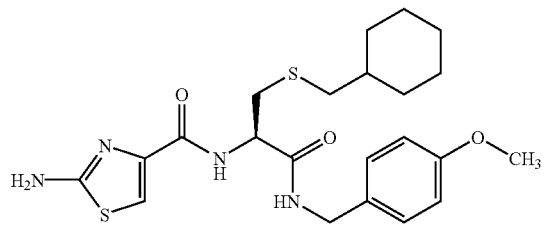

TLC: Rf 0.30 (methylene chloride:methanol=19:1); (CDCl$_3$+3drops of CD$_3$OD) δ 7.33 (1H, s), 7.27–7.17 (2H, m), 6.90–6.80 (2H, m), 4.64 (1H, t, J=6 Hz), 4.41 (1H, d, J=15 Hz), 4.35 (1H, d, J=15 Hz), 3.80 (3H, s), 3.08–2.84 (2H, m), 2.44 (2H, d, J=7 Hz), 1.87–0.78 (11H, m).

Example 17(3)

(2R)-N-(4-methoxybenzyl)-3-cyclohexylmethylthio-2-(thiazolidin-2-ylcarbonylamino)propanamide

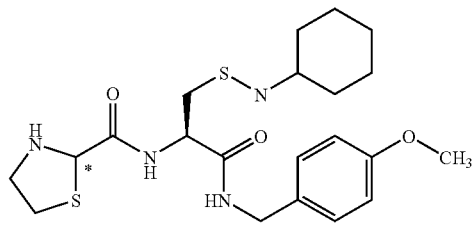

(The absolute configuration of * carbon is not determined, but the above compound is a single optical isomer.)

[α]$_D$=−71.7 (c 0.21, CHCl$_3$);

TLC: Rf 0.27 (hexane:ethyl acetate=1:2); NMR (CDCl$_3$): δ 7.65 (1H, d, J=7.4 Hz), 7.21 (2H, d, J=8.8 Hz), 6.86 (2H, d J=8.8 Hz), 6.80–6.73 (1H, br), 4.99 (1H, s), 4.50–4.38 (3H, m), 3.80 (3H,s), 3.51–3.40 (1H, m), 3.15–2.94 (3H, m), 2.88–2.75 (2H, m), 2.44 (2H, d, J=7.0 Hz), 1.83–1.30 (6H, m), 1.28–0.78 (5H, m).

Example 17(4)

(2R)-N-(4-methoxybenzyl)-3-cyclohexylmethylthio-2-(thiazolidin-2-ylcarbonylamino)propanamide

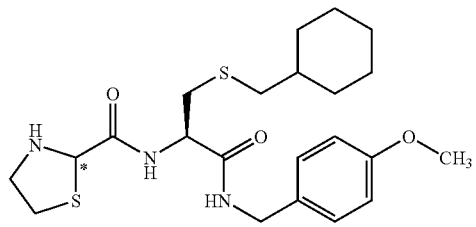

(The absolute configuration of * carbon is not determined, but the above compound is a single optical isomer.)

[α]$_D$=+51.5 (c 0.19, CHCl$_3$); TLC: Rf 0.16 (hexane:ethyl acetate=1:2); NMR (CDCl$_3$): δ 7.69 (1H, d, J=7.0 Hz), 7.21 (2H, d, J=8.8 Hz), 6.86 (2H, d J=8.8 Hz), 6.81–6.69 (1H, br), 5.01 (1H, s), 4.51–4.37 (3H, m), 3.80 (3H, s), 3.52–3.39 (1H, m), 3.08–2.91 (3H, m), 2.89–2.73 (2H, m), 2.53–2.40 (2H, m), 1.83–1.37 (6H, m), 1.34–0.79 (5H, m).

Example 17(5)

(2R)-N-(4-methoxybenzyl)-3-cyclohexylmethylthio-2-((2RS,4R)-2-(2-methylpropyl)thiazolidin-4-ylcarbonylamino)propanamide

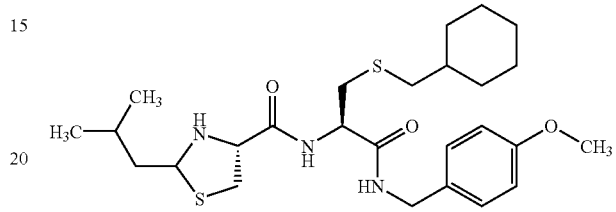

TLC: Rf 0.41 (methanol:methylene chloride=1:19); NMR (CD$_3$OD): δ 7.25–7.18 (2H, m), 6.89–6.82 (2H, m), 4.61–4.46 (2H, m), 4.39–4.24 (2H, m), 4.39–4.24 (m) and 3.84 (t, J=8 Hz) (1H), 3.76 (3H, s), 3.39 (dd, J=10, 3 Hz) and 3.19 (dd, J=10, 8 Hz) (1H), 3.09 (dd, J=10, 8 Hz) and 2.99–2.90 (m) (1H), 2.90–2.76 (2H, m), 2.38 and 2.41 (2H, d, J=6 Hz), 1.90–1.55 (8H, m), 1.49–1.33 (1H, m), 1.33–1.06 (3H, m), 1.06–0.83 (8H, m).

Example 17(6)

(2R)-N-(4-methoxybenzyl)-3-cyclohexylmethylthio-2-((2RS,4R)-2-phenylthiazolidin-4-ylcarbony

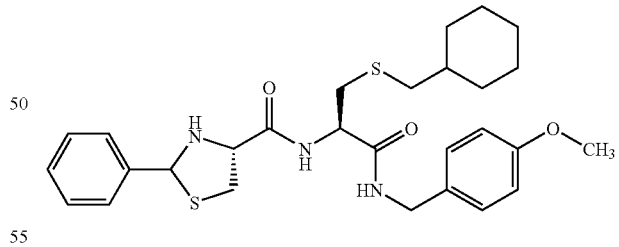

TLC: Rf 0.43 (methanol:methylene chloride=1:19); NMR (CDCl$_3$+5 drops of CD$_3$OD): δ 7.57–7.48 (m, 2H), 7.45–7.33 (m, 3H), 7.25–7.18 (m, 2H), 6.90–6.83 (m, 2H), 5.60 and 5.53 (s, 1H), 4.53–4.29 and 3.99–3.90 (m, 4H), 3.79 (s, 3H), 3.43–3.35 (m) and 3.64 (dd, J=11, 3 Hz) (1H), 3.19 and 3.39 (dd, J=11, 8 Hz, 1H), 2.73 and 2.92 (d, J=7 Hz, 2H), 2.40 and 2.43 (d, J=7 Hz, 2H), 1.85–1.58 (m, 5H), 1.51–1.34 (m, 1H), 1.31–1.03 (m, 3H), 1.00–0.80 (m, 2H).

Example 17(7)

(4R)-N-((1R)-2-cyclohexylmethylthio-1-(4-phenylpiperazin-1-ylcarbonyl)ethyl)-thiazolidin-4-ylcarboxamide

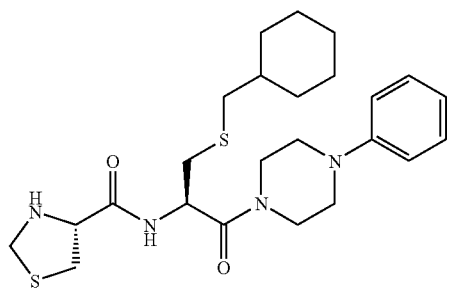

TLC: Rf 0.55 (methanol:chloroform=1:9); NMR (CDCl₃): δ 7.85 (d, J=8.7 Hz, 1H), 7.32–7.26 (m, 2H), 6.94–6.89 (m, 3H), 5.12–5.04 (m, 1H), 4.27 (d, J=9.9 Hz, 1H), 4.15 (dd, J=7.5, 4.2 Hz, 1H), 4.07 (d, J=9.9 Hz, 1H), 3.89–3.74 (m, 4H), 3.44 (dd, J=10.8, 4.2 Hz, 1H), 3.32–3.09 (m, 5H), 2.91 (dd, J=13.5, 3.9 Hz, 1H), 2.76 (dd, J=13.5, 6.3 Hz, 1H), 2.54–2.34 (m, 3H), 1.86–1.60 (m, 5H), 1.50–1.35 (m, 1H), 1.30–1.04 (m, 3H), 1.02–0.84 (m, 2H).

Example 17(8)

(2R)-N-(4-methoxybenzyl)-3-cyclohexylmethylthio-2-((3RS)-thiomorpholin-3-ylcarbonylamino)propanamide

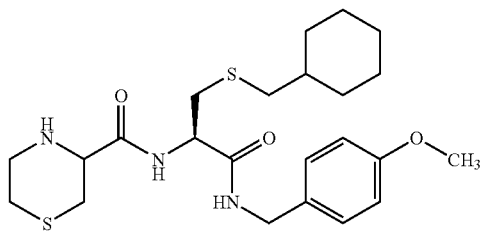

TLC: Rf 0.31 and 0.27 (methylene chloride:methanol=19:1); NMR (CD₃OD): δ 7.26–7.18 (m, 2H), 6.88–6.83 (m, 2H), 4.54–4.46 (m, 1H), 4.38–4.24 (m, 2H), 3.76 (s, 3H), 3.60–3.52 (m, 1H), 3.36–3.28 (m, 1H), 3.02–2.60 (m, 6H), 2.44–2.32 (m, 3H), 1.86–1.60 (m, 5H), 1.50–1.34 (m, 1H), 1.34–1.07 (m, 3H), 1.00–0.83 (m, 2H).

Example 17(9)

(2R)-N-(4-phenoxybenzyl)-3-cyclohexylmethylthio-2-((3RS)-thiomorpholin-3-ylcarbonylamino)propanamide

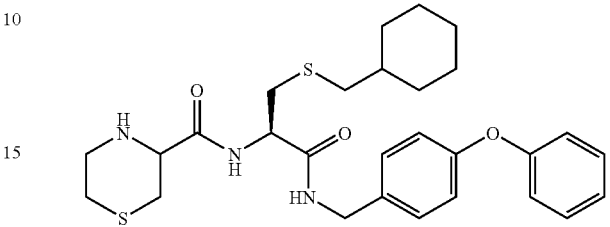

TLC: Rf 0.14 and 0.16 (methylene chloride:methanol=19:1); NMR (CDCl₃): δ 7.69 and 7.62 (d, J=8 Hz, 1H), 7.38–7.30 (m, 2H), 7.28–7.21 (m, 2H), 7.15–7.08 (m, 1H), 7.03–6.93 (m, 4H), 6.91–6.77 (m, 1H), 4.54–4.35 (m, 4H), 3.60–3.51 (m, 1H), 3.38–3.23 (m, 1H), 3.10–2.90 (m, 2H), 2.88–2.76 (m, 2H), 2.75–2.37 (m, 5H), 1.86–1.52 (m, 5H), 1.52–1.35 (m, 1H), 1.30–1.04 (m, 3H), 1.00–0.84 (m, 2H).

Example 17(10)

(2R)-N-(2-phenoxypyridin-5-yl)-3-cyclohexylmethylthio-2-((4R)-thiazolidin-4-ylcarbonylamino)propa

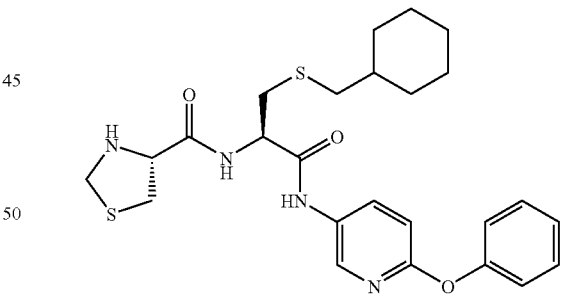

TLC: Rf 0.18 (methanol:chloroform=1:19); NMR (CDCl₃): δ 8.94–8.82 (m, 1H), 8.23 (d, J=2.4 Hz, 1H), 8.05–8.00 (m, 2H), 7.42–7.35 (m, 2H), 7.21–7.16 (m, 1H), 7.12–7.07 (m, 2H), 6.86 (d, J=8.7 Hz, 1H), 4.64–4.57 (m, 1H), 4.30 (d, J=9.9 Hz, 1H), 4.29–4.26 (m, H), 4.07 (d, J=9.9 Hz, 1H), 3.48 (dd, J=10.8, 3.3 Hz, 1H), 3.14 (dd, J=10.8, 8.1, 1H), 3.00 (dd, J=13.8, 7.2 Hz, 1H), 2.92 (dd, J=13.8, 6.9 Hz, 1H), 2.48 (d, J=6.6 Hz, 2H), 1.88–1.60 (m, 5H), 1.54–1.39 (m, 1H), 1.32–1.04 (m, 3H), 1.01–0.84 (m, 2H).

Example 17(11)

(2R)-N-(4-methoxybenzyl)-3-cyclohexylmethylthio-2-((2RS)-thiomorpholin-2-ylcarbonylamino)propanamide

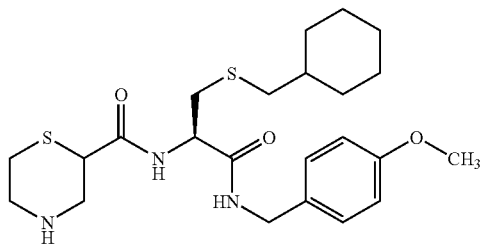

TLC: Rf 0.46 and 0.41 (methylene chloride:methanol=9:1); NMR (CDCl₃): δ 8.92 and 8.62 (d, J=8 Hz, 1H), 7.25–7.17 (m, 2H), 6.90–6.82 (m, 2H), 4.66–4.52 (m, 1H), 4.48–4.29 (m, 2H), 3.79 (s, 3H), 3.61–3.53 (m, 1H), 3.31–2.81 (m, 7H), 2.55–2.40 (m, 2H), 2.36–2.24 (m, 1H), 1.86–1.58 (m, 5H), 1.53–1.35 (m, 1H), 1.31–1.04 (m, 3H), 1.00–0.83 (m, 2H).

Example 17(12)

(2R)-N-(4-methoxybenzyl)-3-cyclohexylmethylthio-2-((4RS)-1,3-perhydrothiazin-4-ylcarbonylamino)propanamide

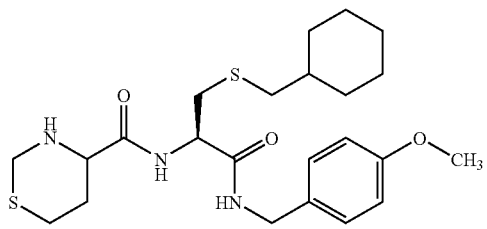

TLC: Rf 0.22 and 0.19 (methylene chloride:methanol=49:1); NMR (CDCl₃): δ 7.66–7.56 (m, 1H), 7.24–7.16 (m, 2H), 6.90–6.82 (m, 2H), 6.78–6.65 (m, 1H), 4.52–4.41 (m, 1H), 4.41–4.30 (m, 2H), 4.17–4.01 (m, 2H), 3.80 (s, 3H), 3.36–3.28 (m, 1H), 2.99–2.73 (m, 4H), 2.49–2.42 (m, 2H), 2.31–2.20 (m, 1H), 1.85–1.35 (m, 7H), 1.30–1.03 (m, 3H), 1.00–0.83 (m, 2H).

Example 17(13)

(2R)-N-(2-phenoxypyridin-5-ylmethyl)-3-cyclohexylmethylthio-2-((4R)-thiazolidin-4-ylcarbonylamino)propanamide

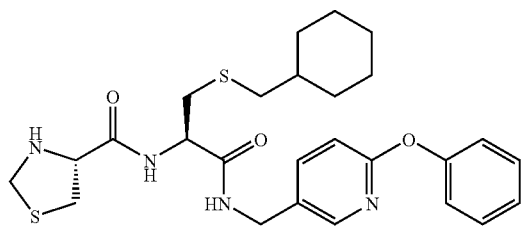

TLC: Rf 0.41 (methanol:chloroform=1:19); NMR (CDCl₃): δ 8.09 (d, J=2.1 Hz, 1H), 7.87 (d, J=7.5 Hz, 1H), 7.64 (dd, J=8.4, 2.4 Hz, 1H), 7.43–7.37 (m, 2H), 7.20 (tt, J=7.2, 1.2 Hz, 1H), 7.14–7.09 (m, 2H), 6.94 (t, J=6.0 Hz, 1H), 6.87 (d, J=8.4 Hz, 1H), 4.43 (dd, J=13.8, 7.2 Hz, 1H), 4.40 (d, J=6.0 Hz, 2H), 4.27 (d, J=9.9 Hz, 1H), 4.18 (dd, J=7.8, 4.2 Hz, 1H), 4.04 (d, J=9.9 Hz, 1H), 3.42 (dd, J=11.1, 3.9 Hz, 1H), 3.10 (dd, J=11.1, 7.8 Hz, 1H), 2.92 (dd, J=13.8, 6.6 Hz, 1H), 2.82 (dd, J=13.8, 7.2 Hz, 1H), 2.43 (d, J=9.3 hz, 2H), 1.86–1.58 (m, 5H), 1.48–1.35 (m, 1H), 1.30–1.04 (m, 3H), 0.98–0.82 (m, 2H).

Example 17(14)

(2R)-N-(4-(morpholin-4-yl)benzyl)-3-cyclohexylmethylthio-2-((4R)-thiazolidin-4-ylcarbonylamino)propanamide

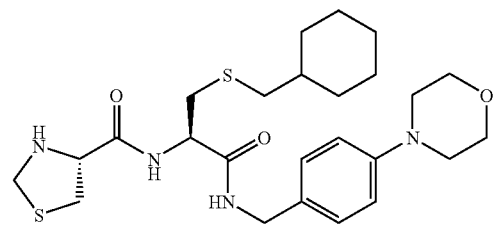

TLC: Rf 0.46 (methanol:chloroform=1:19); NMR (CDCl₃): δ 7.86 (d, J=7.5 Hz, 1H), 7.21–7.16 (m, 2H), 6.89–6.84 (m, 2H), 6.71 (t, J=5.1 Hz, 1H), 4.44 (dd, J=13.8, 6.9 Hz, 1H), 4.40 (dd, J=14.7, 5.7 Hz, 1H), 4.34 (dd, J=14.7, 5.4 Hz, 1H), 4.26 (d, J=9.9 Hz, 1H), 4.14 (dd, J=7.5, 3.9 Hz, 1H), 4.04 (d, J=9.9 Hz, 1H), 3.87–3.84 (m, 4H), 3.40 (dd, J=11.1, 4.2 Hz, 1H), 3.16–3.12 (m, 4H), 3.09 (dd, J=11.1, 7.8 Hz, 1H), 2.92 (dd, J=13.8, 6.3 Hz, 1H), 2.82 (dd, J=13.8, 7.2 Hz, 1H), 2.43 (d, J=6.9 Hz, 2H), 1.85–1.58 (m, 5H), 1.51–1.35 (m, 1H), 1.30–1.04 (m, 3H), 0.98–0.82 (m, 2H).

Example 17(15)

(2R)-N-(4-phenoxybenzyl)-3-cyclohexylmethylthio-2-((4RS)-1,3-perhydrothiazin-4-ylcarbonylamino)propanamide

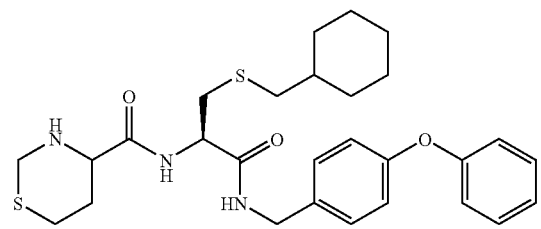

TLC: Rf 0.39 and 0.30 (methylene chloride:methanol=19:1); NMR (CDCl₃): δ 7.68–7.56 (m, 1H), 7.38–7.29 (m, 2H), 7.29–7.20 (m, 2H), 7.14–7.07 (m, 1H), 7.05–6.90 (m, 4H), 6.87–6.82 (m, 1H), 4.54–4.34 (m, 3H), 4.18–4.00 (m, 2H), 3.37–3.29 (m, 1H), 3.00–2.74 (m, 4H), 2.50–2.43 (m, 2H), 2.32–2.20 (m, 1H), 1.86–1.35 (m, 8H), 1.31–1.03 (m, 3H), 1.03–0.83 (m, 2H).

Example 17(16)

(2R)-N-(1-methylpiperidin-4-yl)-3-cyclohexylmethylthio-2-((4R)-thiazolidin-4-ylcarbonylamino)propanamide

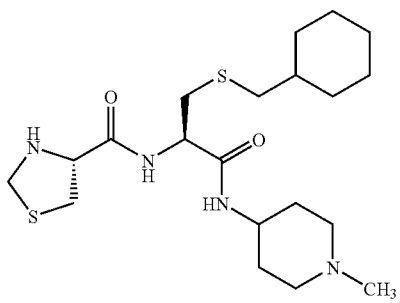

TLC: Rf 0.24 (chloroform:methanol=9:1); NMR (CD$_3$OD): δ 4.46–4.39 (m, 1H), 4.23–4.09 (m, 3H), 3.75–3.64 (m, 1H), 3.23 (dd, J=10.2, 4.4 Hz, 1H), 3.03 (dd, J=10.2, 7.2 Hz, 1H), 2.93–2.70 (m, 4H), 2.43 (d, J=6.6 Hz, 2H), 2.27 (s, 3H), 2.22–2.06 (m, 2H), 1.94–1.10 (m, 13H), 1.03–0.82 (m, 2H).

Example 18

(2R)-N-((1R)-1-(4-nitrophenyl)ethyl)-3-cyclohexylmethylthio-2-((4R)-3-(2-methylpropylcarbonyl)thiazolidin-4-ylcarbonylamino)propanamide

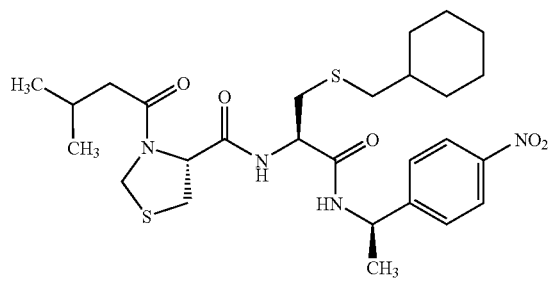

Under cooling with ice, isovaleryl chloride (0.025 ml) was added to a solution of the compound prepared in Example 9(6) (98 mg) and triethylamine (0.06 ml) in methylene chloride (3 ml). The mixture was stirred for 1 hour. The reaction mixture was washed with saturated aqueous sodium hydrogencarbonate, 1N hydrochloric acid, water and saturated aqueous sodium chloride, successively, dried over anhydrous magnesium sulfate. The organic layer was concentrated and the residue was purified by silica gel column chromatography (ethyl acetate:hexane=1:2) to give the compound of the present invention (81 mg) having the following physical data.

TLC: Rf 0.48 (ethyl acetate:hexane=1:1); NMR (CDCl$_3$): δ 8.16 (2H, d, J=8.8 Hz), 7.56 (2H, d, J=8.8 Hz), 7.45 (1H, d J=7.6 Hz), 6.95 (1H, d, J=8.2 Hz), 5.20–5.06 (1H, m), 4.87 (1H, t, J=5.6 Hz), 4.66–4.56 (3H, m) 3.33 (2H, d, J=5.6 Hz), 3.23 (1H, dd, J=13.8, 4.0 Hz), 2.75 (1H, dd, J=13.8, 5.8 Hz), 2.34 (2H, d, J=7.0 Hz), 2.24–2.01 (3H, m), 1.72–0.60 (20H, m).

Example 18(1)–Example 18(5)

By the same desired procedure as Example 18, using the compounds prepared in Example 16, Example 17 and Example 17(1), the following compounds of the present invention were obtained.

Example 18(1)

(2R)-N-(4-methoxybenzyl)-3-cyclohexylmethylthio-2-((2RS)-3-acetylthiazolidin-2-ylcarbonylamino)propanamide

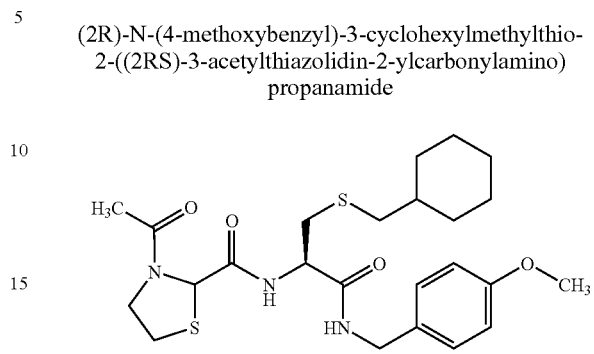

TLC: Rf 0.40 (ethyl acetate); NMR (CDCl$_3$): δ 7.46 (1H, t, J=6.2 Hz), 7.27–7.21 (2H, m), 6.89–6.77 (3H, m), 5.49–5.29 (1H, m), 4.62–4.34 (3H, m), 4.06–3.94 (1H, m), 3.88–3.72 (4H, m), 3.64–3.00 (3H, m), 2.85–2.74 (1H, m), 2.49–2.27 (2H, m), 2.18–2.03 (3H, m), 1.85–0.74 (11H, m).

Example 18(2)

(2R)-N-(4-phenoxybenzyl)-3-cyclohexylmethylthio-2-((4R)-3-methoxycarbonylthiazolidin-4-ylcarbonylamino)propanamide

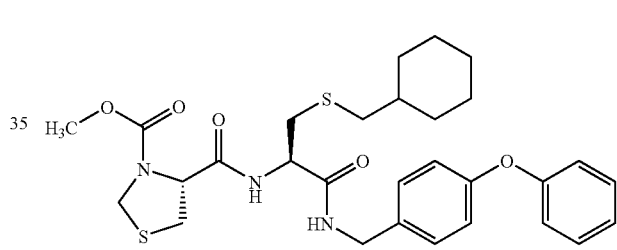

TLC: Rf 0.39 (hexane:ethyl acetate=1:1); NMR (CDCl$_3$): δ 7.37–6.93 (m, 11H), 4.73–4.32 (m, 6H), 3.67 (s, 3H), 3.32 (dd, J=12.0, 3.9 Hz, 1H), 3.28 (dd, J=12.0, 6.9 Hz, 1H), 3.23–3.01 (br, 1H), 2.82 (dd, J=13.8, 6.6 Hz, 1H), 2.48–2.34 (m, 2H), 1.82–1.52 (m, 5H), 1.49–1.04 (m, 4H), 0.96–0.81 (m, 2H).

Example 18(3)

(2R)-N-(4-phenoxybenzyl)-3-cyclohexylmethylthio-2-((4R)-3-(2-methylpropoxycarbonyl)thiazolidin-4-ylcarbonilamino)propanamide

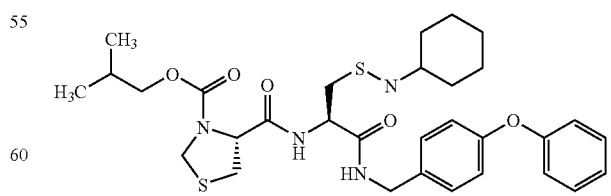

TLC: Rf 0.32 (hexane:ethyl acetate=2:1); NMR (CDCl$_3$): δ 7.37–6.92 (m, 11H), 4.73–4.29 (m, 6H), 3.84 (d, J=6.6 Hz, 2H), 3.32 (dd, J=12.3, 4.5 Hz, 1H), 3.29 (dd, J=12.3, 6.6 Hz, 1H), 3.24–3.17 (br, 1H), 2.81 (dd, J=13.5, 6.6 Hz, 1H), 2.44–2.32 (m, 2H), 1.99–1.54 (m, 6H), 1.49–1.04 (m, 4H), 0.95–0.86 (m, 8H).

Example 18(4)

(2R)-N-(4-methoxybenzyl)-3-cyclohexylmethylthio-2-((4R)-3-methoxycarbonylthiazolidin-4-ylcarbonyl)propanamide

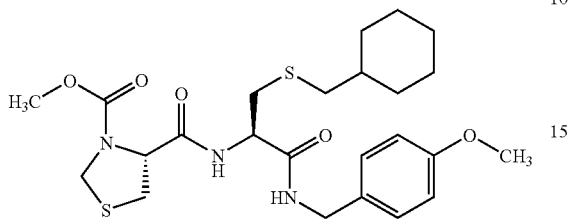

TLC: Rf 0.31 (hexane:ethyl acetate=1:1); NMR (CDCl$_3$): δ 7.22 (d, J=8.7 Hz, 2H), 7.10 (d, J=7.8 Hz, 2H), 6.85 (d, J=8.7 Hz, 2H), 4.72–4.24 (m, 6H), 3.79 (s, 3H), 3.65 (brs, 3H), 3.31 (dd, J=12.0, 4.2 Hz, 1H), 3.26 (dd, J=12.0, 6.9 Hz, 1H), 3.18–3.00 (br, 1H), 2.81 (dd, J=13.8, 6.6 Hz, 1H), 2.46–2.32 (m, 2H), 1.78–1.60 (m, 5H), 1.48–1.04 (m, 4H), 0.94–0.80 (m, 2H).

Example 18(5)

(2R)-N-(4-methoxybenzyl)-3-cyclohexylmethylthio-2-((4R)-3-(2-methylpropoxycarbonyl)thiazolidin-4-ylcarbonyl)propanamide

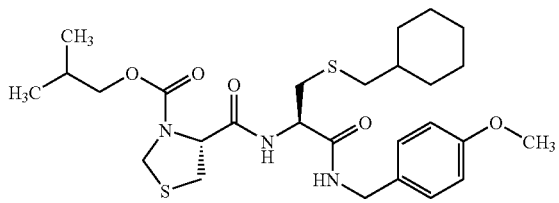

TLC: Rf 0.17 (hexane:ethyl acetate=2:1); NMR (CDCl$_3$): δ 7.21 (d, J=8.4 Hz, 2H), 7.11 (d, J=8.1 Hz, 2H), 6.84 (d, J=8.4 Hz, 2H), 4.72–4.21 (m, 6H), 3.78 (s, 5H), 3.31 (dd, J=12.3, 4.2 Hz, 1H), 3.28 (dd, J=12.3, 6.6 Hz, 1H), 3.25–3.17 (br, 1H), 2.80 (dd, J=13.8, 6.6 Hz, 1H), 2.45–2.30 (m, 2H), 1.94–1.62 (m, 6H), 1.47–1.04 (m, 4H), 0.98–0.80 (br, 8H).

Example 19~Example 19(1)

By the same desired procedure as Reference Example 4→Example 5→Example 17, using the compound prepared in Example 2(99), the following compounds of the present invention were obtained.

Also, (−)-3-t-butoxycarbonylthiazolidin-2-ylcarboxylic acid was used for the preparation of the compound of Example 19.

(+)-3-t-butoxycarbonylthiazolidin-2-ylcarboxylic acid was used for the preparation of the compound of Example 19(1).

Example 19

(2R)-N-(4-dimethylaminobenzyl)-3-cyclohexylmethylthio-2-(thiazolidin-2-ylcarbonylamino)propanamide

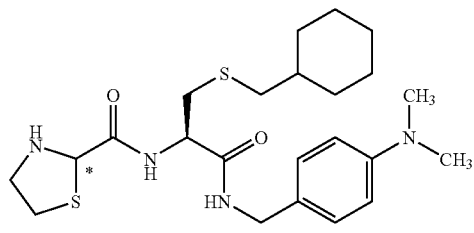

(The absolute configuration of * carbon is not determined, but the above compound is a single optical isomer.)
[α]$_D$=−77.07 (c 0.99, CHCl$_3$); TLC: Rf 0.46 (ethyl acetate:hexane=2:1); NMR (CDCl$_3$): δ 7.68 (1H, d, J=7.2 Hz), 7.19–7.12 (2H, m), 6.73–6.65 (3H, m), 4.98 (1H, s), 4.49–4.39 (1H, m), 4.34 (2H, d, J=5.4 Hz), 3.51–3.39 (1H, m), 3.15–2.74 (11H, m) 2.44 (2H, d, J=6.6 Hz), 1.88–0.77 (11H, m).

Example 19(1)

(2R)-N-(4-dimethylaminobenzyl)-3-cyclohexylmethylthio-2-(thiazolidin-2-ylcarbonylamino)propanamide

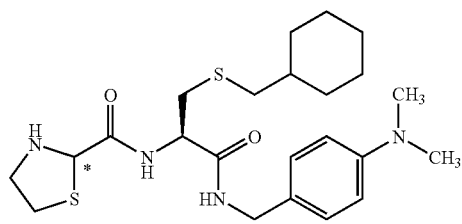

(The absolute configuration of * carbon is not determined, but the above compound-is a single optical isomer.)
[α]$_D$=+70.27 (c 1.06, CHCl$_3$);
TLC: Rf 0.41 (ethyl acetate:hexane=2:1); NMR (CDCl$_3$): δ 7.69 (1H, d, J=7.4 Hz), 7.19–7.12 (2H, m), 6.73–6.65 (2H, m), 6.60 (1H, d, J=5.2 Hz), 5.00 (1H, s), 4.49–4.39 (1H, m), 4.34 (2H, d, J=5.4 Hz), 3.49–3.38 (1H, m), 3.09–2.72 (11H, m) 2.51 (1H, dd, J=12.4, 6.6 Hz), 2.44 (1H, dd, J=12.4, 7.0 Hz), 1.88–0.77 (11H, m).

Example 20

(2R)-N-(4-methoxybenzyl)-3-cyclohexylmethylthio-2-(((4R)-3-t-butoxycarbonylthiazolidin-4-ylmethyl)amino)propanamide

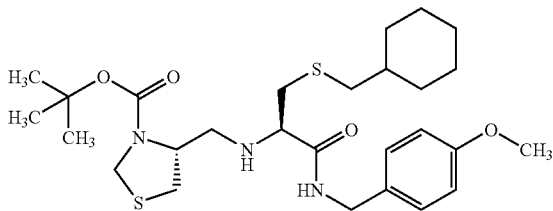

N-methyl morpholine (0.18 ml), (4R)-3-t-butoxycarbonyl-4-formylthiazolidine (355 mg) and sodium cyanoborohydride (206 mg) were added to a suspention of the compound (611 mg) (obtained by the same desired procedure as Reference Example 4 using the compound prepared in Example 2(80)) in ethanol (2 ml). The mixture was stirred for 3.5 hours at room temperature. The reaction mixture was concentrated. Saturated aqueous sodium hydrogencarbonate was added to the residue. The mixture was extracted with ethyl acetate. The extract was washed with saturated aqueous sodium chloride, dried over anhydrous sodium sulfate. The organic layer was concentrated and the residue was purified by silica gel column chromatography (ethyl acetate:hexane=2:1→1:1) to give the compound of the present invention (637.5 mg) having the following physical data.

TLC: Rf 0.30 (ethyl acetate:hexane=1:2); NMR (CD$_3$OD) δ 7.27–7.20 (m, 2H), 6.89–6.83 (m, 2H), 4.54 (d, J=9 Hz, 1H), 4.37 (d, J=14 Hz, 1H), 4.33–4.21 (m, 2H), 4.17 (d, J=9 Hz, 1H), 3.77 (3H, s), 3.25 (dd, J=8, 5 Hz), 3.14–3.05 (m, 1H), 2.98–2.80 (m, 2H), 2.77–2.60 (m, 3H), 2.41 (dd, J=12, 8 Hz, 1H), 2.40 (dd, J=12, 8 Hz, 1H), 1.88–1.60 (m, 5H), 1.55–1.35 (m, 10H), 1.35–1.07 (m, 3H), 1.03–0.85 (2H, m).

Example 20(1)~Example 20(7)

By the same desired procedure as Example 20, using the compound (obtained by the same desired procedure as Reference Example 4, using the compound prepared in Example 2(103)) or the compound (obtained by the same desired procedure as Reference Example 4, using the compound prepared in Example 2 (80)), the following compounds of the present invention were obtained.

Example 20(1)

(2R)-N-(4-phenoxybenzyl)-3-cyclohexylmethylthio-2-(((4R)-3-t-butoxycarbonylthiazolidin-4-ylmethyl)amino)propanamide

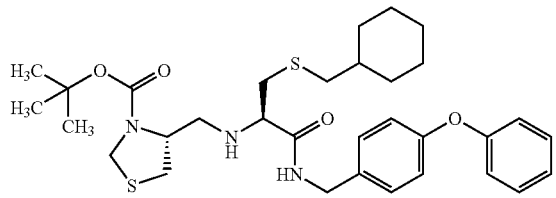

TLC: Rf 0.60 (methylene chloride:ethyl acetate=9:1); NMR (CD$_3$OD): δ 7.39–7.28 (m, 4H), 7.14–7.04 (m, 1H), 6.99–6.88 (m, 4H), 4.54 (d, J=9.0 Hz, 1H), 4.43 (d, J=14.7 Hz, 1H), 4.37–4.21 (m, 1H), 4.33 (d, J=14.7 Hz, 1H), 4.15 (d, J=9.0 Hz, 1H), 3.26 (dd, J=7.6, 5.4 Hz, 1H), 3.16–2.60 (m, 6H), 2.41 (d, J=6.6 Hz, 2H), 1.45 (s, 9H), 1.90–0.80 (m, 11H).

Example 20(2)

(2R)-N-(4-methoxybenzyl)-3-cyclohexylmethylthio-2-((thiophen-2-ylmethyl)amino)propanamide

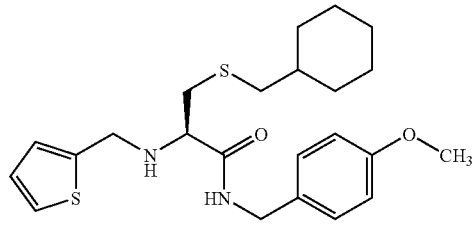

TLC: Rf 0.19 (hexane:ethyl acetate=4:1); NMR (CDCl$_3$): δ 7.64 (t, J=5.4 Hz, 1H), 7.22–7.18 (m, 3H), 6.95–6.84 (m, 4H), 4.39 (dd, J=14.4, 6.0 Hz, 1H), 4.37 (dd, J=14.4, 6.0 Hz, 1H), 3.93 (s, 2H), 3.80 (s, 3H), 3.30 (dd, J=9.3, 3.9 Hz, 1H), 3.03 (dd, J=13.8, 3.9 Hz, 1H), 2.63 (dd, J=13.8, 9.3 Hz, 1H), 2.31 (dd, J=12.3, 6.9 Hz, 1H), 2.25 (dd, J=12.3, 6.9 Hz, 1H), 1.83–1.32 (m, 6H), 1.28–1.04 (m, 3H), 0.95–0.80 (m, 2H).

Example 20(3)

(2R)-N-(4-methoxybenzyl)-3-cyclohexylmethylthio-2-((cyclohexylmethyl)-amino)propanamide

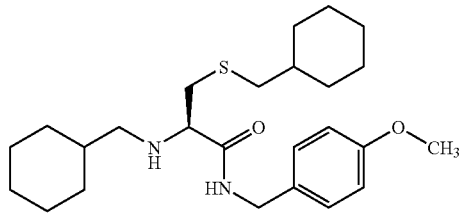

TLC: Rf 0.24 (hexane:ethyl acetate=4:1); NMR (CDCl$_3$): δ 7.67 (t, J=5.5 Hz, 1H), 7.23–7.16 (m, 2H), 6.90–6.83 (m, 2H), 4.40 (dd, J=14.4, 6.2 Hz, 1H), 4.35 (dd, J=14.6, 5.8 Hz, 1H), 3.80 (s, 3H), 3.17–3.02 (m, 2H), 2.60–2.24 (m, 5H), 1.87–0.70 (m, 22H).

Example 20(4)

(2R)-N-(4-methoxybenzyl)-3-cyclohexylmethylthio-2-(((4RS)-3-t-butoxycarbonyl-1,3-perhydrothiazin-4-ylmethyl)amino)propanamide

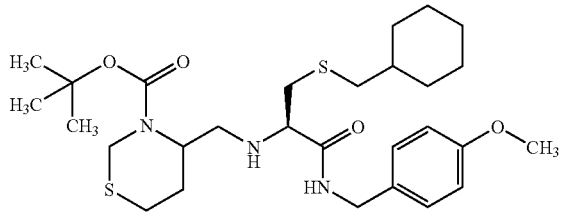

TLC: Rf 0.17 (ethyl acetate:hexane=1:2); NMR (CD$_3$OD) δ 7.29–7.20 (m, 2H), 6.91–6.81 (m, 2H), 4.71–4.50 (m, 1H), 4.41–4.22 (m, 4H), 3.77 (s, 3H), 3.28–3.19 (m, 1H), 3.03–2.75 (m, 3H), 2.71–2.35 (m, 5H), 2.00–1.60 (m, 7H), 1.52–1.34 (m, 10 H), 1.33–1.10 (m, 3H), 1.02–0.84 (m, 2H).

Example 20(5)

(2R)-N-(4-phenoxybenzyl)-3-cyclohexylmethylthio-2-((thiophen-2-ylmethyl)-amino)propanamide

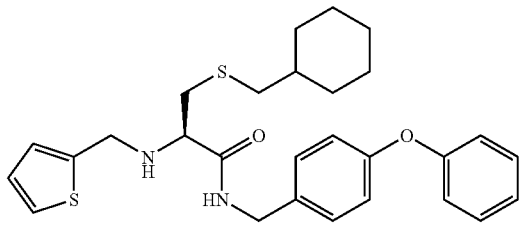

TLC: Rf 0.41 (hexane:ethyl acetate=2:1); NMR (CD$_3$OD): δ 7.37–7.25 (m, 5H), 7.12–7.05 (m, 1H), 7.00–6.91 (m, 6H), 4.42 (d, J=14.6 Hz, 1H), 4.34 (d, J=14.6 Hz, 1H), 3.98 (d, J=14.1 Hz, 1H), 3.86 (d, J=14.1 Hz, 1H), 3.33–3.28 (m, 1H), 2.83 (dd, J=13.4, 6.0 Hz, 1H), 2.68 (dd, J=13.4, 7.4 Hz, 1H), 2.32 (dd, J=12.6, 6.9 Hz, 1H), 2.26 (dd, J=12.6, 6.9 Hz, 1H), 1.84–1.59 (m, 5H), 1.47–1.06 (m, 4H), 0.99–0.80 (m, 2H).

Example 20(6)

(2R)-N-(4-phenoxybenzyl)-3-cyclohexylmethylthio-2-((cyclohexylmethyl)-amino)propanamide

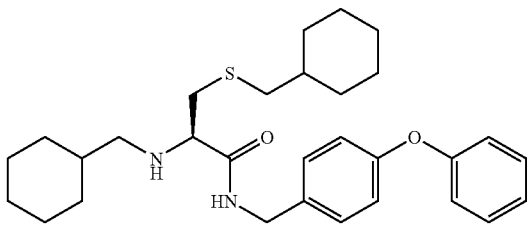

TLC: Rf 0.52 (hexane:ethyl acetate=2:1); NMR (CD$_3$OD) δ 7.38–7.27 (m, 4H), 7.13–7.04 (m, 1H), 6.98–6.89 (m, 4H), 4.45 (d, J=14.6 Hz, 1H), 4.30 (d, J=14.6 Hz, 1H), 3.17 (dd, J=7.4, 6.2 Hz, 1H), 2.83 (dd, J=13.2, 6.2 Hz, 1H), 2.65 (dd, J=13.2, 7.4 Hz, 1H), 2.42–2.23 (m, 0.4H) 1.90–0.70 (m, 22H).

Example 20(7)

(2R)-N-(4-methoxybenzyl)-3-cyclohexylmethylthio-2-(((4R)-3-(3-methylbutyryl)-thiazolidin-4-ylmethyl)amino)propanamide

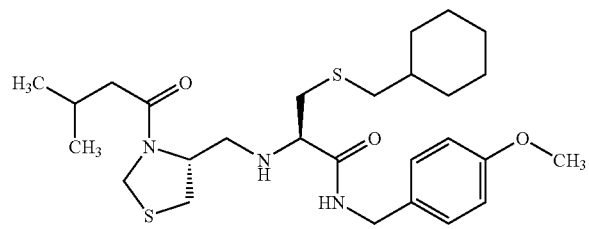

TLC: Rf 0.33 (hexane:ethyl acetate=1:1); NMR (DMSO-d$_6$) δ 8.06–8.00 (br, 1H), 7.20 (d, J=8.0 Hz, 2H), 6.85 (d, J=8.0 Hz, 2H), 4.76–4.68 (br, 1H), 4.53–4.42 (br, 1H), 4.28–4.18 (m, 3H), 3.74 (s, 3H), 3.24–3.21 (m, 1H), 3.09–2.95 (m, 2H), 2.77–2.60 (m, 4H), 2.45–2.38 (m, 2H), 2.28–2.17 (m, 3H), 2.09–2.00 (m, 1H), 1.79–1.73 (m, 2H), 1.69–1.58 (m, 3H), 1.46–1.38 (m, 1H), 1.26–1.10 (m, 3H), 0.99–0.91 (m, 8H).

Example 21~Example 21(2)

By the same desired procedure as Example 17, using the compounds prepared in Example 20~Example 20(1) and Example 20(4), the following compounds of the present invention were obtained.

Example 21

(2R)-N-(4-methoxybenzyl)-3-cycloyhexylmethylthio-2-(((4R)-thiazolidin-4-ylmethyl)amino)propanamide

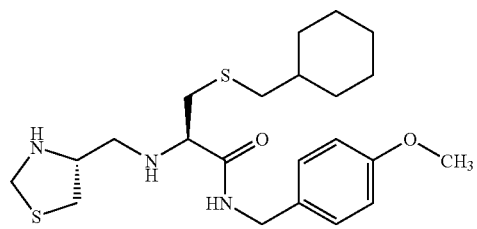

TLC: Rf 0.34 (methylene chloride:methanol=19:1); NMR (CDCl$_3$): δ 7.76–7.66 (m, 1H), 7.23–7.16 (m, 2H), 6.89–6.83 (m, 2H), 4.37 (d, J=6 Hz, 2H), 4.16 (d, J=10 Hz, 1H), 4.10 (d, J=10 Hz, 1H), 3.80 (3H, s), 3.39 (quintet, J=7 Hz, 1H), 3.19 (dd, J=10, 3 Hz, 1H), 3.08 (dd, J=14, 3 Hz, 1H), 2.96 (dd, J=10, 7 Hz, 1H), 2.68 (d, J=7 Hz, 2H), 2.61 (dd, J=14, 10 Hz, 1H), 2.47(dd, J=10, 7 Hz, 1H), 2.42 (dd, J=13, 7 Hz, 1H), 2.39(dd, J=13, 7 Hz, 1H), 2.00–1.58 (m, 7H), 1.53–1.36 (m, 1H), 1.32–1.05 (m, 3H), 1.02–0.83 (2H, m).

Example 21(1)

(2R)-N-(4-phenoxybenzyl)-3-cyclohexylmethylthio-2-(((4R)-thiazolidin-4-ylmethyl)amino)propanamide

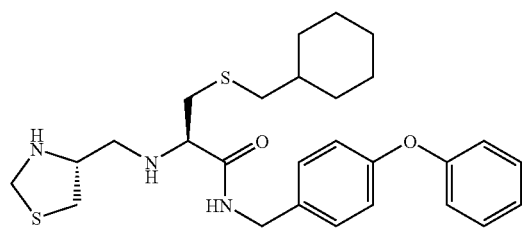

TLC: Rf 0.47 (chloroform:methanol=19:1); NMR (CD$_3$OD): δ 7.40–7.29 (m, 4H), 7.15–7.04 (m, 1H), 7.00–6.90 (m, 4H), 4.43 (d, J=14.6 Hz, 1H), 4.34 (d, J=14.6 Hz, 1H), 4.13 (d, J=9.2 Hz, 1H), 4.02 (d, J=9.2 Hz, 1H), 3.78–3.54 (m, 1H), 3.33–3.23 (m, 1H), 2.99–2.60 (m, 6H), 2.52 (dd, J=9.8, 7.0 Hz, 1H), 2.41 (d, J=6.6 Hz, 2H), 1.90–0.80 (m, 11H).

Example 21(2)

(2R)-N-(4-methoxybenzyl)-3-cyclohexylmethylthio-2-(((4RS)-1,3-perhydrothiazin-4-ylmethyl)amino) propanamide

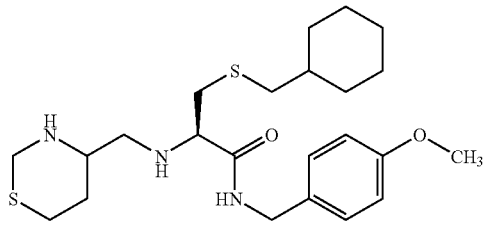

TLC: Rf 0.37 (methylene chloride:methanol=9:1); NMR (CD₃OD) δ 7.28–7.21 (m, 2H), 6.90–6.83 (m, 2H), 4.42–4.25 (m, 2H), 4.08–3.97 (m, 1H), 3.95–3.86 (m, 1H), 3.77 (s, 3H), 3.23–3.13 (m, 1H), 3.01–2.76 (m, 2H), 2.76–2.56 (m, 3H), 2.56–2.32 (m, 4H), 1.87–1.60 (m, 6H), 1.50–1.08 (m, 5H), 1.03–0.84 (m, 2H).

Example 22

(2R)-N-(4-methoxybenzyl)-3-((1S,2R,4R)-bicyclo[2.2.1]heptan-2-ylmethylthio)-2-((4R)-3-t-butoxycarbonylthiazildin-4-ylcarbonylamino) propanamide

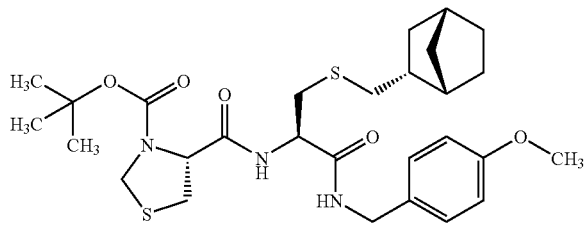

By the same desired procedure as Example 6, using the compound prepared in Example 10(10), the compound of the present invention having the following physical data was obtained.

TLC: Rf 0.50 (ethyl acetate:hexane=1:1); NMR (CD₃OD): δ 7.27–7.15 (2H, m), 6.90–6.79 (2H, m), 4.67–4.43 (4H, m), 4.334 (1H, d, J=15 Hz), 4.31 (1H, d, J=15 Hz), 3.76 (3H, s), 3.43–3.25 (1H, m), 3.14 (1H, dd, J=12, 4 Hz), 3.02–2.70 (2H, m), 2.57 (1H, dd, J=12, 8 Hz), 2.55 (1H, dd, J=12, 8 Hz), 2.22–2.10 (2H, m), 2.10–1.69 (2H, m), 1.61–1.03 (6H, m), 1.45 (9H, s), 0.68 (1H, ddd, j=12, 5, 2 Hz).

Example 23

(2R)-N-(4-methoxybenzyl)-3-((1S,2R,4R)-bicyclo[2.2.1]heptan-2-ylmethylthio)-2-((4R)-3-t-butoxycarbonylthiazildin-4-ylcarbonylamino) propanamide. hydrochloride

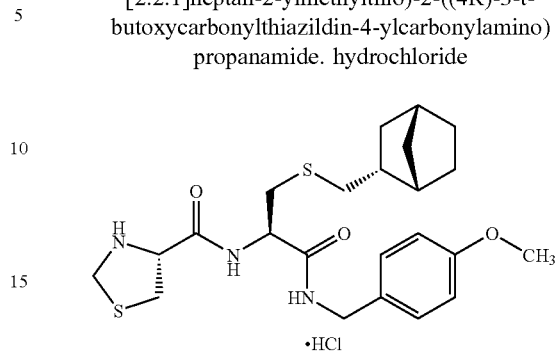

By the same desired procedure as Example 9, using the compound prepared in Example 22, the compound of the present invention having the following physical data was obtained.

TLC: Rf 0.51 (methylene chloride:methanol=19:1); NMR (CD₃OD): δ 7.30–7.18 (2H, m), 6.93–6.83 (2H, m), 4.60–4.46 (2H, m), 4.39 (2H, s), 4.36–4.24 (2H, m), 3.50 (1H, dd j=12, 7 Hz), 3.24 (1H, dd, J=12, 7 Hz), 2.94 (1H, dd, J=13, 6 Hz), 2.82 (1H, dd, J=13, 8 Hz), 2.59 (1H, dd, J=12, 8 Hz), 2.57 (1H, dd, J=12, 8 Hz), 2.22–2.11 (2H, m), 2.10–1.89 (1H, m), 1.89–1.70 (1H, m), 1.62–1.03 (6H, m), 0.68 (1H, ddd, J=12, 5, 2 Hz).

Formulation Example

Fomulation Example 1

The following components were admixed in conventional method and punched out to obtain 100 tablets each containing 50 mg of active ingredient.

| | |
|---|---|
| (2R)-N-(4-methoxybenzyl)-3-cyclohexylmethylthio-2-((4R)-3-t-butoxycarbonylthiazolidin-4-ylcarbonylamino)propanamide | 5.0 g |
| carboxymethylcellulose calcium (disintegrating agent) | 0.2 g |
| Magnesium stearate (Lubricating agent) | 0.1 g |
| Microcrystaline cellulose | 4.7 g |

Formulation Example 2

The following components were admixed in conventional manner. The solution was sterilized in conventional manner, placed 5 ml portions into ampoules and freezed-dried to obtain 100 ampouls each containing 20 mg of active ingredient.

| | |
|---|---|
| (2R)-N-(4-methoxybenzyl)-3-cyclohexylmethylthio-2-((4R)-3-t-butoxycarbonylthiazolidin-4-ylcarbonylamino)propanamide | 2.00 g |
| mannitol | 20 g |
| distilled water | 500 ml |

What is claimed is:

1. An amino acid compound of the formula (I):

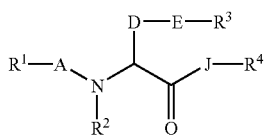

wherein $R^1$ is a 5–15 membered saturated, partially saturated or unsaturated mono-cyclic or bi-cyclic hetero ring containing 1–2 nitrogen atoms, 1–2 oxygen atoms and/or one sulfur atom, (with the proviso that, all 5–15 membered saturated, partially saturated or unsaturated mono-cyclic or bi-cyclic hetero rings containing 1–2 nitrogen atoms, 1–2 oxygen atoms and/or one sulfur atom in the $R^1$ group may be substituted by 1~3 substituents selected from the following (i)~(xi);

(i) C1–4 alkyl,
(ii) C1–4 alkoxy,
(iii) phenyl,
(iv) phenoxy,
(v) benzyloxy,
(vi) —$SR^5$ (in which $R^5$ is hydrogen or C1–4 alkyl),
(vii) C2–5 acyl,
(viii) halogen,
(ix) C1–4 alkoxycarbonyl,
(x) nitro,
(xi) —$NR^6R^7$ (in which $R^6$ and $R^7$ each independently, is hydrogen, C1–4 alkyl or C1–4 alkoxycarbonyl, or $R^6$ and $R^7$ taken together with the nitrogen atom to which they are attached may represent a 5~7 membered saturated hetero ring optionally containing another one nitrogen atom or one oxygen atom));

A is bond, —CO— or —$SO_2$—, $R^2$ is hydrogen or C1–4 alkyl optionally substituted by one phenyl;

D is C1–4 alkylene or C2–4 alkenylene;

E is

1) —OCO—,
2) —$CONR^8$— (in which $R^8$ is hydrogen or C1–4 alkyl),
3) —$NR^9CO$— (in which $R^9$ is hydrogen or C1–4 alkyl),
4) —O—,
5) —S—,
6) —SO—,
7) —$SO_2$—,
8) —$NR^{10}$— (in which $R^{10}$ is hydrogen or C1–4 alkyl),
9) —CO—,
10) —$SO_2NR^{11}$— (in which $R^{11}$ is hydrogen or C1–4 alkyl), or
11) —$NR^{12}SO_2$— (in which $R^{12}$ is hydrogen or C1–4 alkyl);

$R^3$ is

C1–4 alkyl substituted by C3–10 mono-, bi- and bridged carbocyclic ring (with the proviso that, all C3–10 mono-, bi- and bridged carbocyclic rings in $R^3$, may be substituted by 1~3 substituents selected from the following (i)~(xi);

(i) C1–4 alkyl,
(ii) C1–4 alkoxy,
(iii) phenyl,
(iv) phenoxy,
(v) benzyloxy,
(vi) —$SR^{13}$ (in which $R^{13}$ is hydrogen or C1–4 alkyl),
(vii) C2–5 acyl,
(viii) halogen,
(ix) C1–4 alkoxycarbonyl,
(x) nitro,
(xi) —$NR^{14}R^{15}$ (in which $R^{14}$ and $R^{15}$ each independently, is hydrogen, C1–4 alkyl or C1–4 alkoxycarbonyl, or $R^{14}$ and $R^{15}$ taken together with the nitrogen atom to which they are attached may represent a 5~7 membered saturated hetero ring optionally containing another one nitrogen atom or one oxygen atom));

J is —O— or —$NR^{16}$— (in which $R^{16}$ is hydrogen or C1–4 alkyl);

$R^4$ is a C1–8 alkyl substituted by C3–10 mono-, bi- and bridged carbocyclic ring (with the proviso that, all C3–10 mono-, bi- and bridged carbocyclic rings in $R^4$, may be substituted by 1~3 of substituents selected from the following (i)~(xi);

(i) C1–4 alkyl,
(ii) C1–4 alkoxy,
(iii) phenyl,
(iv) phenoxy,
(v) benzyloxy,
(vi) —$SR^{20}$ (in which $R^{20}$ is hydrogen or C1–4 alkyl),
(vii) C2–5 acyl,
(viii) halogen,
(ix) C1–4 alkoxycarbonyl,
(x) nitro,
(xi) —$NR^{21}R^{22}$ (in which $R^{21}$ and $R^{22}$ each independently, is hydrogen, C1–4 alkyl or C1–4 alkoxycarbonyl, or $R^{21}$ and $R^{22}$ taken together with the nitrogen atom to which they are attached may represent a 5~7 membered saturated hetero ring optionally containing another one nitrogen atom or one oxygen atom))

a non-toxic salt thereof, or a hydrate thereof.

2. A compound according to claim 1, wherein E is —OCO—, —$CONR^8$—, —$NR^9CO$—, —$NR^{10}$—, —CO—, —$SO_2NR^{11}$, or —$NR^{12}SO_2$—, (in which $R^8$, $R^9$, $R^{10}$, $R^{11}$ and $R^{12}$ are the same meanings as described in claim 1).

3. The compound according to claim 1, wherein E is —O—, —S—, —SO—, or —$SO_2$—.

4. A compound according to claim 1, which is (1) (2R)-N-(4-methoxybenzyl)-3-cyclohexylmethylthio-2-((2RS)-3-t-butoxy-carbonylthiazolidin-2-ylcarbonylamino)propanamide, (2) (2R)-N-(4-methoxybenzyl)-3-cyclohexylmethylthio-2-(1-(t-butoxy-carbonyl)piperidin-4-ylcarbonylamino)propanamide, (3) (2R)-N-(4-methoxybenzyl)-3-cyclohexylmethylthio-2-(tetrahydrofuran-2-ylcarbonylamino)propanamide, (4) (2R)-N-(4-methoxybenzyl)-3-cyclohexylmethylthio-2-((4R)-3-t-butoxy-carbonylthiazolidin-4-ylcarbonylamino)propanamide, (5) (2R)-N-(4-methoxybenzyl)-3-cyclohexylmethylthio-2-((2S)-1-t-butoxy-carbonylpyrrolidin-2-ylcarbonylamino)propanamide, (6) (2R)-N-(4-methoxybenzyl)-3-cyclohexylmethylthio-2-(thiazol-4-ylcarbonylamino)propanamide, (7) (2R)-N-((1R)-1-(4-nitrophenyl)ethyl)-3-cyclohexylmethylthio-2-((4R)-3-t-butoxycarbonyithazolidin-4-ylcarbonylamino)propanamide, (8) (2S)-N-((1R)-1-(4-nitrophenyl)ethyl)-3-cyclohexylmethylthio-2-((4R)-3-t-butoxycarbonylthiazolidin-4-ylcarbonylamino)propanamide, (9) (2R)-N-(4-methoxybenzyl)-3-cyclohexylmethylthio-2-(2-t-butoxycarbonylaminothiazol-4-ylcarbonylamino)propanamide

(10) (2R)-N-(4-methoxybenzyl)-3-cyclohexylmethylthio-2-((4S)-3-t-butoxy-carbonylthiazolidin-4-ylcarbonylamino)propanamide,

(11) (2R)-N-(4-nitrobenzyl)-3-cyclohexylmethylthio-2-((4R)-3-t-butoxycarbonylthiazolidin-4-ylcarbonylamino)propanamide,

(12) (2R)-N-(4-nitrobenzyl)-3-cyclohexylmethylthio-2-((2RS)-3-t-butoxycarbonylthiazolidin-2-ylcarbonylamino)propanamide,

(13) (2R)-N-(4-nitrobenzyl)-3-cyclohexylmethylthio-2-((4R)-3-methylthiazolidin-4-ylcarbonylamino)propanamide,

(14) (2R)-N-(4-dimethylaminobenzyl)-3-cyclohexylmethylthio-2-((4R))-3-t-butoxycarbonylthiazolidin-4-ylcarbonylamino)propanamide,

(15) (2R)-N-(4-dimethylaminobenzyl)-3-cyclohexylmethylthio-2-((2RS)-3-t-butoxycarbonylthiazolidin-2-ylcarbonylamino)propanamide,

(16) (2R)-N-(4-nitrobenzyl)-3-cyclohexylmethylthio-2-(1-t-butoxycarbonyl-imidazol-4-ylcarbonylamino)propanamide,

(17) (2R)-N-(4-nitrobenzyl)-3-cyclohexylmethylthio-2-((4R)-2,2-dimethylthiazolidin-4-ylcarbonylamino)propanamide,

(18) (2R)-N-(4-nitrobenzyl)-3-cyclohexylmethylthio-2-(thiophen-2-ylcarbonylamino)propanamide,

(19) (2R)-N-(4-nitrobenzyl)-3-cyclohexylmethylthio-2-(5-methyloxazol-2-ylcarbonylamino)propanamide,

(20) (2R)-N-(4-methoxybenzyl)-3-cyclohexylmethylthio-2-(3-t-butoxycarbonylthiazolidin-2-ylcarbonylamino)propanamide,

(21) (2R)-N-(4-methoxybenzyl)-3-cyclobexylmetbylthio-2-(3-t-butoxycarbonylthiazolidin-2-ylcarbonylamino)propanamide,

(22) (2S)-N-(4-methoxybenzyl)-3-cyclohexylmethylthio-2-(3-t-butoxycarbonylthiazolidin-2-ylcarbonylamino)propanamide,

(23) (2S)-N-(4-methoxybenzyl)-3-cyclohexylmethylthio-2-((4S)-3-t-butoxycarbonylthiazolidin-4-ylcarbonylamino)propanamide,

(24) (2S)-N-(4-methoxybenzyl)-3-cyclohexylmethylthio-2-((4R)-3-t-butoxycarbonylthiazolidin-4-ylcarbonylamino)propanamide,

(25) (2R)-N-methyl-N-(4-methoxybenyl)-3-cyclohexylmethylthio-2-((4R)-3-t-butoxycarbonylthiazolidin-4-ylcarbonylamino)propanamide,

(26) (2R)-N-(4-methoxybenzyl)-3-cyclohexylmethylthio-2-((4R)-N'-methyl-N'-(3-t-butoxycarbonytthiazolidn-4-ylcarbonyl)amino)propanamide,

(27) (2R)-N-(4-phenoxybenzyl)-3-cyclohexylmethylthio-2-((4R)-3-t-butoxycarbonylthiazolidin-4-ylcarbonylamino)propanamide,

(28) (2R)-N-(4-methoxybenzyl)-3-cyclohexylmethylthio-2-((2RS,4R)-3-t-butoxycarbonyl-2-(2-methylpropyl)thiazolidin-4-ylcarbonylamino)propanamide,

(29) (2R)-N-(4-metboxybenzyl)-3-cyclohexylmethylthio-2-(pyridin-3-ylcarbonylamino)propanamide,

(30) (2R)-N-(4-benzyloxybenzyl)-3-cyclohexylmethylthio-2-((4R)-3-t-butoxycarbonylthiazolidin-4-ylcarbonylamino)propanamide,

(31) (2R)-N-(3-benzyloxy-4-methoxybenzyl)-3-cyclohexylmethylthio-2-((4R)-3-t-butoxycarbonylthiazolidin-4-ylcarbonylamino)propanamide,

(32) (2R)-N-(4-methoxybenzyl)-3-cyclohexylmethylthio-2-(pyridin-4-ylcarbonylamino)propanamde,

(33) (2R)-N-(4-methoxybenzyl)-3-cyclohexylmethylthio-2-((2RS,4R)-3-t-butoxycarbonyl-2-phenylthiazolidin-4-ylcarbonylamino)propanamide,

(34) (2R)-N-(4-methoxybenzyl)-3-cyclohexylmethylthio-2-((3RS)-4-t-butoxycarbonylthiomorpholin-3-ylcarbonylamino)propanamide,

(35) (2R)-N-(4-phenoxybenzyl)-3-cyclohexylmethylthio-2-((3RS)-4-t-butoxycarbonylthiomorpholin-3-ylcarbonylamino)propanamide,

(36) (2R)-N-(4-methoxybenzyl)-3-cyclohexylmethylthio-2-((2RS)-4-t-butoxycarbonylthiomorpholin-2-ylcarbonylamino)propanamide,

(37) (2R)-N-(4-methoxybenzyl)-3cyclohexylmethylthio-2-(4RS)-3-t-butoxycarbonyl-1,3-perhydrothiazin-4-ylcarbonylamino)propanamide,

(38) (2R)-N-(4-(morpholin-4-yl)benzyl)-3-cyclohexylmethylthio-2-((4R)-3-t-butoxycarbonylthiazolidin-4-ylcarbonylamino)propanamide,

(39) (2R)-N-(4-phenoxybenzyl)-3-cyclohexylmethylthio-2-((4RS)-3-t-butoxycarbonyl-1,3-perhydrothiazin-4-ylcarbonylamino)propanamide,

(40) (2R)-N-(4-methoxybenzyl)-3-cyclohexylmethylthio-2-(4R)-2oxothiazolidin-4-ylcarbonylamino)propanamide,

(41) (2R)-N-(4-methoxybenzyl)-3-cyclohexylmethylsulfonyl-2-(tetrahydrofuran-2-ylcarbonylamino)propanamide,

(42) (2R)-N-(4-methoxybenzyl)-3-cyclohexylmethylsulfonyl-2-(tetrahydrofuran-3-ylcarbonylamino)propanamide,

(43) (2R)-N-(4-methoxybenzyl)-3-cyclohexylmethylsulfonyl-2-((2RS)-3-t-butoxycarbonylthiazolidin-2-ylcarbonylamino)propanamide,

(44) (2R)-N-(4-methoxybenzyl)-3-cyclohexylmethylsulfonyl-2-((4R)-3-t-butoxycarbonylthiazolidin-4-ylcarbonylamino)propanamide,

(45) (2R)-N-(4-methoxybenzyl)-3-cyclohexylmethylsulfonyl-2-(3-t-butoxycarbonylthiazolidin-2-ylcarbonylamino)propanamide,

(46) (2R)-N-(4-methoxybenzyl)-3-cyclohexylmethylsulfinyl-2-((4R)-3-t-butoxycarbonylthiazolidin-4-ylcarbonylamino)propanamide,

(47) (2R)-N-(4-methoxybenzyl)-3-cyclohexylmethylsulfonyl-2-(1-t-butoxycarbonylpiperidin-4-ylcarbonylamino)propanamide,

(48) (2R)-N-(4-methoxybenzyl)-3-cyclohexylmethylsulfonyl-2-((2RS)-thiazolidin-2-ylcarbonylamino)propanamide,

(49) (2R)-N-(4-methoxybenzyl)-3-cyclohexylmethylthio-2-piperidin-4-ylcarbonylamino)propanamide,

(50) (2R)-N-((1R)-1-(4-nitrophenyl)ethyl)-3-cyclohexylmethylhio-2-((4R)-thiazolidin-4-ylcarbonylamino)propanamide,

(51) (2R)-N-(4-methoxybenzyl)-3-cyclohexylmethylthio-2-((4S)thiazolidin-4-ylcarbonylamino)propanamide,

(52) (2R)-N-(4-nitrobenzyl)-3-cyclohexylmethylhio-2-((4R)thiazolidin-4-ylcarbonylamino)propanamide,

(53) (2R)-N-(4-nitrobenzyl)-3-cyclohexylmethylthio-2-((2RS)thiazolidin-2-ylcarbonylamino)propanamide,

(54) (2R)-N-(4-nitrobenzyl)-3-cyclohexylmethylthio-2-(imidazol-4-ylcarbonylamino)propanamide,

(55) (2R)-N-(4-dimethylaminobenzyl)-3-cyclohexylmethylthio-2-((4R)thiazolidin-4-ylcarbonylamino)propanamide,

(56) (2R)-N-(4-dimethylaminobenzyl)-3-cyclohexylmethylthio-2-((2RS)-thiazolidin-2-ylcarbonylamino)propanamide,

(57) (2R)-N-(4-benzyloxybenzyl)-3-cyclohexylmethylthio-2-((4R)-thiazolidin-4-ylcarbonylamino)propanamide, 58) (2R)-N-(3-benzyloxy-4-methoxybenzyl)-3-cyclohexylmethylthio-2-((4R)-thiazolidin-4-ylcarbonylamino)propanamide,

(59) (2R)-N-(4-phenoxybenyl)-3cyclohexylmethylthio-2-((4R)-thiolidin-4-ylcarbonylamino)propanamide,

(60) (2R)-N-(4-methoxybenzyl)-3-cyclohexylmethylthio-2-((2RS)-thiolidin-2-ylcarbonylamino)propanamide,

(61) (2R)-N-(4-methoxybenzyl)-3-cyclohexylmethylthio-2-((4R)-thiolidin-4-ylcarbonylamino)propanamide,

(62) (2R)-N-(4-methoxybenzyl)-3cyclohexylmethylthio-2-(2-aminothiazol-4-ylcarbonylamino)propanamide,

(63) (2R)-N-(4-methoxybenyl)-3-cyclohexylmethylthio-2-(thiolidin-2-ylcarbonylanhino)propanamide,

(64) (2R)-N-(4-methoxybenzyl)-3-cyclohexylmethylthio-2-((2RS,4R)-2-(2-methylpropyl)thiazolidin-4-ylcarbonylamino)propanamide,

(65) (2R)-N-(4-methoxybenzyl)-3-cyclohexylmethylthio-2-((2RS,4R)-2-phenylthiazolidin-4-yl carbonylamino)propanamide,

(66) (2R)-N-(4-methoxybenzyl)-3-cyclohexylmethylthio-2-((3RS)thiomorpholin-3-ylcarbonylamino)propanamide,

(67) (2R)-N-(4-phenoxybenzyl)-3-cyclohexylmethylthio-2-((3RS)thiomorpholin-3-ylcarbonylamino)propanainide,

(68) (2R)-N-(4-methoxybenzyl)-3cyclohexylmethylthio-2-((2RS)thiomorpholin-2-ylcarbonylamino)propanamide,

(69) (2R)-N-(4-methoxybenzyl)-3-cyclohexylmethylthio-2-((4RS)-1,3-perhydrothiazin-4-ylcarbonylamino)propanamide,

(70) (2R)-N-(4-morpholin-4-yl)-3-cyclohexylmethylthio-2-((4R)-thiozolidin-4-ylcarbonylamino)propanamide,

(71) (2R)-N-(4-phenoxybenzyl)-3-cyclohexylmetbylthio-2-((4RS)-1,3-perhydrothiazin-4-ylcarbonylamino)propanamide,

(72) (2R)-N-((1R)-1-(4-nitrophenyl)ethyl)-3-cyclohexylmethylthio-2-(4R)-3-(2-methylpropylcarbonyl)thiazolidin-4-ylcarbonylamino)propanamide,

(73) (2R)-N-(4-methoxybenzyl)-3-cyclohexylmethylthio-2-((2RS)-3-acetylthiazolidin-2-ylcarbonylamino)propanamide

(74) (2R)-N-(4-phenoxybenzyl)-3-cyclohexylmethylthio-2-((4R)-3-methoxycarbonylthiazolidin-4-ylcarbonylamino)propanamide,

(75) (2R)-N-(4-phenoxybenzyl)-3-cyclohexylmethylthio-2-(4R)-3-(2-methylpropoxycarbonyl)thiazolidin-4-ylcarbonylamino)propanamide,

(76) (2R)-N-(4-methoxybenzyl)-3-cyclohexylmethylthio-2-((4R)-3-methoxycarbonylthiazolidin-4-ylcarbonylamino)propanamide,

(77) (2R)-N-(4-methoxybenzyl)-3-cyclohexylmethylthio-2-((4R)-3-(2-methylpropoxycarbonyl)thiazolidin-4-ylcarbonylamino)propanamide,

(78) (2R)-N-(4-dimethylaminobenzyl)-3-cyclohexylmethylthio-2-(thiazolidin-2-ylcarbonylamino)propanamide,

(79) (2R)-N-(4-methoxybenzyl)-3-((1S,2R,4R)-bicyclo[2.2.1]heptan-2-ylmethylthio)-2-((4R)-3-t-butoxycarbonylthiazolidin-4-ylcarbonylamino)propanamide, or

(80) (2R)-N-(4-methoxybenzyl)-3-((1S,2R,4R)-bicyclo[2.2.1]heptan-2-ylmethylthio-2-((4R)-thiazolidin-4-ylcarbonylamino)propanamide, or a non-toxic salt thereof, or a hydrate thereof.

5. A pharmaceutical composition comprising, as an active ingredient, an amino acid compound of formula (I) depicted in claim 1, a non-toxic salt thereof or a hydrate thereof.

6. A method for treating a disease induced by an excessive release of neurotransmitters from N-type calcium channels, comprising administering, to a host in need of such treatment, an effective amount of an amino acid compound of formula (I) depicted in claim 1, a non-toxic salt thereof or a hydrate thereof.

7. The method according to claim 6, wherein the disease induced by an excessive release of neurotransmitters from N-type calcium channels is selected from the group consisting of cerebral infarct, transient ischemic attack, encephalomyelopathy after cardiac operation, spinal angiopathy, hypertension with stress, neurosis and epilepsy.

8. A method for the treatment of pain induced by an excessive release of neurotransmitters from N-type calcium channels, comprising administering to a host in need of such treatment, an effective amount of an amino acid compound of formula (I) depicted in claim 1, a non-toxic salt thereof or a hydrate thereof.

* * * * *